United States Patent
Suto et al.

(10) Patent No.: US 10,653,682 B2
(45) Date of Patent: May 19, 2020

(54) OXADIAZOLES AND THIADIAZOLES AS TGF-β INHIBITORS

(71) Applicants: Southern Research Institute, Birmingham, AL (US); UAB Research Foundation, Birmingham, AL (US)

(72) Inventors: Mark J. Suto, Homewood, AL (US); Vandana V. Gupta, Birmingham, AL (US); Bini Mathew, Hoover, AL (US); Joanne Murphy-Ullrich, Birmingham, AL (US)

(73) Assignees: Southern Research Institute, Birmingham, AL (US); UAB Research Foundation, Birmingham, AL (US)

(*) Notice: Subject to any disclaimer, the term of this patent is extended or adjusted under 35 U.S.C. 154(b) by 0 days.

(21) Appl. No.: 16/172,312

(22) Filed: Oct. 26, 2018

(65) Prior Publication Data

US 2019/0125730 A1    May 2, 2019

Related U.S. Application Data

(60) Provisional application No. 62/577,608, filed on Oct. 26, 2017.

(51) Int. Cl.
| | |
|---|---|
| *A61K 31/433* | (2006.01) |
| *A61K 31/4245* | (2006.01) |
| *A61P 37/06* | (2006.01) |
| *A61K 31/4709* | (2006.01) |
| *A61P 35/00* | (2006.01) |
| *A61K 31/4439* | (2006.01) |

(52) U.S. Cl.
CPC ........ *A61K 31/433* (2013.01); *A61K 31/4245* (2013.01); *A61K 31/4439* (2013.01); *A61K 31/4709* (2013.01); *A61P 35/00* (2018.01); *A61P 37/06* (2018.01)

(58) Field of Classification Search
CPC ............................ C07D 285/10; A61K 31/433
See application file for complete search history.

(56) References Cited

U.S. PATENT DOCUMENTS

| | | |
|---|---|---|
| 2004/0157861 A1 | 8/2004 | Scarborough et al. |
| 2006/0264415 A1 | 11/2006 | Leit de Moradei et al. |
| 2012/0232268 A1 | 9/2012 | Burgess |
| 2015/0252032 A1 | 9/2015 | Bolli et al. |
| 2017/0101387 A1 | 4/2017 | Sasikumar et al. |

FOREIGN PATENT DOCUMENTS

WO PCT/US2018/057798    10/2018

OTHER PUBLICATIONS

Yanagisawa et al. CAS: 165: 458319, 2016.*
Tran et al. CAS: 152: 168885, 2009.*
Mcgaughey et al. CAS: 166:373123, 2012.*
Rajapakse et al. CAS: 145: 230579, 2006.*
Adams and Lawler "The thrombospondins", (2004) Int J Biochem Cell Biol 36:961-968.
Adams and Lawler "The Thrombospondins", (2011) Cold Spring Harb Perspect Biol 3:a009712.
Agah et al. "The Lack of Thrombospondin-1 (TSP1) Dictates the Course of Wound Healing in Double-TSP1/TSP2-Null Mice", (2002) Am J Pathol 161:831-839.
Belmadani et al. ""A Thrombospondin-1 Antagonist of Transforming Growth Factor-β Activation Blocks Cardiomyopathy in Rats with Diabetes and Elevated Angiotensin II"" (2007) Am J Pathol 171:777-789.
Breitkopf et al. "Thrombospondin 1 acts as a strong promoter of transforming growth factor β effects via two distinctmechanisms in hepatic stellate cells" (2005) Gut 54:673-681.
Chen et al. "Thrombospondin 1 is a key mediator of transforming growth factor β-mediated cell contractility in systemic sclerosis via a mitogen-activated protein kinase kinase (MEK)/extracellular signal-regulated kinase (ERK)-dependent mechanism", (2011) Fibrogenesis Tissue Repair 4:9.
Chipev, et al. ""Myofibroblast phenotype and apoptosis in keloid and palmar fibroblasts in vitro"" (2000) Cell Death Differ 7:166-176.
Connolly et al. "Outgrowth of Drug-Resistant Carcinomas Expressing Markers of Tumor Aggression after Long-term TβRI/II Kinase Inhibition with LY2109761", (2011) Cancer Res 71:2339-2349.
Crawford et al. "Thrombospondin-1 is a major activator of TGF-beta1 in vivo", (1998) Cell 93:1159-1170.
Daniel et al. "Thrombospondin-1 is a major activator of TGF-β in fibrotic renal disease in the rat in vivo", (2004) Kidney Int 65:459-468.
Daniel et al. "Thrombospondin-1 Is an Endogenous Activator of TGF-β in Experimental Diabetic Nephropathy In Vivo", (2007) Diabetes 56:2982-2989.
DiPietro et al. "Thrombospondin 1 synthesis and function in wound repair", (1996) Am J Pathol 148:1851-1860.
Dropmann et al. "TGF-β1 and TGF-β2 abundance in liver diseases of mice and men", (2016) Oncotarget 7:19499-19518.
Fabregat et al. "TGF-β signalling and liver disease", (2016) The FEBS journal 283:2219-2232.
Hayashi et al. "Thrombospondin-1 Is a Novel Negative Regulator of Liver Regeneration After Partial Hepatectomy Through Transforming Growth Factor-beta1 Activation in Mice" (2012) Hepatology 55:1562-1573.

(Continued)

*Primary Examiner* — Rei Tsang Shiao
(74) *Attorney, Agent, or Firm* — Ballard Spahr LLP

(57) ABSTRACT

The present disclosure is concerned with oxadiazole and thiadiazole analogs that are capable of inhibiting TGF-β and methods of treating cancers such as, for example, multiple myeloma and a hematologic malignancy, and methods of treating fibrotic conditions using these compounds. This abstract is intended as a scanning tool for purposes of searching in the particular art and is not intended to be limiting of the present invention.

23 Claims, 30 Drawing Sheets

(56) References Cited

OTHER PUBLICATIONS

Hugo "The thrombospondin 1-TGF-β axis in fibrotic renal disease", (2003) Nephrol Dial Transplant 18:1241-1245.
Katz et al. "TGF-β signaling in liver and gastrointestinal cancers" (2016) Cancer letters 379(2):166-172.
Kondou et al. "A blocking peptide for transforming growth factor-beta1 activation prevents hepatic fibrosis in vivo", (2003) J Hepatol 39:742-748.
Kumar R et al, "TGF-β activation by bone marrow-derived thrombospondin-1 causes Schistosoma- and hypoxia-induced pulmonary hypertension", (2017) Nature Commun. 8: 15494.
Lu et al. "Blockade of TSP1-Dependent TGF-β Activity Reduces Renal Injury and Proteinuria in a Murine Model of Diabetic Nephropathy", (2011) Am J Pathol 178:2573-2586.
Ludlow et al."Characterization of integrin β6 and thrombospondin 1 double-null mice" , (2005) J Cell Mol Med 9:421-437.
Mimura et al. "Constitutive thrombospondin-1 overexpression contributes to autocrine transforming growth factor-β signaling in cultured scleroderma fibroblsts", (2005) Am J Pathol 166:1451-1463.
Murphy-Ullrich and Mosher "Localization of thrombospondin in clots formed in situ", (1985) Blood 66:1098-1104.
Murphy-Ullrich and Poczatek "Activation of latent TGF-beta by thrombospondin-1: mechanisms and physiology", (2000) Cytokine Growth Factor Rev 11:59-69.
Narmada "HGF regulates the activation of TGF-β1 in rat hepatocytes and hepatic stellate cells", (2013) J Cell Physiol 228:393-401.
Nor et al. "Activation of Latent TGF-β1 by Thrombospondin-1 is a Major Component of Wound Repair" (2005) Oral Biosci Med 2:153-161.
Nyström A et al, "Losartan ameliorates dystrophic epidermolysis bullosa and uncovers new disease mechanisms" (2015) EMBO Mol Medicine 7: 1211-1228.
Poczatek et al. Glucose Stimulation of Transforming Growth Factor-β Bioactivity in Mesangial Cells Is Mediated by Thrombospondin-1 (2000) Am J Pathol 157:1353-1363.
Prud'homme, "Pathobiology of transforming growth factor β in cancer, fibrosis and immunologic disease, and therapeutic considerations" (2007) Lab Invest 87:1077-1091.
Raugi et al. "Thrombospondin in early human wound tissue" (1987) J Invest Dermatol 89:551-554.
Reed et al. "Differential expresion of SPARC and Thrombospondin 1 in wound repair Immunolocatization and in situ hybridization" (1993) J Histochem Cytochem 41:1467-1477.
Schultz-Cherry and Murphy-Ullrich "Thrombospondin causes activation of latent transforming growth factor-beta secreted by endothelial cells by a novel mechanism" (1993) J Cell Biol 122:923-932.
Wang et al. "Nitric Oxide and cGMP-dependent Protein Kinase Regulation of Glucose-mediated Thrombospondin 1-dependent Transforming Growth Factor-β Activation in Mesangial Cells" (2002) J Biol Chem 277:9880-9888.
Wang et al. Glucose Up-regulates Thrombospondin 1 Gene Transcription and Transforming Growth Factor-β Activity through Antagonism of cGMP-dependent Protein Kinase Repression via Upstream Stimulatory Factor 2 (2004) J Biol Chem 279:34311-34322.
Xu et al. "TGF-β/SMAD Pathway and Its Regulation in Hepatic Fibrosis" (2016) J Histochem Cytochem 64:157-167.
Yang et al. "Deficiency of thrombospondin-1 reduces Th17 differentiation and attenuates experimental autoimmune encephalomyelitis" (2009) J Autoimmun 32: 94-103.
Yehualaeshet et al. "A CD36 synthetic peptide inhibits bleomycin-induced pulmonary inflammation and connective tissue synthesis in the rat" (2000) Am. J. Respir. Cell Mol. Biol. 23: 204-12.
Yehualaeshet et al. "Activation of rat alveolar macrophage-derived latent transforming growth factor beta-1 by plasmin requires interaction with thrombospondin-1 and its cell surface receptor, CD36" (1999) Am J Pathol 155:841-851.
Yevdokimova et al. "Thrombospondin-1 is the key activator of TGF-β1 in human mesangial cells exposed to high glucose" (2001) J Am Soc Nephrol 12:703-712.
Yoshida et al. "TGF-β/Smad signaling during hepatic fibrocarcinogenesis" (2014) Int J Oncol 45:1363-1371.
Zhou et al. THY-1 expression regulates the ability of rat lung fibroblasts to activate transforming growth factor β in response to fibrogenic stimuli (2004) Am J Pathol 165:659-669.
International Search Report and Written Opinion dated Jan. 17, 2019 by the International Searching Authority for International Application No. PCT/US2018/057798, filed on Oct. 26, 2018 (Applicant—Southern Research Insitute) (9 Pages).
U.S. Appl. No. 62/577,608, filed Oct. 26, 2017, Mark J. Suto.

* cited by examiner

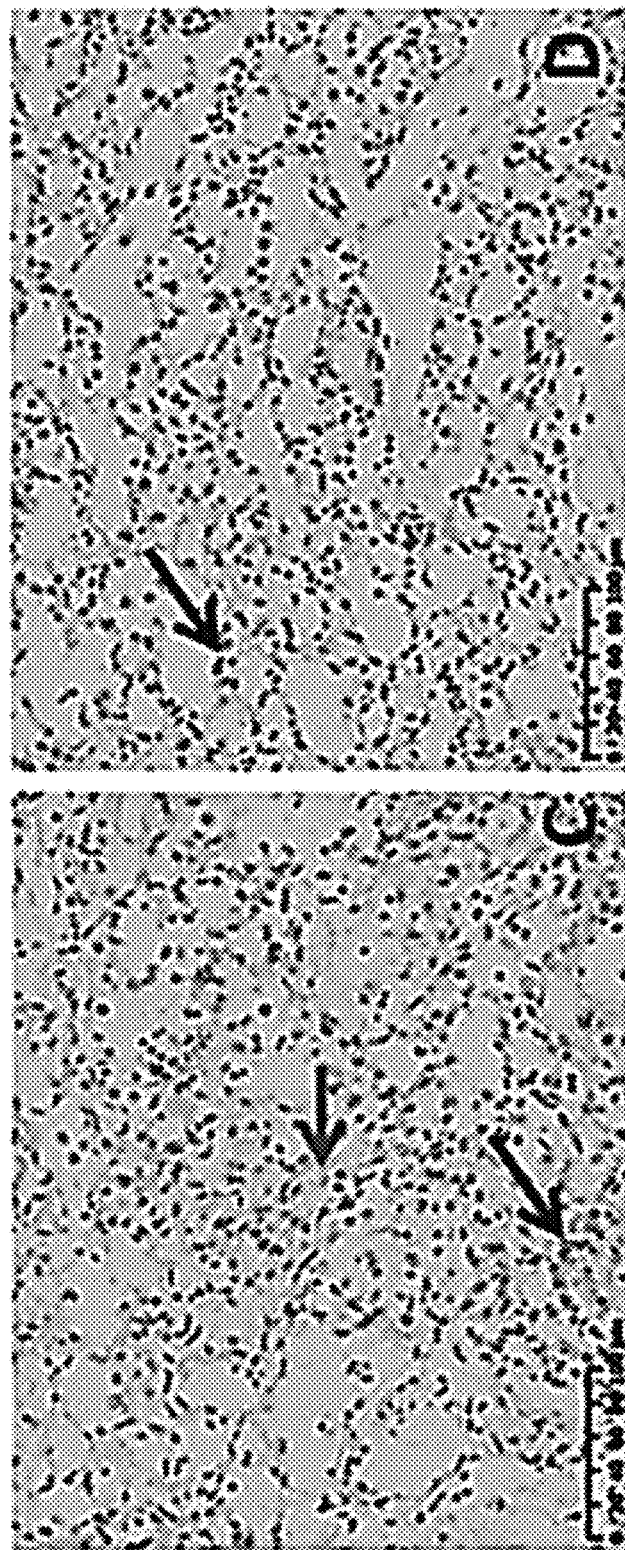

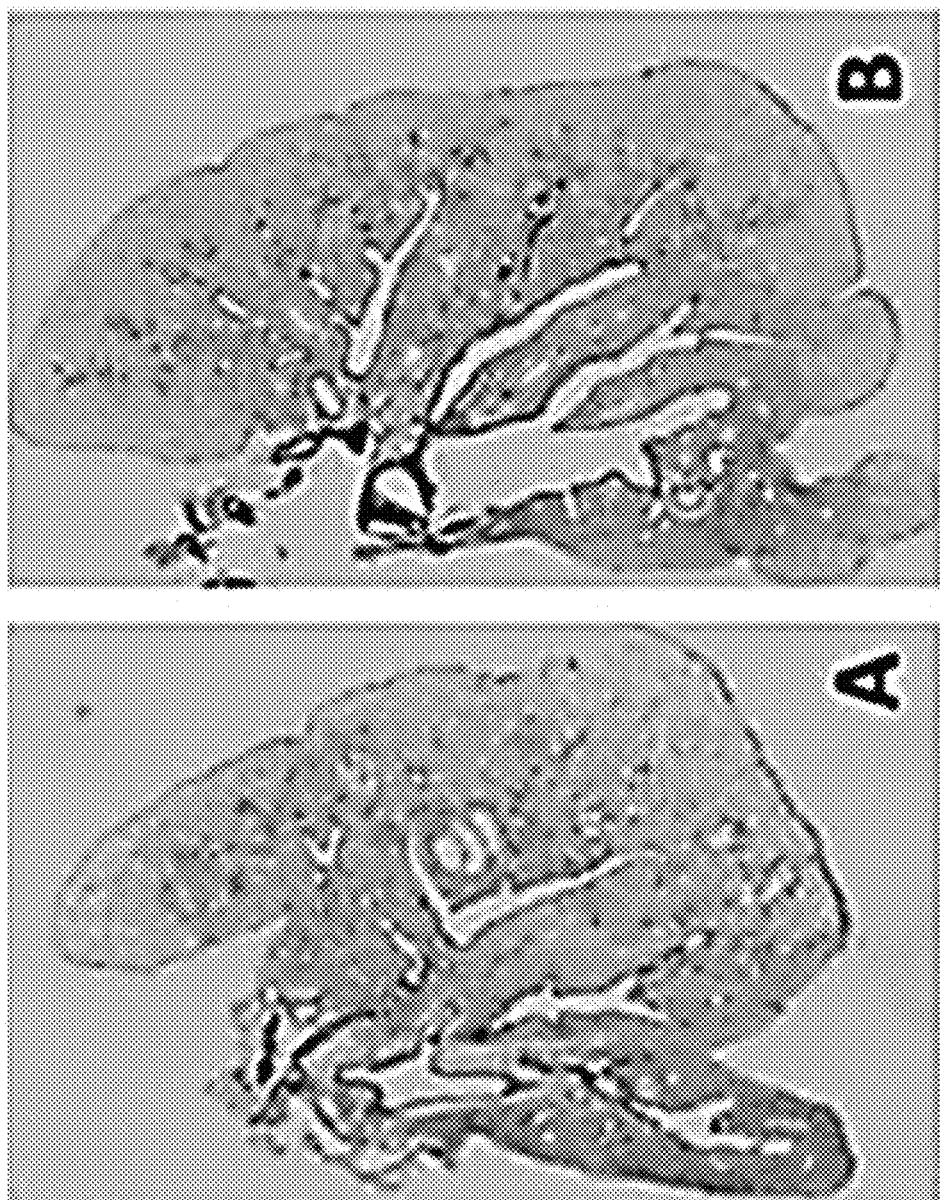

OXADIAZOLES AND THIADIAZOLES AS TGF-β INHIBITORS

CROSS-REFERENCE TO RELATED APPLICATIONS

This Application claims the benefit of U.S. Provisional Application No. 62/577,608, filed on Oct. 26, 2017, the contents of which are incorporated herein by reference in their entirety.

STATEMENT REGARDING FEDERALLY SPONSORED RESEARCH

This invention was made with government support under grant number 1R01 CA175012 awarded by the National Institutes of Health. The government has certain rights in the invention.

BACKGROUND

TGF-β is a central regulator of chronic liver disease through induction of fibrogenic responses (Weiskirchen and Tacke (2016) *Dig Dis* 34:410-422; Katz et al. (2016) *Cancer letters* 379:166-172; Yoshida et al. (2014) *Int J Oncol* 45:1363-1371; Fabregat et al. (2016) *The FEBS journal* 283:2219-2232; Xu et al. (2016) *J Histochem Cytochem* 64:157-167). Although infiltrating macrophages are a source of TGF-β, hepatic stellate cells are a significant source of TGF-β in liver fibrosis. TGF-β stimulates induction of myofibroblast-like properties of hepatic stellate cells to produce extracellular matrix, leading to fibrosis. Although TGF-β inhibits hepatocyte proliferation under basal conditions, it has pro-oncogenic properties during malignant progression through stimulating epithelial to mesenchymal transition, cell survival and migration, and reduced immune surveillance.

TSP1 expression is increased in human liver disease with the THBS1 gene identified as part of the characteristic gene signature of chronic liver disease, including cirrhosis, in humans (Smalling et al. (2013) *Am J Physiol Gastrointest Liver Physiol* 305:G364-374). In vitro studies show that bile acids increase expression of TSP1 by hepatocytes, resulting in increased TGF-β signaling in co-cultured hepatic stellate cells (Myung et al. (2007) *Biochem Biophys Res Commun* 353:1091-1096). Both TSP1 and TGF-β are increased in congenital hepatic fibrosis (El-Youssef (1999) *Journal of pediatric gastroenterology and nutrition* 28:386-392). THBS1 message levels are increased in human liver specimens from patients with alcohol cirrhosis, NASH cirrhosis, and fibrosis and in mouse models of liver fibrosis induced by carbon tetrachloride or DDC (Smalling et al., (2013) *Am J Physiol Gastrointet Liver Physiol* 305: G364-G374.) TSP1 regulated TGF-β activation prevented hepatocyte proliferation and liver regeneration after partial hepatectomy in Thbs1 deficient mice (Hayashi et al. (2012) *Hepatology* 55:1562-1573) and TSP1 induction by obstructed portal flow in mice is thought to lead to TGF-β-dependent liver atrophy (Hayashi et al. (2016) *Hepatol Res* 55: 1562-1573). TSP1 has been shown to regulate latent TGF-β activation in animal models of liver fibrosis and in cell culture models (reviewed in Li et al. (2016) *Hepatol Res*, doi: 10.1111/hepr.12787). Treatment of rats with the TSP1 antagonist peptide LSKL prevented TGF-β activation and reduced liver fibrosis in the dimethylnitrosamine model (Kondou et al. (2003) *J Hepatol* 39:742-748). TSP1 is required for TGF-β signaling in both cultured hepatocytes and hepatic stellate cells, which is blocked by LSKL peptide (Breitkopf et al. (2005) *Gut* 54:673-681; Narmada (2013) *J Cell Physiol* 228:393-401). Interestingly, TSP1-dependent latent TGF-β activation might play a role in hepatitis C induced fibrosis and carcinogenesis as the hepatitis C core protein induces TSP1 expression by hepatocytes to increase active TGF-β and LSKL peptide blocks hepatitis C core protein activation of TGF-β (Benzoubir et al. (2013) *J Hepatol* 59:1160-1168). LSKL peptide administered early after injury also accelerated liver regeneration in mice following partial hepatectomy through blocking TGF-β activation and signaling (Kuroki et al. (2015) *Br J Surg* 102:813-825). Both the TGF-β1 and the TGF-β2 isoforms are upregulated in mouse models and in human tissues with liver fibrosis and also hepatocellular carcinoma (Dropmann et al. (2016) *Oncotarget* 7:19499-19518): this is interesting since TSP1 can activate both the β1 and β2 isoforms of latent TGF-β, whereas β2 cannot be activated by integrin-dependent mechanisms.

Genetic ablation of TGF-β, its receptors, or its signaling mediators results in developmental defects, inflammation, and increased carcinomas. Thus, it is therapeutically advantageous to target only adverse TGF-β activity in liver disease and spare homeostatic activity. Current anti-TGF-β therapeutics target the molecule itself or downstream signaling pathways and provide no mechanism for distinguishing between homeostatic and disease-related TGF-β activity, thereby increasing the potential for adverse effects. In fact, Smad 2 resistance and increased papilloma incidence in mice treated for 20 weeks with a TGF-β receptor kinase inhibitor have been identified (Connolly et al. (2011) *Cancer Res* 71:2339-2349) and the 1D11 pan-specific anti-TGF-β neutralizing antibody shows epithelial hyperplasia and progression to carcinoma in some models (Prud'homme (2007) *Lab Invest* 87:1077-1091).

TGF-β is secreted as a biologically inactive growth factor and control of the conversion of latent TGF-β to a biologically active growth factor is a major regulatory node. Binding of the N-terminal latency associated peptide (LAP) prevents TGF-β binding to its receptors and this interaction must be disrupted for TGF-β signaling to occur. Latent TGF-β can be converted to the active form through multiple mechanisms that include proteolysis, binding to integrins, mechanical forces, modifications of the latent complex by viral enzymes or by reactive oxygen species, or by binding to the secreted and ECM protein TSP1 (Sweetwyne and Murphy-Ullrich (2012) *Matrix Biol* 31:178-186; Murphy-Ullrich and Poczatek (2000) *Cytokine Growth Factor Rev* 11:59-69). The mechanism that regulates latent TGF-β activation can vary with tissue, cell type, and specific disease milieu. Blockade of the major activation mechanism in a particular disease typically attenuates adverse effects of TGF-β. Thus, it is important to identify the predominant mechanism of TGF-β activation in multiple myeloma.

Thrombospondin 1 (TSP1) is a complex multi-functional protein released from platelet α-granules, incorporated into the fibrin clot, and expressed by cell types that participate in wound healing responses in a temporally regulated manner (Agah et al. (2002) *Am J Pathol* 161:831-839; Murphy-Ullrich and Mosher (1985) *Blood* 66:1098-1104; DiPietro et al. (1996) *Am J Pathol* 148:1851-1860; Reed et al. (1993) *J Histochem Cytochem* 41:1467-1477; Raugi et al. (1987) *J Invest Dermatol* 89:551-554). TSP1 regulates multiple cellular events involved in tissue repair including hemostasis, cell adhesion, migration, proliferation, ECM expression and organization, and regulation of growth factor activity (Adams and Lawler (2004) *Int J Biochem Cell Biol* 36:961-968;

Adams and Lawler (2011) *Cold Spring Harb Perspect Biol* 3:a009712). In addition to physiologic repair, TSP1 is also expressed at elevated levels in many tissues undergoing fibro-proliferative remodeling and blockade of specific actions of TSP1 or loss of TSP1 expression can attenuate pathologic tissue remodeling (Hugo (2003) *Nephrol Dial Transplant* 18:1241-1245; Poczatek et al. (2000) *Am J Pathol* 157:1353-1363; Daniel et al. (2007) Diabetes 56:2982-2989). TSP1 is a major regulator of latent TGF-β activation (Murphy-Ullrich and Poczatek (2000) *Cytokine Growth Factor Rev* 11:59-69). TSP1 also has TGF-β-independent functions in hemostasis, cell adhesion, migration, and growth factor regulation, e.g. regulation of epidermal growth factor (EGF), VEGF, and fibroblast growth factor (FGF) (Adams and Lawler (2011) *Cold Spring Harb Perspect Biol* 3:a009712). TSP1 is an endogenous angiogenesis inhibitor via inhibition of VEGF and FGF signaling. TSP1 binding to Cluster of Differentiation 47 (CD47) and Cluster of Differentiation 36 (CD36) blocks nitric oxide signaling.

TSP1 is a secreted ECM protein that controls TGF-β activity by binding and activating latent TGF-β (Sweetwyne and Murphy-Ullrich (2012) *Matrix Biol* 31:178-186; Murphy-Ullrich and Poczatek (2000) *Cytokine Growth Factor Rev* 11:59-69). TSP1 binds to latent TGF-β to activate TGF-β at the cell surface or in the extracellular milieu (Sweetwyne and Murphy-Ullrich (2012) *Matrix Biol* 31:178-186). Activation occurs through binding of the KRFK (-lysine-arginine-phenylalanine-lysine-) sequence in the TSP1 type 1 repeats (TSRs) to LSKL (-leucine-serine-lysine-leucine-) in the LAP of the latent complex, which disrupts LAP-mature domain interactions to expose the receptor binding sequences on the mature domain, rendering TGF-β capable of signaling (Young and Murphy-Ullrich (2004) *J Biol Chem* 279:38032-38039). Peptide mimetics of sequences involved in TSP1-TGF-β binding competitively inhibit TSP1-TGF-β activation and studies with these peptides have established TSP1 as a primary regulator of TGF-β bioactivity in different diseases (Sweetwyne and Murphy-Ullrich (2012) *Matrix Biol* 31:178-186). The tetrapeptide LSKL, which competitively blocks TSP-LAP binding, has been used in rodent models to inhibit TSP1-TGF-β activation and attenuate disease. Dose dependent intraperitoneal injection (i.p.) of LSKL improves end organ function in murine diabetic nephropathy and rat cardiomyopathy by blocking TGF-β signaling in target tissues (Belmadani et al. (2007) *Am J Pathol* 171:777-789; Lu et al. (2011) *Am J Pathol* 178:2573-2586). Animals necropsied after 15 weeks of treatment with 30 mg/kg i.p. LSKL, 3 times weekly, showed no inflammation, no tumors in all major organs, and no impairment of wound healing (Lu et al. (2011) *Am J Pathol* 178:2573-2586).

In vitro studies have shown that TSP1 activates latent TGF-β secreted by multiple cell types including endothelial cells, mesangial cells, hepatic stellate cells and skin, lung, and cardiac fibroblasts, T cells, and macrophages (Breitkopf et al. (2005) *Gut* 54:673-681; Murphy-Ullrich and Poczatek (2000) *Cytokine Growth Factor Rev* 11:59-69; et al. (2000) *Am J Pathol* 157:1353-1363; Mimura et al. (2005) *Am J Pathol* 166:1451-1463; Yehualaeshet et al. (1999) *Am J Pathol* 155:841-851; Zhou et al. (2006) *Biochem Biophys Res Commun* 339:633-641; Schultz-Cherry and Murphy-Ullrich (1993) *J Cell Biol* 122:923-932; Yevdokimova et al. (2001) *J Am Soc Nephrol* 12:703-712; Yang et al. (2009) *J Autoimmun* 32: 94-103; Zhou et al. (2004) *Am J Pathol* 165:659-669). Peptides such as LSKL or WxxW which block TSP1 binding to the latent complex or antibodies which block TSP1-dependent TGF-β activation such as monoclonal antibody 133 (Mab 133) have been used to establish the involvement of endogenous TSP1 in TGF-β activation in a number of disease conditions and physiologic processes (Belmadani et al. (2007) *Am J Pathol* 171:777-789; Lu et al. (2011) *Am J Pathol* 178:2573-2586; Crawford et al. (1998) *Cell* 93:1159-1170; Daniel et al. (2004) *Kidney Int* 65:459-468; Kondou et al. (2003) *J Hepatol* 39:742-748).

Initial evidence for an in vivo role of TSP1 in latent TGF-β activation was shown by the ability of the KRFK peptide administered in the perinatal period to partially rescue the abnormal TSP-1 null phenotype, in particular airway epithelial hyperplasia and pancreatic islet hyperplasia/acinar hypoplasia (Crawford et al. (1998) *Cell* 93:1159-1170). Furthermore, treatment of wild type mice with the LSKL blocking peptide in the perinatal period replicated features of the TSP1 knockout phenotype in the airways and pancreas. Double knockout of both $β_6$ integrin and TSP1 results in a phenotype distinct from either single knockout that is characterized by severe inflammation, cardiac degeneration, and epithelial hyperplasia, suggesting both separate and synergistic roles in regulating latent TGF-β activation (Ludlow et al. (2005) *J Cell Mol Med* 9:421-437). However, it is likely that the primary role for TSP1 in controlling TGF-β activation is during injury, under stress, and in pathologic conditions, rather than during development. The expression of TSP1 is induced by factors associated with systemic diseases with fibrotic end organ involvement including high glucose, reactive oxygen species, and angiotensin II (Zhou et al. (2006) *Biochem Biophys Res Commun* 339:633-641; Yevdokimova et al. (2001) *J Am Soc Nephrol* 12:703-712; Wang et al. (2002) *J Biol Chem* 277:9880-9888; Wang et al. (2004) *J Biol Chem* 279:34311-34322). Indeed there is evidence from studies utilizing TSP1 antagonist peptides and diabetic TSP1 knockout mice that TSP1 is a major factor in the development of fibrotic end organ complications in diabetes (Daniel et al. (2007) *Diabetes* 56:2982-2989; Belmadani et al. (2007) *Am J Pathol* 171: 777-789; Lu et al. (2011) *Am J Pathol* 178:2573-2586). Treatment with i.p. injections of LSKL, but not LSAL (leucine-serine-alanine-leucine) control peptide, reduced cardiac fibrosis, Smad phosphorylation, and improved left ventricular function (Belmadani et al. (2007) *Am J Pathol* 171:777-789). Similarly, treatment of Akita mice, a model of type 1 diabetes, with i.p. LSKL reduced urinary TGF-β activity and renal phospho-Smad 2/3 levels and improved markers of tubulointerstitial injury and podocyte function. (Lu et al. (2011) *Am J Pathol* 178:2573-2586). Both TSP1 and TGF-β are upregulated in pulmonary arterial hypertension due to chronic hypoxia, Schistosomiasis, and in scleroderma: recent studies show that TSP1 knockout or treatment with the blocking peptide LSKL protected against development of pulmonary hypertension due to hypoxia or Schistosome infection and also reduced active TGF-β (Kumar R et al, (2017) *Nature Commun.* 8: 15494). Epidermolysis bullosa is a disfiguring, blistering skin disease due to genetic defects in collagen and collagen anchoring fibrils that link the epidermis to the dermis. It has a fibrotic phenotype associated with increased TGF-β activity and thus TGF-β antagonists have been proposed as therapeutic agents (Nystroem A et al, (2015) *EMBO Mol Medicine* 7: 1211-1228). Losartan reduces TGF-β activity, inflammation, and the increased TSP-1 expression in a collagen VII hypomorphic model of epidermolysis bullosa (Nystroem A, et al). Interestingly, several studies have shown that TSP1 is involved in alveolar macrophage-dependent TGF-β activation in mouse and rat models of bleomycin-induced pulmonary fibrosis and treatment with either TSP1 or CD36 antagonist peptides can ameliorate lung fibrosis and reduce active TGF-β (Chen et al. (2009) *Exp. Toxicol. Pathol.* 61: 59-65; Yehualaeshet et al. (2000) *Am. J. Respir. Cell Mol. Biol.* 23: 204-12).

One of the roles of TSP1 in dermal wound healing appears to be regulating the activation of latent TGF-β. The phenotype of excisional wound healing in the TSP1 null mouse is consistent with a decrease in local TGF-β activation (Agah et al. (2002) *Am J Pathol* 161:831-839) and is characterized by a delay in macrophage recruitment and capillary angiogenesis and a persistence of granulation tissue, neovascularization, and inflammation (Nor et al. (2005) *Oral Biosci Med* 2:153-161). Topical treatment of TSP1 null wounds with the KRFK activating peptide largely rescued the TSP1 null wound phenotype (Nor et al. (2005) *Oral Biosci Med* 2:153-161). TGF-β levels in these wounds were increased following KRFK treatment and the effects of the KRFK peptide were blocked by a pan-specific anti-TGF-β antibody. While these data suggest that TSP1 plays a role in local activation of TGF-β during wounding, the studies of Agah et al., concluded that the decreased active and total TGF-β in the wounds of TSP1 or TSP1/TSP2 null mice is indirect and primarily due to defects in macrophage recruitment to wounds (a maj or source of TGF-β in wounds) leading to an overall reduction in TGF-β rather than a defect in activation (Agah et al. (2002) *Am J Pathol* 161:831-839). Despite this controversy, it is clear that TSP1 has the potential to modify the wound healing process. Subcutaneous implantation of TSP1 soaked sponges increased levels of active TGF-β, gel contraction and fibroblast migration (Sakai et al. (2003) *J Dermatol Sci* 31:99-109). Overexpression of TSP1 in keloids and in scleroderma correlates with increased TGF-β activity (Mimura et al. (2005) *Am J Pathol* 166:1451-1463; et al. (2000) *Cell Death Differ* 7:166-176; Chen et al. (2011) *Fibrogenesis Tissue Repair* 4:9). Others have used a derivative of the KRFK sequence, KFK (lysine-phenylalanine-lysine) coupled to a fatty acyl moiety to locally activate TGF-β and increase TIMP-1, which reduces MMP-induced elastin and collagen degradation when applied to dermal fibroblast cultures (Cauchard et al. (2004) *Biochem Pharmacol* 67:2013-2022). Systemic administration of the LSKL blocking peptide did not reduce Smad signaling or impair dermal wound healing in diabetic mice, although, these studies did not address the effects of direct LSKL administration to the wounds and it is not known if local dermal levels of LSKL following systemic intraperitoneal peptide administration are sufficient to alter local TGF-β activation (Lu et al. (2011) *Am J Pathol* 178:2573-2586).

Although peptides comprising the amino acid sequence LSKL capable of stimulating TGF-β activity are known, these peptides are often costly and difficult to synthesize. Moreover, small molecules such as LSKL have an extremely short plasma stability half-life, only 2.1 minutes. Thus, there remains a need for small molecules capable of altering TGF-β activity that are less expensive, easier to synthesize, and have an extended plasma stability half-life and methods of making and using same.

SUMMARY

In accordance with the purpose(s) of the invention, as embodied and broadly described herein, the invention, in one aspect, relates to oxadiazole and thiadiazole compounds useful in the treatment of disorders associated with a dysregulation of TGF-β including, but not limited to, cancers, in particular, multiple myeloma and hematologic malignancies, immune dysfunction, and fibrotic disorders, in particular, liver fibrosis, diabetic nephropathy, muscular dystrophy, amyotrophic lateral sclerosis, PAH, NASH, epidermolysis bullosa, and glaucoma.

Disclosed are compounds having a structure represented by a formula selected from:

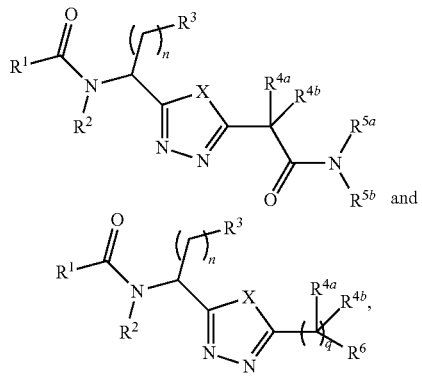

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)(C1-C4$ alkyl), —$(CH_2)_m N(C1-C4$ alkyl)(C=O)(C1-C4 alkyl), and $Cy^5$; wherein m is selected from 0 and 1; wherein $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and Cy$^6$, wherein Cy$^6$, when present, C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

Also disclosed are compounds having a structure represented by a formula selected from:

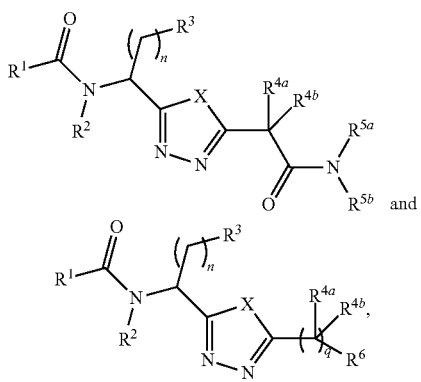

wherein n is selected from 1, 2, 3, and 4; wherein q is selected from 0 and 1; wherein X is selected from O and S; wherein R$^1$ is selected from C1-C8 alkyl and Cy$^1$; wherein Cy$^1$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^2$ is selected from hydrogen, C1-C4 alkyl, and amine protecting group; wherein R$^3$ is selected from NR$^{20a}$R$^{20b}$, NHCOR$^{21}$, and Ar$^1$; wherein each of R$^{20a}$ and R$^{20b}$, when present, is independently selected from hydrogen, C1-C4 alkyl, Cy$^2$, and amine protecting group; wherein Cy$^2$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^{21}$, when present, is selected from C1-C4 alkyl, cycloalkyl, and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino); wherein m is selected from 0 and 1; wherein each of R$^{4a}$ and R$^{4b}$ is independently selected from hydrogen and C1-C4 alkyl; or wherein each of R$^{4a}$ and R$^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof.

Also disclosed are pharmaceutical compositions comprising a therapeutically effective amount of at least one disclosed compound and a pharmaceutically acceptable carrier.

Also disclosed are methods for inhibiting TGF-β activity in a subject, the method comprising the step of administering to the subject an effective amount of at least one compound having a structure represented by a formula selected from:

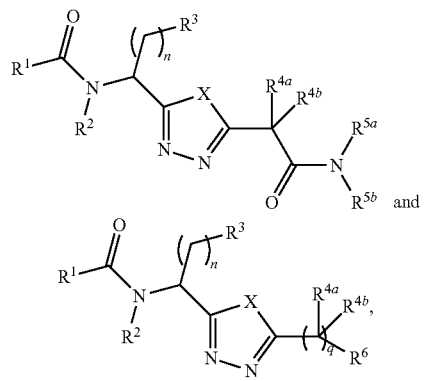

wherein n is selected from 1, 2, 3, and 4; wherein q is selected from 0 and 1; wherein X is selected from O and S; wherein R$^1$ is selected from C1-C8 alkyl and Cy$^1$; wherein Cy$^1$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^2$ is selected from hydrogen, C1-C4 alkyl, and amine protecting group; wherein R$^3$ is selected from NR$^{20a}$R$^{20b}$, NHCOR$^{21}$, and Ar$^1$; wherein each of R$^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_mNH_2$ and —$(CH_2)_m$(C1-C4 alkylamino); wherein m is selected from 0 and 1; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby inhibiting TGF-β activity in the subject.

Also disclosed are methods for inhibiting TGF-β activity in at least one cell, the method comprising the step of contacting the cell with an effective amount of at least one compound having a structure represented by a formula selected from:

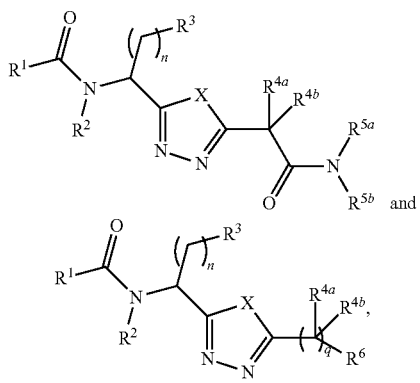

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, and $Ar^1$; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_mNH_2$ and —$(CH_2)_m$(C1-C4 alkylamino); wherein m is selected from 0 and 1; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby TGF-β activity in the cell.

Also disclosed are kits comprising at least one compound of claim 1 and one or more of: (a) at least one agent known to increase TGF-β activity; (b) at least one agent known to treat cancer; (c) at least one agent known to treat a fibrotic disorder; (d) at least one agent known to an immune dysfunction; (e) instructions for treating a disorder associated with TGF-β dysfunction; (f) instructions for treating cancer; (g) instructions for treating a fibrotic disorder; and (h) instructions for treating an immune dysfunction.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF THE DRAWINGS

The accompanying figures, which are incorporated in and constitute a part of this specification, illustrate several aspects and together with the description serve to explain the principles of the invention.

(FIG. 6B), and both IV and p.o. (FIG. 6C) administration.

(FIG. 7B), and both IV and p.o. (FIG. 7C) administration.

FIG. 13A-D show representative images illustrating bronchial, arteriole, and alveolar damages in fibrotic core in a model group (FIG. 13A and FIG. 13C) and a CPD-X group (FIG. 13B and FIG. 13D). Specifically, FIG. 13A and FIG. 13B show bronchial ("b") and arteriole ("a") damage in the fibrosis core. FIG. 13C and FIG. 13D show alveolar wall damage with inflammatory cell infiltration (FIG. 13C, bottom arrow and FIG. 13D, arrow) and several alveolar structure disappeared (FIG. 13C, top arrow) and damage in fibrosis core. H&E staining, magnification ×200.

FIG. 16A-D show representative images illustrating the histological changes of lung fibrosis in a model group (FIG. 16A and FIG. 16C) and a CPD-X group (FIG. 16B and FIG. 16D). Specifically, alveolar wall damage with fibrosis (FIG. 16C, top arrow and FIG. 16D, both arrows) and several alveolar structure damages (FIG. 16C, bottom two arrows) with fibrotic mass in fibrosis core is shown. Masson Trichrome staining, magnification ×200.

Figure 1A:
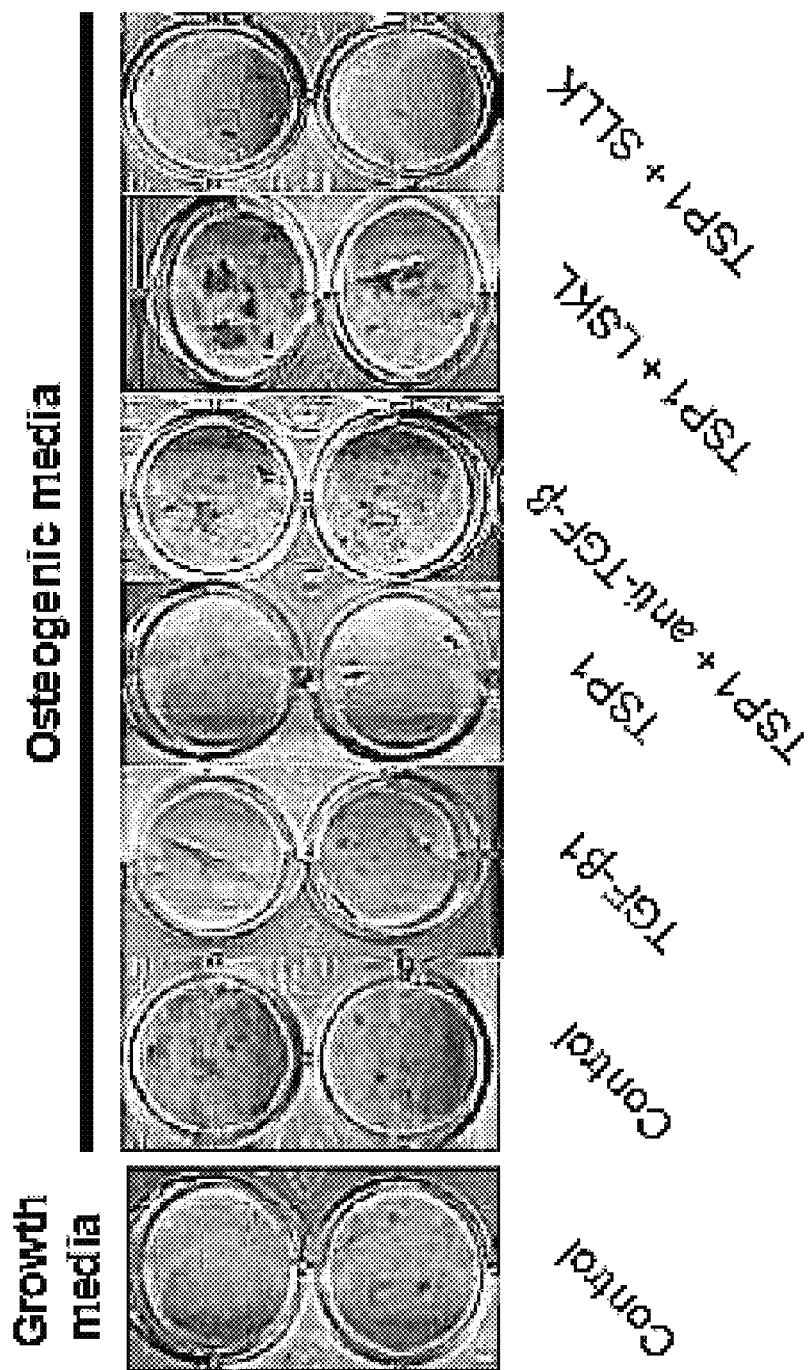
FIG. 1A and FIG. 1B show representative data illustrating the impact of TSP1, LSKL and TGF-β on osteoblast differentiation by MSCs under osteogenic conditions.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In one aspect, the subject is a mammal. A patient refers to a subject afflicted with a viral infection. The term "patient" includes human and veterinary subjects. In some aspects of the disclosed methods, the subject has been diagnosed with a need for treatment of one or more viral infections prior to the administering step. In various aspects, the one or more disorders is selected from chikungunya, Venezuelan equine encephalitis, dengue, influenza, and zika.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit, or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. In some aspects of the disclosed methods, the subject has been diagnosed with a need for treatment of a viral infection prior to the administering step. As used herein, the phrase "identified to be in need of treatment for a disorder," or the like, refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "comprising" (and its grammatical variations) as used herein is used in the inclusive sense of "having" or "including" and not in the exclusive sense of "consisting of."

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —$N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —$OC(O)A^1$ or —$C(O)OA^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -$(A^1O(O)C-A^2-C(O)O)_a$— or -$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —NO$_2$.

The term "nitrile" as used herein is represented by the formula —CN.

The term "silyl" as used herein is represented by the formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$—C(O)OSiR°$_3$; —(CH$_2$)$_{0-4}$C(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$C(O)NR°$_2$; —C(O)N(OR)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$S(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_1$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR*, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

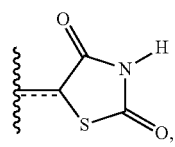

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. "Solvates" refers to the compound formed by the interaction of a solvent and a solute and includes hydrates. Solvates are usually crystalline solid adducts containing solvent molecules within the crystal structure, in either stoichiometric or nonstoichiometric proportions. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

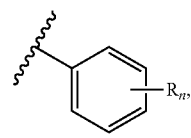

which is understood to be equivalent to a formula:

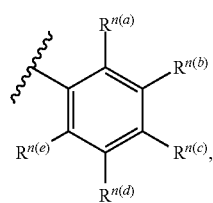

wherein n is typically an integer. That is, $R''$ is understood to represent five independent substituents, $R''^{(a)}$, $R''^{(b)}$, $R''^{(c)}$, $R''^{(d)}$, $R''^{(e)}$. In each such case, each of the five $R''$ can be hydrogen or a recited substituent. By "independent substituents," it is meant that each R substituent can be independently defined. For example, if in one instance $R''^{(a)}$ is halogen, then $R''^{(b)}$ is not necessarily halogen in that instance.

In some yet further aspects, a structure of a compound can be represented by a formula:

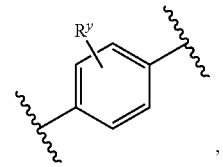

wherein $R^y$ represents, for example, 0-2 independent substituents selected from $A^1$, $A^2$, and $A^3$, which is understood to be equivalent to the groups of formulae:

wherein $R^y$ represents 0 independent substituents

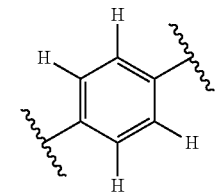

wherein $R^y$ represents 1 independent substituent

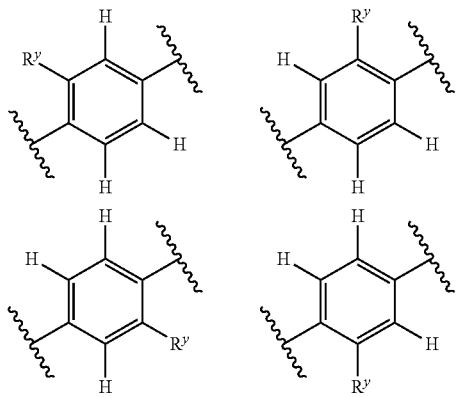

wherein $R^y$ represents 2 independent substituents

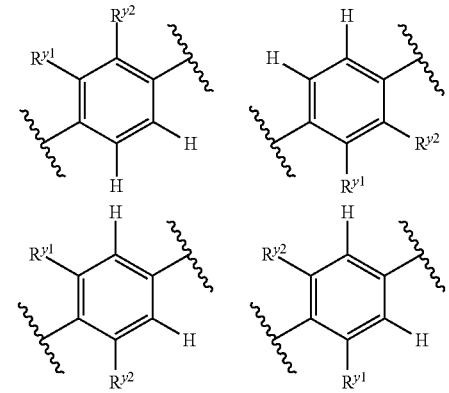

-continued

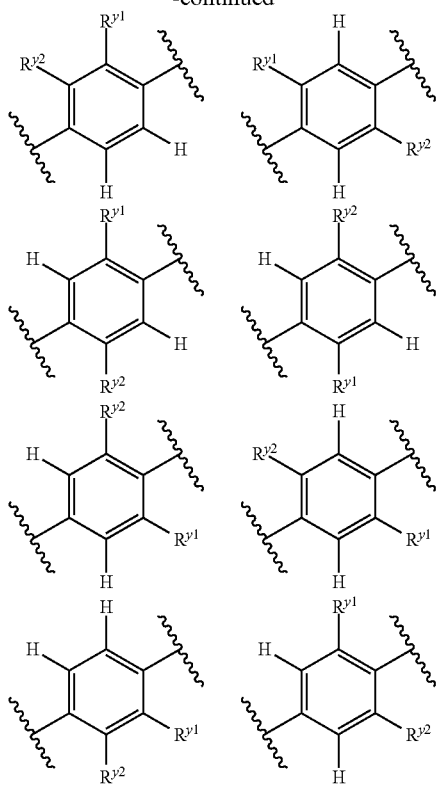

Again, by "independent substituents," it is meant that each R substituent can be independently defined. For example, if in one instance $R^{y1}$ is $A^1$, then $R^{y2}$ is not necessarily $A^1$ in that instance.

In some further aspects, a structure of a compound can be represented by a formula,

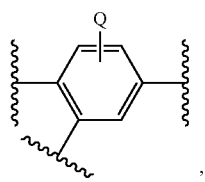

, wherein, for example, Q comprises three substituents independently selected from hydrogen and A, which is understood to be equivalent to a formula:

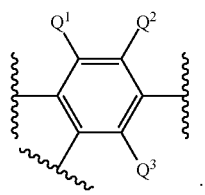

.

Again, by "independent substituents," it is meant that each Q substituent is independently defined as hydrogen or A, which is understood to be equivalent to the groups of formulae:

wherein Q comprises three substituents independently selected from H and A

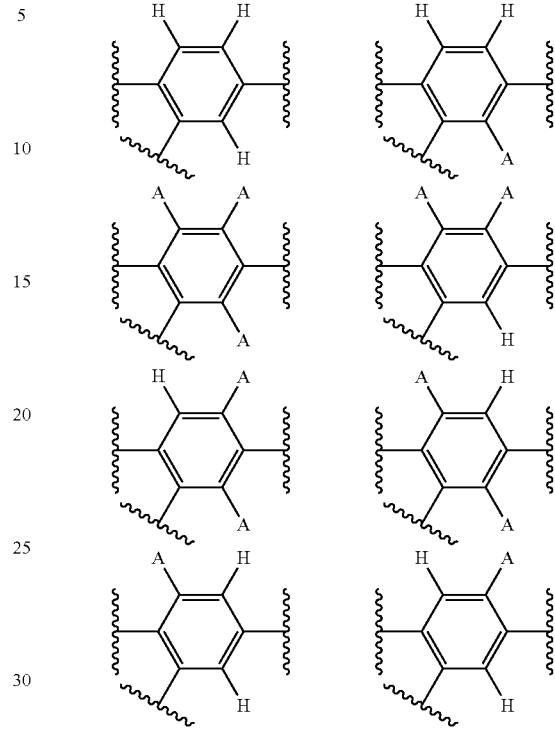

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein.

These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful in treating disorders associated with dysregulation of TGF-β, in particular, cancers, immune dysfunction, and fibrotic conditions. In a further aspect, the invention relates to compounds useful in treating cancers, in particular, multiple myeloma and hematologic malignancies, immune dysfunction, and fibrotic disorders, in particular, liver fibrosis, diabetic nephropathy, muscular dystrophy, amyotrophic lateral sclerosis, PAH, NASH, epidermolysis bullosa, and glaucoma.

In one aspect, the disclosed compounds exhibit inhibition of TGF-β.

In one aspect, the compounds of the invention are useful in inhibiting TGF-β in a mammal. In a further aspect, the compounds of the invention are useful in inhibiting TGF-β activity in at least one cell.

In one aspect, the compounds of the invention are useful in the treatment of cancers, as further described herein.

In one aspect, the compounds of the invention are useful in the treatment of fibrotic conditions including, but not limited to, liver fibrosis, diabetic nephropathy, muscular dystrophy, amyotrophic lateral sclerosis, PAH, NASH, epidermolysis bullosa, and glaucoma, and as further described herein.

In one aspect, the compounds of the invention are useful in the treatment of immune dysfunction, as described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

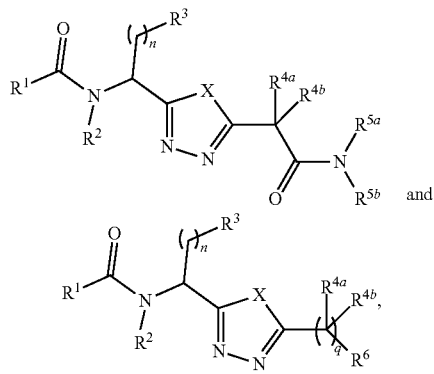

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), —$(CH_2)_m$[(C1-C4)(C1-C4) dialkylamino], —$(CH_2)_m$NH(C=O)(C1-C4 alkyl), —$(CH_2)_m$N(C1-C4 alkyl)(C=O)(C1-C4 alkyl), and $Cy^5$; wherein m is selected from 0 and 1; wherein $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and Cy$^6$, wherein Cy$^6$, when present, C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are compounds having a structure represented by a formula selected from:

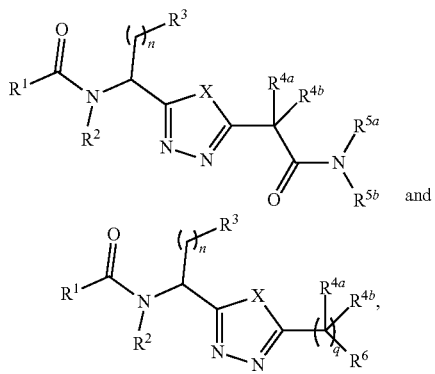

wherein n is selected from 1, 2, 3, and 4; wherein q is selected from 0 and 1; wherein X is selected from O and S; wherein R$^1$ is selected from C1-C8 alkyl and Cy$^1$; wherein Cy$^1$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^2$ is selected from hydrogen, C1-C4 alkyl, and amine protecting group; wherein R$^3$ is selected from NR$^{20a}$R$^{20b}$, NHCOR$^{21}$, and Ar$^1$; wherein each of R$^{20a}$ and R$^{20b}$, when present, is independently selected from hydrogen, C1-C4 alkyl, Cy$^2$, and amine protecting group; wherein Cy$^2$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^{21}$, when present, is selected from C1-C4 alkyl, cycloalkyl, and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino); wherein m is selected from 0 and 1; wherein each of R$^{4a}$ and R$^{4b}$ is independently selected from hydrogen and C1-C4 alkyl; or wherein each of R$^{4a}$ and R$^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof.

In a further aspect, R$^3$ is selected from NR$^{20a}$R$^{20b}$, NHCOR$^{21}$, and Ar$^1$; wherein Ar$^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino]; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino.

In a further aspect, each of R$^2$, R$^{5a}$, and R$^{5b}$ is hydrogen.

In a further aspect, the compound has a structure represented by a formula selected from:

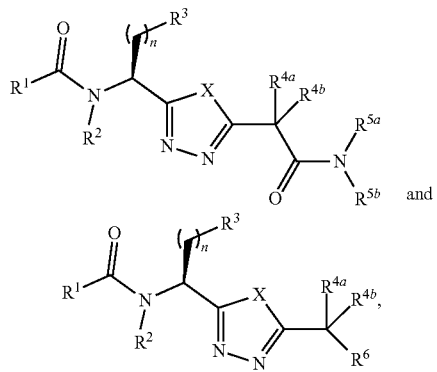

In a further aspect, the compound has a structure represented by a formula:

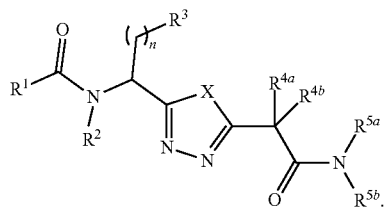

In a further aspect, the compound has a structure represented by a formula:

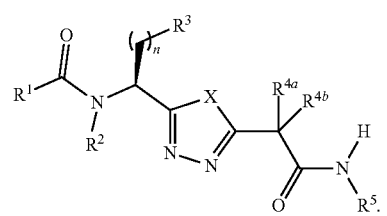

In a further aspect, the compound has a structure represented by a formula:

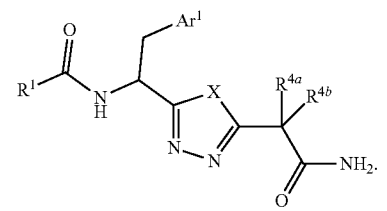

In a further aspect, the compound has a structure represented by a formula:

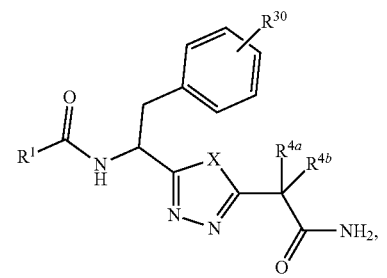

wherein $R^{30}$ is selected from —$(CH_2)_m NH_2$ and —$(CH_2)_m$(C1-C4 alkylamino).

In a further aspect, the compound has a structure represented by a formula:

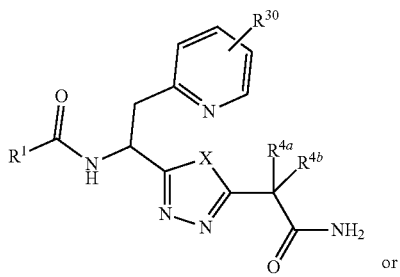

or

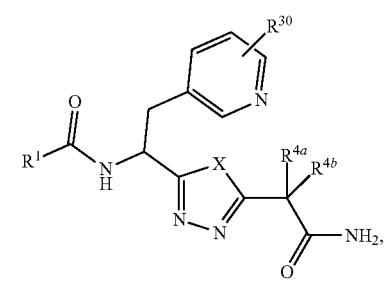

wherein $R^{30}$ is selected from —$(CH_2)_m NH_2$ and —$(CH_2)_m$(C1-C4 alkylamino).

In a further aspect, the compound has a structure represented by a formula:

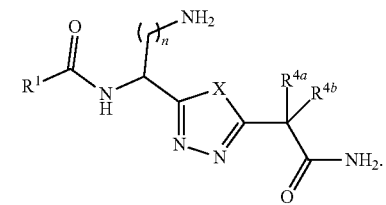

In a further aspect, the compound is selected from:

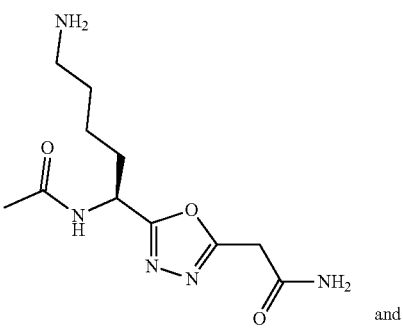

and

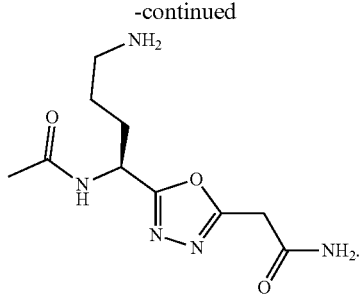

In a further aspect, the compound is:

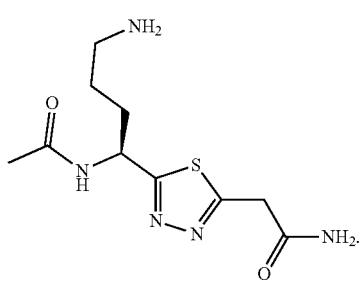 [SMILES: CC(=O)N[C@@H](CCCN)c1nnc(CC(N)=O)s1]

In a further aspect, the compound has a structure represented by a formula:

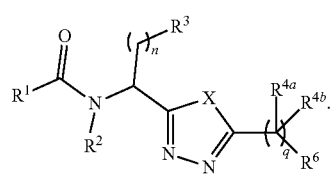

In a further aspect, the compound has a structure represented by a formula:

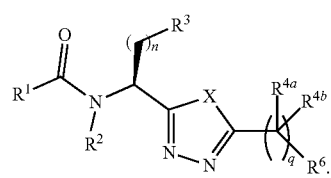

In a further aspect, the compound has a structure represented by a formula:

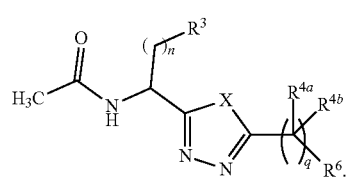

In a further aspect, the compound is selected from:

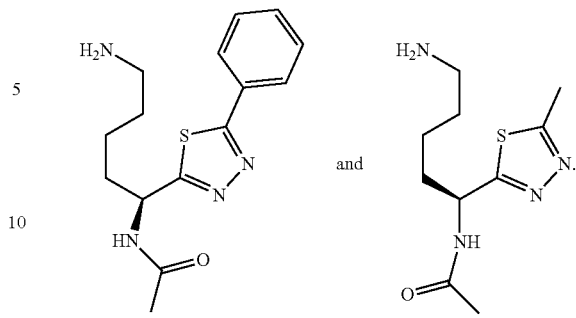

In a further aspect, the compound is:

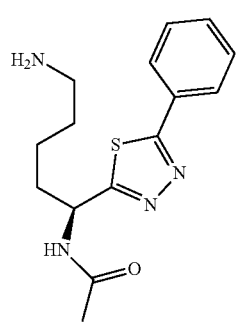

In a further aspect, the compound has a structure represented by a formula:

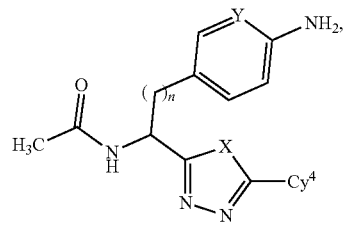

wherein n is selected from 1 and 2; and Y is selected from N and CH.

In a further aspect, the compound has a structure represented by a formula:

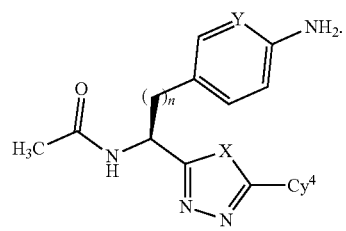

In one aspect, n is selected from 1, 2, 3, and 4. In a further aspect, n is selected from 1, 2, and 3. In a still further aspect, n is selected from 1 and 2. In yet a further aspect, n is 4. In an even further aspect, n is 3. In a still further aspect, n is 2.

In yet a further aspect, n is 1.

In one aspect, m is selected from 0 and 1. In a further aspect, m is 1. In a still further aspect, m is 0.

In one aspect, q is selected from 0 and 1. In a further aspect, q is 1. In a still further aspect, q is 0.

a. $PG^1$ Groups

In one aspect, $PG^1$ is an amine protecting group. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. In a still further aspect, $PG^1$ is 9-fluorenylmethyloxycarbonyl.

b. X Groups

In one aspect, X is selected from O and S. In a further aspect, X is O. In a still further aspect, X is S.

c. Y Groups

In one aspect, Y is selected from N and CH. In a further aspect, X is N. In a still further aspect, X is CH.

d. $R^1$ Groups

In one aspect, $R^1$ is selected from C1-C8 alkyl and $Cy^1$. In a further aspect, $R^1$ is selected from C1-C4 alkyl and $Cy^1$. In a still further aspect, $R^1$ is selected from methyl, ethyl, n-propyl, i-propyl, and $Cy^1$. In yet a further aspect, $R^1$ is selected from methyl, ethyl, and $Cy^1$. In an even further aspect, $R^1$ is selected from ethyl and $Cy^1$. In a still further aspect, $R^1$ is selected from methyl and $Cy^1$.

In a further aspect, $R^1$ is C1-C8 alkyl. In a still further aspect, $R^1$ is selected from methyl, ethyl, n-propyl, i-propyl, n-butyl, i-butyl, s-butyl, and t-butyl. In yet a further aspect, $R^1$ is selected from methyl, ethyl, n-propyl, and i-propyl. In an even further aspect, $R^1$ is selected from methyl and ethyl. In a still further aspect, $R^1$ is ethyl. In yet a further aspect, $R^1$ is methyl.

In a further aspect, $R^1$ is $Cy^1$.

e. $R^2$ Groups

In one aspect, $R^2$ is selected from hydrogen, C1-C4 alkyl, and amine protecting group. In a further aspect, $R^2$ is hydrogen.

In a further aspect, $R^2$ is selected from hydrogen, methyl, ethyl, n-propyl, i-propyl, n-butyl, i-butyl, s-butyl, t-butyl, and amine protecting group. In a still further aspect, $R^2$ is selected from hydrogen, methyl, ethyl, n-propyl, i-propyl, and amine protecting group. In yet a further aspect, $R^2$ is selected from hydrogen, methyl, ethyl, and amine protecting group. In an even further aspect, $R^2$ is selected from hydrogen, ethyl, and amine protecting group. In a still further aspect, $R^2$ is selected from hydrogen, methyl, and amine protecting group.

In a further aspect, $R^2$ is selected from hydrogen, methyl, ethyl, n-propyl, i-propyl, n-butyl, i-butyl, s-butyl, and t-butyl. In a still further aspect, $R^2$ is selected from hydrogen, methyl, ethyl, n-propyl, and i-propyl. In yet a further aspect, $R^2$ is selected from hydrogen, methyl, and ethyl. In an even further aspect, $R^2$ is selected from hydrogen and ethyl. In a still further aspect, $R^2$ is selected from hydrogen and methyl.

In a further aspect, $R^2$ is selected from methyl, ethyl, n-propyl, i-propyl, n-butyl, i-butyl, s-butyl, and t-butyl. In a still further aspect, $R^2$ is selected from methyl, ethyl, n-propyl, and i-propyl. In yet a further aspect, $R^2$ is selected from methyl and ethyl. In an even further aspect, $R^2$ is ethyl. In a still further aspect, $R^2$ is methyl.

In a further aspect, $R^2$ is amine protecting group. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. In a still further aspect, $R^2$ is t-butyloxycarbonyl.

In a further aspect, each of $R^2$ and $R^5$ is hydrogen.

f. $R^3$ Groups

In one aspect, $R^3$ is selected from $NR^{20a}R^{20b}$, $NHCOR^{21}$, and $Ar^1$. In a further aspect, $R^3$ is selected from $NR^{20a}R^{20b}$ and $Ar^1$.

In one aspect, $R^3$ is selected from $NR^{20a}R^{20b}$, $NHCOR^{21}$, $NHPG^1$, and $Ar^1$. In a further aspect, $R^3$ is $NHPG^1$.

In a further aspect, $R^3$ is $NR^{20a}R^{20b}$. In a still further aspect, $R^3$ is $NHR^{20a}$. In yet a further aspect, $R^3$ is $-NH_2$. In an even further aspect, $R^3$ is $NHCOR^{21}$.

In a further aspect, $R^3$ is selected from $NR^{20a}R^{20b}$ and $NHCOR^{21}$. In a still further aspect, $R^3$ is selected from $NHCOR^{21}$ and Ar.

In a further aspect, $R^3$ is $Ar^1$.

g. $R^{4a}$ and $R^{4b}$ Groups

In one aspect, each of $R^{4a}$ and $R^{4b}$ is independently selected from hydrogen and C1-C4 alkyl; or each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, each of $R^{4a}$ and $R^{4b}$ is independently selected from hydrogen and C1-C4 alkyl. In a still further aspect, each of $R^{4a}$ and $R^{4b}$ is independently selected from hydrogen, methyl, ethyl, n-propyl, and i-propyl. In yet a further aspect, each of $R^{4a}$ and $R^{4b}$ is independently selected from hydrogen, methyl, and ethyl. In an even further aspect, each of $R^{4a}$ and $R^{4b}$ is independently selected from hydrogen and ethyl. In a still further aspect, each of $R^{4a}$ and $R^{4b}$ is independently selected from hydrogen and methyl.

In a further aspect, each of $R^{4a}$ and $R^{4b}$ is hydrogen.

In a further aspect, each of $R^{4a}$ and $R^{4b}$ is independently C1-C4 alkyl. In a still further aspect, each of $R^{4a}$ and $R^{4b}$ is independently selected from methyl, ethyl, n-propyl, and i-propyl. In yet a further aspect, each of $R^{4a}$ and $R^{4b}$ is independently selected from methyl and ethyl. In an even further aspect, each of $R^{4a}$ and $R^{4b}$ is ethyl. In a still further aspect, each of $R^{4a}$ and $R^{4b}$ is methyl.

In a further aspect, each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of $R^{4a}$ and $R^{4b}$ are optionally covalently bonded together and, together with the intermediate atoms, comprise a 3- to 7-membered cycloalkyl substituted with 0-3 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of $R^{4a}$ and $R^{4b}$ are optionally covalently bonded together and, together with the intermediate atoms, comprise a 3- to 7-membered cycloalkyl substituted with 0-2 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of $R^{4a}$ and $R^{4b}$ are optionally covalently bonded together and, together with the intermediate atoms, comprise a 3- to 7-membered cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{4a}$ and R$^{4b}$ are optionally covalently bonded together and, together with the intermediate atoms, comprise a 3- to 7-membered cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{4a}$ and R$^{4b}$ are optionally covalently bonded together and, together with the intermediate atoms, comprise an unsubstituted 3- to 7-membered cycloalkyl.

In a further aspect, each of R$^{4a}$ and R$^{4b}$ are optionally covalently bonded together and, together with the intermediate atoms, comprise a 3- to 6-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{4a}$ and R$^{4b}$ are optionally covalently bonded together and, together with the intermediate atoms, comprise a 3- to 5-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{4a}$ and R$^{4b}$ are optionally covalently bonded together and, together with the intermediate atoms, comprise a 3- to 4-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of R$^{4a}$ and R$^{4b}$ are optionally covalently bonded together and, together with the intermediate atoms, comprise a 4- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{4a}$ and R$^{4b}$ are optionally covalently bonded together and, together with the intermediate atoms, comprise a 5- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{4a}$ and R$^{4b}$ are optionally covalently bonded together and, together with the intermediate atoms, comprise a 6- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, each of R$^{4a}$ and R$^{4b}$ are optionally covalently bonded together and, together with the intermediate atoms, comprise a cyclopropyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{4a}$ and R$^{4b}$ are optionally covalently bonded together and, together with the intermediate atoms, comprise a cyclopropyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{4a}$ and R$^{4b}$ are optionally covalently bonded together and, together with the intermediate atoms, comprise a cyclopropyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, each of R$^{4a}$ and R$^{4b}$ are optionally covalently bonded together and, together with the intermediate atoms, comprise a cyclopropyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, each of R$^{4a}$ and R$^{4b}$ are optionally covalently bonded together and, together with the intermediate atoms, comprise a cyclopropyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, each of R$^{4a}$ and R$^{4b}$ are optionally covalently bonded together and, together with the intermediate atoms, comprise an unsubstituted cyclopropyl.

h. R$^{5a}$ and R$^{5b}$ Groups

In one aspect, each of R$^{5a}$ and R$^{5b}$ is independently selected from hydrogen, C1-C4 alkyl, and Cy$^3$.

In a further aspect, each of R$^{5a}$ and R$^{5b}$ is independently selected from hydrogen, methyl, ethyl, n-propyl, i-propyl, n-butyl, i-butyl, s-butyl, t-butyl, and Cy$^3$. In a still further aspect, each of R$^{5a}$ and R$^{5b}$ is independently selected from hydrogen, methyl, ethyl, n-propyl, i-propyl, and Cy$^3$. In yet a further aspect, each of R$^{5a}$ and R$^{5b}$ is independently selected from hydrogen, methyl, ethyl, and Cy$^3$. In an even further aspect, each of R$^{5a}$ and R$^{5b}$ is independently selected from hydrogen, methyl, and Cy$^3$.

In a further aspect, each of R$^{5a}$ and R$^{5b}$ is independently selected from hydrogen, methyl, ethyl, n-propyl, i-propyl, n-butyl, i-butyl, s-butyl, and t-butyl. In a still further aspect, each of R$^{5a}$ and R$^{5b}$ is independently selected from hydrogen, methyl, ethyl, n-propyl, and i-propyl. In yet a further aspect, each of R$^{5a}$ and R$^{5b}$ is independently selected from hydrogen, methyl, and ethyl. In an even further aspect, each of R$^{5a}$ and R$^{5b}$ is independently selected from hydrogen and ethyl. In a still further aspect, each of R$^{5a}$ and R$^{5b}$ is independently selected from hydrogen and methyl.

In a further aspect, each of R$^{5a}$ and R$^{5b}$ is independently selected from methyl, ethyl, n-propyl, i-propyl, n-butyl, i-butyl, s-butyl, and t-butyl. In a still further aspect, each of R$^{5a}$ and R$^{5b}$ is independently selected from methyl, ethyl, n-propyl, and i-propyl. In yet a further aspect, each of R$^{5a}$ and R$^{5b}$ is independently selected from methyl and ethyl. In an even further aspect, each of R$^{5a}$ and R$^{5b}$ is ethyl. In a still further aspect, each of R$^{5a}$ and R$^{5b}$ is methyl.

In a further aspect, each of R$^{5a}$ and R$^{5b}$ is independently selected from hydrogen and Cy$^3$. In a still further aspect, each of R$^{5a}$ and R$^{5b}$ is Cy$^3$.

i. R$^6$ Groups

In one aspect, R$^6$ is selected from C1-C4 alkyl and Cy$^4$. In a further aspect, R$^6$ is selected from methyl, ethyl, n-propyl, i-propyl, and Cy$^4$. In a still further aspect, R$^6$ is selected from methyl, ethyl, and Cy$^4$. In yet a further aspect, R$^6$ is selected from methyl and Cy$^4$. In an even further aspect, R$^6$ is selected from ethyl and Cy$^4$.

In a further aspect, R$^6$ is selected from methyl, ethyl, n-propyl, i-propyl, n-butyl, i-butyl, s-butyl, and t-butyl. In a still further aspect, R$^6$ is selected from methyl, ethyl, n-propyl, and i-propyl. In yet a further aspect, R$^6$ is selected from methyl and ethyl. In an even further aspect, $R^6$ is methyl. In a still further aspect, $R^6$ is ethyl.

In a further aspect, $R^6$ is $Cy^4$.

j. $R^{20a}$ and $R^{20b}$ Groups

In one aspect, each of $R^{20a}$ and $R^{20b}$, when present, is independently selected from hydrogen, C1-C4 alkyl, $Cy^2$, and amine protecting group. In a further aspect, each of $R^{20a}$ and $R^{20b}$, when present, is hydrogen.

In a further aspect, each of $R^{20a}$ and $R^{20b}$, when present, is independently selected from hydrogen and C1-C4 alkyl. In a still further aspect, each of $R^{20a}$ and $R^{20b}$, when present, is independently selected from hydrogen, methyl, ethyl, n-propyl, and i-propyl. In yet a further aspect, each of $R^{20a}$ and $R^{20b}$, when present, is independently selected from hydrogen, methyl, and ethyl. In an even further aspect, each of $R^{20a}$ and $R^{20b}$, when present, is independently selected from hydrogen and ethyl. In a still further aspect, each of $R^{20a}$ and $R^{20b}$, when present, is independently selected from hydrogen and methyl.

In a further aspect, each of $R^{20a}$ and $R^{20b}$, when present, is independently selected from methyl, ethyl, n-propyl, i-propyl, n-butyl, i-butyl, s-butyl, and t-butyl. In a still further aspect, each of $R^{20a}$ and $R^{20b}$, when present, is independently selected from methyl, ethyl, n-propyl, and i-propyl. In yet a further aspect, each of $R^{20a}$ and $R^{20b}$, when present, is independently selected from methyl and ethyl. In an even further aspect, each of $R^{20a}$ and $R^{20b}$ when present, is ethyl. In a still further aspect, each of $R^{20a}$ and $R^{20b}$, when present, is methyl.

In a further aspect, each of $R^{20a}$ and $R^{20b}$, when present, is independently selected from hydrogen and $Cy^2$. In a still further aspect, each of $R^{20a}$ and $R^{20b}$, when present, is $Cy^2$.

In a further aspect, each of $R^{20a}$ and $R^{20b}$, when present, is independently selected from hydrogen and amine protecting group. Examples of amine protecting groups include, but are not limited to, carbobenzyloxy, p-methoxybenzyl carbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, and 4-nitrobenzenesulfonyl. In a still further aspect, each of $R^{20a}$ and $R^{20b}$, when present, is independently selected from hydrogen and t-butyloxycarbonyl.

k. $R^{21}$ Groups

In one aspect, $R^{21}$, when present, is selected from C1-C4 alkyl, cycloalkyl, and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $R^{21}$, when present, is selected from methyl, ethyl, n-propyl, i-propyl, n-butyl, i-butyl, s-butyl, and t-butyl. In a still further aspect, $R^{21}$, when present, is selected from methyl, ethyl, n-propyl, and i-propyl. In yet a further aspect, $R^{21}$, when present, is selected from methyl and ethyl. In an even further aspect, $R^{21}$, when present, is ethyl. In a still further aspect, $R^{21}$, when present, is methyl.

In a further aspect, $R^{21}$, when present, is selected from cycloalkyl and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is selected from cycloalkyl and heterocycloalkyl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is selected from cycloalkyl and heterocycloalkyl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $R^{21}$, when present, is selected from cycloalkyl and heterocycloalkyl and is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is selected from cycloalkyl and heterocycloalkyl and is monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is selected from cycloalkyl and heterocycloalkyl and is unsubstituted.

In a further aspect, $R^{21}$, when present, is cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $R^{21}$, when present, is cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is unsubstituted cycloalkyl.

In a further aspect, $R^{21}$, when present, is heterocycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is heterocycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is heterocycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $R^{21}$, when present, is heterocycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $R^{21}$, when present, is heterocycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $R^{21}$, when present, is unsubstituted heterocycloalkyl.

In a further aspect, $R^{21}$, when present, is C3-C8 cycloalkyl. In a still further aspect, $R^{21}$, when present, is C2-C7 heterocycloalkyl.

l. $R^{30}$ Groups

In one aspect, $R^{30}$ is selected from —$(CH_2)_m NH_2$ and —$(CH_2)_m$(C1-C4 alkylamino). In a further aspect, $R^{30}$ is selected from —$CH_2NH_2$, —$NH_2$, —$CH_2$(C1-C4 alkylamino), and (C1-C4) alkylamino. In a still further aspect, $R^{30}$ is selected from —$CH_2NH_2$ and —$CH_2$(C1-C4 alkylamino). In yet a further aspect, $R^{30}$ is selected from —$NH_2$ and (C1-C4) alkylamino.

In a further aspect, $R^{30}$ is —$(CH_2)_m NH_2$. In a still further aspect, $R^{30}$ is —$CH_2NH_2$. In yet a further aspect, $R^{30}$ is —$NH_2$.

In a further aspect, $R^{30}$ is —$(CH_2)_m$(C1-C4 alkylamino). In a still further aspect, $R^{30}$ is —$CH_2$(C1-C4 alkylamino). In yet a further aspect, $R^{30}$ is (C1-C4) alkylamino.

m. $Cy^1$ Groups

In one aspect, $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^1$, when present, is selected from C3-C8 cycloalkyl and aryl and is substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is selected from C3-C8 cycloalkyl and aryl and is substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is selected from C3-C8 cycloalkyl and aryl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is selected from C3-C8 cycloalkyl and aryl and is monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is selected from C3-C8 cycloalkyl and aryl and is unsubstituted.

In a further aspect, $Cy^1$, when present, is C3-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C3-C8 cycloalkyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is C3-C8 cycloalkyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is C3-C8 cycloalkyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C3-C8 cycloalkyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is unsubstituted C3-C8 cycloalkyl.

In a further aspect, $Cy^1$, when present, is C3-C7 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C3-C6 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is C3-C5 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is C3-C4 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C4-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is C5-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is C6-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is C7-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $Cy^1$, when present, is cyclohexyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is cyclohexyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is cyclohexyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is cyclohexyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is cyclohexyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is unsubstituted cyclohexyl.

In a further aspect, $Cy^1$, when present, is aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is aryl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is unsubstituted aryl.

In a further aspect, $Cy^1$, when present, is phenyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is phenyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is phenyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^1$, when present, is phenyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^1$, when present, is phenyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^1$, when present, is unsubstituted phenyl.

n. $Cy^2$ Groups

In one aspect, $Cy^2$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^2$, when present, is selected from C3-C8 cycloalkyl and aryl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is selected from C3-C8 cycloalkyl and aryl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$, when present, is selected from C3-C8 cycloalkyl and aryl and is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$, when present, is selected from C3-C8 cycloalkyl and aryl and is monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is selected from C3-C8 cycloalkyl and aryl and is unsubstituted.

In a further aspect, $Cy^2$, when present, is C3-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is C3-C8 cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$, when present, is C3-C8 cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$, when present, is C3-C8 cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is C3-C8 cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$, when present, is unsubstituted C3-C8 cycloalkyl.

In a further aspect, $Cy^2$, when present, is C3-C7 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is C3-C6 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$, when present, is C3-C5 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$, when present, is C3-C4 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^2$, when present, is C4-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^2$, when present, is C5-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^2$, when present, is C6-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is C7-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, Cy$^2$, when present, is cyclohexyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is cyclohexyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is cyclohexyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^2$, when present, is cyclohexyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is cyclohexyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is unsubstituted cyclohexyl.

In a further aspect, Cy$^2$, when present, is aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^2$, when present, is aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is aryl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is unsubstituted aryl.

In a further aspect, Cy$^2$, when present, is phenyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is phenyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is phenyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^2$, when present, is phenyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^2$, when present, is phenyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^2$, when present, is unsubstituted phenyl.

o. Cy$^3$ Groups

In one aspect, Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, Cy$^3$, when present, is selected from C3-C8 cycloalkyl and aryl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$, when present, is selected from C3-C8 cycloalkyl and aryl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^3$, when present, is selected from C3-C8 cycloalkyl and aryl and is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^3$, when present, is selected from C3-C8 cycloalkyl and aryl and is monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$, when present, is selected from C3-C8 cycloalkyl and aryl and is unsubstituted.

In a further aspect, Cy$^3$, when present, is C3-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$, when present, is C3-C8 cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, Cy$^3$, when present, is C3-C8 cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, Cy$^3$, when present, is C3-C8 cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, Cy$^3$, when present, is C3-C8 cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-

C4)(C1-C4) dialkylamino. In yet a further aspect, $Cy^3$, when present, is unsubstituted C3-C8 cycloalkyl.

In a further aspect, $Cy^3$, when present, is C3-C7 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is C3-C6 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is C3-C5 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$, when present, is C3-C4 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is C4-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is C5-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$, when present, is C6-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is C7-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $Cy^3$, when present, is cyclohexyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is cyclohexyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is cyclohexyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$, when present, is cyclohexyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is cyclohexyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is unsubstituted cyclohexyl.

In a further aspect, $Cy^3$, when present, is aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$, when present, is aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is aryl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is unsubstituted aryl.

In a further aspect, $Cy^3$, when present, is phenyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is phenyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is phenyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^3$, when present, is phenyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^3$, when present, is phenyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^3$, when present, is unsubstituted phenyl.

p. $Cy^4$ Groups

In one aspect, $Cy^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a further aspect, $Cy^4$, when present, is selected from C3-C8 cycloalkyl, C2-C7 heterocycloalkyl, aryl, and heteroaryl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is selected from C3-C8 cycloalkyl, C2-C7 heterocycloalkyl, aryl, and heteroaryl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is selected from C3-C8 cycloalkyl, C2-C7 heterocycloalkyl, aryl, and heteroaryl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is selected from C3-C8 cycloalkyl, C2-C7 heterocycloalkyl, aryl, and heteroaryl and is unsubstituted.

In one aspect, $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, C1-C4)(C1-C4) dialkylamino, and $Cy^6$. In a further aspect, $Cy^4$, when present, is selected from C3-C8 cycloalkyl, C2-C7 heterocycloalkyl, aryl, and heteroaryl and is substituted with 0-3 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, C1-C4)(C1-C4) dialkylamino, and $Cy^6$. In a still further aspect, $Cy^4$, when present, is selected from C3-C8 cycloalkyl, C2-C7 heterocycloalkyl, aryl, and heteroaryl and is substituted with 0-2 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, C1-C4)(C1-C4) dialkylamino, and $Cy^6$. In yet a further aspect, $Cy^4$, when present, is selected from C3-C8 cycloalkyl, C2-C7 heterocycloalkyl, aryl, and heteroaryl and is substituted with 0-1 non-hydrogen group selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, C1-C4)(C1-C4) dialkylamino, and $Cy^6$. In an even further aspect, $Cy^4$, when present, is selected from C3-C8 cycloalkyl, C2-C7 heterocycloalkyl, aryl, and heteroaryl and is monosubstituted with a —CN group. In a still further aspect, $Cy^4$, when present, is selected from C3-C8 cycloalkyl, C2-C7 heterocycloalkyl, aryl, and heteroaryl and is monosubstituted with a $Cy^6$ group.

In a further aspect, $Cy^4$, when present, is selected from C3-C8 cycloalkyl and C2-C7 heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is selected from C3-C8 cycloalkyl and C2-C7 heterocycloalkyl and is substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is selected from C3-C8 cycloalkyl and C2-C7 heterocycloalkyl and is substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is selected from C3-C8 cycloalkyl and C2-C7 heterocycloalkyl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is selected from C3-C8 cycloalkyl and C2-C7 heterocycloalkyl and is unsubstituted.

In a further aspect, $Cy^4$, when present, is C3-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is C3-C8 cycloalkyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is C3-C8 cycloalkyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is C3-C8 cycloalkyl is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted C3-C8 cycloalkyl.

In a further aspect, $Cy^4$, when present, is cyclohexyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is cyclohexyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is cyclohexyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is cyclohexyl is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted cyclohexyl.

In a further aspect, $Cy^4$, when present, is C2-C7 heterocycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is C2-C7 heterocycloalkyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is C2-C7 heterocycloalkyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is C2-C7 heterocycloalkyl is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted C2-C7 heterocycloalkyl.

In a further aspect, $Cy^4$, when present, is tetrahydro-2H-pyranyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is tetrahydro-2H-pyranyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is tetrahydro-2H-pyranyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is tetrahydro-2H-pyranyl is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted tetrahydro-2H-pyranyl.

In a further aspect, $Cy^4$, when present, is selected from aryl and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is selected from aryl and heteroaryl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is selected from aryl and heteroaryl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is selected from aryl and heteroaryl and is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is selected from aryl and heteroaryl and is unsubstituted.

In a further aspect, $Cy^4$, when present, is aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted aryl.

In a further aspect, $Cy^4$, when present, is phenyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is phenyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is phenyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is phenyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted phenyl.

In a further aspect, $Cy^4$, when present, is heteroaryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is heteroaryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is heteroaryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is heteroaryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted heteroaryl.

In a further aspect, $Cy^4$, when present, is pyridinyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is pyridinyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4) (C1-C4) dialkylamino. In yet a further aspect, $Cy^4$, when present, is pyridinyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4) (C1-C4) dialkylamino. In an even further aspect, $Cy^4$, when present, is pyridinyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted pyridinyl.

In a further aspect, $Cy^4$, when present, is pyrimidinyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is pyrimidinyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is pyrimidinyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is pyrimidinyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted pyrimidinyl.

In a further aspect, $Cy^4$, when present, is thiazolyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is thiazolyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In yet a further aspect, $Cy^4$, when present, is thiazolyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In an even further aspect, $Cy^4$, when present, is thiazolyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino. In a still further aspect, $Cy^4$, when present, is unsubstituted thiazolyl.

q. $Cy^5$ Groups

In one aspect, $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^5$, when present, is selected from C3-C8 cycloalkyl and aryl and is substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is selected from C3-C8 cycloalkyl and aryl and is substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is selected from C3-C8 cycloalkyl and aryl and is substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is selected from C3-C8 cycloalkyl and aryl and is monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is selected from C3-C8 cycloalkyl and aryl and is unsubstituted.

In a further aspect, $Cy^5$, when present, is C3-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is C3-C8 cycloalkyl substituted with 0-3 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is C3-C8 cycloalkyl substituted with 0-2 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is C3-C8 cycloalkyl substituted with 0-1 non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is C3-C8 cycloalkyl monosubstituted with a non-hydrogen group selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is unsubstituted C3-C8 cycloalkyl.

In a further aspect, $Cy^5$, when present, is C3-C7 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is C3-C6 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is C3-C5 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is C3-C4 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is C4-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is C5-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is C6-C8 cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is C7-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $Cy^5$, when present, is cyclohexyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is cyclohexyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is cyclohexyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is cyclohexyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is cyclohexyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is unsubstituted cyclohexyl.

In a further aspect, $Cy^5$, when present, is aryl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is aryl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is aryl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is aryl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is aryl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is unsubstituted aryl.

In a further aspect, $Cy^5$, when present, is phenyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is phenyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is phenyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^5$, when present, is phenyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^5$, when present, is phenyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^5$, when present, is unsubstituted phenyl.

r. $Cy^6$ Groups

In one aspect, $Cy^6$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a further aspect, $Cy^6$, when present, is selected from C3-C8 cycloalkyl and aryl and is substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is selected from C3-C8 cycloalkyl and aryl and is substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is selected from C3-C8 cycloalkyl and aryl and is substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is selected from C3-C8 cycloalkyl and aryl and is monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is selected from C3-C8 cycloalkyl and aryl and is unsubstituted.

In a further aspect, $Cy^6$, when present, is C3-C8 cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is C3-C8 cycloalkyl substituted with 0-3 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is C3-C8 cycloalkyl substituted with 0-2 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is C3-C8 cycloalkyl substituted with 0-1 non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is C3-C8 cycloalkyl monosubstituted with a non-hydrogen group selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is unsubstituted C3-C8 cycloalkyl.

In a further aspect, $Cy^6$, when present, is C3-C7 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is C3-C6 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is C3-C5 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is C3-C4 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is C4-C8 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is C5-C8 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is C6-C8 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is C7-C8 cycloalkyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino.

In a further aspect, $Cy^6$, when present, is cyclohexyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is cyclohexyl substituted with 0-3 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is cyclohexyl substituted with 0-2 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is cyclohexyl substituted with 0-1 non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is cyclohexyl monosubstituted with a non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is unsubstituted cyclohexyl.

In a further aspect, $Cy^6$, when present, is aryl substituted with 0-4 non-hydrogen groups independently selected from halogen, $—NH_2$, C1-C4 alkyl, C1-C4 haloalkyl, C1-C4 alkoxy, C1-C4 alkylamino, and (C1-C4)(C1-C4) dialkylamino. In a still further aspect, $Cy^6$, when present, is aryl substituted with 0-3 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is aryl substituted with 0-2 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is aryl substituted with 0-1 non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is aryl monosubstituted with a non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is unsubstituted aryl.

In a further aspect, $Cy^6$, when present, is phenyl substituted with 0-4 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is phenyl substituted with 0-3 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is phenyl substituted with 0-2 non-hydrogen groups independently selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In an even further aspect, $Cy^6$, when present, is phenyl substituted with 0-1 non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In a still further aspect, $Cy^6$, when present, is phenyl monosubstituted with a non-hydrogen group selected from halogen, $—NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino. In yet a further aspect, $Cy^6$, when present, is unsubstituted phenyl.

s. $Ar^1$ Groups

In one aspect, $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, $—(CH_2)_m NH_2$, $—(CH_2)_m$(C1-C4 alkylamino), and $—(CH_2)_m$[(C1-C4)(C1-C4) dialkylamino], provided that $Ar^1$, when present, is substituted with at least one non-hydrogen group selected from $—(CH_2)_m NH_2$ and $—(CH_2)_m$(C1-C4 alkylamino). In a further aspect, $Ar^1$, when present, is selected from aryl and heteroaryl and is substituted with 1-3 non-hydrogen groups independently selected from halogen, C1-C4 alkyl, C1-C4 haloalkyl, C1-C4 hydroxyalkyl, C1-C4 alkoxy, $—(CH_2)_m NH_2$, $—(CH_2)_m$(C1-C4 alkylamino), and $—(CH_2)_m$[(C1-C4)(C1-C4) dialkylamino], provided that $Ar^1$, when present, is substituted with at least one non-hydrogen group selected from $—(CH_2)_m NH_2$ and $—(CH_2)_m$(C1-C4 alkylamino). In a still further aspect, $Ar^1$, when present, is selected from aryl and heteroaryl and is substituted with 1-2 non-hydrogen groups independently selected from halogen, C1-C4 alkyl, C1-C4 haloalkyl, C1-C4 hydroxyalkyl, C1-C4 alkoxy, $—(CH_2)_m NH_2$, $—(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In yet a further aspect, $Ar^1$, when present, is selected from aryl and heteroaryl and is monosubstituted with a non-hydrogen group selected from —$(CH_2)_m NH_2$ and —$(CH_2)_m$(C1-C4 alkylamino).

In one aspect, $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)$(C1-C4 alkyl), —$(CH_2)_m N$(C1-C4 alkyl)(C=O)(C1-C4 alkyl), and $Cy^5$. In a further aspect, $Ar^1$, when present, is selected from aryl and heteroaryl and is substituted with 0-3 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)$(C1-C4 alkyl), —$(CH_2)_m N$(C1-C4 alkyl)(C=O)(C1-C4 alkyl), and $Cy^5$. In a still further aspect, $Ar^1$, when present, is selected from aryl and heteroaryl and is substituted with 0-2 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)$(C1-C4 alkyl), —$(CH_2)_m N$(C1-C4 alkyl)(C=O)(C1-C4 alkyl), and $Cy^5$. In yet a further aspect, $Ar^1$, when present, is selected from aryl and heteroaryl and is substituted with 0-1 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)$(C1-C4 alkyl), —$(CH_2)_m N$(C1-C4 alkyl)(C=O)(C1-C4 alkyl), and $Cy^5$.

In a further aspect, $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), —$(CH_2)_m$[(C1-C4)(C1-C4) dialkylamino], —$(CH_2)_m NH(C=O)$(C1-C4 alkyl), —$(CH_2)_m N$(C1-C4 alkyl)(C=O)(C1-C4 alkyl), and $Cy^5$, provided that $Ar^1$, when present, is substituted with at least one non-hydrogen group selected from —CN, —$(CH_2)_m NH_2$, and —$(CH_2)_m$(C1-C4 alkylamino).

In a further aspect, $Ar^1$, when present, is aryl substituted with 1-4 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In a still further aspect, $Ar^1$, when present, is aryl substituted with 1-3 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In yet a further aspect, $Ar^1$, when present, is aryl substituted with 1-2 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In an even further aspect, $Ar^1$, when present, is aryl monosubstituted with a non-hydrogen group selected from —$(CH_2)_m NH_2$ and —$(CH_2)_m$(C1-C4 alkylamino).

In a further aspect, $Ar^1$, when present, is aryl monosubstituted with a non-hydrogen group selected from —$NH_2$, —$CH_2 NH_2$, —$CH_2 NHCH_3$, and —$NHCH_3$. In a still further aspect, $Ar^1$, when present, is aryl monosubstituted with a non-hydrogen group selected from —$NH_2$ and —$NHCH_3$. In yet a further aspect, $Ar^1$, when present, is aryl monosubstituted with a —$NH_2$ group. In an even further aspect, $Ar^1$, when present, is aryl monosubstituted with a —$CH_2 NH_2$ group. In a still further aspect, $Ar^1$, when present, is aryl monosubstituted with a —$CH_2 NHCH_3$ group. In yet a further aspect, $Ar^1$, when present, is aryl monosubstituted with a —$NHCH_3$ group.

In a further aspect, $Ar^1$, when present, is phenyl substituted with 1-4 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In a still further aspect, $Ar^1$, when present, is phenyl substituted with 1-3 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In yet a further aspect, $Ar^1$, when present, is phenyl substituted with 1-2 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In an even further aspect, $Ar^1$, when present, is phenyl monosubstituted with a non-hydrogen group selected from —$(CH_2)_m NH_2$ and —$(CH_2)_m$(C1-C4 alkylamino).

In a further aspect, $Ar^1$, when present, is phenyl monosubstituted with a non-hydrogen group selected from —$NH_2$, —$CH_2 NH_2$, —$CH_2 NHCH_3$, and —$NHCH_3$. In a still further aspect, $Ar^1$, when present, is phenyl monosubstituted with a non-hydrogen group selected from —$NH_2$ and —$NHCH_3$. In yet a further aspect, $Ar^1$, when present, is phenyl monosubstituted with a —$NH_2$ group. In an even further aspect, $Ar^1$, when present, is phenyl monosubstituted with a —$CH_2 NH_2$ group. In a still further aspect, $Ar^1$, when present, is phenyl monosubstituted with a —$CH_2 NHCH_3$ group. In yet a further aspect, $Ar^1$, when present, is phenyl monosubstituted with a —$NHCH_3$ group.

In a further aspect, $Ar^1$, when present, is heteroaryl substituted with 1-4 non-hydrogen groups independently selected from halogen, C1-C4 alkyl, C1-C4 haloalkyl, C1-C4 hydroxyalkyl, C1-C4 alkoxy, —$(CH_2)_m NH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_m NH_2$ and —$(CH_2)_m$(C1-C4 alkylamino). In a still further aspect, $Ar^1$, when present, is heteroaryl substituted with 1-3 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino). In yet a further aspect, Ar$^1$, when present, is heteroaryl substituted with 1-2 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino). In an even further aspect, Ar$^1$, when present, is heteroaryl monosubstituted with a non-hydrogen group selected from —(CH$_2$)$_m$NH$_2$ and —(CH$_2$)$_m$(C1-C4 alkylamino).

In a further aspect, Ar$^1$, when present, is heteroaryl monosubstituted with a non-hydrogen group selected from —NH$_2$, —CH$_2$NH$_2$, —CH$_2$NHCH$_3$, and —NHCH$_3$. In a still further aspect, Ar$^1$, when present, is aryl monosubstituted with a non-hydrogen group selected from —NH$_2$ and —NHCH$_3$. In yet a further aspect, Ar$^1$, when present, is heteroaryl monosubstituted with a —NH$_2$ group. In an even further aspect, Ar$^1$, when present, is heteroaryl monosubstituted with a —CH$_2$NH$_2$ group. In a still further aspect, Ar$^1$, when present, is heteroaryl monosubstituted with a —CH$_2$NHCH$_3$ group. In yet a further aspect, Ar$^1$, when present, is heteroaryl monosubstituted with a —NHCH$_3$ group.

In a further aspect, Ar$^1$, when present, is pyridinyl substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino). In a still further aspect, Ar$^1$, when present, is pyridinyl substituted with 1-3 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino). In yet a further aspect, Ar$^1$, when present, is pyridinyl substituted with 1-2 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino). In an even further aspect, Ar$^1$, when present, is pyridinyl monosubstituted with a non-hydrogen group selected from —(CH$_2$)$_m$NH$_2$ and —(CH$_2$)$_m$(C1-C4 alkylamino).

In a further aspect, Ar$^1$, when present, is pyridinyl monosubstituted with a non-hydrogen group selected from —NH$_2$, —CH$_2$NH$_2$, —CH$_2$NHCH$_3$, and —NHCH$_3$. In a still further aspect, Ar$^1$, when present, is pyridinyl monosubstituted with a non-hydrogen group selected from —NH$_2$ and —NHCH$_3$. In yet a further aspect, Ar$^1$, when present, is pyridinyl monosubstituted with a —NH$_2$ group. In an even further aspect, Ar$^1$, when present, is pyridinyl monosubstituted with a —CH$_2$NH$_2$ group. In a still further aspect, Ar$^1$, when present, is pyridinyl monosubstituted with a —CH$_2$NHCH$_3$ group. In yet a further aspect, Ar$^1$, when present, is pyridinyl monosubstituted with a —NHCH$_3$ group.

2. Example Compounds

In one aspect, a compound can be present as one or more of the following structures:

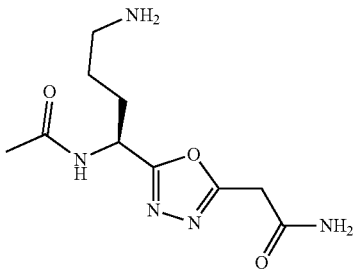

and

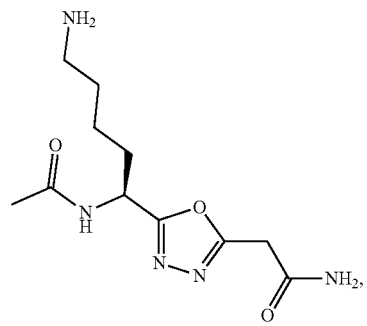

or a pharmaceutically acceptable salt thereof.

In one aspect, a compound can be present as the following structure:

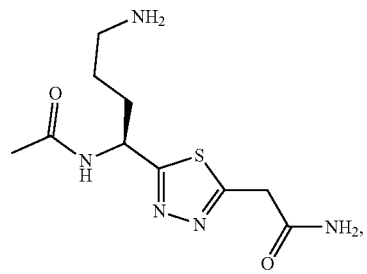 [SMILES: CC(=O)N[C@@H](CCCN)c1nnc(CC(N)=O)s1]

or a pharmaceutically acceptable salt thereof.

In one aspect, a compound can be present as the following structure:
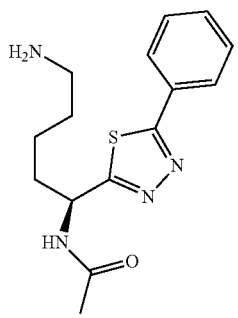
or a pharmaceutically acceptable salt thereof.
In one aspect, a compound can be present as the following structure:
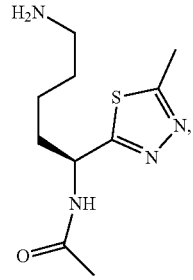 [SMILES: CC(=O)N[C@@H](CCCCN)c1nnc(C)s1]
or a pharmaceutically acceptable salt thereof.
In one aspect, a compound can be present as one or more of the following structures:
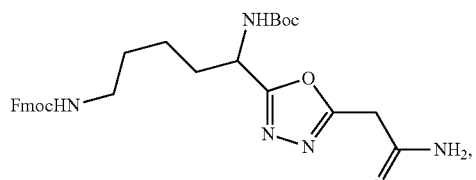
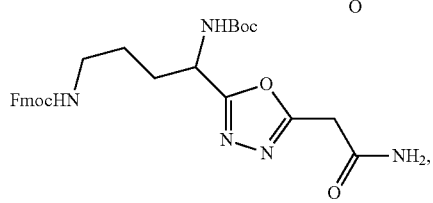
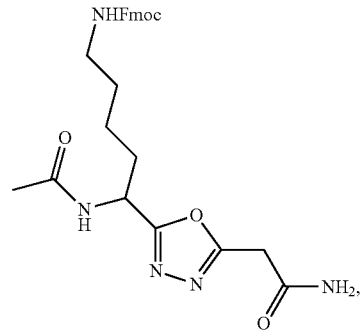
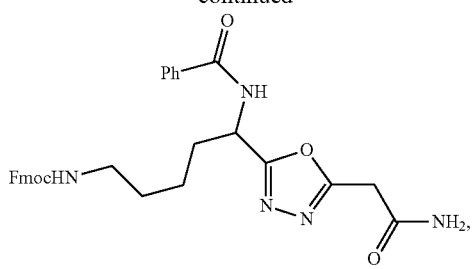
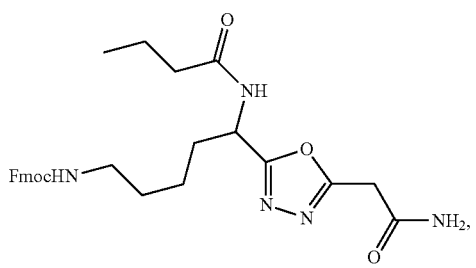
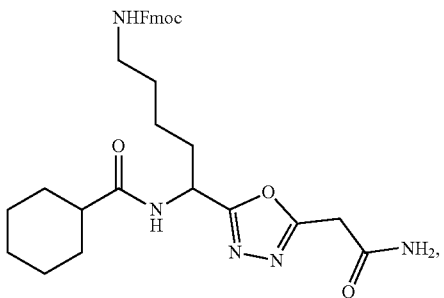
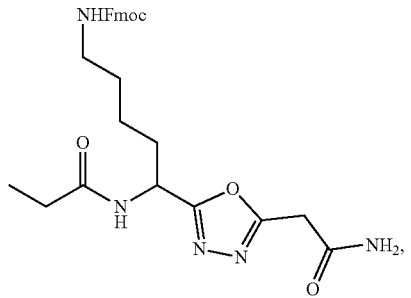
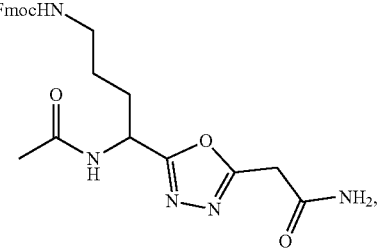
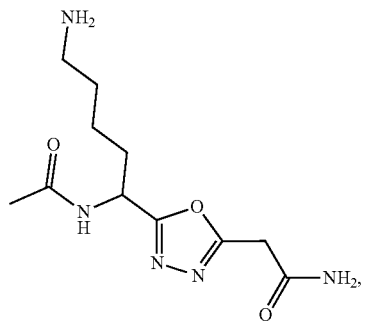

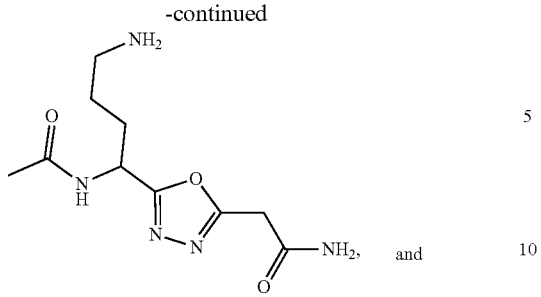
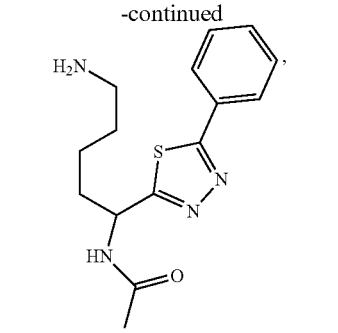
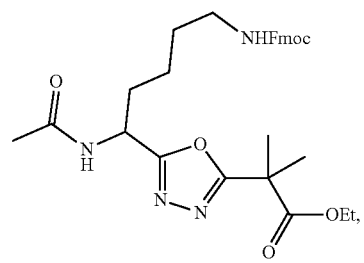
, and
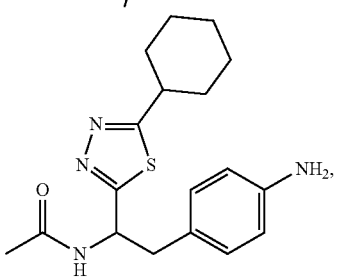
or a pharmaceutically acceptable salt thereof.
In one aspect, a compound can be present as one or more of the following structures:
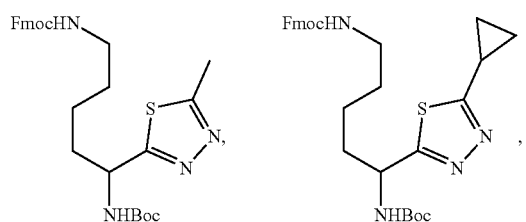
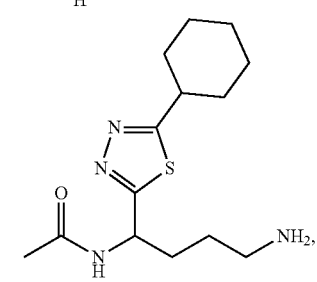
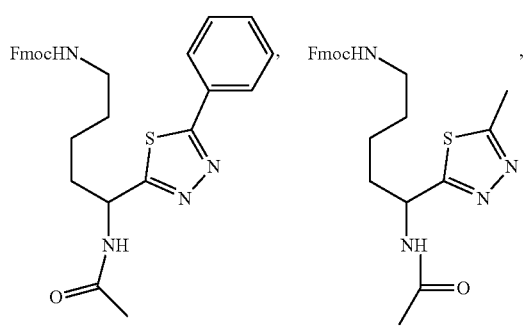
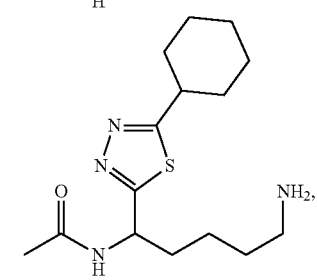
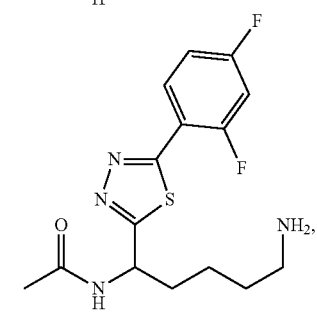
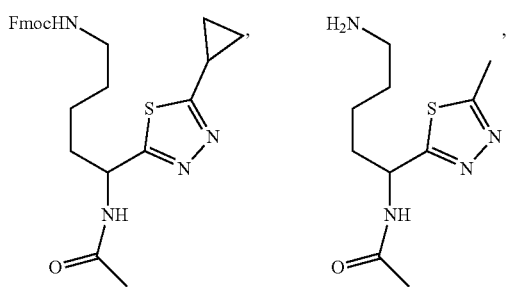
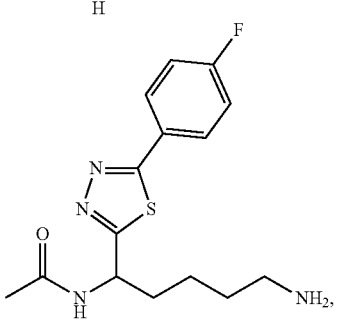

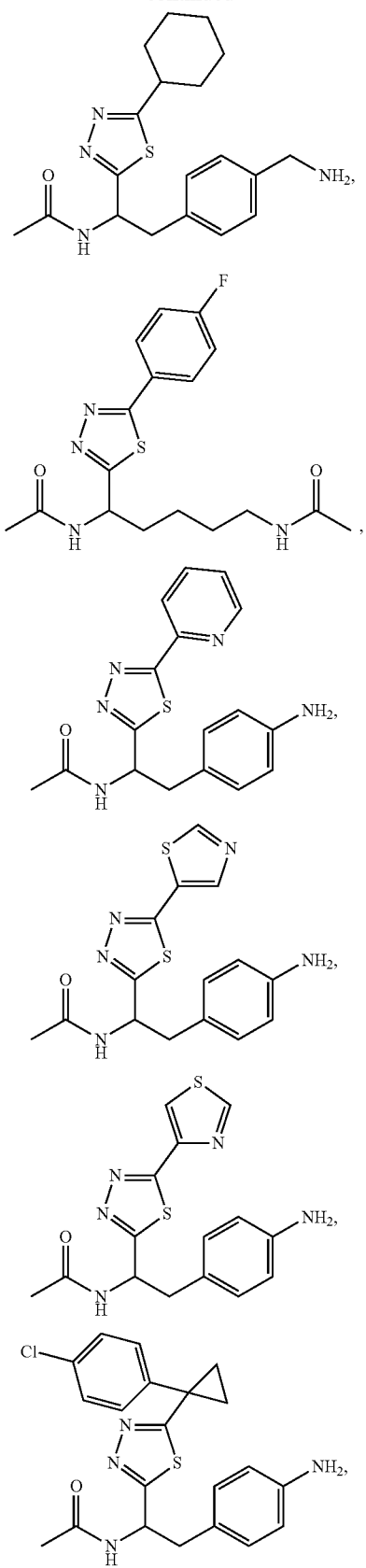
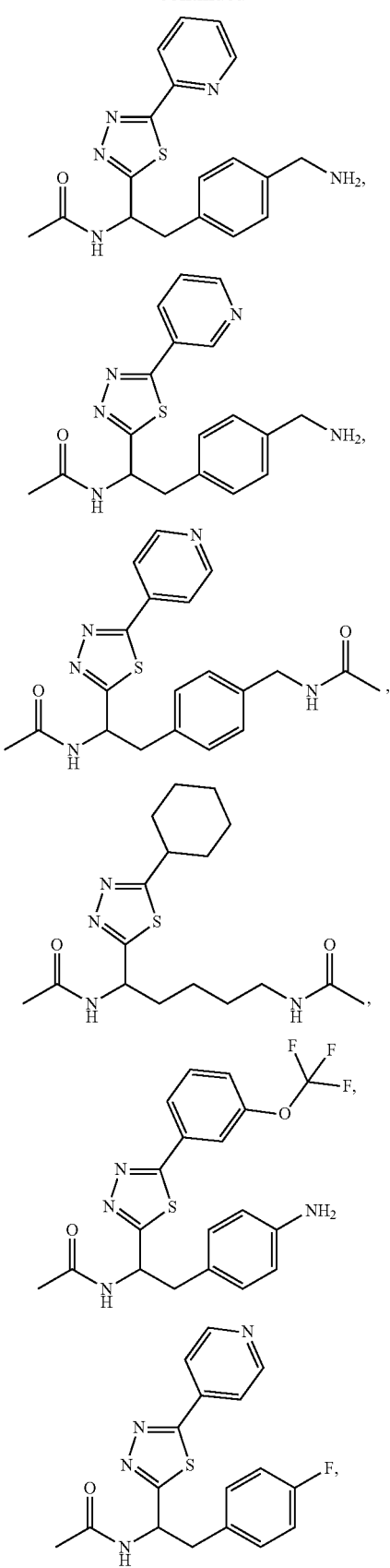

73
-continued
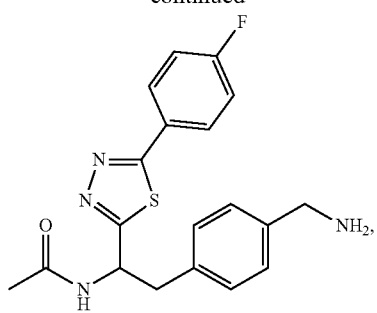
74
-continued
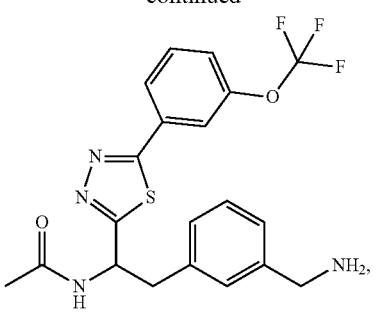
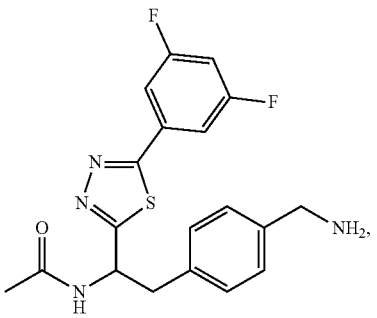
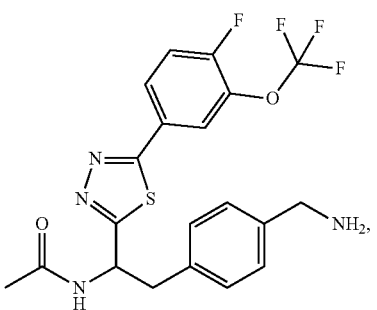
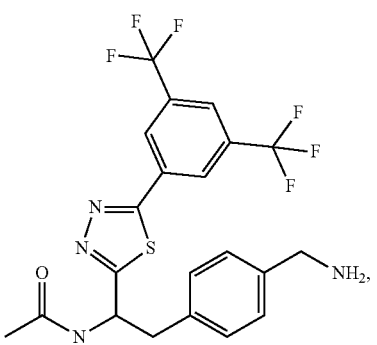
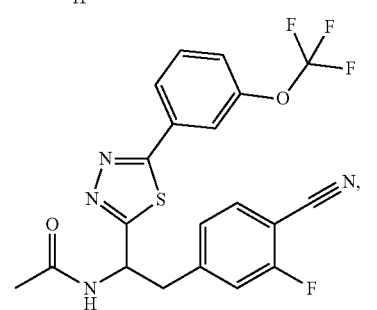

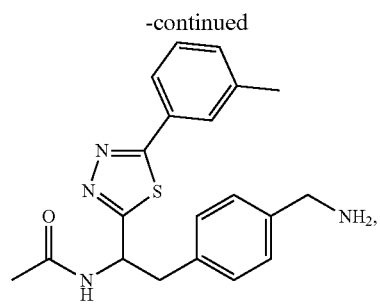
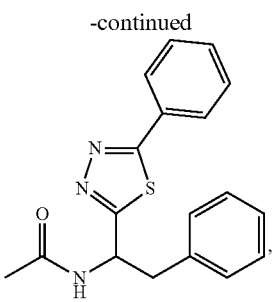

77
-continued
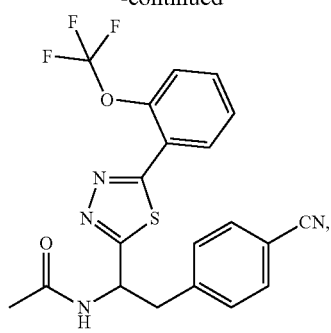
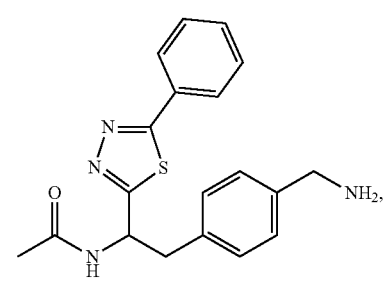
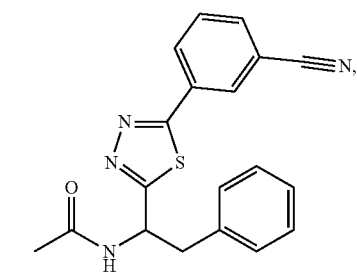
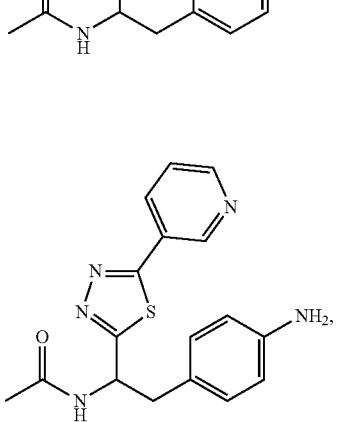
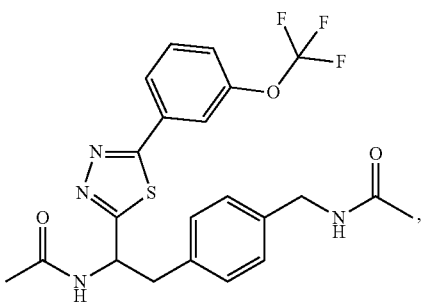
78
-continued
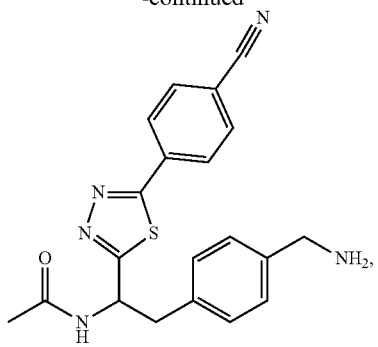
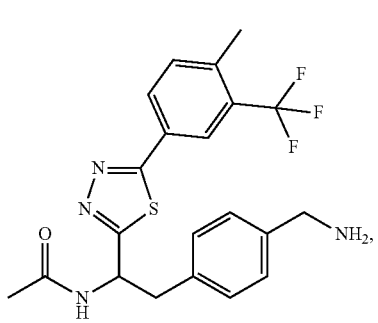
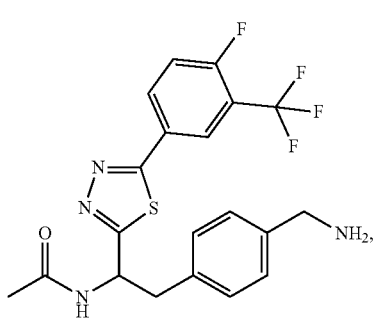
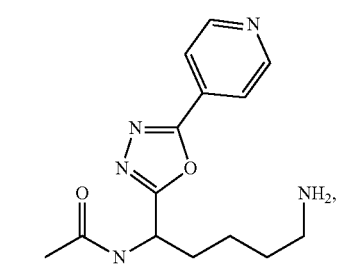
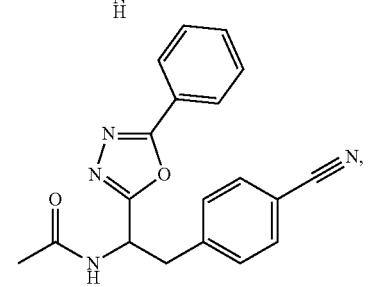

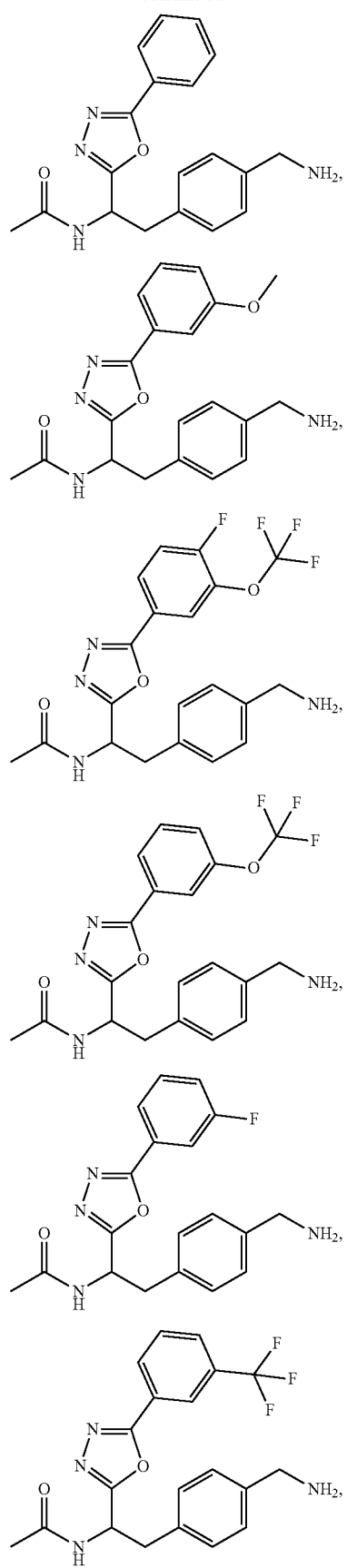
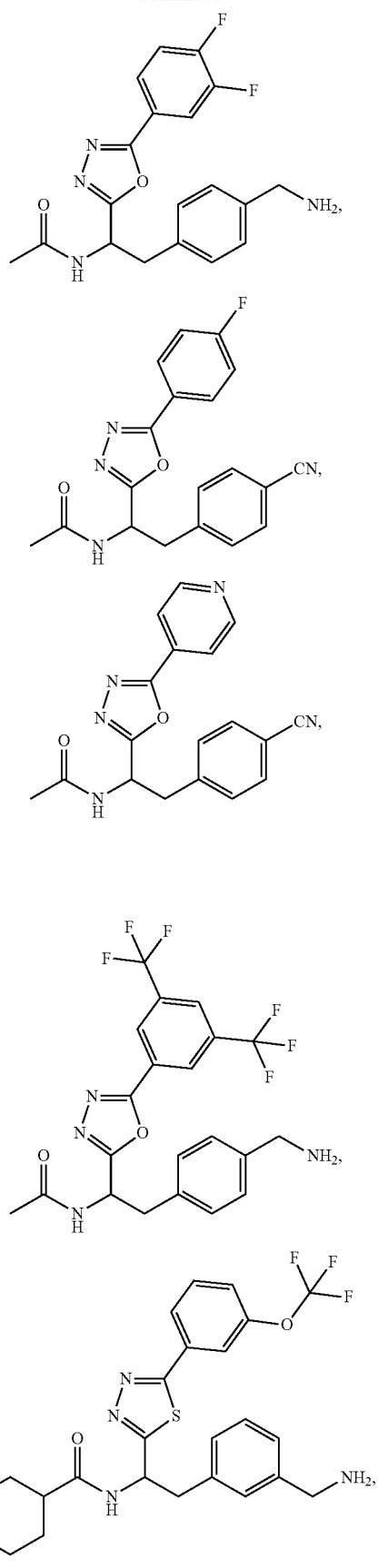

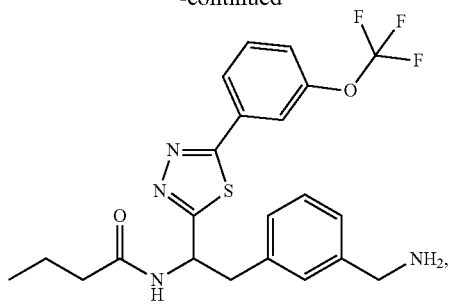
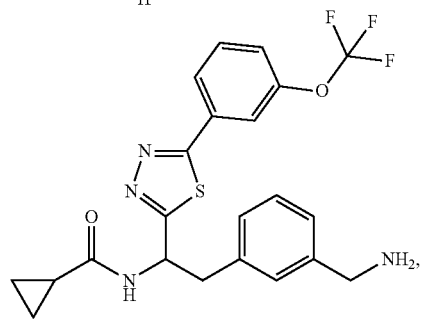
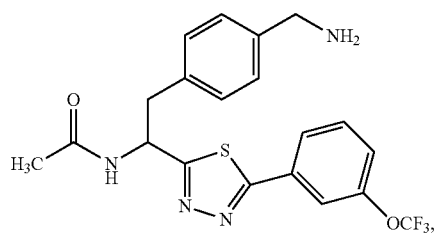
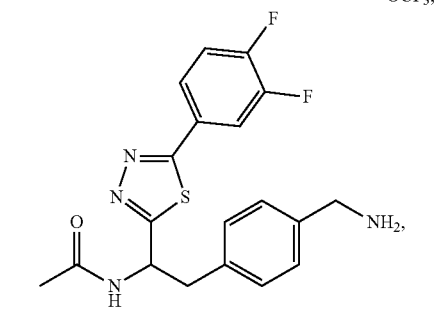
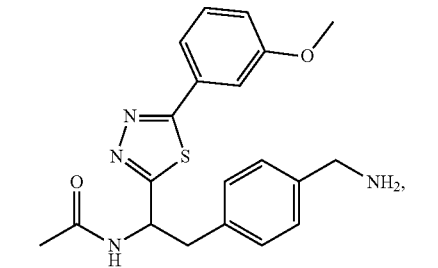
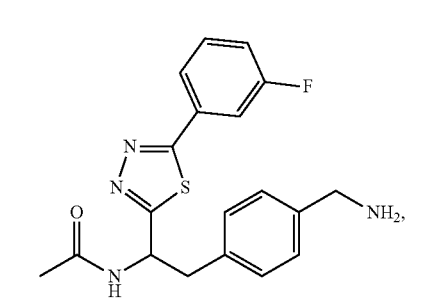
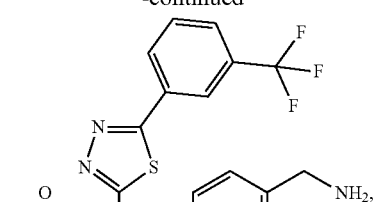
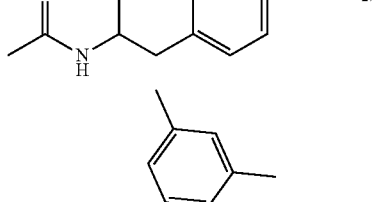
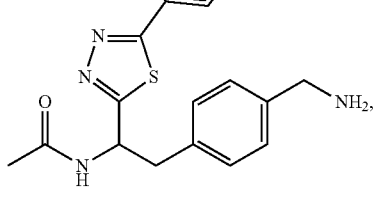
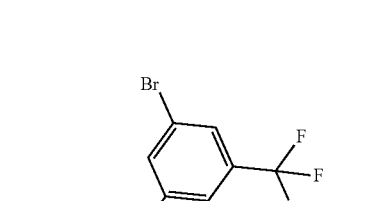
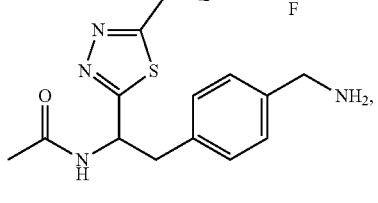
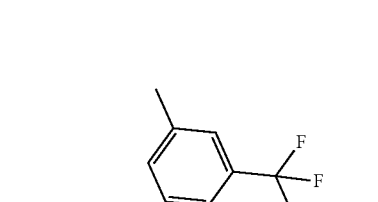

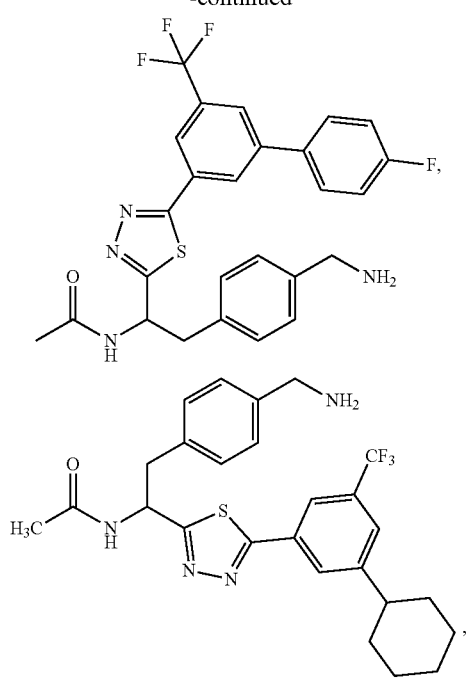
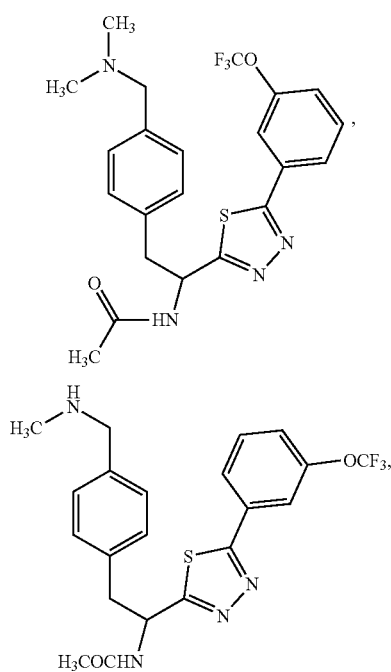
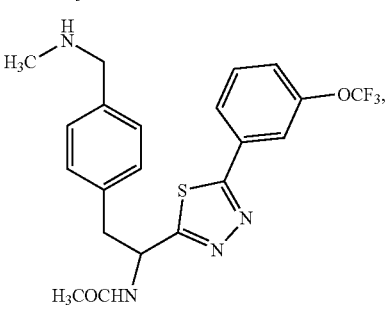
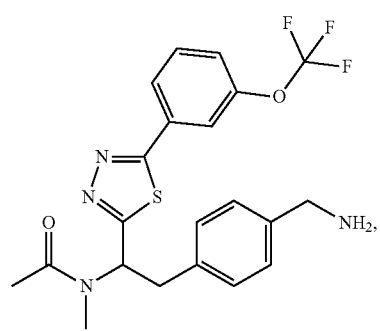
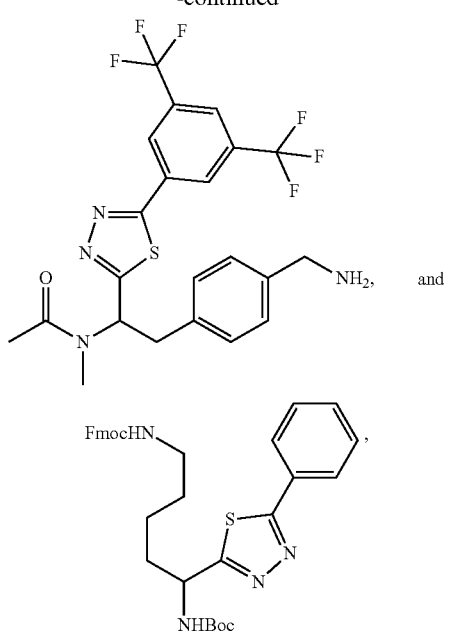
or a pharmaceutically acceptable salt thereof.
In one aspect, a compound can be present as one or more of the following structures:
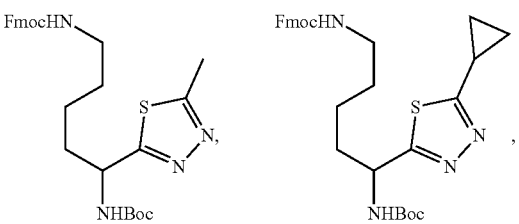

85
-continued
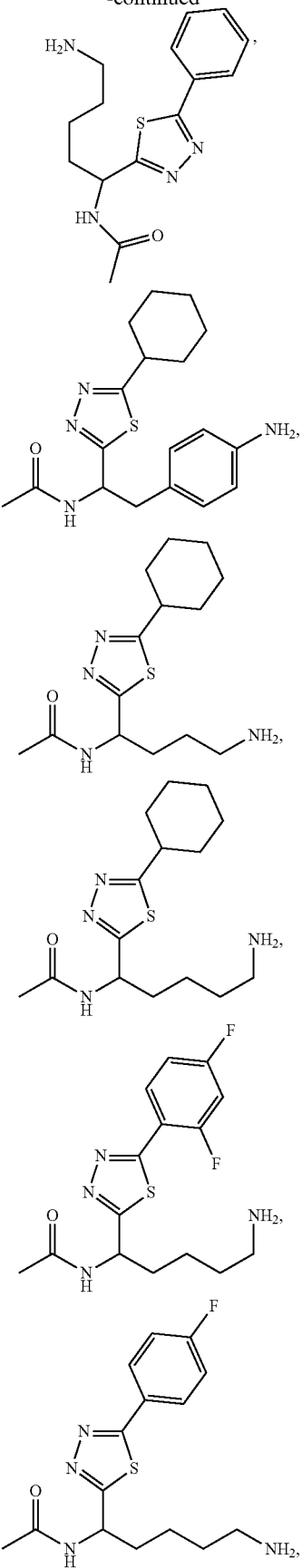
86
-continued
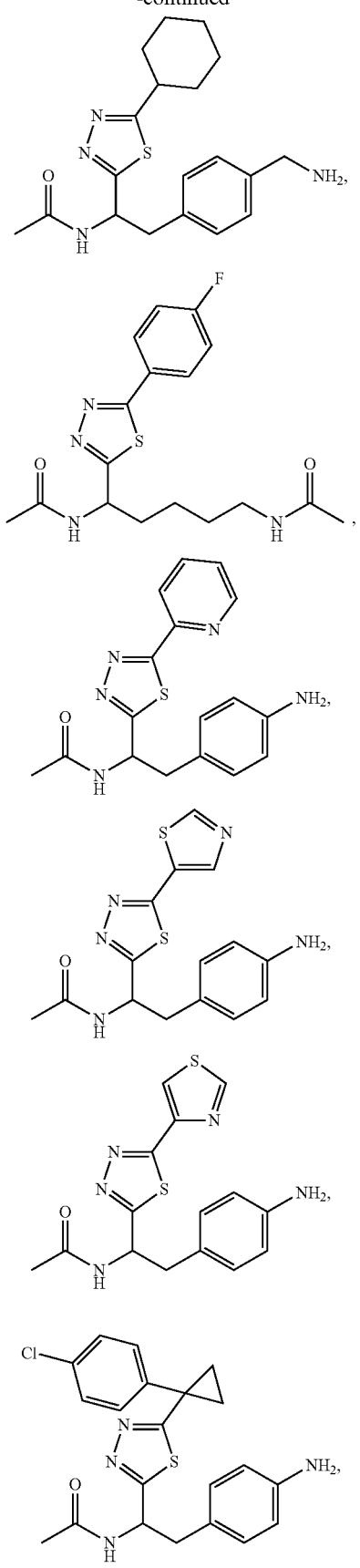

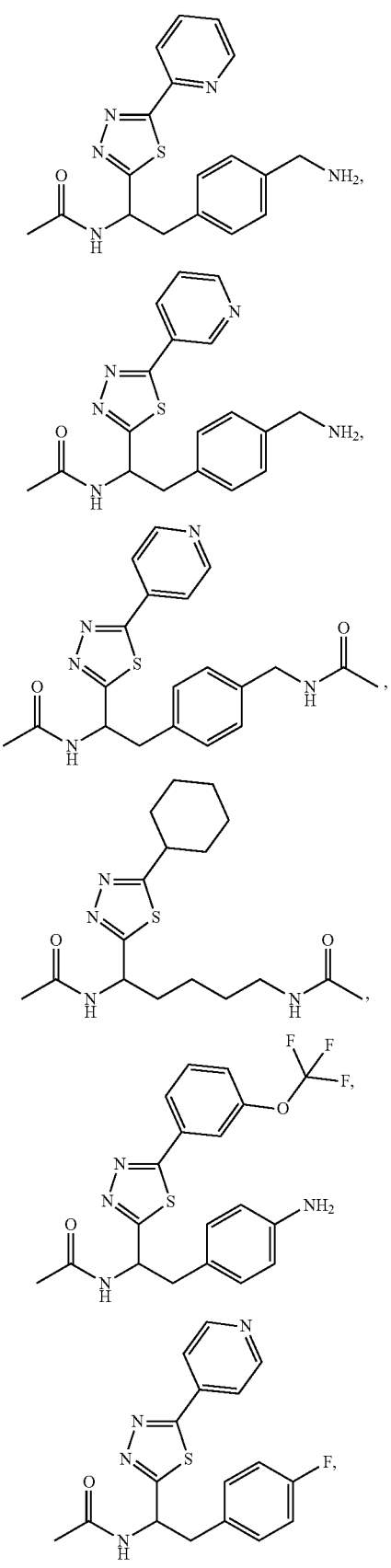
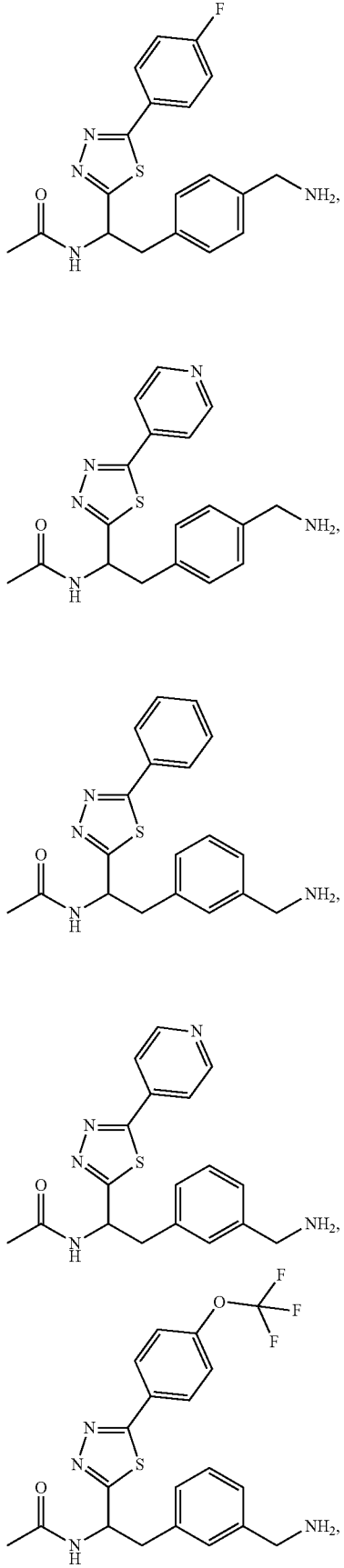

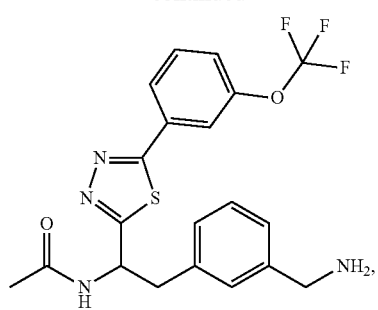
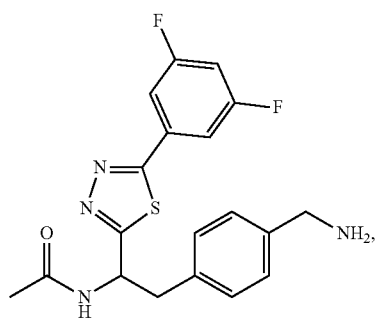
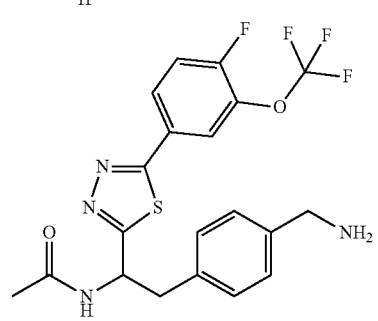
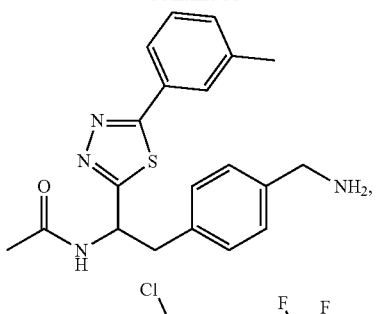
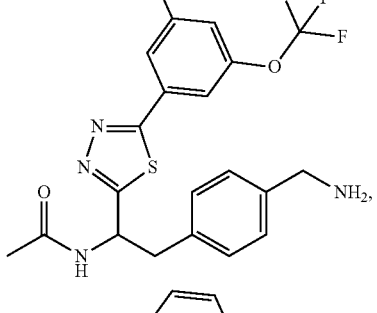
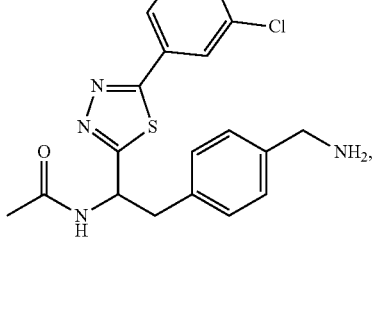

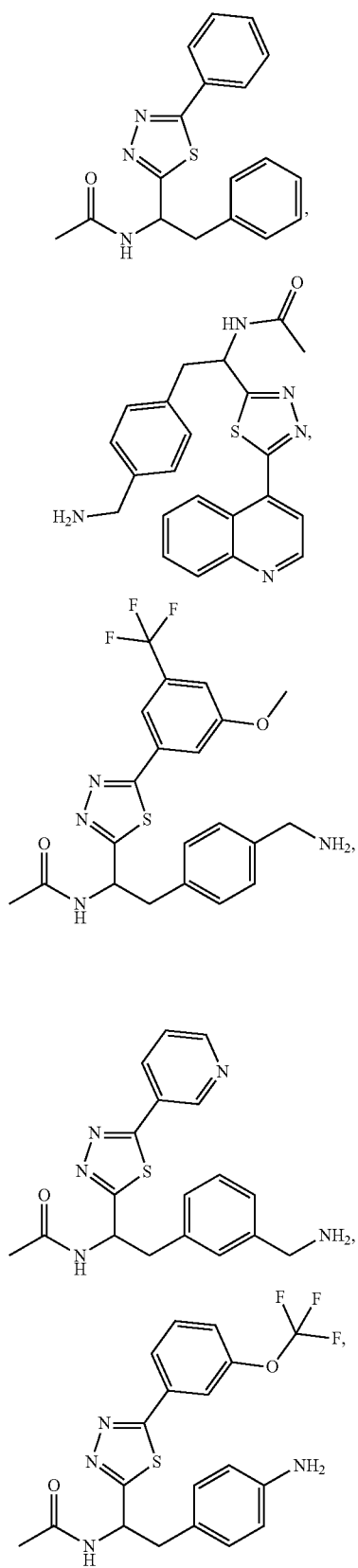
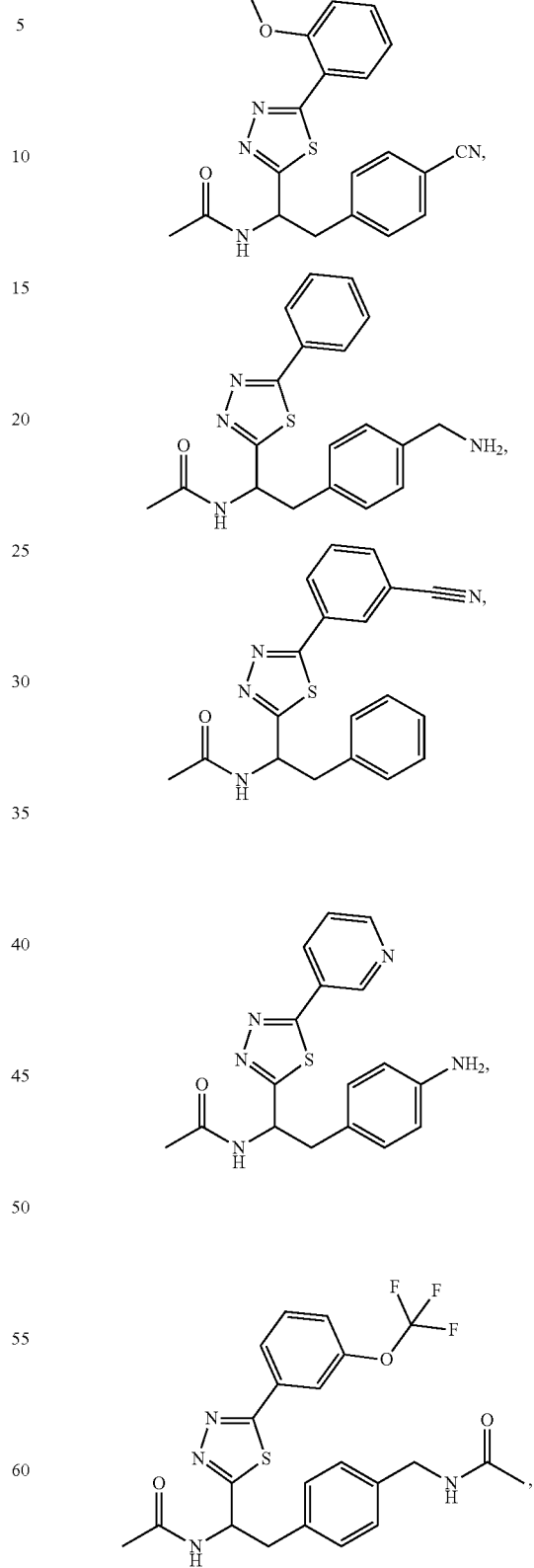

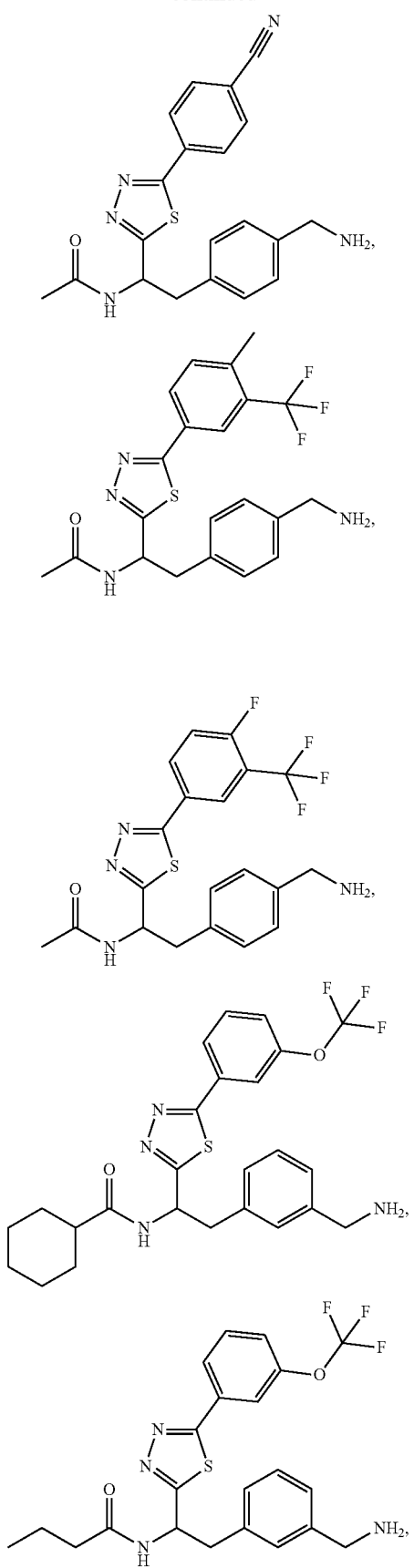
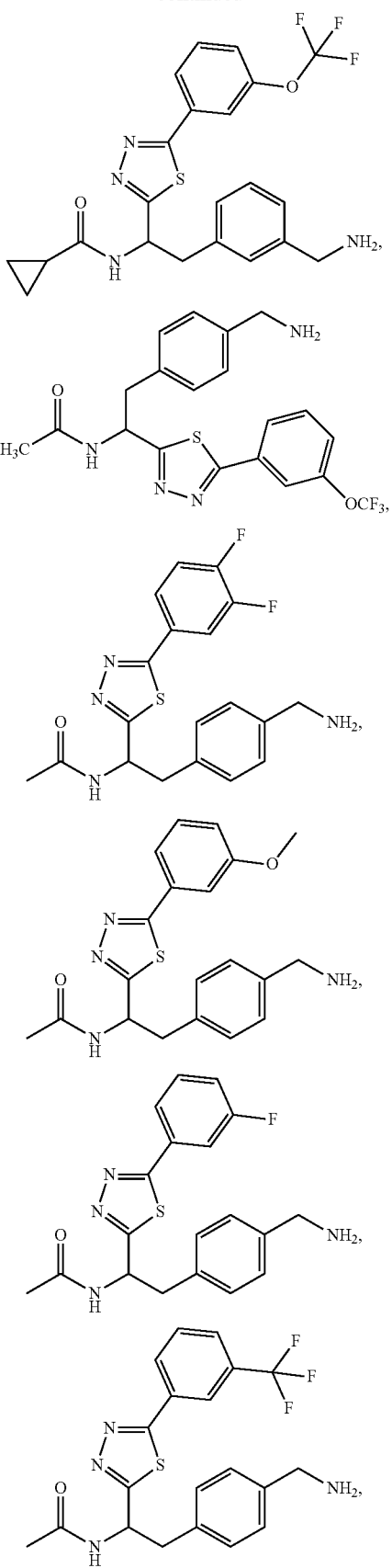

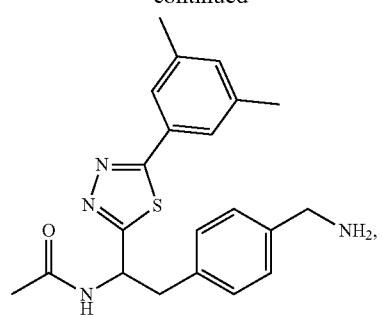
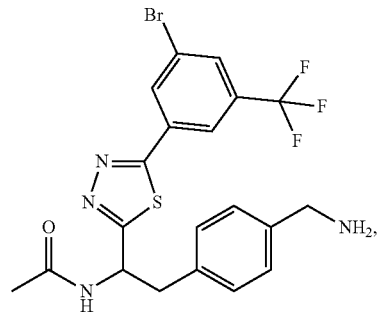
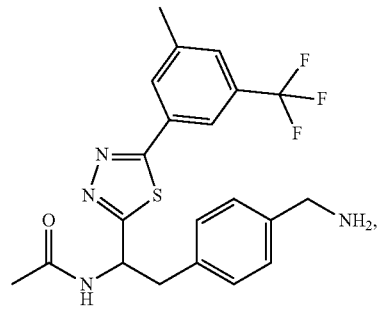
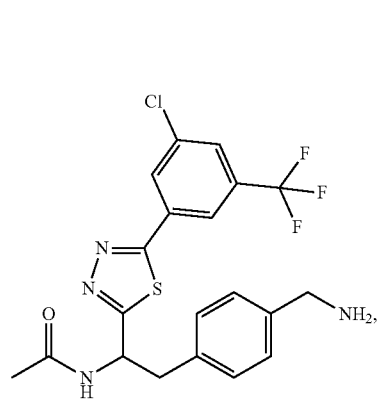
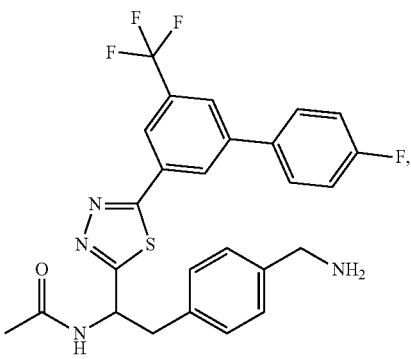
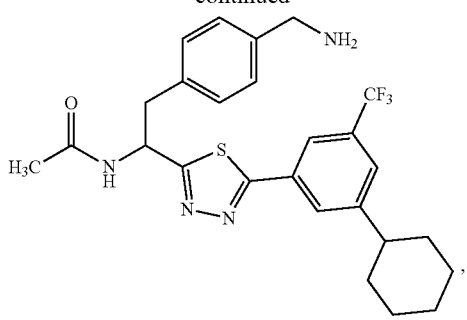
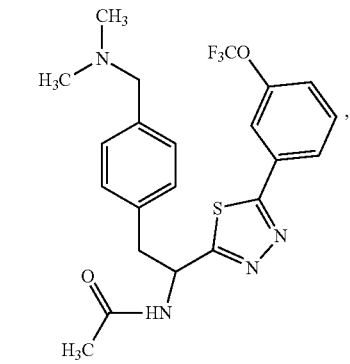
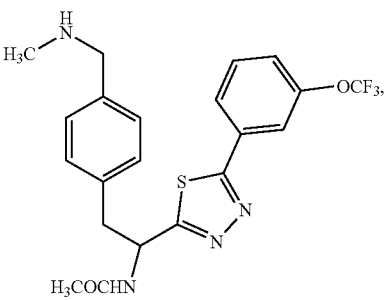
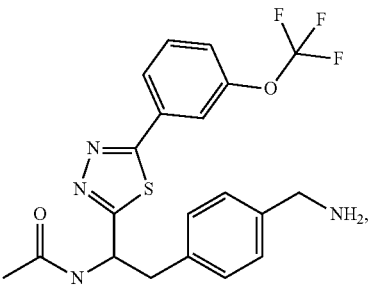
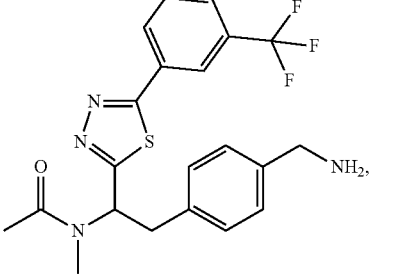

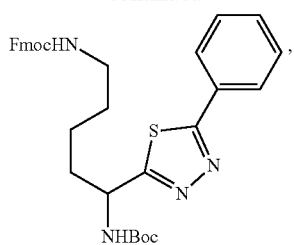
or a pharmaceutically acceptable salt thereof.
In one aspect, a compound can be present as one or more of the following structures:
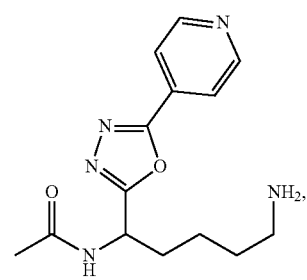
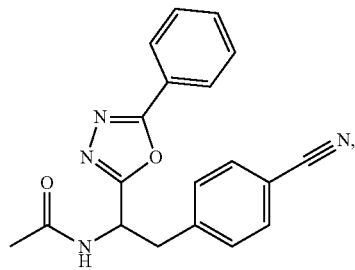
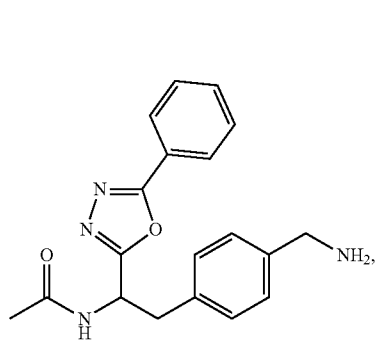
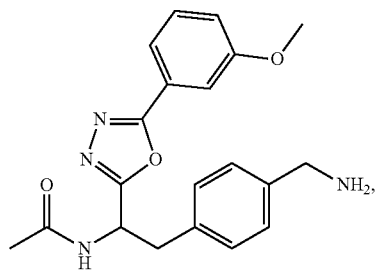
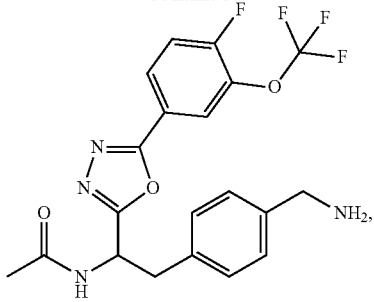
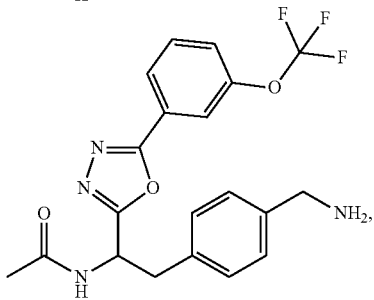
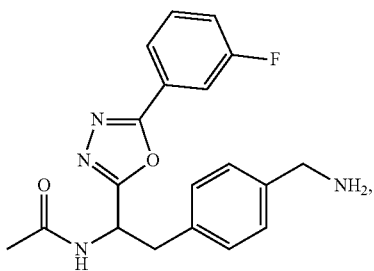
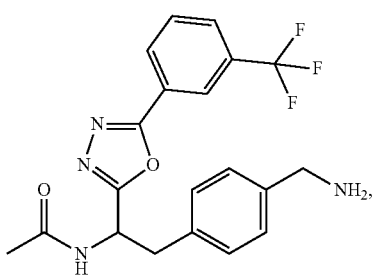
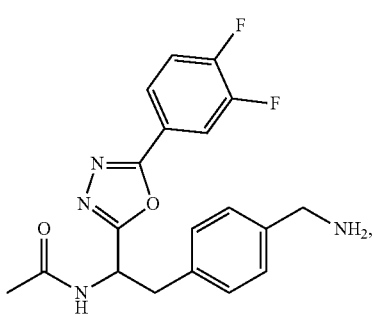

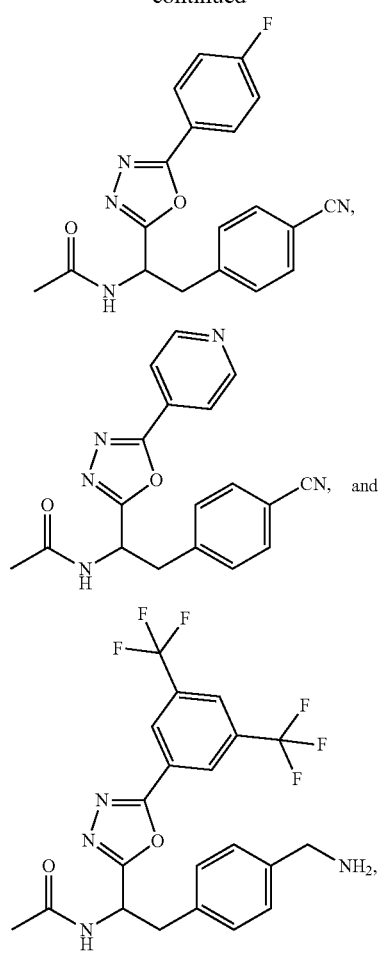

or a pharmaceutically acceptable salt thereof.

3. Prophetic Compound Examples

The following compound examples are prophetic, and can be prepared using the synthesis methods described herein above and other general methods as needed as would be known to one skilled in the art. It is anticipated that the prophetic compounds would be active as inhibitors of TGF-β, and such activity can be determined using the assay methods described herein.

In one aspect, a compound can be selected from:

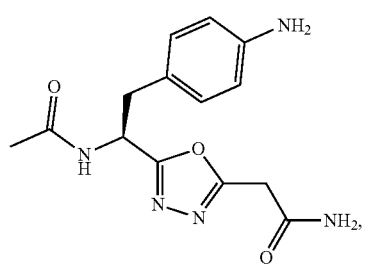

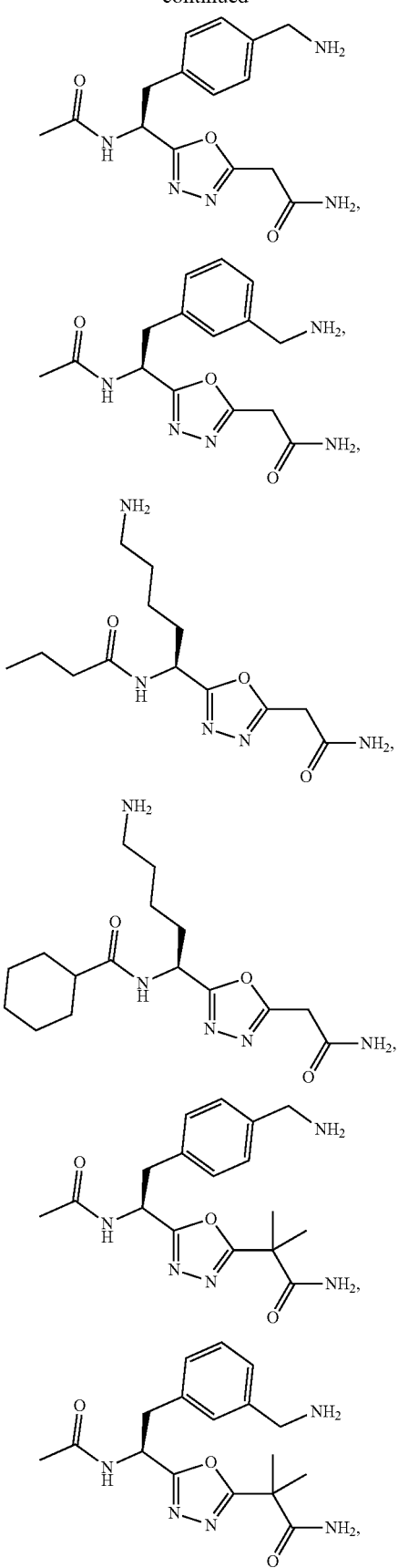

-continued
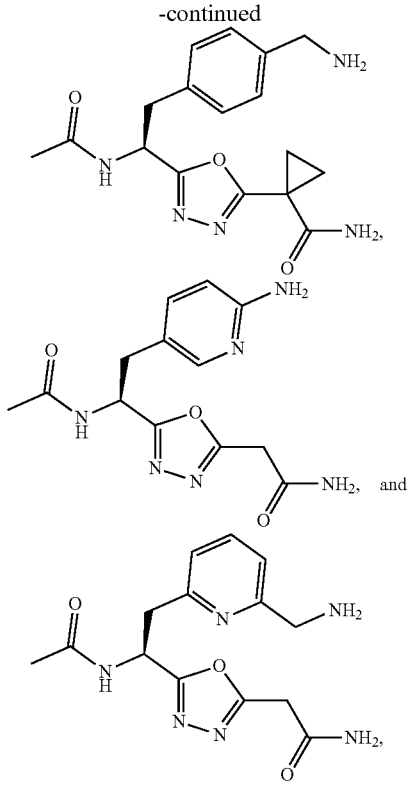
or a pharmaceutically acceptable salt thereof.
In one aspect, a compound can be selected from:
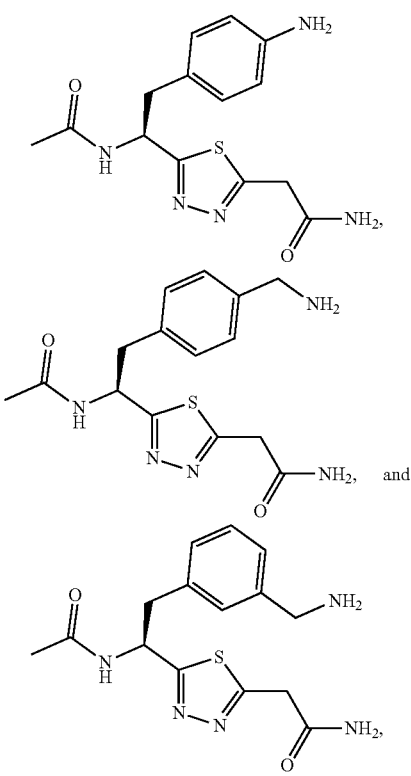
or a pharmaceutically acceptable salt thereof.
In one aspect, a compound can be selected from:
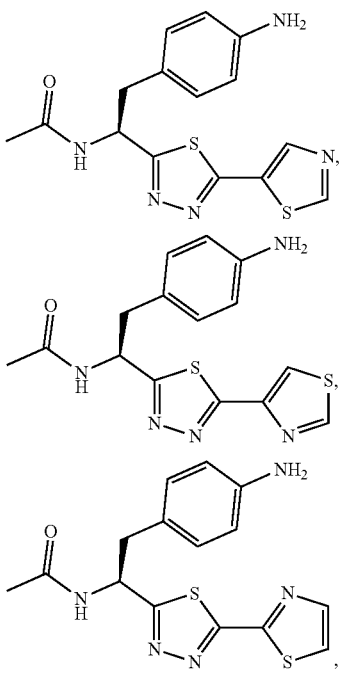
or a pharmaceutically acceptable salt thereof.

103
In one aspect, a compound can be selected from:
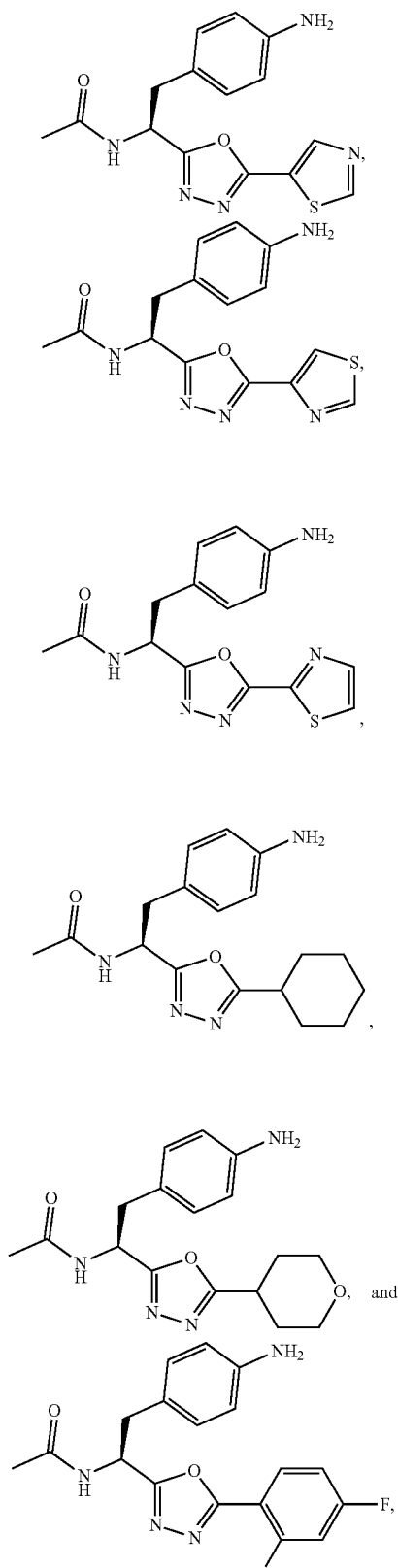
and
or a pharmaceutically acceptable salt thereof.
104
In one aspect, a compound can be selected from:
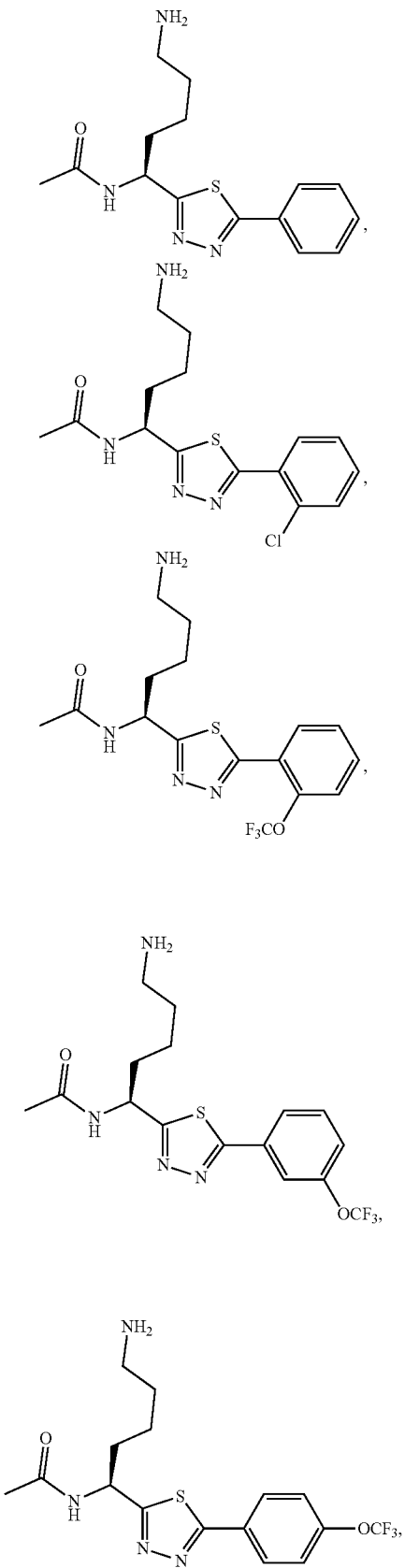

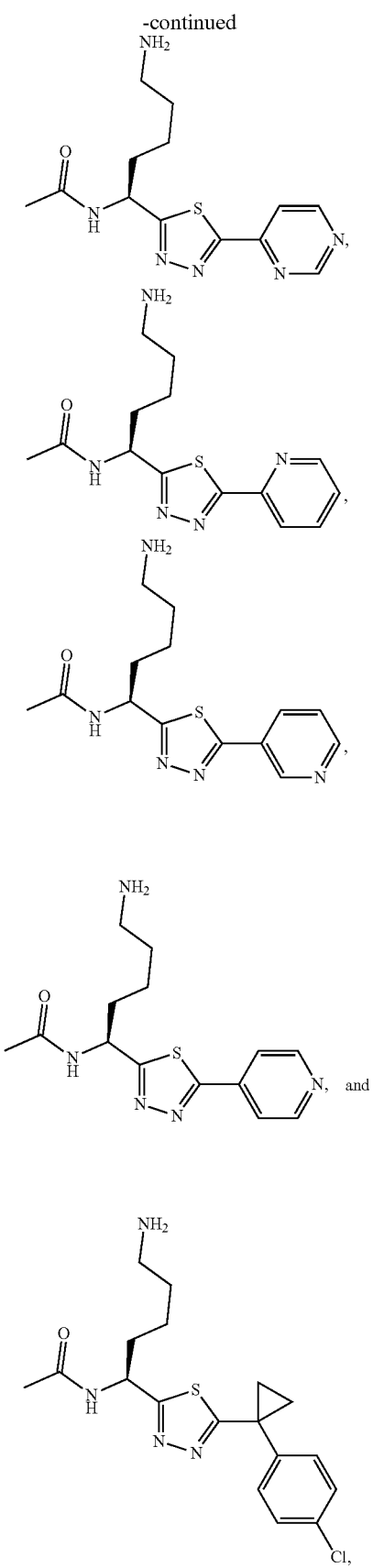
or a pharmaceutically acceptable salt thereof.
In one aspect, a compound can be selected from:
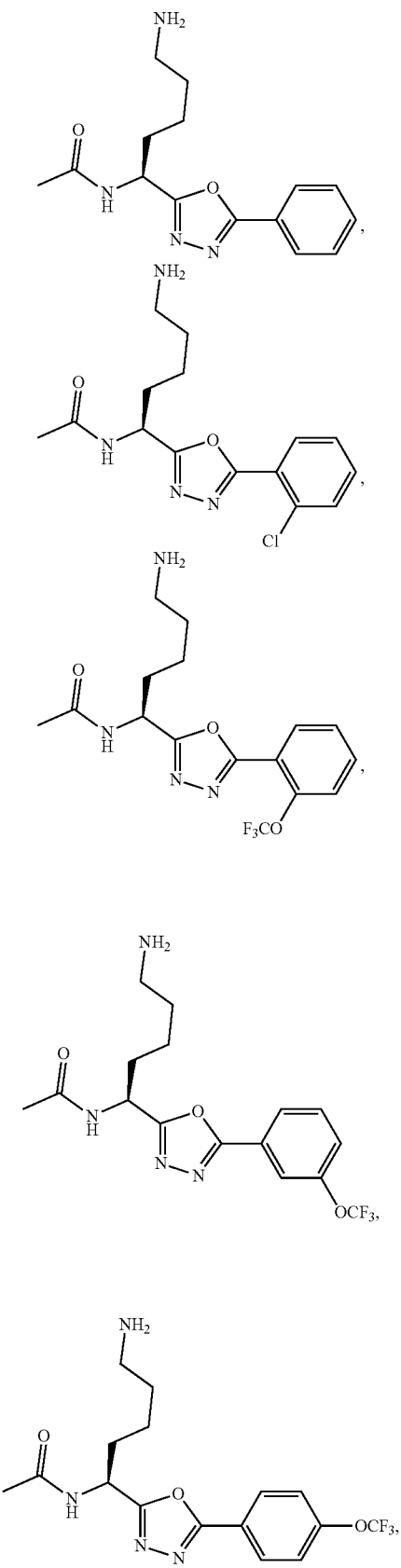

-continued
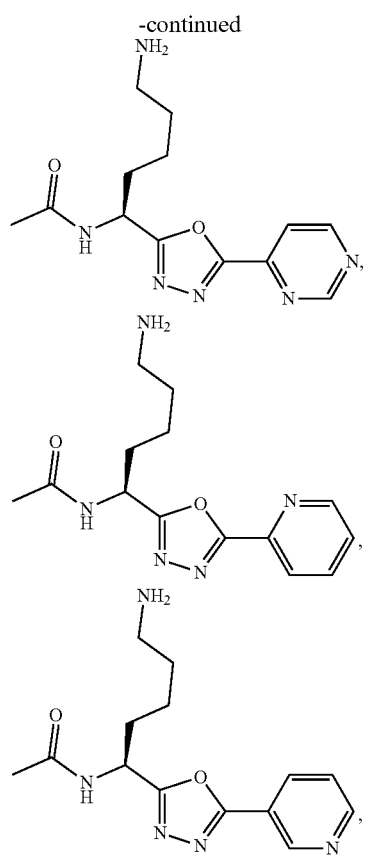
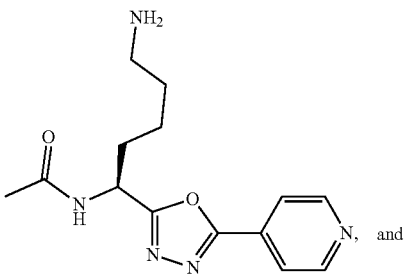
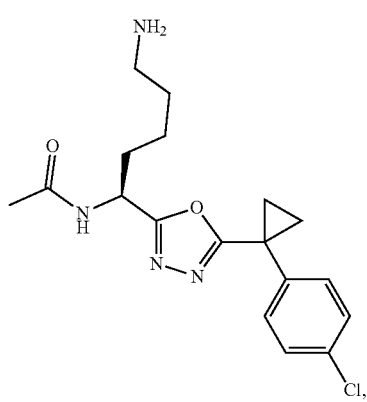
or a pharmaceutically acceptable salt thereof.
In one aspect, a compound can be selected from:
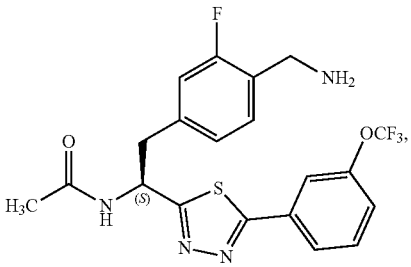
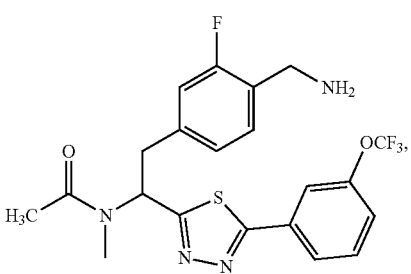
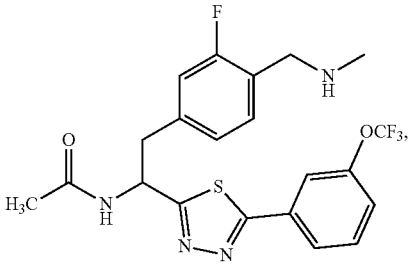
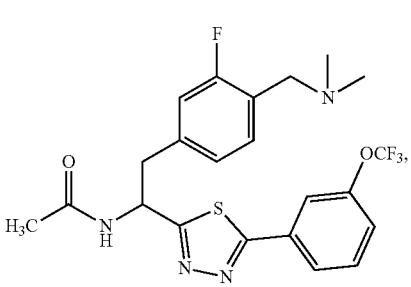
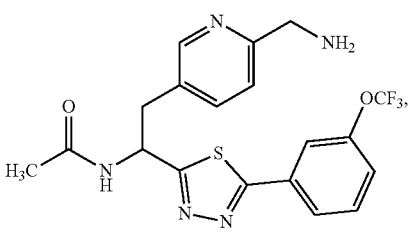
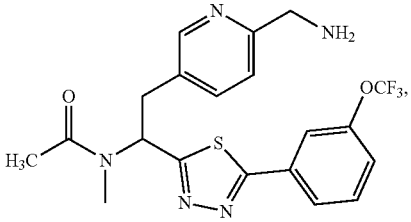

-continued

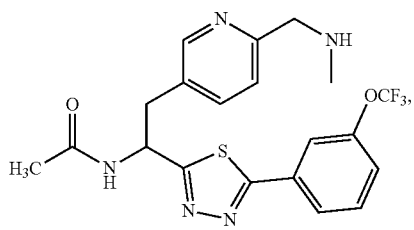
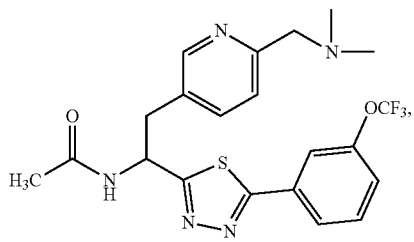
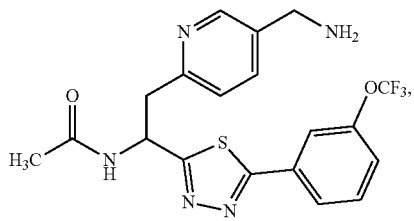
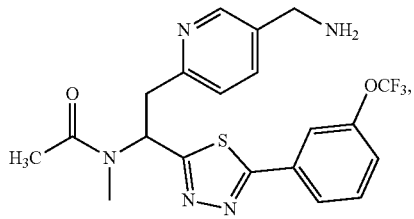
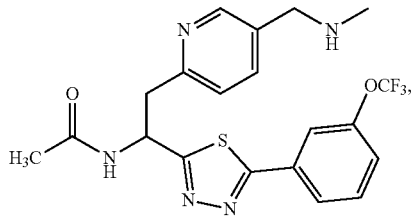
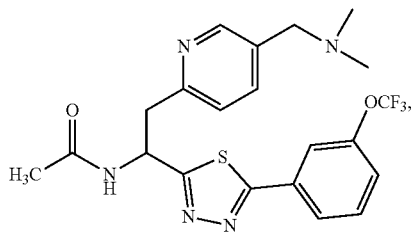
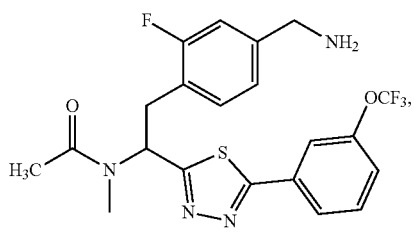

-continued

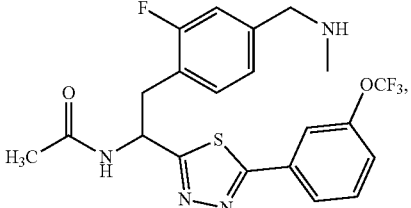
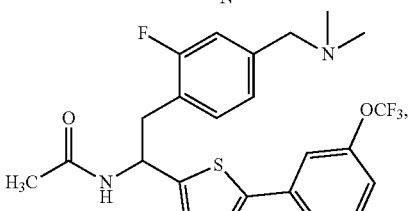
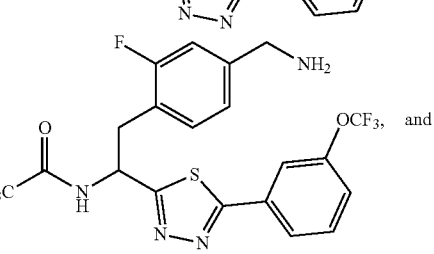
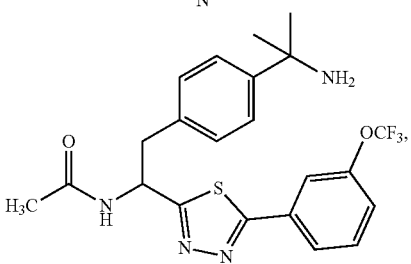

or a pharmaceutically acceptable salt thereof.

C. Pharmaceutical Compositions

In one aspect, the invention relates to pharmaceutical compositions comprising a therapeutically effective amount at least one disclosed compound and a pharmaceutically acceptable carrier. In a further aspect, a pharmaceutical composition can be provided comprising a therapeutically effective amount of at least one disclosed compound. In a still further aspect, a pharmaceutical composition can be provided comprising a prophylactically effective amount of at least one disclosed compound. In yet a further aspect, the invention relates to pharmaceutical compositions comprising a pharmaceutically acceptable carrier and a compound, wherein the compound is present in an effective amount.

Pharmaceutically acceptable salts of the compounds are conventional acid-addition salts or base-addition salts that retain the biological effectiveness and properties of the compounds and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Example base-addition salts include those derived from ammonium, potassium, sodium and, quaternary ammonium hydroxides, such as for example, tetramethylammonium hydroxide. Chemical modification of a pharmaceutical compound into a salt is a known technique to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456-1457.

The pharmaceutical compositions comprise the compounds in a pharmaceutically acceptable carrier. A pharmaceutically acceptable carrier refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. The compounds can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In a further aspect, the pharmaceutical composition is administered to a mammal. In a still further aspect, the mammal is a human. In an even further aspect, the human is a patient.

In a further aspect, the pharmaceutical composition is administered following identification of the mammal in need of treatment of cancer. In a still further aspect, the mammal has been diagnosed with a need for treatment of cancer prior to the administering step.

In a further aspect, the pharmaceutical composition is administered following identification of the mammal in need of treatment of a fibrotic disorder. In a still further aspect, the mammal has been diagnosed with a need for treatment of a fibrotic disorder prior to the administering step. In yet a further aspect, the fibrotic disorder is selected from PAH, NASH, ALS, and MD.

In a further aspect, the pharmaceutical composition is administered following identification of the mammal in need of immunotherapy. In a still further aspect, the mammal has been diagnosed with a need for immunotherapy prior to the administering step.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of TGF-β. The method also includes the administration of a therapeutically effect amount of the compound for the treatment of patient having a predisposition for being afflicted with a disorder associated with TGF-β activity. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the virus.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

In a further aspect, the composition further comprises at least one agent known to treat cancer. In a still further aspect, the cancer is selected from multiple myeloma and a hematologic malignancy.

In a further aspect, the composition further comprises at least one agent known to have a side effect of increasing the risk of cancer.

In a further aspect, the composition further comprises at least one agent known to treat a fibrotic disorder. In a still further aspect, the fibrotic disorder is found in the liver, the lung, the cardiac muscle, the kidney, the skin, the pulmonary artery, or the eye. In yet a further aspect, the fibrotic disorder is found in the liver. In an even further aspect, fibrotic disorder is glaucoma, amyotropic lateral sclerosis, pulmonary arterial hypertension (PAH), non-alcoholic steatohepatitis (NASH), epidermolysis bullosa, or muscular dystrophy.

In a further aspect, the composition further comprises at least one agent known to have a side effect of increasing the risk of a fibrotic disorder.

In a further aspect, the composition further comprises at least one agent known to treat an immune dysfunction.

In a further aspect, the composition further comprises at least one agent known to have a side effect of increasing the risk of an immune dysfunction.

It is understood that the disclosed compositions can be prepared from the disclosed compounds. It is also understood that the disclosed compositions can be employed in the disclosed methods of using.

D. Methods of Making the Compounds

In various aspects, the inventions relates to methods of making compounds useful to treat disorders associated with TGF-β activity such as, for example, cancers, in particular, multiple myeloma and hematologic malignancies, immune dysfunction, and fibrotic disorders, in particular, liver fibrosis, diabetic nephropathy, muscular dystrophy, amyotrophic lateral sclerosis, PAH, NASH, epidermolysis bullosa, and glaucoma. Thus, in one aspect, disclosed are methods of making a disclosed compound.

Compounds according to the present disclosure can, for example, be prepared by the several methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, oxadiazole analogs can be prepared as shown below.

SCHEME 1A.

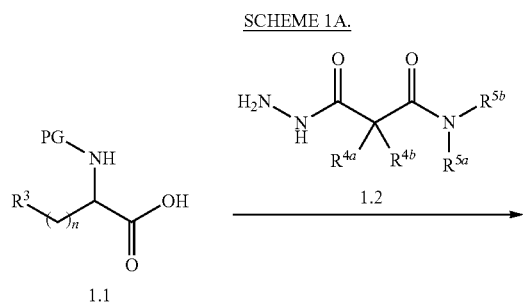

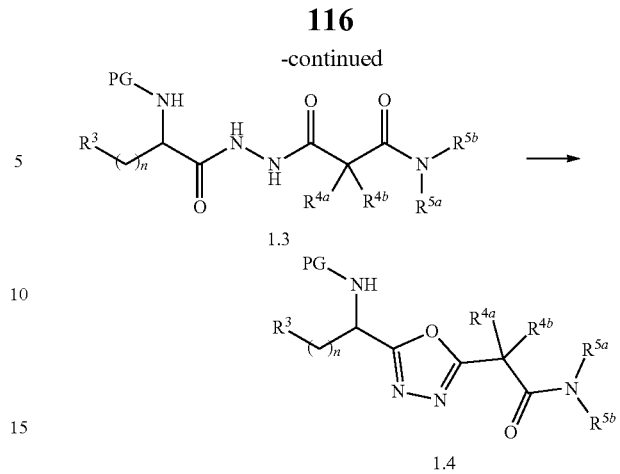

Compounds are represented in generic form, with substituents as noted in compound descriptions elsewhere herein and wherein PG is an amine protecting group. A more specific example is set forth below.

SCHEME 1B.

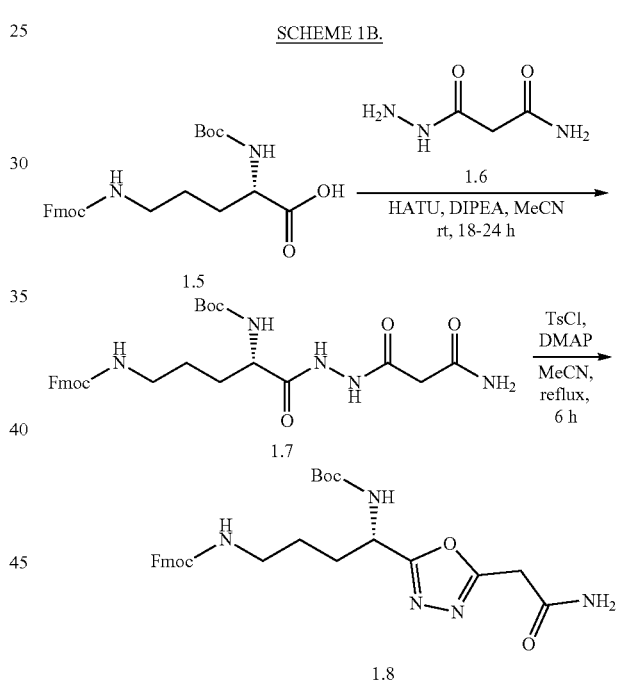

In one aspect, compounds of type 1.4, and similar compounds, can be prepared according to reaction Scheme 1B above. Thus, compounds of type 1.7 can be prepared by a coupling reaction of an appropriate carboxylic acid, e.g., 1.5 as shown above, and an appropriate hydrazide, e.g., 1.6 as shown above. Appropriate carboxylic acids and appropriate hydrazides are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., acetonitrile, for an appropriate period of time, e.g., 18-24 hours. Compounds of type 1.8 can be prepared by cyclization of an appropriate hydrazide, e.g., 1.7 as shown above. The cyclization is carried out in the presence of an appropriate sulfonyl halide, e.g., 4-toluenesulfonyl chloride, and an appropriate activating agent, e.g., 4-dimethylaminopyridine, in an appropriate solvent, e.g., acetonitrile, for an appropriate period of time, e.g., 6 hours. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted oxadiazole analogs similar to Formula 1.4.

2. Route II

In one aspect, thiadiazole analogs can be prepared as shown below.

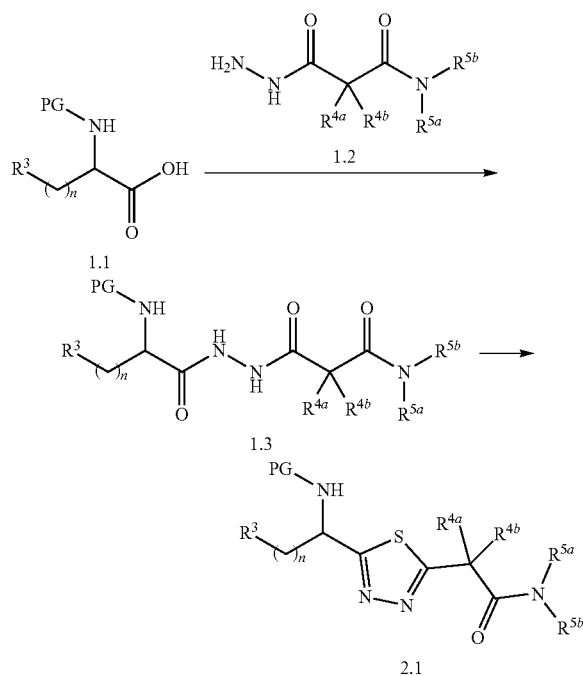

Compounds are represented in generic form, with substituents as noted in compound descriptions elsewhere herein and wherein PG is an amine protecting group. A more specific example is set forth below.

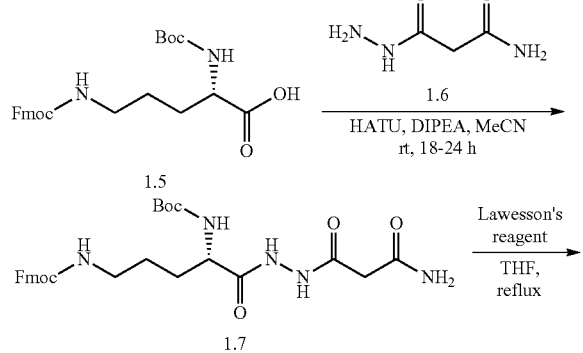

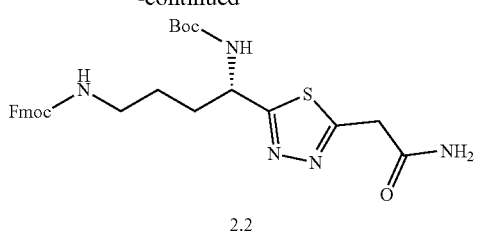

In one aspect, compounds of type 2.1, and similar compounds, can be prepared according to reaction Scheme 2B above. Thus, compounds of type 1.7 can be prepared by a coupling reaction of an appropriate carboxylic acid, e.g., 1.5 as shown above, and an appropriate hydrazide, e.g., 1.6 as shown above. Appropriate carboxylic acids and appropriate hydrazides are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine (DIPEA), in an appropriate solvent, e.g., acetonitrile, for an appropriate period of time, e.g., 18-24 hours. Compounds of type 2.2 can be prepared by thionation and subsequent cyclization of an appropriate hydrazide, e.g., 1.7 as shown above. The thionation/cyclization is carried out in the presence of an appropriate thionating agent, e.g., Lawesson's reagent, in an appropriate solvent, e.g., tetrahydrofuran (THF), at an appropriate temperature, e.g., refluxing conditions. As can be appreciated by one skilled in the art, the above reaction provides an example of a generalized approach wherein compounds similar in structure to the specific reactants above (compounds similar to compounds of type 1.1, 1.2, and 1.3), can be substituted in the reaction to provide substituted thiadiazole analogs similar to Formula 2.1.

3. Route III

In one aspect, oxadiazole and thiadiazole analogs can be prepared as shown below.

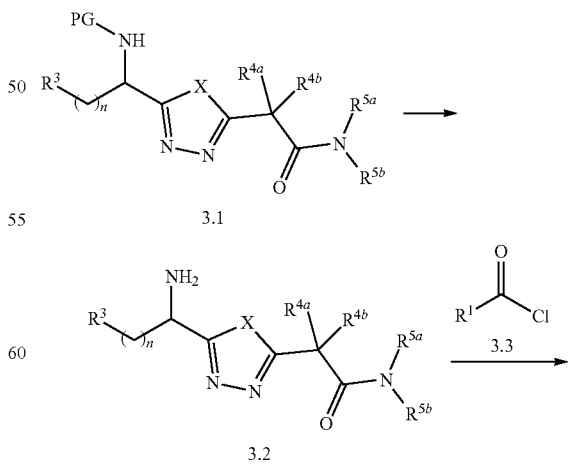

-continued

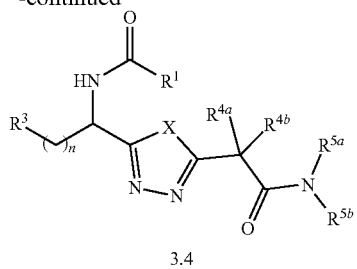

3.4

Compounds are represented in generic form, with substituents as noted in compound descriptions elsewhere herein and wherein PG is an amine protecting group. A more specific example is set forth below.

SCHEME 3B.

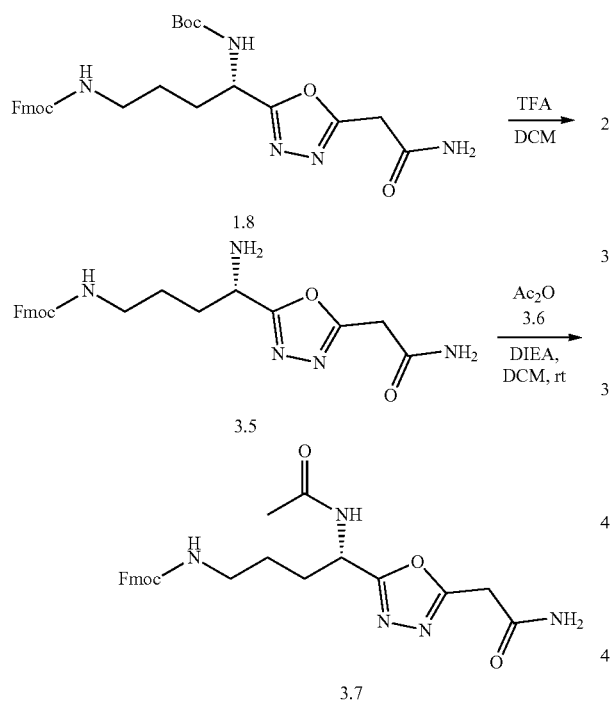

In one aspect, compounds of type 3.4, and similar compounds, can be prepared according to reaction Scheme 3B above. Thus, compounds of type 3.5 can be prepared by a deprotection of an appropriate amine, e.g., 1.8 as shown above. Appropriate amines are commercially available or prepared by methods known to one skilled in the art. The deprotection is carried out in the presence of an appropriate acid, e.g., trifluoroacetic acid, in an appropriate solvent, e.g., dichloromethane (DCM). Compounds of type 3.7 can be prepared by a coupling reaction of an appropriate amine, e.g., 3.5 as shown above, and an appropriate carboxylate, e.g., 3.6 as shown above. Appropriate carboxylates are commercially available or prepared by methods known to one skilled in the art. The coupling reaction is carried out in the presence of an appropriate base, e.g., diisopropylethylamine (DIEA), in an appropriate solvent, e.g., dichloromethane. As can be appreciated by one skilled in the art, the above reaction provides an example of a generalized approach wherein compounds similar in structure to the specific reactants above (compounds similar to compounds of type 3.1, 3.2, and 3.3), can be substituted in the reaction to provide substituted oxadiazole and thiadiazole analogs similar to Formula 3.4.

4. Route IV

In one aspect, oxadiazole and thiadiazole analogs can be prepared as shown below.

SCHEME 4A.

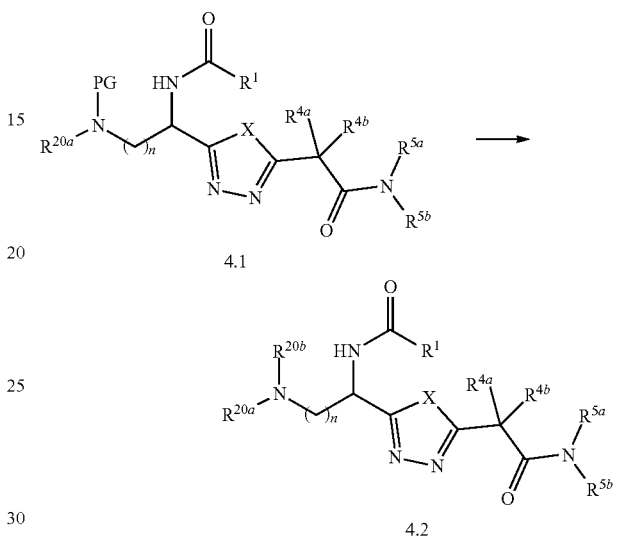

Compounds are represented in generic form, with substituents as noted in compound descriptions elsewhere herein and wherein PG is an amine protecting group. A more specific example is set forth below.

SCHEME 4B.

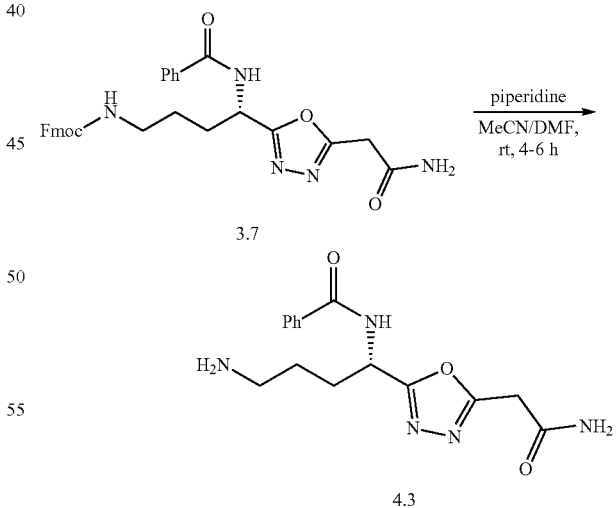

In one aspect, compounds of type 4.2, and similar compounds, can be prepared according to reaction Scheme 4B above. Thus, compounds of type 4.3 can be prepared by deprotection of an appropriate amine, e.g., 3.7 as shown above. The deprotection is carried out in the presence of an appropriate base, e.g., piperidine, in an appropriate solvent, e.g., acetonitrile, for an appropriate period of time, e.g., 4-6 hours. As can be appreciated by one skilled in the art, the above reaction provides an example of a generalized approach wherein compounds similar in structure to the specific reactants above (compounds similar to compounds of type 4.1), can be substituted in the reaction to provide substituted oxadiazole and thiadiazole analogs similar to Formula 4.2.

5. Route V

In one aspect, oxadiazole analogs can be prepared as shown below.

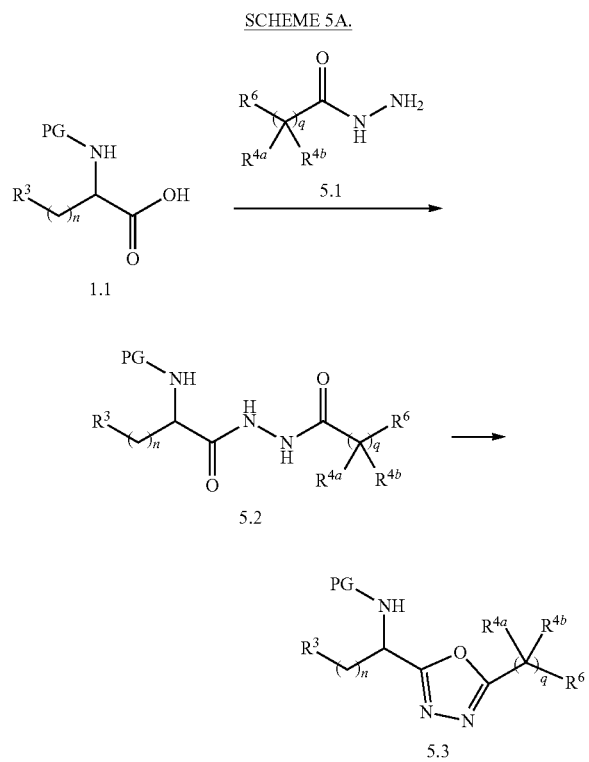

Compounds are represented in generic form, with substituents as noted in compound descriptions elsewhere herein and wherein PG is an amine protecting group. A more specific example is set forth below.

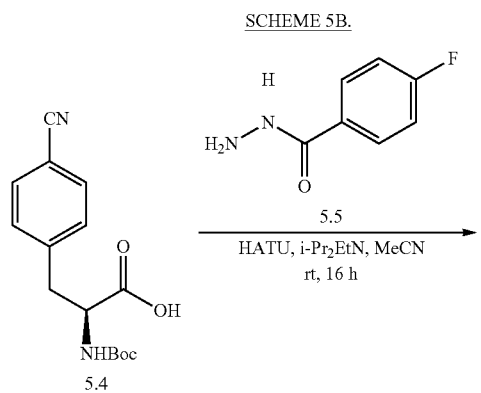

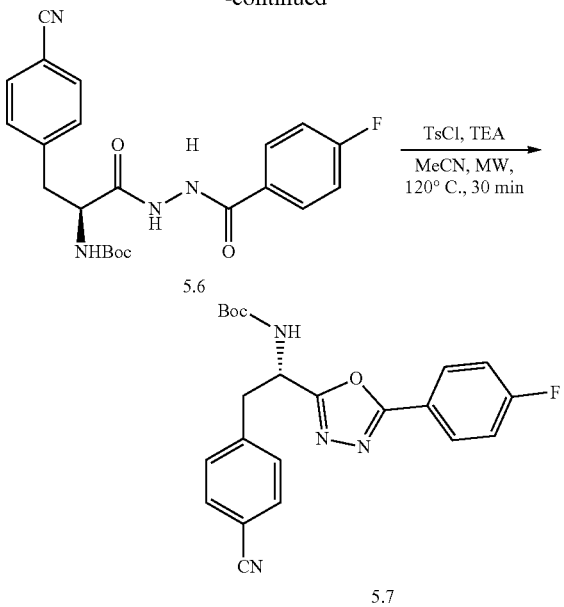

In one aspect, compounds of type 5.3, and similar compounds, can be prepared according to reaction Scheme 5B above. Thus, compounds of type 5.7 can be prepared by a coupling reaction of an appropriate carboxylic acid, e.g., 5.4 as shown above, and an appropriate hydrazide, e.g., 5.5 as shown above. Appropriate carboxylic acids and appropriate hydrazides are commercially available or prepared by methods known to one skilled in the art. The coupling reaction is carried out in the presence of an appropriate coupling agent, e.g., 1-[bis(dimethylamino)methylene]-1H-1,2,3-triazolo[4,5-b]pyridinium 3-oxid hexafluorophosphate (HATU), and an appropriate base, e.g., diisopropylethylamine, in an appropriate solvent, e.g., acetonitrile, for an appropriate period of time, e.g., 16 hours. Compounds of type 5.7 can be prepared by cyclization of an appropriate hydrazide, e.g., 5.6 as shown above. The cyclization is carried out in the presence of an appropriate sulfonyl halide, e.g., 4-toluenesulfonyl chloride, and an appropriate base, e.g., triethylamine, in an appropriate solvent, e.g., acetonitrile, for an appropriate period of time, e.g., 30 minutes, at an appropriate temperature, e.g., 120° C. As can be appreciated by one skilled in the art, the above reaction provides an example of a generalized approach wherein compounds similar in structure to the specific reactants above (compounds similar to compounds of type 1.1, 5.1, and 5.2), can be substituted in the reaction to provide substituted oxadiazole analogs similar to Formula 5.3.

6. Route VI

In one aspect, thiadiazole analogs can be prepared as shown below.

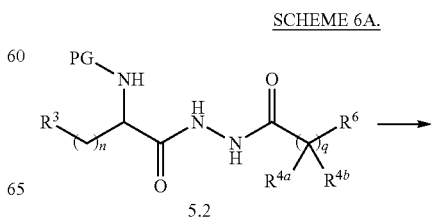

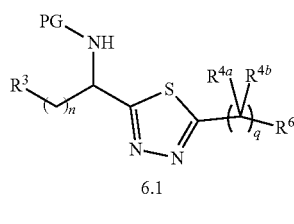

6.1

Compounds are represented in generic form, with substituents as noted in compound descriptions elsewhere herein and wherein PG is an amine protecting group. A more specific example is set forth below.

SCHEME 6B.

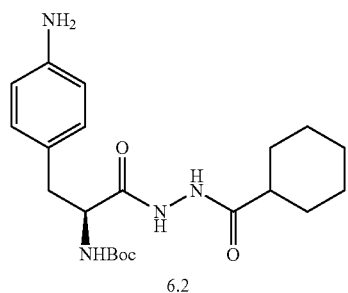

6.2

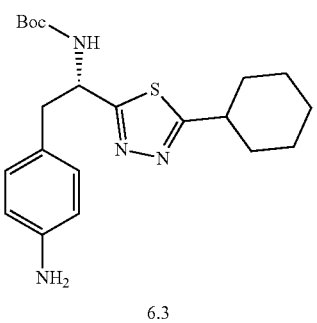

6.3

In one aspect, compounds of type 6.1, and similar compounds, can be prepared according to reaction Scheme 6B above. Thus, compounds of type 6.3 can be prepared by thionation and subsequent cyclization of an appropriate hydrazide, e.g., 6.2 as shown above. The thionation/cyclization is carried out in the presence of an appropriate thionating agent, e.g., Lawesson's reagent, in an appropriate solvent, e.g., tetrahydrofuran (THF), at an appropriate temperature, e.g., refluxing conditions, for an appropriate period of time, e.g., 3 hours. As can be appreciated by one skilled in the art, the above reaction provides an example of a generalized approach wherein compounds similar in structure to the specific reactants above (compounds similar to compounds of type 5.2), can be substituted in the reaction to provide substituted thiadiazole analogs similar to Formula 6.3.

7. Route VII

In one aspect, oxadiazole and thiadiazole analogs can be prepared as shown below.

SCHEME 7A.

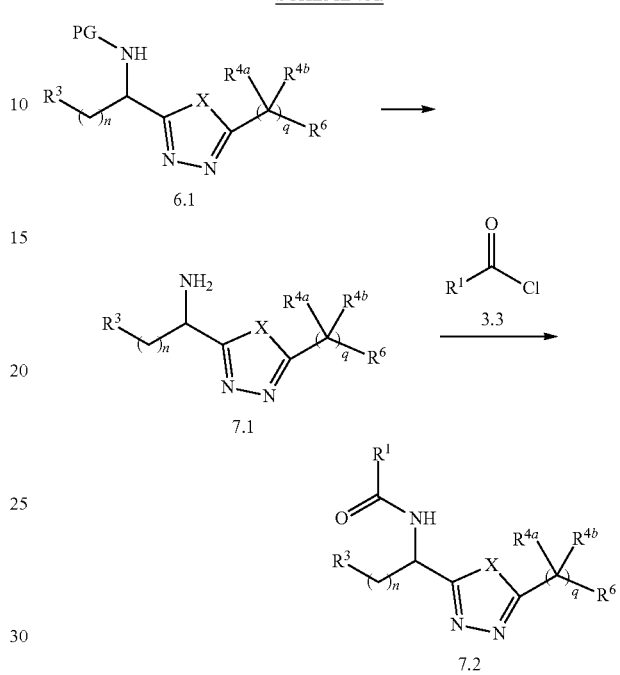

Compounds are represented in generic form, with substituents as noted in compound descriptions elsewhere herein and wherein PG is an amine protecting group. A more specific example is set forth below.

SCHEME 7B.

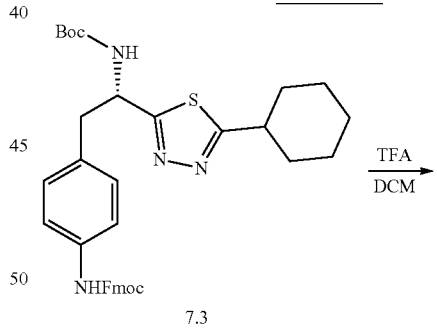

7.3

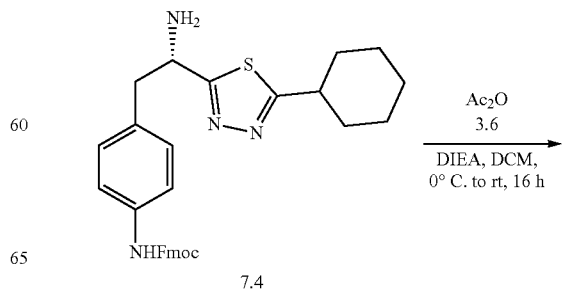

7.4

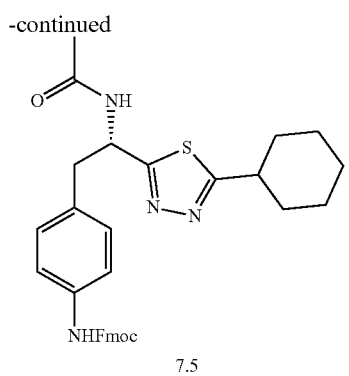

7.5

In one aspect, compounds of type 7.2, and similar compounds, can be prepared according to reaction Scheme 7B above. Thus, compounds of type 7.4 can be prepared by a deprotection of an appropriate amine, e.g., 7.3 as shown above. Appropriate amines are commercially available or prepared by methods known to one skilled in the art. The deprotection is carried out in the presence of an appropriate acid, e.g., trifluoroacetic acid, in an appropriate solvent, e.g., dichloromethane (DCM). Compounds of type 7.5 can be prepared by a coupling reaction of an appropriate amine, e.g., 7.4 as shown above, and an appropriate carboxylate, e.g., 3.6 as shown above. Appropriate carboxylates are commercially available or prepared by methods known to one skilled in the art. The coupling reaction is carried out in the presence of an appropriate base, e.g., diisopropylethylamine (DIEA), in an appropriate solvent, e.g., dichloromethane, for an appropriate period of time 16 h. As can be appreciated by one skilled in the art, the above reaction provides an example of a generalized approach wherein compounds similar in structure to the specific reactants above (compounds similar to compounds of type 3.3, 6.1, and 7.1), can be substituted in the reaction to provide substituted oxadiazole and thiadiazole analogs similar to Formula 7.2.

8. Route VIII

In one aspect, oxadiazole and thiadiazole analogs can be prepared as shown below.

SCHEME 8A.

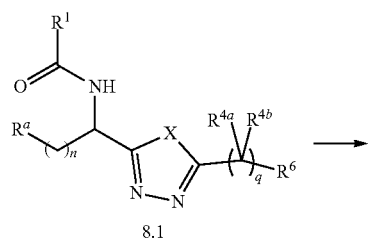

8.1

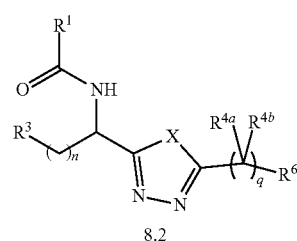

8.2

Compounds are represented in generic form, with substituents as noted in compound descriptions elsewhere herein and wherein $R^a$ is $R^3$ with a protected amine group. A more specific example is set forth below.

SCHEME 8B.

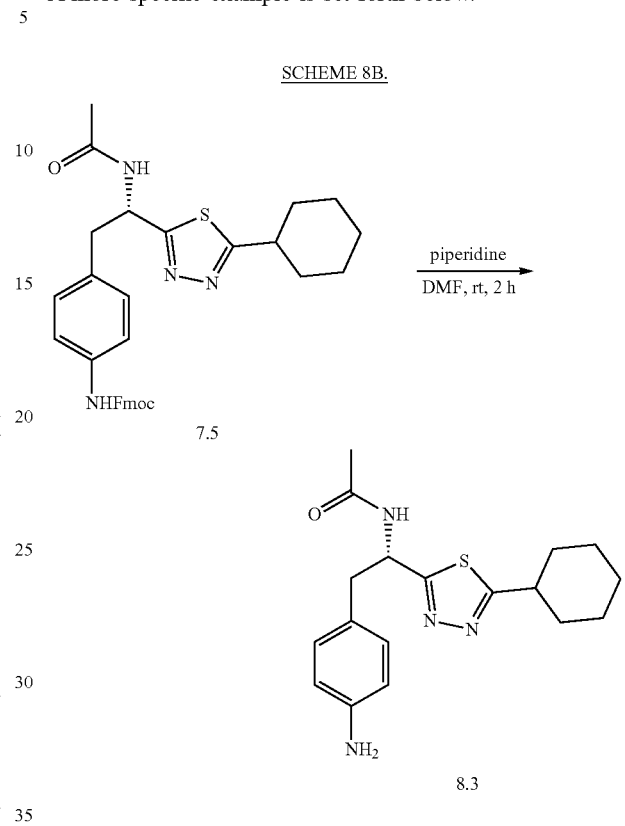

In one aspect, compounds of type 8.2, and similar compounds, can be prepared according to reaction Scheme 8B above. Thus, compounds of type 8.3 can be prepared by deprotection of an appropriate amine, e.g., 7.5 as shown above. The deprotection is carried out in the presence of an appropriate base, e.g., piperidine, in an appropriate solvent, e.g., dimethylformamide, for an appropriate period of time, e.g., 2 hours. As can be appreciated by one skilled in the art, the above reaction provides an example of a generalized approach wherein compounds similar in structure to the specific reactants above (compounds similar to compounds of type 8.1), can be substituted in the reaction to provide substituted oxadiazole and thiadiazole analogs similar to Formula 8.2.

9. Route IX

In one aspect, oxadiazole and thiadiazole analogs can be prepared as shown below.

SCHEME 9A.

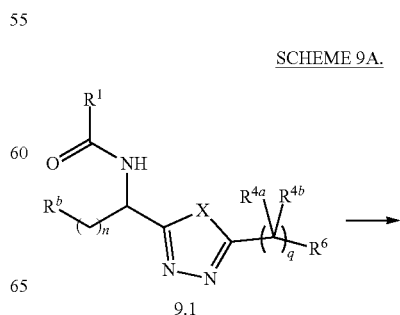

9.1

127

-continued

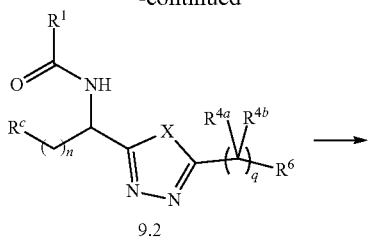
9.2

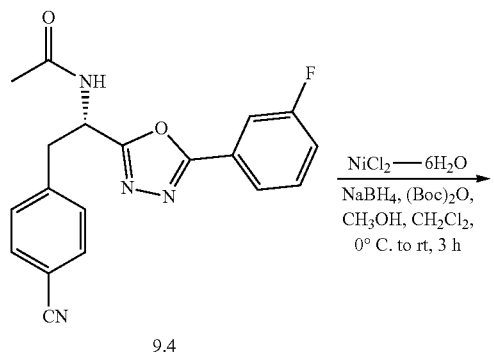
9.3

Compounds are represented in generic form, with substituents as noted in compound descriptions elsewhere herein and wherein $R^b$ is $R^3$ with a cyano substituent and $R^c$ is $R^3$ with a protected amine group. A more specific example is set forth below.

SCHEME 9B.

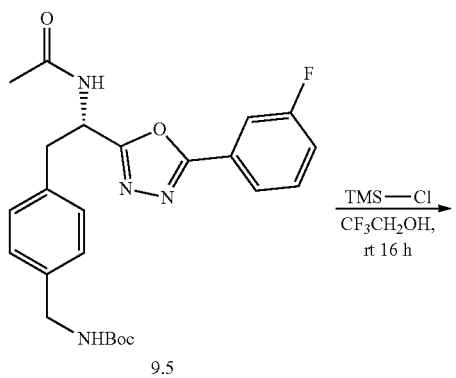
9.4

|
9.5

128

-continued

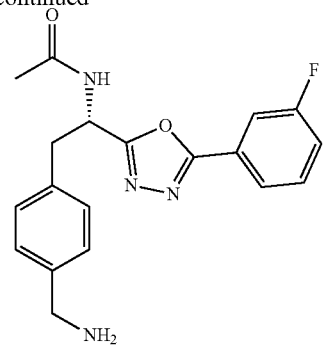
9.6

In one aspect, compounds of type 9.3, and similar compounds, can be prepared according to reaction Scheme 9B above. Thus, compounds of type 9.5 can be prepared by reduction of an appropriate cyanide, e.g., 9.4 as shown above. The reduction is carried out in the presence of an appropriate catalyst, e.g., nickel (II) chloride hexahydrate, an appropriate reducing agent, e.g., sodium borohydride, and an appropriate amine protecting agent, e.g., di-tert-butyl-dicarbonate, in an appropriate solvent, e.g., methanol and dichloromethane, for an appropriate period of time, e.g., 3 hours. Compounds of type 9.6 can be prepared by deprotection of an appropriate protected amine, e.g., 9.5 as shown above. The deprotection is carried out in the presence of an appropriate deprotecting agent, e.g., trimethylsilyl chloride, in an appropriate solvent, e.g., 2,2,2-trifluoroethanol, for an appropriate period of time, e.g., 16 hours. As can be appreciated by one skilled in the art, the above reaction provides an example of a generalized approach wherein compounds similar in structure to the specific reactants above (compounds similar to compounds of type 9.1 and 9.2), can be substituted in the reaction to provide substituted oxadiazole and thiadiazole analogs similar to Formula 9.6.

10. Route X

In one aspect, oxadiazole and thiadiazole analogs can be prepared as shown below.

SCHEME 10A.

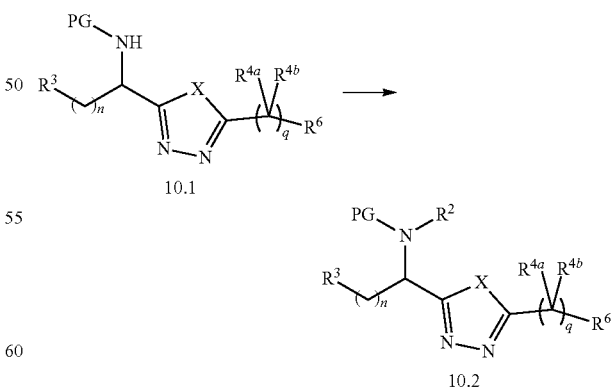
10.1

10.2

Compounds are represented in generic form, with substituents as noted in compound descriptions elsewhere herein and wherein PG is an amine protecting group. A more specific example is set forth below.

SCHEME 10B.

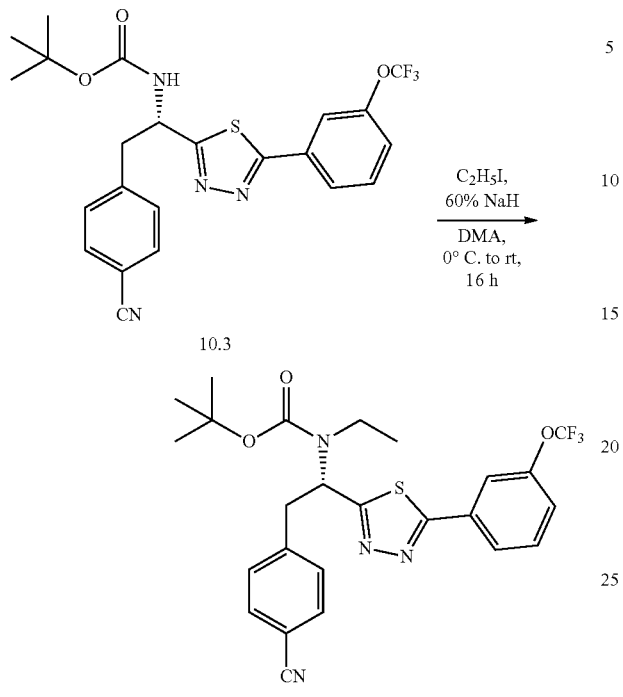

10.3

10.4

In one aspect, compounds of type 10.2, and similar compounds, can be prepared according to reaction Scheme 10B above. Thus, compounds of type 10.4 can be prepared by alkylation of an appropriate amine, e.g., 10.3 as shown above. The alkylation is carried out in the presence of an appropriate alkyl halide, e.g., ethyl iodide, and an appropriate base, e.g., 60% sodium hydride, in an appropriate solvent, e.g., N,N'-dimethylacetamide, for an appropriate period of time, e.g., 16 hours. Deprotection of the amine can subsequently be achieved by methods known in the art. As can be appreciated by one skilled in the art, the above reaction provides an example of a generalized approach wherein compounds similar in structure to the specific reactants above (compounds similar to compounds of type 10.1), can be substituted in the reaction to provide substituted oxadiazole and thiadiazole analogs similar to Formula 10.2.

11. Route XI

In one aspect, oxadiazole and thiadiazole analogs can be prepared as shown below.

SCHEME 11A.

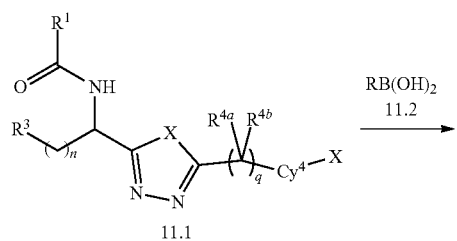

11.1

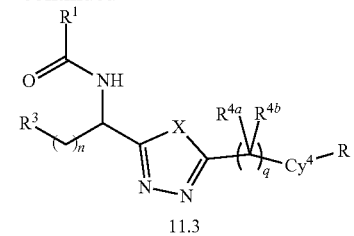

11.3

Compounds are represented in generic form, with substituents as noted in compound descriptions elsewhere herein and wherein X is a halogen and R is aryl or a vinylic substituent, as defined elsewhere herein. A more specific example is set forth below.

SCHEME 11B.

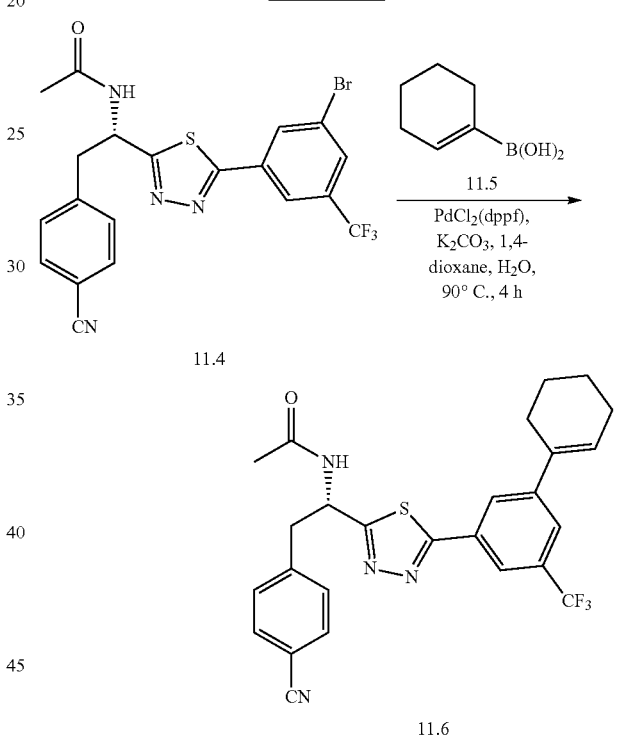

11.4

11.6

In one aspect, compounds of type 11.3, and similar compounds, can be prepared according to reaction Scheme 11B above. Thus, compounds of type 11.6 can be prepared by a coupling reaction between an appropriate aryl halide, e.g., 11.4 as shown above, and an appropriate borane, e.g., 11.5 as shown above. The coupling reaction is carried out in the presence of an appropriate catalyst, e.g., [1,1'-bis(diphenylphosphino)ferrocene]dichloropalladium(II), and an appropriate base, e.g., potassium carbonate, in an appropriate solvent system, e.g., 1,4-dioxane and water, at an appropriate temperature, e.g., 90° C., for an appropriate period of time, e.g., 4 hours. As can be appreciated by one skilled in the art, the above reaction provides an example of a generalized approach wherein compounds similar in structure to the specific reactants above (compounds similar to compounds of type 11.1 and 11.2), can be substituted in the reaction to provide substituted oxadiazole and thiadiazole analogs similar to Formula 11.3.

12. Route XII

In one aspect, oxadiazole and thiadiazole analogs can be prepared as shown below.

SCHEME 12A.

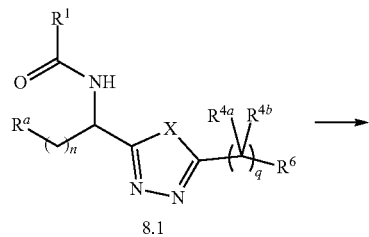

8.1

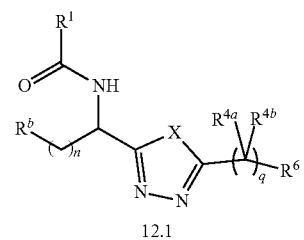

12.1

Compounds are represented in generic form, with substituents as noted in compound descriptions elsewhere herein and wherein $R^a$ is $R^3$ with a primary amine group and $R^b$ is $R^3$ with a tertiary amine group. A more specific example is set forth below.

SCHEME 12B.

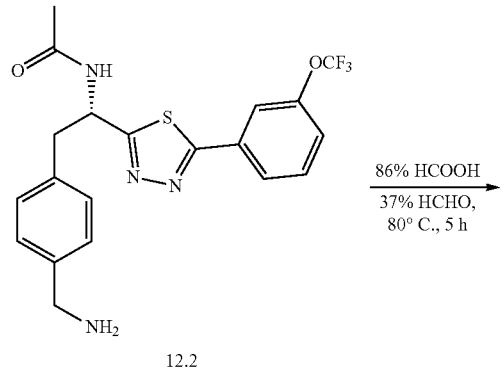

12.2

86% HCOOH
37% HCHO,
80° C., 5 h

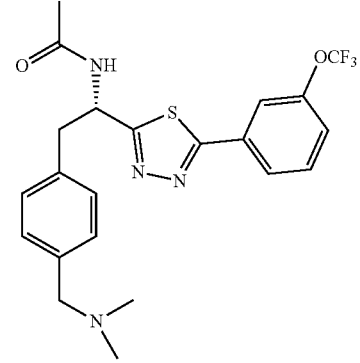

12.3

In one aspect, compounds of type 12.1, and similar compounds, can be prepared according to reaction Scheme 12B above. Thus, compounds of type 12.3 can be prepared by alkylation of an appropriate amine, e.g., 12.2 as shown above. The alkylation is carried out in the presence of an appropriate acid, e.g., 86% formic acid, and an appropriate aldehyde, e.g., 37% formaldehyde, at an appropriate temperature, e.g., 80° C., for an appropriate period of time, e.g., 5 hours. As can be appreciated by one skilled in the art, the above reaction provides an example of a generalized approach wherein compounds similar in structure to the specific reactants above (compounds similar to compounds of type 8.1), can be substituted in the reaction to provide substituted oxadiazole and thiadiazole analogs similar to Formula 12.1.

13. Route XIII

In one aspect, oxadiazole and thiadiazole analogs can be prepared as shown below.

SCHEME 13A.

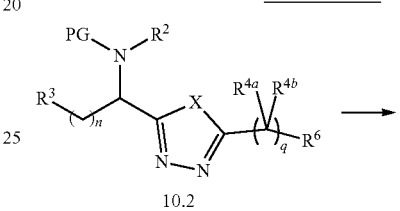

10.2

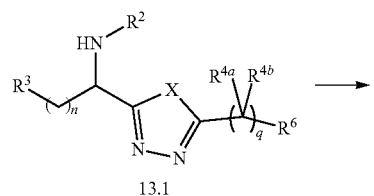

13.1

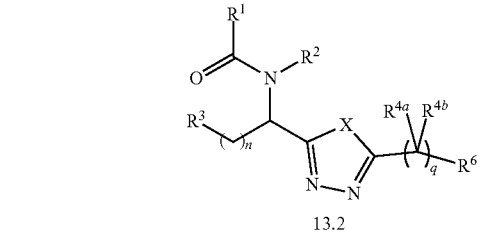

13.2

Compounds are represented in generic form, with substituents as noted in compound descriptions elsewhere herein and wherein PG is an amine protecting group. A more specific example is set forth below.

SCHEME 13B.

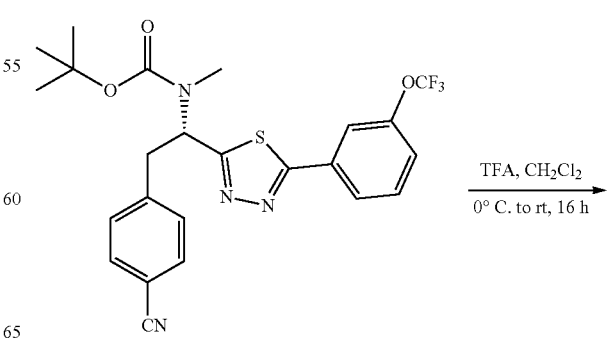

TFA, CH₂Cl₂
0° C. to rt, 16 h 10.5

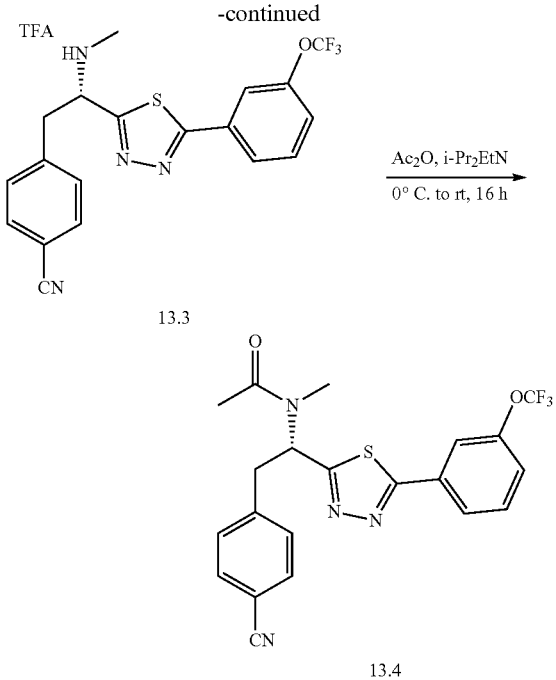

In one aspect, compounds of type 13.2, and similar compounds, can be prepared according to reaction Scheme 13B above. Thus, compounds of type 13.3 can be prepared by deprotection of an appropriate protected amine, e.g., 10.5 as shown above. The deprotection is carried out in the presence of an appropriate deprotecting agent, e.g., trifluoroacetic acid, in an appropriate solvent, e.g., dichloromethane, for an appropriate period of time, e.g., 16 hours. Compounds of type 13.4 can be prepared by acylation of an appropriate amine, e.g., 13.3 as shown above. The acylation is carried out in the presence of an appropriate acylating agent, e.g., acetic anhydride, and an appropriate base, e.g., diisopropylethylamine, for an appropriate period of time, e.g., 16 hours. As can be appreciated by one skilled in the art, the above reaction provides an example of a generalized approach wherein compounds similar in structure to the specific reactants above (compounds similar to compounds of type 10.2 and 13.1), can be substituted in the reaction to provide substituted oxadiazole and thiadiazole analogs similar to Formula 13.2.

E. Methods of Using the Compounds

The compounds and pharmaceutical compositions of the invention are useful in treating or controlling disorders associated with TGF-β activity, in particular, cancers such as, for example, multiple myeloma and hematologic malignancies, immunotherapy, and fibrotic disorders such as, for example, liver fibrosis, amyoptrophic lateral sclerosis, diabetic nephropathy, muscular dystrophy, PAH, NASH, epidermolysis bullosa, and glaucoma.

Examples of cancers for which the compounds and compositions can be useful in treating, include, but are not limited to carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

Examples of fibrotic disorders for which the compounds and compositions can be useful in treating, include, but are not limited to, pulmonary fibrosis, glomerulonephritis, liver cirrhosis, diabetic nephropathy, proliferative vitreoretinopathy, systemic sclerosis, scleroderma, muscular dystrophy, amyotrophic lateral sclerosis, PAH, NASH, epidermolysis bullosa, and glaucoma.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a cancer or of a fibrotic disorder.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a cancer, immune dysfunction, or a fibrotic disorder.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The compounds disclosed herein are useful for treating or controlling disorders associated with TGF-β activity, in particular, cancers, immune dysfunction, and fibrotic disorders. Thus, provided is a method comprising administering a therapeutically effective amount of a composition comprising a disclosed compound to a subject. In a further aspect, the method can be a method for treating cancer. In a still further aspect, the method can be a method for treating a fibrotic disorder. In a still further aspect, the method can be a method for treating immune dysfunction.

a. Treating Cancer

In one aspect, disclosed are methods of treating cancer associated with TGF-β activity in a mammal, the method comprising the step of administering to the mammal an effective amount of at least one disclosed compound, or a pharmaceutically acceptable salt thereof.

In one aspect, disclosed are methods for treating cancer in a subject, the method comprising the step of administering to the subject an effective amount of at least one compound having a structure represented by a formula selected from:

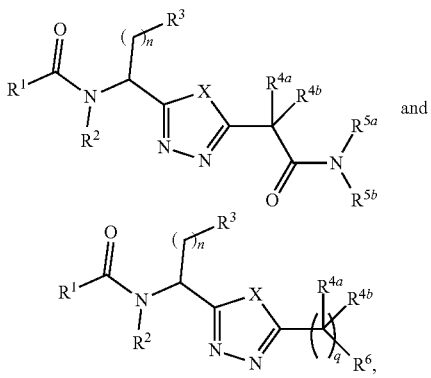

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), —$(CH_2)_m$[(C1-C4)(C1-C4) dialkylamino], —$(CH_2)_m$NH(C=O)(C1-C4 alkyl), —$(CH_2)_m$N(C1-C4 alkyl)(C=O)(C1-C4 alkyl), and $Cy^5$; wherein m is selected from 0 and 1; wherein $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and $Cy^6$, wherein $Cy^6$, when present, C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are methods for treating cancer in a subject, the method comprising the step of administering to the subject an effective amount of at least one compound having a structure represented by a formula selected from:

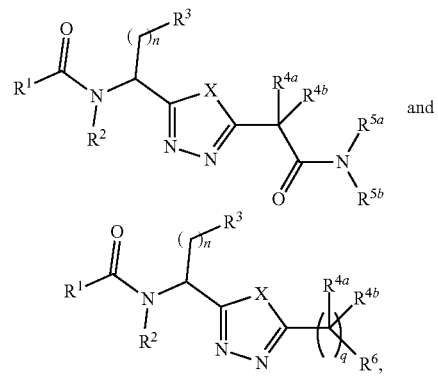

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^2$ is selected from hydrogen, C1-C4 alkyl, and amine protecting group; wherein R$^3$ is selected from NR$^{20a}$R$^{20b}$, NHCOR$^{21}$, and Ar$^1$; wherein each of R$^{20a}$ and R$^{20b}$, when present, is independently selected from hydrogen, C1-C4 alkyl, Cy$^2$, and amine protecting group; wherein Cy$^2$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^{21}$, when present, is selected from C1-C4 alkyl, cycloalkyl, and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino); wherein m is selected from 0 and 1; wherein each of R$^{4a}$ and R$^{4b}$ is independently selected from hydrogen and C1-C4 alkyl; or wherein each of R$^{4a}$ and R$^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby treating cancer in the subject.

Examples of cancers include, but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, liver, kidney, lymphatic system, stomach, lung, pancreas, and skin. In a yet further aspect, the cancer is selected from a cancer of the lung and liver. In an even further aspect, the cancer is selected from a cancer of the breast, ovary, testes, and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In a further aspect, the cancer is selected from a cancer of the breast, cervix, gastrointestinal tract, colorectal tract, brain, skin, prostate, ovary, thyroid, testes, genitourinary tract, pancreas, and endometrias. In a still further aspect, the cancer is a cancer of the breast. In yet a further aspect, the cancer of the breast is a hormone resistant cancer. In an even further aspect, the cancer of the breast is a hormone resistant cancer. In a still further aspect, the cancer is a cancer of the cervix. In yet a further aspect, the cancer is a cancer of the ovary. In an even further aspect, the cancer is a cancer of the endometrias. In a still further aspect, the cancer is a cancer of the genitourinary tract. In yet a further aspect, the cancer is a cancer of the colorectal tract. In an even further aspect, the cancer of the colorectal tract is a colorectal carcinoma. In a still further aspect, the cancer is a cancer of the gastrointestinal tract. In yet a further aspect, the cancer of the gastrointestinal tract is a gastrointestinal stromal tumor. In an even further aspect, the cancer is a cancer of the skin. In a still further aspect, the cancer of the skin is a melanoma. In yet a further aspect, the cancer is a cancer of the brain. In an even further aspect, the cancer of the brain is a glioma. In a still further aspect, the glioma is glioblastoma multiforme. In yet a further aspect, glioma is selected from is selected from an ependymoma, astrocytoma, oligodendroglioma, and oligoastrocytoma. In an even further aspect, the cancer of the brain is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, and hemangiopericytoma. In a still further aspect, the hematological cancer is selected from a leukemia, lymphoma, chronic myeloproliferative disorder, myelodysplastic syndrome, myeloproliferative neoplasm, and plasma cell neoplasm (myeloma). In yet a further aspect, the hematological cancer is leukemia. In an even further aspect, the leukemia is selected from acute leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, and chronic lymphocytic leukemia. In a still further aspect, the leukemia is acute lymphocytic leukemia. In yet a further aspect, the hematological cancer is lymphoma. In an even further aspect, the hematological cancer is myeloma. In a still further aspect, the myeloma is multiple myeloma.

In a further aspect, the carcinoma is selected from colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, bile duct carcinoma, choriocarcinoma, seminoma, embryonal carcinoma, lung carcinoma, small cell lung carcinoma, bladder carcinoma, and epithelial carcinoma.

In a further aspect, the cancer is selected from breast cancer, cervical cancer, gastrointestinal cancer, colorectal cancer, brain cancer, skin cancer, prostate cancer, ovarian cancer, thyroid cancer, testicular cancer, pancreatic cancer, endometrial cancer, melanoma, glioma, leukemia, lymphoma, chronic myeloproliferative disorder, myelodysplastic syndrome, myeloproliferative neoplasm, and plasma cell neoplasm (myeloma).

In a further aspect, the subject has been diagnosed with a need for treatment of cancer prior to the administering step.

In a further aspect, the subject is a mammal. In a still further aspect, the mammal is a human.

In a further aspect, the method further comprises the step of identifying a subject in need of treatment of cancer.

In a further aspect, the method further comprises the step of administering a therapeutically effective amount of at least one chemotherapeutic agent. Examples of chemotherapeutic agents include, but are not limited to, alkylating agents such as busulfan, cis-platin, mitomycin C, and carboplatin; antimitotic agents such as colchicine, vinblastine, paclitaxel (e.g., TAXOL®), and docetaxel; topoisomerase I inhibitors such as camptothecin and topotecan; topoisomerase II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea, gemcitabine, capecitabine and thioguanine; antibodies such as HERCEPTIN® and RITUXAN®, as well as other known chemotherapeutics such as photofrin, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

b. Treating a Fibrotic Disorder

In one aspect, disclosed are methods of treating a fibrotic disorder associated with TGF-β activity in a mammal, the method comprising the step of administering to the mammal an effective amount of at least one disclosed compound, or a pharmaceutically acceptable salt thereof.

In one aspect, disclosed are methods for treating a fibrotic disorder in a subject, the method comprising the step of administering to the subject an effective amount of at least one compound having a structure represented by a formula selected from:

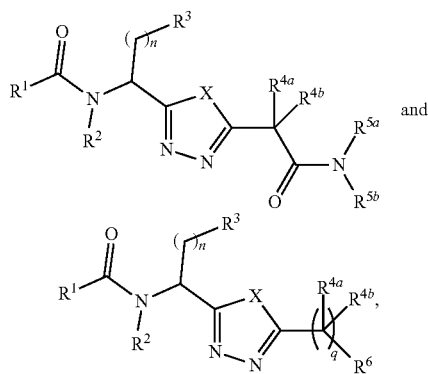

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), —$(CH_2)_m$[(C1-C4)(C1-C4) dialkylamino], —$(CH_2)_mNH(C=O)$(C1-C4 alkyl), —$(CH_2)_mN$(C1-C4 alkyl)(C=O)(C1-C4 alkyl), and $Cy^5$; wherein m is selected from 0 and 1; wherein $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and $Cy^6$, wherein $Cy^6$, when present, C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are methods for treating a fibrotic disorder in a subject, the method comprising the step of administering to the subject an effective amount of at least one compound having a structure represented by a formula selected from:

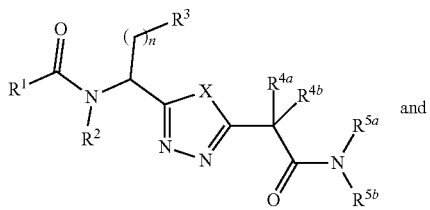

and

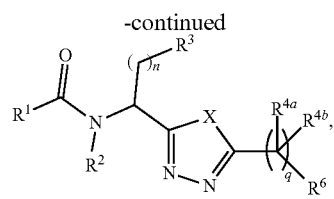

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, and $Ar^1$; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), and —$(CH_2)_m$[(C1-C4)(C1-C4) dialkylamino], provided that $Ar^1$, when present, is substituted with at least one non-hydrogen group selected from —$(CH_2)_mNH_2$ and —$(CH_2)_m$(C1-C4 alkylamino); wherein m is selected from 0 and 1; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby treating the fibrotic disorder in the subject.

Examples of fibrotic disorders for which the compounds and compositions can be useful in treating, include, but are not limited to, pulmonary fibrosis, diabetic nephropathy, glomerulonephritis, liver cirrhosis, muscular dystrophy, proliferative vitreoretinopathy, systemic sclerosis, scleroderma, amyotrophic lateral sclerosis, PAH, NASH, epidermolysis bullosa, and glaucoma.

In a further aspect, the subject has been diagnosed with a need for treatment of the disorder prior to the administering step.

In a further aspect, the subject is a mammal. In a still further aspect, the mammal is a human.

In a further aspect, the method further comprises the step of identifying a subject in need of treatment of the fibrotic disorder.

In a further aspect, the method further comprises the step of administering a therapeutically effective amount of at least one agent known to treat a fibrotic disorder. In a still further aspect, the at least one agent is selected from pirfenidone, nintedanib, a prostaglandin such as latanoprost and bimaotoprost, a beta blocker such as timolol and betaxolol, an alpha-adrenergic agonist such as apraclonidine and brimonidine, a carbonic anhydrase inhibitor such as dorzolamide and brinzolamide, a moitic or cholinergic agent such as pilocarpine, a diuretic, an angiotenisin-converting enzyme (ACE) inhibitor, an angiotensin II receptor blocker, an anti-inflammatory agent, and an anti-fibrotic agent.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

c. Treating an Immune Dysfunction

In one aspect, disclosed are methods of treating an immune dysfunction associated with TGF-β activity in a mammal, the method comprising the step of administering to the mammal an effective amount of at least one disclosed compound, or a pharmaceutically acceptable salt thereof.

In one aspect, disclosed are methods for treating an immune dysfunction in a subject, the method comprising the step of administering to the subject an effective amount of at least one compound having a structure represented by a formula selected from:

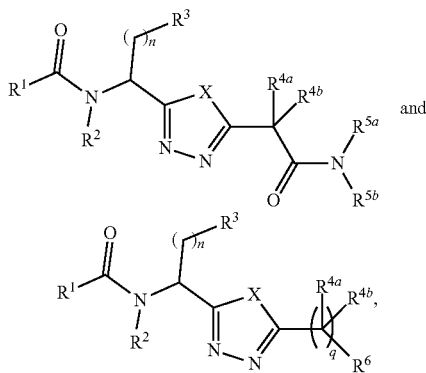

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —$(CH_2)_mNH_2$, —$(CH_2)_m$(C1-C4 alkylamino), —$(CH_2)_m$[(C1-C4)(C1-C4) dialkylamino], —$(CH_2)_mNH(C=O)(C1-C4$ alkyl), —$(CH_2)_mN(C1-C4$ alkyl)(C=O)(C1-C4 alkyl), and $Cy^5$; wherein m is selected from 0 and 1; wherein $Cy^5$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, —$NH_2$, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and $Cy^6$, wherein $Cy^6$, when present, C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are methods for treating an immune dysfunction in a subject, the method comprising the step of administering to the subject an effective amount of at least one compound having a structure represented by a formula selected from:

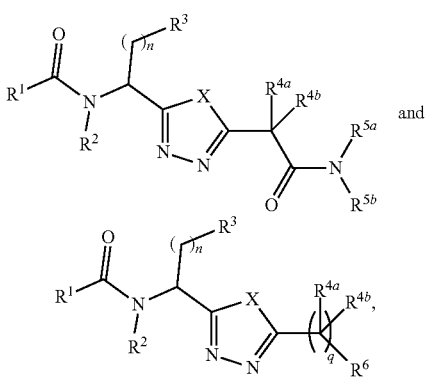

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, and $Ar^1$; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, $-(CH_2)_mNH_2$, $-(CH_2)_m$(C1-C4 alkylamino), and $-(CH_2)_m$[(C1-C4)(C1-C4) dialkylamino], provided that $Ar^1$, when present, is substituted with at least one non-hydrogen group selected from $-(CH_2)_mNH_2$ and $-(CH_2)_m$(C1-C4 alkylamino); wherein m is selected from 0 and 1; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby treating the immune dysfunction in the subject.

In a further aspect, the subject has been diagnosed with a need for immunotherapy prior to the administering step. Examples of immunotherapy include, but are not limited to injection immunotherapy, topical immunotherapy, BCG immunotherapy, dendritic cell-based pump-priming, T-cell adoptive transfer, administration of an immunomodulator, immune enhancement therapy, use of genetically engineered T-cells, antimicrobial immunotherapy, and immunosuppression.

In a further aspect, the subject is a mammal. In a still further aspect, the mammal is a human.

In a further aspect, the method further comprises the step of identifying a subject in need of immunotherapy.

In a further aspect, the method further comprises the step of administering a therapeutically effective amount of at least one agent known to treat an immune dysfunction. Examples of agents known to treat immune dysfunction include, but are not limited to, interleukins (i.e., IL-2, IL-7, and IL-12), cytokines (i.e., interferons, G-CSF, imiquimod), chemokines (i.e., CCL3, CCL26, and CXCL7), immunomodulatory imide drugs (i.e., thalidomide, lenalidomide, pomalidomide, and apremilast), cytosine phosphate-guanosine, oligodeoxynulceotides, glucans, cytostatic drugs, glucocorticoids, and immunosuppressive antibodies.

In a further aspect, the at least one compound and the at least one agent are administered sequentially. In a still further aspect, the at least one compound and the at least one agent are administered simultaneously.

In a further aspect, the at least one compound and the at least one agent are co-formulated. In a still further aspect, the at least one compound and the at least one agent are co-packaged.

2. Methods of Inhibiting TGF-b Activity in a Subject

In one aspect, disclosed are methods of inhibiting TGF-β activity in a mammal, the method comprising the step of administering to the mammal a therapeutically effective amount of at least one disclosed compound, or a pharmaceutically acceptable salt thereof.

In one aspect, disclosed are methods for inhibiting TGF-β activity in a subject, the method comprising the step of administering to the subject an effective amount of at least one compound having a structure represented by a formula selected from:

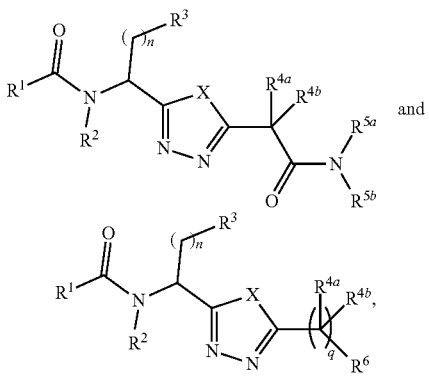

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, $NHPG^1$, and $Ar^1$; wherein $PG^1$ is an amine protecting group; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 0-4 non-hydrogen groups independently selected from halogen, $-CN$, C1-C4 alkyl, C1-C4 haloalkyl, C1-C4 hydroxyalkyl, C1-C4 alkoxy, $-(CH_2)_mNH_2$, $-(CH_2)_m(C1-C4\ alkylamino)$, $-(CH_2)_m[(C1-C4)(C1-C4)\ dialkylamino]$, $-(CH_2)_mNH(C=O)(C1-C4\ alkyl)$, $-(CH_2)_mN(C1-C4\ alkyl)(C=O)(C1-C4\ alkyl)$, and $Cy^5$; wherein m is selected from 0 and 1; wherein $Cy^5$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^6$ is selected from C1-C4 alkyl and $Cy^4$; and wherein $Cy^4$, when present, is selected from C3-C8 cycloalkyl, C2-C7 heterocycloalkyl, aryl, and heteroaryl and is substituted with 0-4 non-hydrogen groups independently selected from halogen, $-NH_2$, $-CN$, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and $Cy^6$, wherein $Cy^6$, when present, C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are methods for inhibiting TGF-β activity in a subject, the method comprising the step of administering to the subject an effective amount of at least one compound having a structure represented by a formula selected from:

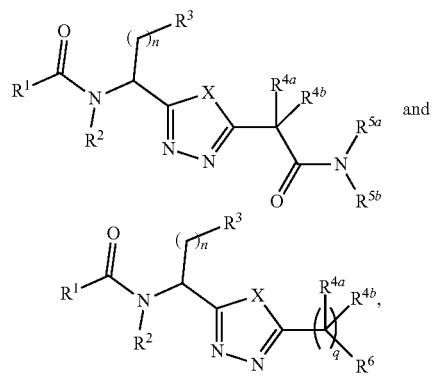

wherein n is selected from 1, 2, 3, and 4; wherein q is selected from 0 and 1; wherein X is selected from O and S; wherein $R^1$ is selected from C1-C8 alkyl and $Cy^1$; wherein $Cy^1$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^2$ is selected from hydrogen, C1-C4 alkyl, and amine protecting group; wherein $R^3$ is selected from $NR^{20a}R^{20b}$, $NHCOR^{21}$, and $Ar^1$; wherein each of $R^{20a}$ and $R^{20b}$, when present, is independently selected from hydrogen, C1-C4 alkyl, $Cy^2$, and amine protecting group; wherein $Cy^2$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $R^{21}$, when present, is selected from C1-C4 alkyl, cycloalkyl, and heterocycloalkyl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, $-(CH_2)_mNH_2$, $-(CH_2)_m(C1-C4\ alkylamino)$, and $-(CH_2)_m[(C1-C4)(C1-C4)\ dialkylamino]$, provided that $Ar^1$, when present, is substituted with at least one non-hydrogen group selected from $-(CH_2)_mNH_2$ and $-(CH_2)_m(C1-C4\ alkylamino)$; wherein m is selected from 0 and 1; wherein each of $R^{4a}$ and $R^{4b}$ is independently selected from hydrogen and C1-C4 alkyl; or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of $R^{5a}$ and $R^{5b}$ is independently selected from hydrogen, C1-C4 alkyl, and $Cy^3$; wherein $Cy^3$, when present, is selected from C3-C8 cycloalkyl and aryl and is substituted with 0-4 non-hydrogen groups independently selected from halogen, $-NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R⁶ is selected from C1-C4 alkyl and Cy⁴; and wherein Cy⁴, when present, is selected from C3-C8 cycloalkyl, C2-C7 heterocycloalkyl, aryl, and heteroaryl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby inhibiting TGF-β activity in the subject.

In a further aspect, inhibiting TGF-β is inhibiting cancer. In a still further aspect, the cancer is selected from multiple myeloma or a hematologic malignancy.

In a further aspect, the subject has been diagnosed with a need for treatment of cancer prior to the administering step. In a still further aspect, the method further comprises the step of identifying a subject in need of treatment of cancer.

In a further aspect, inhibiting TGF-β is inhibiting a fibrotic disorder. In a still further aspect, the fibrotic disorder is found in the liver, the lung, the cardiac muscle, the kidney, the skin, or the eye. In yet a further aspect, the fibrotic disorder is glaucoma, amyotropic lateral sclerosis, pulmonary arterial hypertension, NASH, epidermolysis bullosa, or muscular dystrophy.

In a further aspect, the subject has been diagnosed with a need for treatment of the disorder prior to the administering step. In a still further aspect, the method further comprises the step of identifying a subject in need of treatment of the disorder.

In a further aspect, inhibiting TGF-β is associated with immunotherapy.

In a further aspect, the subject has been diagnosed with a need for immunotherapy prior to the administering step. In a still further aspect, the method further comprises the step of identifying a subject in need of immunotherapy.

In a further aspect, the compound exhibits inhibition of TGF-β activity. In a still further aspect, the compound exhibits a decrease in TGF-β activity.

In a further aspect, the subject is a mammal. In a still further aspect, the subject is a human.

In a further aspect, the effective amount is a therapeutically effective amount. In a still further aspect, the effective amount is a prophylactically effective amount.

In a further aspect, the subject has been diagnosed with a need for treatment of the disorder prior to the administering step. In a still further aspect, the method further comprises the step of identifying a subject in need of treatment of the disorder.

3. Methods of Inhibiting a TGF-b in at Least One Cell

In one aspect, disclosed are methods for inhibiting TGF-β activity in at least one cell, the method comprising the step of contacting the at least one cell with an effective amount of at least one disclosed compound, or a pharmaceutically acceptable salt thereof.

In one aspect, disclosed are methods for inhibiting TGF-β activity in at least one cell, the method comprising the step of contacting the cell with an effective amount of at least one compound having a structure represented by a formula selected from:

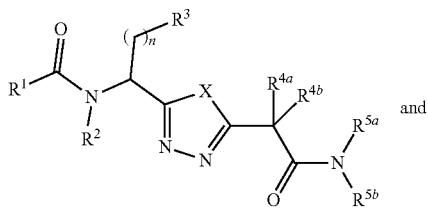

and

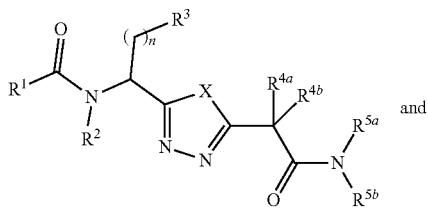

wherein n is selected from 1, 2, 3, and 4; wherein q is selected from 0 and 1; wherein X is selected from O and S; wherein R¹ is selected from C1-C8 alkyl and Cy¹; wherein Cy¹, when present, is selected from C3-C8 cycloalkyl and aryl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R² is selected from hydrogen, C1-C4 alkyl, and amine protecting group; wherein R³ is selected from NR²⁰ᵃR²⁰ᵇ, NHCOR²¹, NHPG¹, and Ar¹; wherein PG¹ is an amine protecting group; wherein each of R²⁰ᵃ and R²⁰ᵇ, when present, is independently selected from hydrogen, C1-C4 alkyl, Cy², and amine protecting group; wherein Cy², when present, is selected from C3-C8 cycloalkyl and aryl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R²¹, when present, is selected from C1-C4 alkyl, cycloalkyl, and heterocycloalkyl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar¹, when present, is selected from aryl and heteroaryl and is substituted with 0-4 non-hydrogen groups independently selected from halogen, —CN, C1-C4 alkyl, C1-C4 haloalkyl, C1-C4 hydroxyalkyl, C1-C4 alkoxy, —(CH₂)ₘNH₂, —(CH₂)ₘ(C1-C4 alkylamino), —(CH₂)ₘ[(C1-C4)(C1-C4) dialkylamino], —(CH₂)ₘNH(C=O)(C1-C4 alkyl), —(CH₂)ₘN(C1-C4 alkyl)(C=O)(C1-C4 alkyl), and Cy⁵; wherein m is selected from 0 and 1; wherein Cy⁵, when present, is selected from C3-C8 cycloalkyl and aryl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R⁴ᵃ and R⁴ᵇ is independently selected from hydrogen and C1-C4 alkyl; or wherein each of R⁴ᵃ and R⁴ᵇ are optionally covalently bonded together and, together with the intermediate atoms, comprise a 3- to 7-membered cycloalkyl substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R⁵ᵃ and R⁵ᵇ is independently selected from hydrogen, C1-C4 alkyl, and Cy³; wherein Cy³, when present, is selected from C3-C8 cycloalkyl and aryl and is substituted with 0-4 non-hydrogen groups independently selected from halogen, —NH₂, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R⁶ is selected from C1-C4 alkyl and Cy⁴; and wherein Cy⁴, when present, is selected from C3-C8 cycloalkyl, C2-C7 heterocycloalkyl, aryl, and heteroaryl and is substituted with 0-4 non-hydrogen groups independently selected from halogen, —NH₂, —CN, C1-C4 alkyl, C1-C4 haloalkyl, C1-C4 hydroxyalkyl, C1-C4 alkoxy, C1-C4 alkoxyhaloalkyl, C1-C4 alkylamino, (C1-C4)(C1-C4) dialkylamino, and Cy$^6$, wherein Cy$^6$, when present, C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; or a pharmaceutically acceptable salt thereof.

In one aspect, disclosed are methods for inhibiting TGF-β activity in at least one cell, the method comprising the step of contacting the cell with an effective amount of at least one compound having a structure represented by a formula selected from:

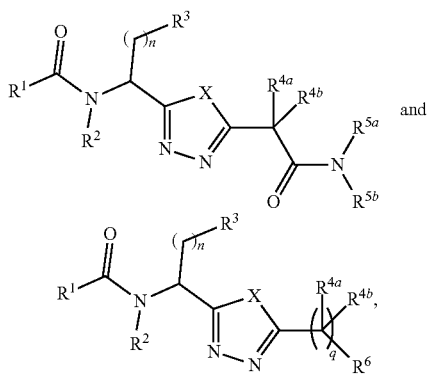

wherein n is selected from 1, 2, 3, and 4; wherein q is selected from 0 and 1; wherein X is selected from O and S; wherein R$^1$ is selected from C1-C8 alkyl and Cy$^1$; wherein Cy$^1$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^2$ is selected from hydrogen, C1-C4 alkyl, and amine protecting group; wherein R$^3$ is selected from NR$^{20a}$R$^{20b}$, NHCOR$^{21}$, and Ar$^1$; wherein each of R$^{20a}$ and R$^{20b}$, when present, is independently selected from hydrogen, C1-C4 alkyl, Cy$^2$, and amine protecting group; wherein Cy$^2$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^{21}$, when present, is selected from C1-C4 alkyl, cycloalkyl, and heterocycloalkyl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein Ar$^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino], provided that Ar$^1$, when present, is substituted with at least one non-hydrogen group selected from —(CH$_2$)$_m$NH$_2$ and —(CH$_2$)$_m$(C1-C4 alkylamino); wherein m is selected from 0 and 1; wherein each of R$^{4a}$ and R$^{4b}$ is independently selected from hydrogen and C1-C4 alkyl; or wherein each of R$^{4a}$ and R$^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein each of R$^{5a}$ and R$^{5b}$ is independently selected from hydrogen, C1-C4 alkyl, and Cy$^3$; wherein Cy$^3$, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino; wherein R$^6$ is selected from C1-C4 alkyl and Cy$^4$; and wherein Cy$^4$, when present, is selected from C3-C8 cycloalkyl, C2-C7 heterocycloalkyl, aryl, and heteroaryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkoxyhaloalkyl, C1-C4 alkylamino, and (C1-C4)(C1-C4) dialkylamino, or a pharmaceutically acceptable salt thereof, thereby TGF-β activity in the cell.

In a further aspect, inhibiting TGF-β is associated with treating cancer. In a still further aspect, inhibiting TGF-β is associated with immunotherapy. In yet a further aspect, inhibiting TGF-β is associated with treating a fibrotic disorder.

In a further aspect, the cell is mammalian. In a still further aspect, the cell is human. In yet a further aspect, the cell has been isolated from a mammal prior to the contacting step.

In a further aspect, contacting is via administration to a mammal. In a still further aspect, the mammal has been diagnosed with a need for inhibition of TGF-β prior to the administering step. In yet a further aspect, the mammal has been diagnosed with a need for treatment of a disorder related to dysfunction of TGF-β prior to the administering step.

4. Use of Compounds

In one aspect, the invention relates to the use of a disclosed compound or a product of a disclosed method. In a further aspect, a use relates to the manufacture of a medicament for the treatment of cancer in a mammal. In a still further aspect, a use relates to the manufacture of a medicament for the treatment of a fibrotic disorder in a mammal. In yet a further aspect, the use relates to the manufacture of a medicament for the treatment of immune dysfunction.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for antagonism of TGF-β activity. In one aspect, the use is characterized in that the mammal is a human. In one aspect, the use is characterized in that the disorder is a cancer or a fibrotic disorder. In one aspect, the use is characterized in that the disorder relates to immune dysfunction.

In a further aspect, the use relates to the manufacture of a medicament for the treatment of cancer in a mammal. In a still further aspect, the use relates to the manufacture of a medicament for the treatment of a fibrotic disorder in a mammal. In a still further aspect, the use relates to the manufacture of a medicament for the treatment of immune dysfunction.

In a further aspect, the use relates to antagonism of a TGF-β activity in a mammal. In a further aspect, the use relates to modulating TGF-β activity in a mammal. In a still further aspect, the use relates to modulating TGF-β activity in a cell. In yet a further aspect, the mammal is a human.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of cancer in a mammal. In a further aspect, the cancer is selected from multiple myeloma and hematologic malignancy. In a further aspect, the invention relates to the use of a disclosed compound or a disclosed product in the manufacture of a medicament for the treatment of a fibrotic disorder in a mammal. In a further aspect, the fibrotic disorder is liver fibrosis, diabetic nephropathy, muscular dystrophy, PAH, NASH, epidermolysis bullosa, or glaucoma. In a still further aspect, the use relates to the manufacture of a medicament for the treatment of immune dysfunction.

5. Manufacture of a Medicament

In one aspect, the invention relates to a method for the manufacture of a medicament for treating a disorder associated with TGF-β in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of TGF-β activity. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

6. Kits

In one aspect, disclosed are kits comprising at least one compound of claim 1 and one or more of: (a) at least one agent known to increase TGF-β activity; (b) at least one agent known to treat cancer; (c) at least one agent known to treat a fibrotic disorder; (d) at least one agent known to an immune dysfunction; (e) instructions for treating a disorder associated with TGF-β dysfunction; (f) instructions for treating cancer; (g) instructions for treating a fibrotic disorder; and (h) instructions for treating an immune dysfunction.

Examples of cancers for which the compounds and compositions can be useful in treating, include, but are not limited to carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas.

Examples of fibrotic disorders for which the compounds and compositions can be useful in treating, include, but are not limited to, pulmonary fibrosis, diabetic nephropathy, glomerulonephritis, liver cirrhosis, proliferative vitreoretinopathy, systemic sclerosis, scleroderma, muscular dystrophy, PAH, NASH, epidermolysis bullosa, and glaucoma.

Examples of agents known to treat cancer include, but are not limited to, alkylating agents such as busulfan, cis-platin, mitomycin C, and carboplatin; antimitotic agents such as colchicine, vinblastine, paclitaxel (e.g., TAXOL®), and docetaxel; topoisomerase I inhibitors such as camptothecin and topotecan; topoisomerase II inhibitors such as doxorubicin and etoposide; RNA/DNA antimetabolites such as 5-azacytidine, 5-fluorouracil and methotrexate; DNA antimetabolites such as 5-fluoro-2'-deoxy-uridine, ara-C, hydroxyurea, gemcitabine, capecitabine and thioguanine; antibodies such as HERCEPTIN® and RITUXAN®, as well as other known chemotherapeutics such as photofrin, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

Examples of agents known to treat fibrotic disorders include, but are not limited to, pirfenidone, nintedanib, a prostaglandin such as latanoprost and bimaotoprost, a beta blocker such as timolol and betaxolol, an alpha-adrenergic agonist such as apraclonidine and brimonidine, a carbonic anhydrase inhibitor such as dorzolamide and brinzolamide, a moitic or cholinergic agent such as pilocarpine, a diuretic, an angiotenisin-converting enzyme (ACE) inhibitor, an angiotensin II receptor blocker, an anti-inflammatory agent, and an anti-fibrotic agent.

Examples of agents known to treat immune dysfunction include, but are not limited to, interleukins (i.e., IL-2, IL-7, and IL-12), cytokines (i.e., interferons, G-CSF, imiquimod), chemokines (i.e., CCL3, CCL26, and CXCL7), immuno-modulatory imide drugs (i.e., thalidomide, lenalidomide, pomalidomide, and apremilast), cytosine phosphate-guanosine, oligodeoxynulceotides, glucans, cytostatic drugs, glucocorticoids, and immunosuppressive antibodies.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

F. Examples

The following preparations and examples are given to enable those skilled in the art to more clearly understand and to practice the present invention. They should not be considered as limiting the scope of the invention, but merely as being illustrative and representative.

1. General Experimental Methods

The reactions were performed under a dry argon atmosphere and reaction temperatures were measured externally. Anhydrous solvents over molecular sieves were purchased from Aldrich and used as such in reactions. Purification of compounds was performed on an Isco Teledyne Combiflash Rf200 with four channels to carryout sequential purification. Universal RediSep solid sample loading pre-packed cartridges (5.0 g Silica) were used to absorb crude product and purified on 12 g silica RediSep Rf Gold Silica (20-40 m spherical silica) columns using appropriate solvent gradients. Pure samples were dried overnight under high vacuum over $P_2O_5$ at 78° C. before analyses. The reactions were monitored by thin-layer chromatography (TLC) on pre-coated silica gel ($60F_{254}$) aluminium plates (0.25 mm) from E. Merck and visualized using UV light (254 nm). Pure samples were dried overnight under high vacuum over $P_2O_5$ at 78° C. before analyses. The HR-mass spectral data were obtained on an Agilent LC-MSTOF by electrospray ionization (ESI). $^1$H NMR spectra were recorded at 400 MHz on Agilent/Varian MR-400 spectrometer in $CDCl_3$ or DMSO-$d_6$ as solvents. The chemical shifts (6) are in ppm downfield from standard tetramethylsilane (TMS). Coupling constants (J) are reported in Hertz (Hz). Purity of final compounds was checked by HPLC using Waters HPLC equipped with a 3100 Mass Detector using Sunfire C18 column (5 m, 4.6×150 mm) using Acetonitrile-$H_2O$ (both containing 0.1% formic acid) 10-90% in 15 min.

2. General Synthesis of Oxadiazoles (Route I)

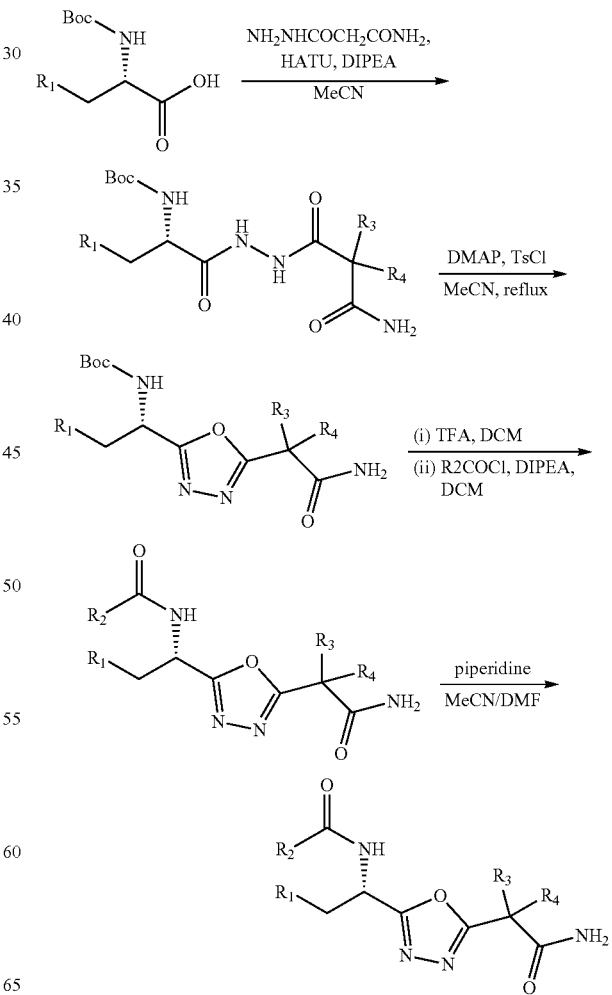

a. General Procedure for the Preparation of Diacyl Hydrazide Analogs

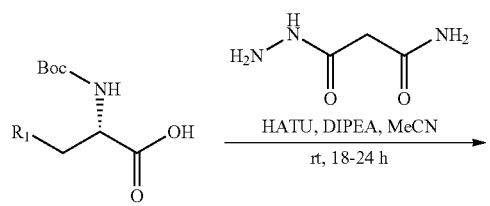

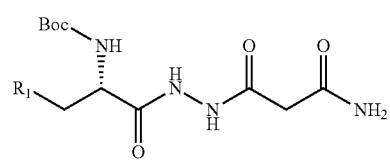

To a dry round-bottom flask equipped with a stir bar was added carboxylic acid (0.85 mmol) and acetonitrile (22 mL). 3-hydrazinyl-3-oxopropanamide (0.85 mmol) was added, followed by DIPEA (1.3 mmol). After stirring for ten minutes under argon at room temperature, HATU (1.0 mmol) was added, and the reaction was stirred for 18-24 hours until deemed complete by TLC. The mixture was concentrated under reduced pressure, then the diacyl hydrazide analogues were obtained by triturating the solid residue with DCM and filtering the resulting heterogeneous mixture.

i. (S)-(9H-Fluoren-9-yl)methyl Tert-butyl (6-(2-(3-amino-3-oxopropanoyl)hydrazinyl)-6-oxohexane-1,5-diyl)dicarbamate (1)

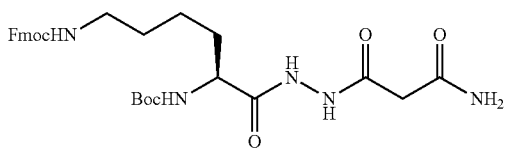

(S)-(9H-fluoren-9-yl)methyl tert-butyl (6-(2-(3-amino-3-oxopropanoyl)hydrazinyl)-6-oxohexane-1,5-diyl)dicarbamate (1) was obtained as a yellow solid in 75% total yield (361 mg) by following the general procedure for the preparation of diacyl hydrazide analogs outlined above; $^1$H NMR (400 MHz, DMSO-$d_6$): δ=10.05-9.96 (brs, 2H), 7.89 (d, J=1.08 Hz, 2H), 7.68 (d, J=1.34 Hz, 2H), 7.45-7.37 (m, 3H), 7.36-7.30 (m, 2H), 7.29-7.23 (m, 1H), 7.11-7.07 (brs, 1H), 6.88 (d, J=2.20 Hz, 1H), 4.32-4.25 (m, 2H), 4.23-4.17 (m, 1H), 3.98-3.90 (m, 1H), 3.04 (s, 2H), 3.00-2.91 (m, 2H), 1.68-1.43 (m, 3H), 1.43-1.27 (m, 12H). MS (APCI): m/z=590.3 [M+Na].

ii. (S)-(9H-Fluoren-9-yl)methyl Tert-butyl (5-(2-(3-amino-3-oxopropanoyl)hydrazinyl)-5-oxopentane-1,4-diyl)dicarbamate (2)

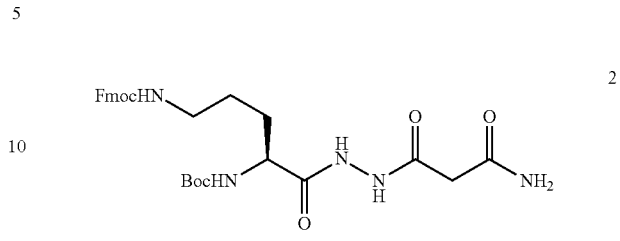

(S)-(9H-fluoren-9-yl)methyl tert-butyl (5-(2-(3-amino-3-oxopropanoyl)hydrazinyl)-5-oxopentane-1,4-diyl)dicarbamate (2) was obtained as a yellow solid in 82% total yield (390 mg) by following the general procedure for the preparation of diacyl hydrazide analogs outlined above; $^1$H NMR (400 MHz, DMSO-$d_6$): δ=10.08-9.99 (brs, 1H), 8.53-8.41 (brs, 1H), 8.32-8.24 (brs, 1H), 7.89 (d, J=10.66 Hz, 2H), 7.68 (d, J=14.7 Hz, 2H), 7.48-7.37 (m, 3H), 7.37-7.23 (m, 4H), 4.32-4.25 (m, 2H), 4.25-4.16 (m, 1H), 4.02-3.90 (m, 1H), 3.04 (s, 2H), 3.00-2.94 (m, 2H), 1.51-1.42 (m, 4H), 1.37 (s, 9H). MS (APCI): m/z=576.3 [M+Na]

iii. Tert-Butyl (S)-(3-(4-((((9H-fluoren-9-yl)methoxy)carbonyl)amino)phenyl)-1-(2-(3-amino-3-oxopropanoyl)hydrazinyl)-1-oxopropan-2-yl)carbamate (3)

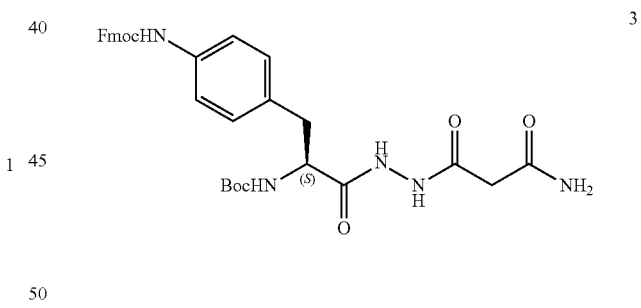

Tert-butyl (S)-(3-(4-((((9H-fluoren-9-yl)methoxy)carbonyl)amino)phenyl)-1-(2-(3-amino-3-oxopropanoyl)hydrazinyl)-1-oxopropan-2-yl)carbamate (3) was obtained as a yellow solid in 48% total yield (246 mg) by following the general procedure for the preparation of diacyl hydrazide analogs outlined above; $^1$H NMR (400 MHz, DMSO-$d_6$): δ=10.21-10.05 (brs, 1H), 9.69-9.56 (brs, 1H), 7.91 (d, J=7.5 Hz, 2H), 7.75 (d, J=7.32 Hz, 2H), 7.46-7.39 (m, 3H), 7.38-7.31 (m, 3H), 7.23-7.16 (m, 2H), 7.12-7.08 (brs, 1H), 6.96-6.90 (brs, 1H), 4.49-4.43 (m, 2H), 4.33-4.27 (m, 1H), 4.22-4.12 (m, 1H), 3.19-3.14 (m, 1H), 3.08-3.05 (m, 1H), 2.94-2.87 (m, 1H), 2.69 (s, 1H), 1.30 (s, 9H). MS (APCI): m/z=624.3 [M+Na].

iv. Tert-Butyl (S)-(3-(4-(((((9H-fluoren-9-yl)methoxy)carbonyl)amino)methyl)phenyl)-1-(2-(3-amino-3-oxopropanoyl)hydrazinyl)-1-oxopropan-2-yl)carbamate (4)

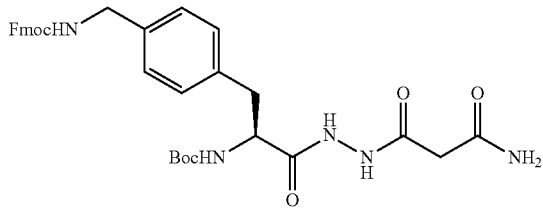

tert-butyl (S)-(3-(4-(((((9H-fluoren-9-yl)methoxy)carbonyl)amino)methyl)phenyl)-1-(2-(3-amino-3-oxopropanoyl)hydrazinyl)-1-oxopropan-2-yl)carbamate (4) was obtained as a yellow solid in 73% total yield (382 mg) by following the general procedure for the preparation of diacyl hydrazide analogs outlined above; $^1$H NMR (400 MHz, DMSO-$d_6$): δ=10.24-10.16 (brs, 1H), 10.13-10.04 (brs, 1H), 7.91-7.85 (m, 2H), 7.83-7.77 (m, 1H), 7.73-7.64 (m, 2H), 7.45-7.39 (m, 2H), 7.35-7.29 (m, 2H), 7.28-7.20 (m, 2H), 7.15-7.07 (m, 2H), 6.99-6.92 (m, 1H), 4.37-4.30 (m, 2H), 4.27-4.17 (m, 2H), 4.17-4.08 (m, 2H), 3.07 (s, 2H), 2.63-2.52 (m, 1H), 2.48-2.38 (m, 1H), 1.29 (s, 9H). MS (APCI): m/z=638.2 [M+Na].

v. Tert-Butyl (S)-(3-(3-(((((9H-fluoren-9-yl)methoxy)carbonyl)amino)methyl)phenyl)-1-(2-(3-amino-3-oxopropanoyl)hydrazinyl)-1-oxopropan-2-yl)carbamate (5)

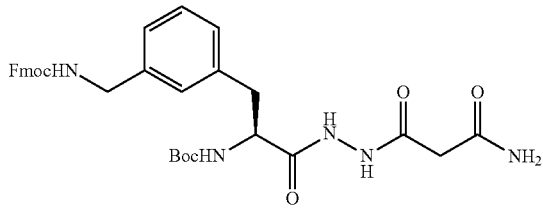

tert-butyl (S)-(3-(3-(((((9H-fluoren-9-yl)methoxy)carbonyl)amino)methyl)phenyl)-1-(2-(3-amino-3-oxopropanoyl)hydrazinyl)-1-oxopropan-2-yl)carbamate (5) was obtained as a yellow solid in 78% total yield (408 mg) by following the general procedure for the preparation of diacyl hydrazide analogs outlined above; $^1$H NMR (400 MHz, DMSO-$d_6$): δ=10.24-10.16 (brs, 1H), 10.11-10.03 (brs, 1H), 7.89 (d, J=7.7 Hz, 2H), 7.85-7.80 (m, 1H), 7.71 (d, J=7.4 Hz, 2H), 7.45-7.38 (m, 3H), 7.35-7.29 (m, 2H), 7.24-7.17 (m, 3H), 7.13-7.04 (m, 2H), 7.03-6.96 (m, 1H), 4.33 (d, J=7 Hz, 2H), 4.26-4.19 (m, 2H), 4.19-4.13 (m, 2H), 3.06 (s, 2H), 3.00-2.93 (m, 1H), 2.79-2.70 (m, 1H), 1.30 (s, 9H). MS (APCI): m/z=638.3 [M+Na].

b. General Procedure for the Preparation of Oxadiazole Analogs

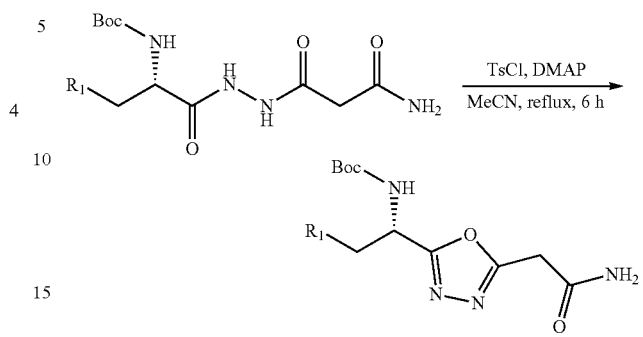

To a solution of diacyl hydrazide (0.388 mmol) in acetonitrile (16.0 mL) was added DMAP (118 mg, 0.969 mmol) followed by TsCl (185 mg, 0.969 mmol)). The reaction was heated to reflux and stirred for 6 hr under argon until the reaction was deemed complete by TLC. The crude mixture was concentrated under reduced pressure, then purified by silica gel chromatography with MeOH/DCM 5:95 to afford the pure oxadiazole.

i. (S)-(9H-Fluoren-9-yl)methyl Tert-butyl (1-(5-(2-amino-2-oxoethyl)-1,3,4-oxadiazol-2-yl)pentane-1,5-diyl)dicarbamate (6)

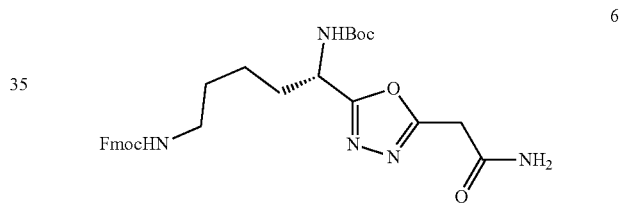

(S)-(9H-fluoren-9-yl)methyl tert-butyl (1-(5-(2-amino-2-oxoethyl)-1,3,4-oxadiazol-2-yl)pentane-1,5-diyl)dicarbamate (6) was obtained as an orange solid in 36% total yield (77.1 mg) by following the general procedure for the preparation of oxadiazole analogs outlined above; $^1$H NMR (400 MHz, CDCl$_3$): δ=7.78-7.72 (m, 2H), 7.62-7.54 (m, 2H), 7.42-7.35 (m, 2H), 7.08-7.01 (brs, 1H), 6.30-6.18 (brs, 1H), 5.70-5.57 (m, 1H), 5.27-5.16 (brs, 1H), 5.03-4.88 (m, 1 H), 4.38-4.31 (m, 2H), 4.24-4.14 (m, 1H), 3.85 (s, 2H), 3.20-3.00 (m, 2H), 1.98-1.78 (m, 2H), 1.56-1.46 (m, 2H), 1.46-1.37 (m, 12H). MS (APCI): m/z=572.2 [M+Na].

ii. (S)-(9H-Fluoren-9-yl)methyl tert-butyl (1-(5-(2-amino-2-oxoethyl)-1,3,4-oxadiazol-2-yl)butane-1,4-diyl)dicarbamate (7)

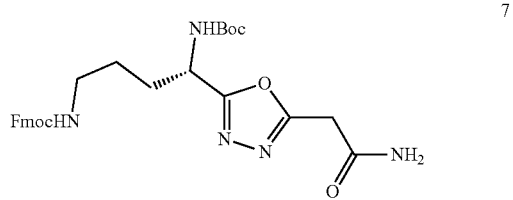

(S)-(9H-fluoren-9-yl)methyl tert-butyl (1-(5-(2-amino-2-oxoethyl)-1,3,4-oxadiazol-2-yl)butane-1,4-diyl)dicarbamate (7) was obtained as an orange solid in 29% total yield (60.3 mg) by following the general procedure for the preparation of oxadiazole analogs outlined above; $^1$H NMR (400 MHz, CDCl$_3$): δ=7.74 (d, J=7.6 Hz, 2H), 7.57 (d, J=7.4 Hz, 2H), 7.41-7.34 (m, 2H), 7.31-7.25 (m, 2H), 6.97-6.90 (brs, 1H), 5.57-5.44 (brs, 1H), 5.28-5.16 (brs, 1H), 5.04-4.87 (brs, 1H), 4.46-4.28 (m, 2H), 4.23-4.11 (m, 1H), 3.83 (s, 2H), 3.25-3.12 (m, 2H), 2.05-1.90 (m, 1H), 1.90-1.78 (m, 1H), 1.65-1.50 (m, 2H), 1.42 (s, 9H). MS (APCI): m/z=558.2 [M+Na].

c. General Procedure for the Preparation of N-acyl Oxadiazole Analogs

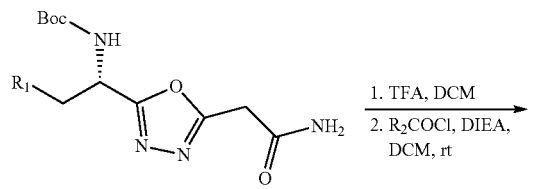

$R_2$ = Me, Et, Pr, Cy, Ph

To a solution of oxadiazole (0.175 mmol) in dichloromethane (4.30 mL) at rt was added 2,2,2-trifluoroacetic acid (0.870 mL, 11.27 mmol) dropwise and stirred at rt for 4 hr. The solvent was removed under reduced pressure until all excess TFA was removed. The resulting oily residue was dissolved in dichloromethane (5.00 mL) and cooled to 0° C. under an atmosphere of argon. Acyl chloride (0.205 mmol) was added, followed by dropwise addition of DIEA (0.392 mmol, 60.0 µL). The mixture was warmed to room temperature, and stirred 6-24 hours under argon until the reaction was deemed complete by TLC. The crude mixture was concentrated under reduced pressure, then the N-acylated products were obtained by triturating the solid residue with DCM and filtering the resulting heterogeneous mixture.

i. (9H-Fluoren-9-yl)methyl (S)-(5-acetamido-5-(5-(2-amino-2-oxoethyl)-1,3,4-oxadiazol-2-yl)pentyl)carbamate (8)

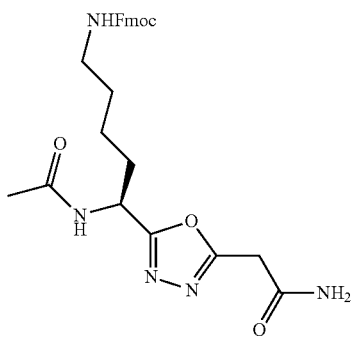

(9H-Fluoren-9-yl)methyl (S)-(5-acetamido-5-(5-(2-amino-2-oxoethyl)-1,3,4-oxadiazol-2-yl)pentyl)carbamate (8) was obtained as a colorless solid in 63% total yield (24.0 mg) by following the general procedure for the preparation of N-acyl oxadiazole analogs outlined above; ESI-MS m/z: 492.2 [M+H]$^+$. $^1$H NMR (400 MHz, DMSO-d$_6$): δ 8.50 (d, 1H, J=8.2 Hz, NH), 7.87 (d, 2H, J=7.3 Hz, ArH), 7.70 (bs, 1H, CONH$_2$), 7.66 (d, J=7.4 Hz, 2H, ArH), 7.41-7.18 (m, 6H, ArH, NHFmoc, CONH$_2$), 5.02-4.99 (m, 1H, NHCH), 4.27 (d, J=6.9 Hz, 2H, FmocCH$_2$), 4.18 (t, J=6.8 Hz, 1H, FmocCH), 3.77 (s, 2H, CH$_2$CONH$_2$), 2.94 (q, J=6.4 Hz, 2H, CH$_2$NHFmoc), 1.84 (s, 3H, Ac), 1.82-1.67 (m, 2H, CH$_2$), 1.43-1.19 (m, 4H, CH$_2$).

ii. (S)-(9H-Fluoren-9-yl)methyl (5-(5-(2-amino-2-oxoethyl)-1,3,4-oxadiazol-2-yl)-5-benzamidopentyl)carbamate (9)

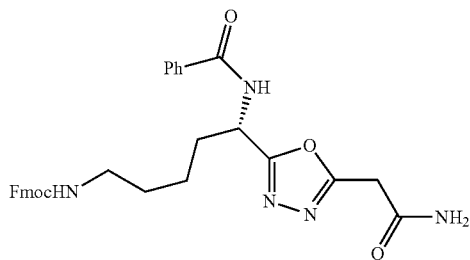

(S)-(9H-Fluoren-9-yl)methyl (5-(5-(2-amino-2-oxoethyl)-1,3,4-oxadiazol-2-yl)-5-benzamidopentyl)carbamate (9) was obtained as a light yellow solid in 69% total yield (65.5 mg) by following the general procedure for the preparation of N-acyl oxadiazole analogs outlined above; $^1$H NMR (400 MHz, CDCl$_3$): δ=7.83-7.77 (m, 2H), 7.77-7.70 (m, 2H), 7.55-7.50 (m, 2H), 7.43-7.35 (m, 4H), 7.34-7.27 (m, 3H), 6.95-6.84 (brs, 1H), 5.94-5.84 (brs, 1H), 5.56-5.42 (m, 1H), 5.10 (t, J=6.0 Hz, 1H), 4.44-4.29 (m, 1H), 4.27-4.18 (m, 1H), 4.18-4.09 (m, 1H), 3.81 (s, 2H), 3.27-3.05 (m, 2H), 2.10-1.93 (m, 3H), 1.55-1.44 (m, 3H). MS (APCI): m/z=554.2 [M+H].

iii. (S)-(9H-Fluoren-9-yl)methyl (5-(5-(2-amino-2-oxoethyl)-1,3,4-oxadiazol-2-yl)-5-butyramidopentyl)carbamate (10)

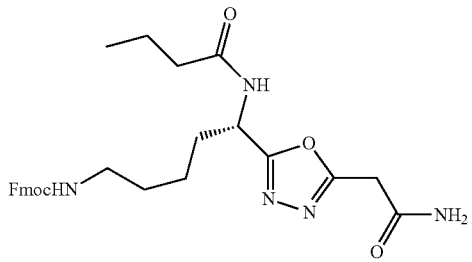

10

(S)-(9H-Fluoren-9-yl)methyl (5-(5-(2-amino-2-oxoethyl)-1,3,4-oxadiazol-2-yl)-5-butyramidopentyl)carbamate (10) was obtained as a white solid in 39% total yield (34.7 mg) by following the general procedure for the preparation of N-acyl oxadiazole analogs outlined above; $^1$H NMR (400 MHz, CDCl$_3$): δ=7.76 (d, J=7.6 Hz, 2H), 7.58 (d, J=7.6 Hz, 2H), 7.39 (t, J=7.4 Hz, 2H), 7.30 (t, J=7.4 Hz, 2H), 6.94-6.82 (m, 2H), 6.64-6.56 (m, 1H), 6.94-6.82 (m, 2H), 5.12-5.01 (m, 1H), 4.46-4.29 (m, 2H), 4.27-4.15 (m, 1H), 3.84 (s, 2H), 3.23-3.11 (m, 2H), 2.25-2.14 (m, 3H), 2.06-1.81 (m, 4H), 1.68-1.60 (m, 3H), 0.90 (t, J=6.9 Hz, 3H). MS (APCI): m/z=520.3 [M+H].

iv. (S)-(9H-Fluoren-9-yl)methyl (5-(5-(2-amino-2-oxoethyl)-1,3,4-oxadiazol-2-yl)-5-(cyclohexanecarboxamido)pentyl)carbamate (11)

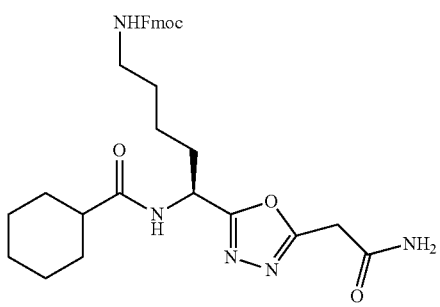

11

(S)-(9H-Fluoren-9-yl)methyl (5-(5-(2-amino-2-oxoethyl)-1,3,4-oxadiazol-2-yl)-5-(cyclohexanecarboxamido)pentyl)carbamate (11) was obtained as a cream solid in 70% total yield (67.0 mg) by following the general procedure for the preparation of N-acyl oxadiazole analogs outlined above; $^1$H NMR (400 MHz, DMSO-d$_6$): δ=8.32 (d, J=8.2 Hz, 1H), 7.88 (d, J=7.4 Hz, 2H), 7.68 (d, J=7.4 Hz, 2H), 7.71-7.64 (brs, 1H), 7.44-7.38 (m, 2H), 7.32 (ddd, J=1.2, 7.5, 8.7 Hz, 2H), 7.29-7.21 (m, 2H), 5.07-4.95 (m, 1H), 4.31-4.23 (m, 2H), 4.23-4.15 (m, 1H), 3.77 (s, 2H), 3.00-2.90 (m, 2H), 2.22-2.09 (m, 1H), 1.72-1.62 (m, 4H), 1.46-1.08 (m, 12H). MS (APCI): m/z=560.3 [M+H].

v. (S)-(9H-Fluoren-9-yl)methyl (5-(5-(2-amino-2-oxoethyl)-1,3,4-oxadiazol-2-yl)-5-propionamidopentyl)carbamate (12)

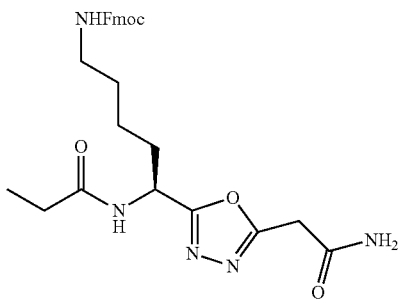

12

(S)-(9H-Fluoren-9-yl)methyl (5-(5-(2-amino-2-oxoethyl)-1,3,4-oxadiazol-2-yl)-5-propionamidopentyl)carbamate (12) was obtained as a white solid in 46% total yield (39.8 mg) by following the general procedure for the preparation of N-acyl oxadiazole analogs outlined above; $^1$H NMR (400 MHz, DMSO-d$_6$): δ=8.42 (d, J=8.2 Hz, 1H), 7.88 (d, J=7.6 Hz, 1H), 7.68 (d, J=7.7 Hz, 1H), 7.74-7.62 (brs, 1H), 7.44-7.38 (m, 2H), 7.33 (ddd, J=1.2, 7.5, 8.6 Hz, 2H), 7.29-7.21 (m, 2H), 5.08-5.00 (m, 1H), 4.32-4.24 (m, 2H), 4.23-4.16 (m, 1H), 3.79 (s, 2H), 2.96 (q, J=6.3 Hz, 2H), 2.19-2.05 (m, 2H), 1.88-1.69 (m, 2H), 1.45-1.35 (m, 2H), 1.35-1.20 (m, 2H), 0.99 (t, J=7.6 Hz). MS (APCI): m/z=506.2 [M+H].

vi. (S)-(9H-Fluoren-9-yl)methyl (4-acetamido-4-(5-(2-amino-2-oxoethyl)-1,3,4-oxadiazol-2-yl)butyl)carbamate (13)

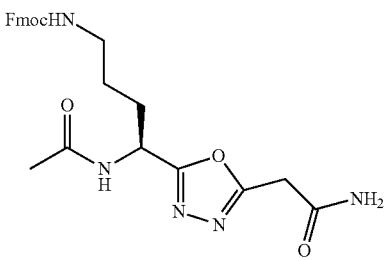

13

(S)-(9H-Fluoren-9-yl)methyl (4-acetamido-4-(5-(2-amino-2-oxoethyl)-1,3,4-oxadiazol-2-yl)butyl)carbamate (13) was obtained as a white solid in 56% total yield (45.7 mg) by following the general procedure for the preparation of N-acyl oxadiazole analogs outlined above; $^1$H NMR (400 MHz, DMSO-d$_6$): δ=8.52 (d, J=8.3 Hz, 1H), 7.88 (d, J=7.4 Hz, 2H), 7.68 (d, J=7.6 Hz, 2H), 7.72-7.60 (brs, 1H), 7.44-7.37 (m, 2H), 7.36-7.28 (m, 3H), 5.10-5.02 (m, 1H), 4.39-4.15 (m, 4H), 3.79 (s, 1H), 3.06-2.90 (m, 3H), 1.89-1.79 (m, 3H), 1.77-1.22 (m, 4H). MS (APCI): m/z=478.2 [M+H].

d. General Procedure for the Preparation of Amino Oxadiazole Analogs

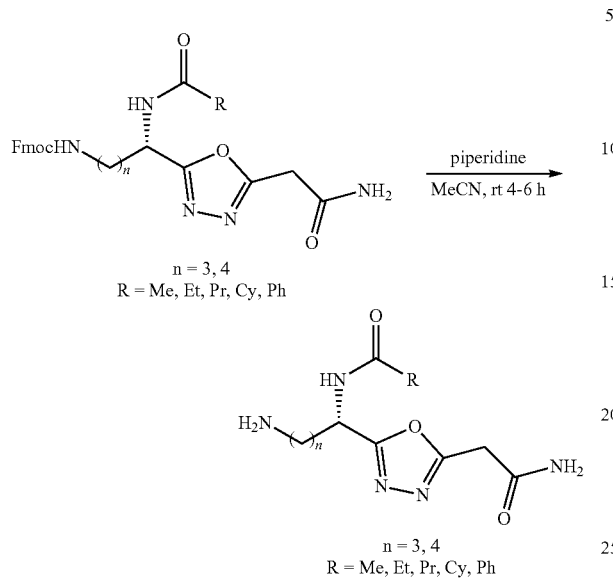

A solution of Fmoc-protected oxadiazole (0.033 mmol) in Acetonitrile (2 ml) or DMF (0.5 mL) was treated with piperidine (6.76 µL, 0.068 mmol). The mixture was stirred at rt for 4-6 hours under argon until deemed complete by TLC. The mixture was concentrated under reduced pressure, then the amino oxadiazole derivatives were obtained by products were obtained by triturating the solid residue with DCM and filtering the resulting heterogeneous mixture.

i. (S)-2-(5-(1-Acetamido-5-aminopentyl)-1,3,4-oxadiazol-2-yl)acetamide (14)

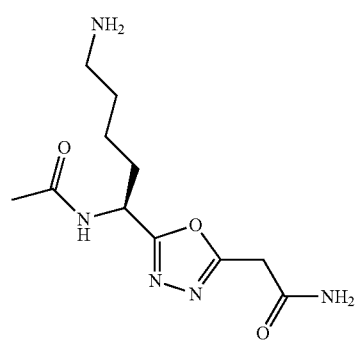

(S)-2-(5-(1-Acetamido-5-aminopentyl)-1,3,4-oxadiazol-2-yl)acetamide (14) was obtained as a colorless solid in 64% total yield (7.0 mg) by following the general procedure for the preparation of amino oxadiazole analogs outlined above; ESI-MS m/z: 270.1 [M+H]$^+$. $^1$H NMR (400 MHz, DMSO-$d_6$): δ 8.53 (d, 1H, J=8.2 Hz, NH), 7.70 (bs, 1H, CONH$_2$), 7.22 (bs, 1H, CONH$_2$), 5.04-4.97 (m, 1H, NHCH), 3.77 (s, 2H, CH$_2$CONH$_2$), 1.84 (s, 3H, Ac), 1.82-1.66 (m, 2H, CH$_2$), 1.39-1.22 (m, 4H, CH$_2$). HRMS calcd for [C$_{11}$H$_{19}$N$_5$O$_3$+H]$^+$: 269.1488, Found: 269.1488.

ii. (S)—N-(5-Amino-1-(5-(2-amino-2-oxoethyl)-1,3,4-oxadiazol-2-yl)pentyl)benzamide (15)

(S)—N-(5-Amino-1-(5-(2-amino-2-oxoethyl)-1,3,4-oxadiazol-2-yl)pentyl)benzamide (15) was obtained as a yellow solid in 80% total yield (8.6 mg) by following the general procedure for the preparation of amino oxadiazole analogs outlined above; MS (APCI): m/z=332.2 [M+H].

3. General Synthesis of Disubstituted Oxadiazoles

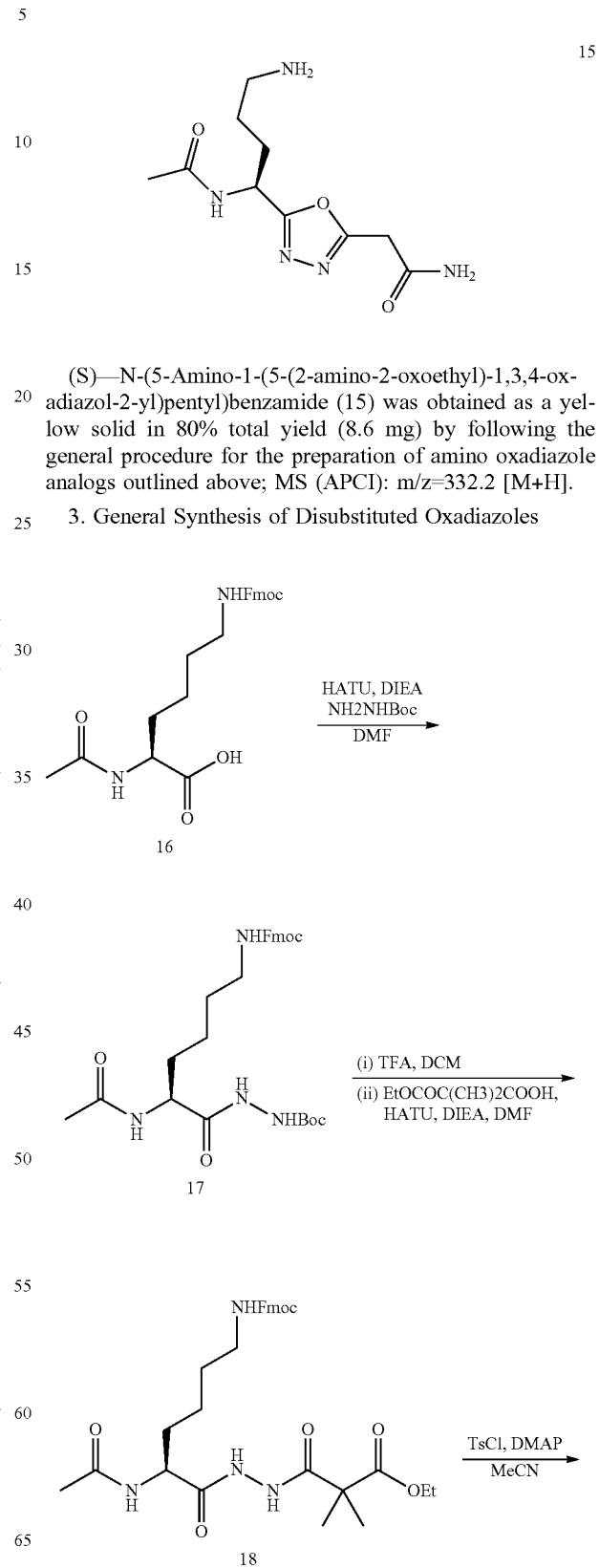

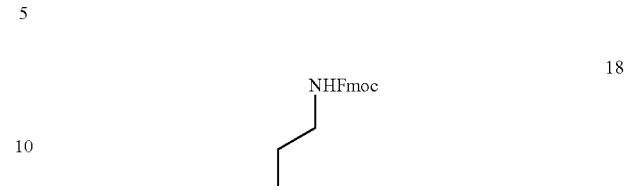

a. Preparation of (S)-tert-Butyl-2-(6-((((9H-fluoren-9-yl)methoxy)carbonyl)amino)-2-acetamido-hexanoyl)hydrazinecarboxylate (17)

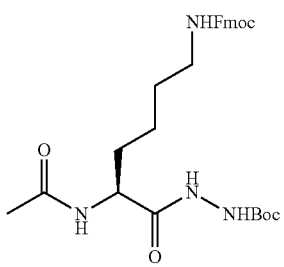

To a rapidly stirring mixture of (S)-6-((((9H-fluoren-9-yl)methoxy)carbonyl)amino)-2-acetamidohexanoic acid (16) (200 mg, 0.487 mmol) in DMF (12.2 mL) was added tert-butyl hydrazinecarboxylate (64.4. mg, 0.487 mmol) followed by DIPEA (128 μL, 0.731 mmol). After stirring for ten minutes, HATU (222 mg, 0.585 mmol) was added, and mixture was stirred overnight. The mixture was concentrated under reduced pressure, then the residue was purified by silica gel chromatography (DCM-MeOH 95:5) to give (S)-tert-butyl2-(6-((((9H-fluoren-9-yl)methoxy)carbonyl)amino)-2-acetamidohexanoyl)hydrazinecarboxylate (17) (96.3 mg, 0.184 mmol, 38%) as a white solid. $^1$H NMR (400 MHz, CDCl$_3$): δ=8.68-8.62 (brs, 1H), 7.74 (d J=7.4 Hz, 2H), 7.60-7.51 (m, 2H), 7.37 (t, J=7.5 Hz, 2H), 7.31-7.26 (m, 2H), 6.90-6.83 (brs, 1H), 6.80 (d J=7.6 Hz, 1H), 4.45-4.29 (m, 3H), 4.22-4.14 (m, 1H), 3.19-3.06 (m, 3H), 2.99-2.90 (brs, 1H), 2.80-2.73 (brs, 1H), 2.17 (s, 3H), 2.01-1.95 (m, 3H), 1.89-1.76 (m, 1H), 1.76-1.63 (m, 1H), 1.55-1.45 (m, 2H), 1.41 (s, 9H). MS (APCI): m/z=547.3 [M+Na]$^+$.

b. Preparation of Ethyl 3-(2-(N6-(((9H-fluoren-9-yl)methoxy)carbonyl)-N2-acetyl-L-lysyl)hydrazinyl)-2,2-dimethyl-3-oxopropanoate (18)

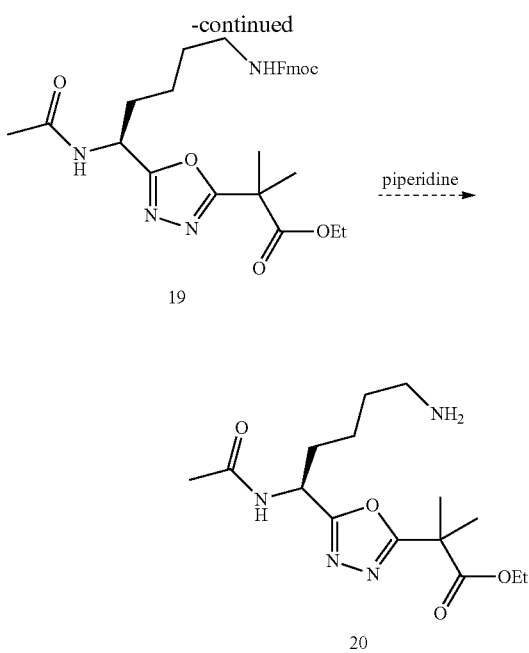

To a solution of (S)-tert-butyl-2-(6-((((9H-fluoren-9-yl)methoxy)carbonyl)amino)-2-acetamidohexanoyl)hydrazinecarboxylate (17) (96 mg, 0.183 mmol) in DCM (4.46 mL) at room temperature was added 2,2,2-trifluoroacetic acid (282 μL, 3.66 mmol) dropwise and stirred at rt for 4 hours. The solvent was removed under reduced pressure until all excess TFA was removed. The resulting oily residue was dissolved in DMf (4.59 mL), then 3-ethoxy-2,2-dimethyl-3-oxopropanoic acid (29.4 mg, 0.184 mmol) was added, followed by DIPEA (99 μL, 0.570 mmol). After stirring for ten minutes, HATU (84.0 mg, 0.220 mmol) was added and the reaction mixture was stirred at room temperature for 18 hours. The mixture was concentrated under reduced pressure, then the residue was purified by silica gel chromatography (DCM-MeOH 95:5) to give ethyl 3-(2-(N6-(((9H-fluoren-9-yl)methoxy)carbonyl)-N2-acetyl-L-lysyl)hydrazinyl)-2,2-dimethyl-3-oxopropanoate (18) (66.0 mg, 0.116 mmol, 63%) as a colorless oil. $^1$H NMR (400 MHz, CDCl$_3$): δ=9.00-8.93 (brs, 1H), 8.89-8.79 (brs, 1H), 7.79-7.73 (m, 2H), 7.60-7.54 (m, 2H), 7.42-7.36 (m, 2H), 7.33-7.28 (m, 2H), 6.46-6.34 (brs, 1H), 5.16-5.03 (brs, 1H), 4.53-4.30 (m, 3H), 4.20 (q, J=7.15 Hz, 2H), 3.25-3.12 (m, 2H), 1.99 (s, 3H), 1.93-1.83 (m, 1H), 1.78-1.67 (m, 1H), 1.57-1.39 (m, 10H), 1.27 (t, J=7.14 Hz, 3H). MS (APCI): m/z=567.3 [M+H].

c. Preparation of Ethyl (S)-2-(5-(5-((((9H-fluoren-9-yl)methoxy)carbonyl)amino)-1-acetamidopentyl)-1,3,4-oxadiazol-2-yl)-2-methylpropanoate (19)

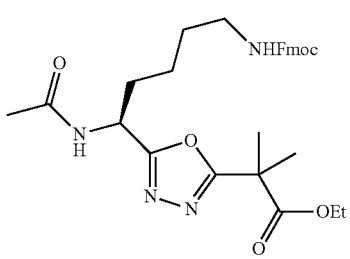

To a solution of (S)-ethyl 3-(2-(6-((((9h-fluoren-9-yl)methoxy)carbonyl)amino)-2-acetamidohexanoyl)hydrazinyl)-2,2-dimethyl-3-oxopropanoate (18) (66 mg, 0.116 mmol) in acetonitrile (4.85 mL) was added DMAP (28.5 mg, 0.233 mmol) followed by tosyl chloride (44.4 mg, 0.233 mmol). The reaction tube was sealed and heated to 120° C. under microwave conditions for 20 minutes. The reaction mixture was cooled to room temperature and concentrated under reduced pressure. The oily residue was purified by silica gel chromatography (DCM-MeOH 95:5) to give ethyl (S)-2-(5-(5-((((9H-fluoren-9-yl)methoxy)carbonyl)amino)-1-acetamidopentyl)-1,3,4-oxadiazol-2-yl)-2-methylpropanoate (19) (17.0 mg, 0.031 mmol, 27%) as a colorless oil. Analysis is in progress MS (APCI): m/z=549.3 [M+H].

4. General Synthesis of Thiadiazoles (Route I)

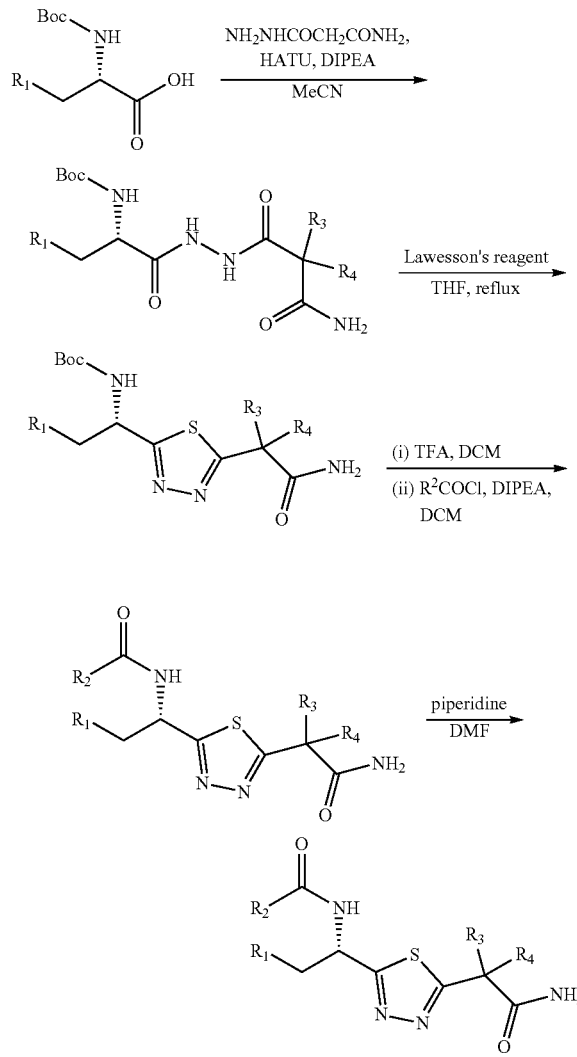

a. General Procedure for the Preparation of Diacyl Hydrazide analogs

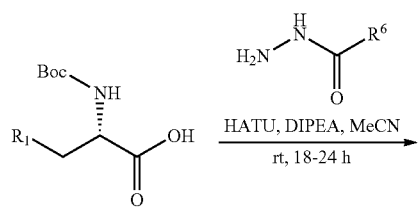

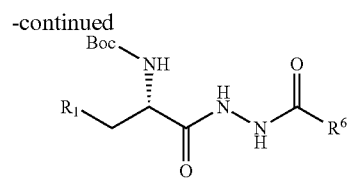

i. (S)-(9H-fluoren-9-yl)methyl tert-butyl (6-(2-acetylhydrazinyl)-6-oxohexane-1,5-diyl)dicarbamate (20)

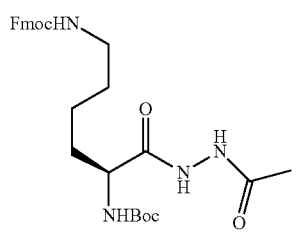

To a stirred solution of (S)-6-((((9H-fluoren-9-yl)methoxy)carbonyl)amino)-2-((tert-butoxycarbonyl)amino)hexanoic acid (0.5 g, 1.067 mmol) in Acetonitrile (15 ml) was added acetohydrazide (0.079 g, 1.067 mmol) followed by HATU (0.406 g, 1.067 mmol) and DIPEA (0.373 ml, 2.134 mmol) and the reaction mixture was stirred at rt for 1 h. Solid crashed out, filtered, filtrate was washed with DCM, dried to afford (S)-(9H-fluoren-9-yl)methyl tert-butyl (6-(2-acetylhydrazinyl)-6-oxohexane-1,5-diyl)dicarbamate (20) (0.460 g, 0.877 mmol, 82% yield). 1H NMR (400 MHz, DMSO-d6) δ 9.83-9.75 (m, 2H), 7.87 (dt, J=7.5, 0.9 Hz, 2H), 7.67 (d, J=7.5 Hz, 2H), 7.42-7.37 (m, 2H), 7.31 (td, J=7.5, 1.1 Hz, 2H), 7.25 (t, J=5.7 Hz, 1H), 6.86 (d, J=8.1 Hz, 1H), 4.27 (d, J=7.0 Hz, 2H), 4.19 (t, J=6.9 Hz, 1H), 3.90 (q, J=8.3 Hz, 1H), 2.94 (d, J=6.9 Hz, 2H), 1.81 (d, J=1.5 Hz, 3H), 1.53 (dd, J=18.9, 10.5 Hz, 2H), 1.48 (s, 2H), 1.34 (s, 10H), 1.18-1.29 (m, 1H). MS m/z 547 [M+Na]+ ii. (S)-(9H-fluoren-9-yl)methyl tert-butyl (6-(2-benzoylhydrazinyl)-6-oxohexane-1,5-diyl)dicarbamate (21)

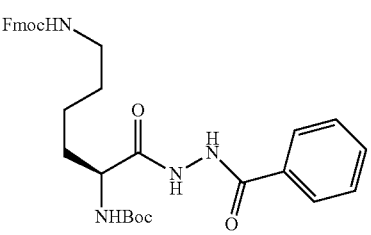

General procedure was followed with 2-(3H-[1,2,3]triazolo[4,5-b]pyridin-3-yl)-1,1,3,3-tetramethylisouronium hexafluorophosphate(V) (0.243 g, 0.640 mmol) and benzohydrazide (0.073 g, 0.534 mmol) to afford (S)-(9H-fluoren-9-yl)methyl tert-butyl (6-(2-benzoylhydrazinyl)-6-oxohexane-1,5-diyl)dicarbamate (21) (0.201 g, 0.343 mmol, 64.2% yield) as white solid. 1H NMR (400 MHz, DMSO-d6) δ 10.34 (s, 1H), 9.90 (s, 1H), 7.88-7.80 (m, 4H), 7.64 (d, J=7.5 Hz, 2H), 7.52 (t, J=7.3 Hz, 1H), 7.44 (t, J=7.5 Hz, 2H), 7.37 (dd, J=8.0, 7.0 Hz, 2H), 7.29 (t, J=7.4 Hz, 2H), 7.24 (t, J=5.8 Hz, 1H), 6.86 (d, J=8.2 Hz, 1H), 4.25 (d, J=6.9 Hz, 2H), 4.17 (t, J=6.9 Hz, 1H), 3.91-4.01 (m, 1H), 2.95 (d, J=6.6 Hz, 2H), 1.58-1.66 (m, 2H), 1.54 (s, 2H), 1.34 (s, 9H), 1.20 (s, 2H). MS m/z 487 [M-Boc+H]$^+$, 609 [M+Na]$^+$.

iii. (S)-(9H-fluoren-9-yl)methyl Tert-butyl (6-(2-(cyclopropanecarbonyl)hydrazinyl)-6-oxohexane-1,5-diyl)dicarbamate (22)

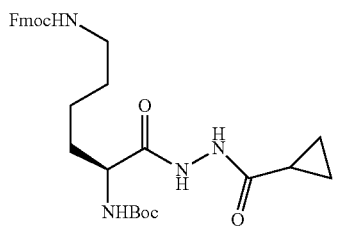

22

General procedure was followed with (S)-6-((((9H-fluoren-9-yl)methoxy)carbonyl)amino)-2-((tert-butoxycarbonyl)amino)hexanoic acid (0.25 g, 0.534 mmol) and cyclopropanecarbohydrazide (0.053 g, 0.534 mmol) to afford (S)-(9H-fluoren-9-yl)methyl tert-butyl (6-(2-(cyclopropanecarbonyl)hydrazinyl)-6-oxohexane-1,5-diyl)dicarbamate (0.211 g, 0.383 mmol, 71.8% yield) to afford (S)-(9H-fluoren-9-yl)methyl tert-butyl (6-(2-(cyclopropanecarbonyl)hydrazinyl)-6-oxohexane-1,5-diyl)dicarbamate (22) (0.211 g, 0.383 mmol, 71.8% yield) as white solid. 1H NMR (400 MHz, DMSO-d6) δ 9.98 (s, 1H), 9.73 (s, 1H), 7.84 (d, J=7.5 Hz, 2H), 7.64 (d, J=7.4 Hz, 2H), 7.41-7.33 (m, 2H), 7.29 (t, J=7.5 Hz, 2H), 7.21 (d, J=5.7 Hz, 1H), 6.8 (d, J=8.1 Hz, 1H), 4.24 (d, J=7.0 Hz, 2H), 4.15 (d, J=7.1 Hz, 1H), 3.87 (d, J=5.9 Hz, 1H), 2.91 (d, J=6.6 Hz, 2H), 1.51 (d, J=27.7 Hz, 3H), 1.32 (s, 12H), 0.71-0.62 (m, 4H). MS m/z 451 [(M-Boc)+H]$^+$.

b. General Procedure for the Preparation of Thiadiazoles

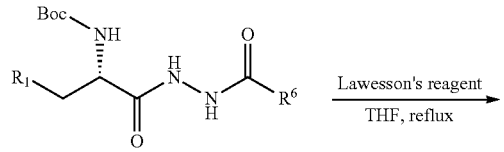

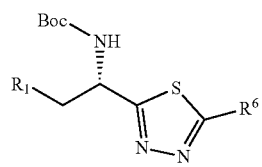

i. (S)-(9H-fluoren-9-yl)methyl Tert-butyl (1-(5-phenyl-1,3,4-thiadiazol-2-yl)pentane-1,5-diyl)dicarbamate (23)

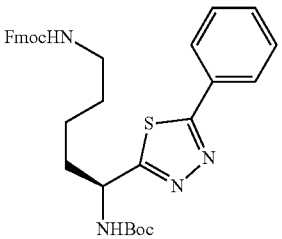

23

To a stirred mixture of (S)-(9H-fluoren-9-yl)methyl tert-butyl (6-(2-benzoylhydrazinyl)-6-oxohexane-1,5-diyl)dicarbamate (0.20 g, 0.341 mmol) in THF (7 ml) was added Lawesson's Reagent (0.145 g, 0.358 mmol) under inert atmosphere and reaction mixture was heated to 70° C. Upon heating mixture turned into clear solution. After 2.5 h at 70° C., TLC showed starting material is still present, another 0.5 eq. of Lawesson's Reagent (0.145 g, 0.358 mmol) was added and reaction mixture was heated for 1 h. Solvents were removed in vacuo and obtained residue was purified through MPLC to afford (S)-(9H-fluoren-9-yl)methyl tert-butyl (1-(5-phenyl-1,3,4-thiadiazol-2-yl)pentane-1,5-diyl)dicarbamate (23) (0.142 g, 0.243 mmol, 71.2% yield) as a white solid. 1H NMR (400 MHz, DMSO-d6) δ 7.93 (d, J=6.3 Hz, 2H), 7.84 (dd, J=14.9, 7.6 Hz, 3H), 7.65 (d, J=7.5 Hz, 2H), 7.56-7.49 (m, 3H), 7.39 (t, J=7.4 Hz, 2H), 7.33-7.22 (m, 3H), 4.87 (s, 1H), 4.27 (d, J=6.9 Hz, 2H), 4-16-4.19 (m, 1H), 2.96 (d, J=6.6 Hz, 2H), 1.91 (s, 1H), 1.83 (s, 1H), 1.4-1.47 (m, 2H), 1.38 (s, 9H), 1.24-1.34 (s, 2H). MS m/z 585 [M+H]$^+$.

ii. (S)-(9H-fluoren-9-yl)methyl tert-butyl (1-(5-methyl-1,3,4-thiadiazol-2-yl)pentane-1,5-diyl)dicarbamate (24)

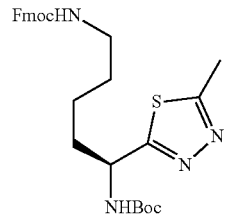

24

To a stirred mixture of (S)-(9H-fluoren-9-yl)methyl tert-butyl (6-(2-acetylhydrazinyl)-6-oxohexane-1,5-diyl)dicarbamate (0.25 g, 0.477 mmol) in THF (7 ml) was added Lawesson's Reagent (0.202 g, 0.500 mmol) under inert atmosphere and reaction mixture was heated to 70° C. Upon heating mixture turned into clear solution. Solvents were removed in vacuo and obtained residue was purified through MPLC to afford (S)-(9H-fluoren-9-yl)methyl tert-butyl (1-(5-methyl-1,3,4-thiadiazol-2-yl)pentane-1,5-diyl)dicarbamate (24) (0.147 g, 0.281 mmol, 59.0% yield). 1H NMR (400 MHz, DMSO-d6) δ 7.84 (d, J=7.5 Hz, 2H), 7.63 (d, J=7.5 Hz, 2H), 7.37 (t, J=7.5 Hz, 2H), 7.28 (tt, J=7.5, 0.9 Hz, 2H), 7.22 (t, J=5.8 Hz, 1H), 6.92-6.94 (m, 1H), 4.76 (d, J=7.7 Hz, 1H), 4.25 (d, J=6.9 Hz, 2H), 4.16 (t, J=6.9 Hz, 1H), 2.92 (q, J=6.4 Hz, 2H), 2.67-2.52 (m, 3H), 1.78 (s, 2H), 1.34 (s, 10H), 1.28 (s, 3H). MS m/z 523 [M+H]$^+$.

iii. (S)-(9H-fluoren-9-yl)methyl Tert-butyl (1-(5-cyclopropyl-1,3,4-thiadiazol-2-yl)pentane-1,5-diyl)dicarbamate (25)

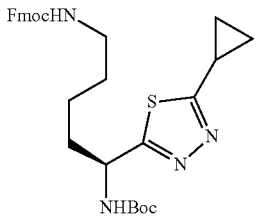

To a stirred mixture of (S)-(9H-fluoren-9-yl)methyl tert-butyl (6-(2-(cyclopropanecarbonyl)hydrazinyl)-6-oxohexane-1,5-diyl)dicarbamate (0.211 g, 0.383 mmol) in THF (7 ml) was added Lawesson's Reagent (0.155 g, 0.383 mmol) under inert atmosphere and reaction mixture was heated to 70° C. Upon heating mixture turned into clear solution. After 2.5 h at 70° C. TLC showed starting material is still present, another 0.5 eq. of Lawesson's Reagent (0.145 g, 0.358 mmol) was added and reaction mixture was heated 70° C. for 1 h. Solvents were removed in vacuo and obtained residue was purified at MPLC to afford (S)-(9H-fluoren-9-yl)methyl tert-butyl (1-(5-cyclopropyl-1,3,4-thiadiazol-2-yl)pentane-1,5-diyl)dicarbamate (25) (0.175 g, 0.319 mmol, 83% yield). 1H NMR (400 MHz, DMSO-d6) δ 7.87 (d, J=7.5 Hz, 2H), 7.73-7.58 (m, 3H), 7.43-7.37 (m, 2H), 7.31 (ddd, J=8.4, 7.0, 1.1 Hz, 2H), 7.25 (t, J=5.7 Hz, 1H), 4.76 (d, J=6.7 Hz, 1H), 4.27 (d, J=7.0 Hz, 2H), 4.18 (t, J=6.8 Hz, 1H), 3.15 (s, 1H), 2.94 (q, J=6.5 Hz, 2H), 2.42 (dt, J=8.6, 4.7 Hz, 1H), 1.36 (s, 9H), 1.32-1.25 (m, 2H), 0.99-0.90 (m, 2H). MS m/z 449 [[(M-Boc)+H]$^+$.

c. General Procedure for the Preparation of N-Acyl Thiadiazole Analogs

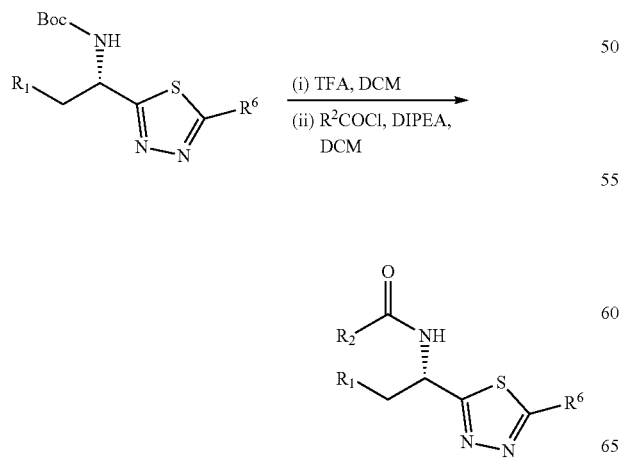

i. (S)-(9H-fluoren-9-yl)methyl (5-amino-5-(5-phenyl-1,3,4-thiadiazol-2-yl)pentyl)carbamate (26)

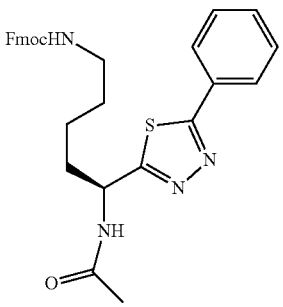

To a stirred solution of (S)-(9H-fluoren-9-yl)methyl tert-butyl (1-(5-phenyl-1,3,4-thiadiazol-2-yl)pentane-1,5-diyl)dicarbamate (0.140 g, 0.239 mmol) in DCM (4 ml) was added trifluoroacetic acid (0.369 mL, 4.79 mmol) under inert atmosphere and the reaction mixture was stirred at rt for 3 h. Solvents were removed in vacuo and obtained sticky solid was used in next step without further purification. Solvents were removed under vacuum and co-evaporated with DCM two times. A sticky solid was obtained and used in the next step without further purification. 1H NMR (400 MHz, DMSO-d6) δ 8.74 (s, 3H), 8.02-7.93 (m, 2H), 7.85 (d, J=7.6 Hz, 2H), 7.64-7.51 (m, 4H), 7.38 (t, J=7.5 Hz, 2H), 7.32-7.25 (m, 2H), 7.23 (t, J=5.8 Hz, 1H), 5.01 (s, 1H), 4.25 (d, J=6.9 Hz, 2H), 4.15 (t, J=6.9 Hz, 1H), 2.95 (d, J=6.4 Hz, 2H), 2.04-1.93 (m, 2H), 1.39 (d, J=16.0 Hz, 2H), 1.25 (d, J=31.9 Hz, 2H). MS m/z 485 [M+H]$^+$.

General procedure was followed to afford (S)-(9H-fluoren-9-yl)methyl (5-acetamido-5-(5-phenyl-1,3,4-thiadiazol-2-yl)pentyl)carbamate (26) (0.092 g, 0.175 mmol, 60.5% yield) as white solid. 1H NMR (400 MHz, DMSO-d6) δ 8.69 (d, J=7.8 Hz, 1H), 7.96-7.89 (m, 2H), 7.86 (d, J=7.5 Hz, 2H), 7.66 (d, J=7.5 Hz, 2H), 7.59-7.47 (m, 3H), 7.39 (t, J=7.4 Hz, 2H), 7.30 (tdd, J=7.4, 1.2, 0.6 Hz, 2H), 7.26 (d, J=5.8 Hz, 1H), 5.18 (td, J=8.6, 5.8 Hz, 1H), 4.27 (d, J=7.2 Hz, 2H), 4.18 (t, J=6.8 Hz, 1H), 2.97 (q, J=6.3 Hz, 2H), 2.02-1.94 (m, 1H), 1.88 (s, 4H), 1.41 (s, 2H), 1.35 (s, 2H). MS m/z 527 [M+H]$^+$.

ii. (S)-(9H-fluoren-9-yl)methyl (5-acetamido-5-(5-methyl-1,3,4-thiadiazol-2-yl)pentyl)carbamate (27)

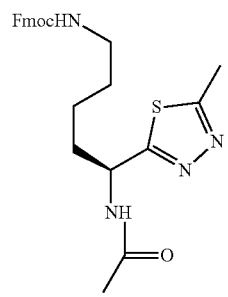

To a stirred solution of (S)-(9H-fluoren-9-yl)methyl tert-butyl (1-(5-methyl-1,3,4-thiadiazol-2-yl)pentane-1,5-diyl)

dicarbamate (0.147 g, 0.281 mmol) in DCM (5 ml) was added TFA (0.433 ml, 5.63 mmol) under inert atmosphere and the reaction mixture was stirred at rt for 2 h. Solvents were removed in vacuo and obtained residue was dissolved in methylene chloride and evaporated once again to afford a residue which was used in next step without further purification. This residue was dissolved in DCM (2 ml) and to this solution was added ACETIC ANHYDRIDE (0.027 ml, 0.284 mmol) followed by DIPEA (0.087 ml, 0.497 mmol) and the reaction mixture was stirred at rt for overnight. TLC showed consumption of starting material. Solvents were removed in vacuo and obtained solid was purified to obtain (S)-(9H-fluoren-9-yl)methyl (5-acetamido-5-(5-methyl-1,3,4-thiadiazol-2-yl)pentyl)carbamate (27) (0.047 g, 0.101 mmol) as a white solid (36% yield over two steps). 1H NMR (400 MHz, Chloroform-d) δ 7.76 (dt, J=7.6, 1.0 Hz, 2H), 7.58 (dt, J=7.5, 1.0 Hz, 2H), 7.35 (dtdd, J=36.7, 7.5, 1.2, 0.7 Hz, 4H), 6.59 (d, J=8.0 Hz, 1H), 5.43-5.32 (m, 1H), 4.93 (s, 1H), 4.46-4.35 (m, 2H), 4.20 (t, J=6.9 Hz, 1H), 3.48 (s, 1H), 3.20 (dq, J=13.8, 6.9 Hz, 2H), 2.73 (s, 3H), 2.09 (dq, J=14.0, 7.4 Hz, 1H), 2.00 (s, 3H), 1.56 (dp, J=14.1, 6.9 Hz, 2H), 1.43 (q, J=7.9 Hz, 2H). MS m/z 465 [M+H]$^+$.

iii. S)-(9H-fluoren-9-yl)methyl (5-acetamido-5-(5-cyclopropyl-1,3,4-thiadiazol-2-yl)pentyl)carbamate (28)

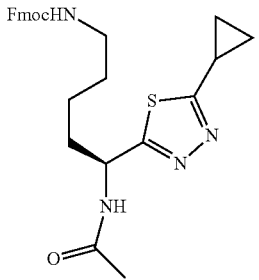

28

To a stirred solution of(S)-(9H-fluoren-9-yl)methyl tert-butyl (1-(5-cyclopropyl-1,3,4-thiadiazol-2-yl)pentane-1,5-diyl)dicarbamate (0.17 g, 0.310 mmol) in DCM (5 ml) was added TRIFLUOROACETIC ACID (0.597 ml, 7.75 mmol) under inert atmosphere and the reaction mixture was stirred at rt for 2 h. Solvents were removed in vacuo and the obtained residue was dissolved in DCM and co-evaporated twice, dried under vacuum and used in next step without further purification. MS m/z 449 [[(M-Boc)+H]$^+$. General procedure was followed to afford (S)-(9H-fluoren-9-yl) methyl (5-acetamido-5-(5-cyclopropyl-1,3,4-thiadiazol-2-yl)pentyl)carbamate (28) (0.099 g, 0.202 mmol, 53.2% yield) as white fluffy solid. 1H NMR (400 MHz, DMSO-d6) δ 8.56 (d, J=7.9 Hz, 1H), 7.87 (d, J=7.5 Hz, 2H), 7.66 (d, J=7.3 Hz, 2H), 7.39 (t, J=7.4 Hz, 2H), 7.31 (td, J=7.5, 1.2 Hz, 2H), 7.25 (t, J=5.7 Hz, 1H), 5.06 (td, J=8.6, 5.8 Hz, 1H), 4.27 (d, J=6.9 Hz, 2H), 4.18 (t, J=6.9 Hz, 1H), 2.94 (q, J=6.5 Hz, 2H), 2.46-2.35 (m, 1H), 1.87 (d, J=13.2 Hz, 1H), 1.83 (s, 3H), 1.74-1.77 (m, 1H), 1.39 (q, J=6.7, 6.1 Hz, 2H), 1.30 (s, 1H), 1.20-1.10 (m, 3H), 0.98-0.91 (m, 2H). MS m/z 491 [M+H]$^+$.

d. General Procedure for the Preparation of Amino Thiadiazole Analogs

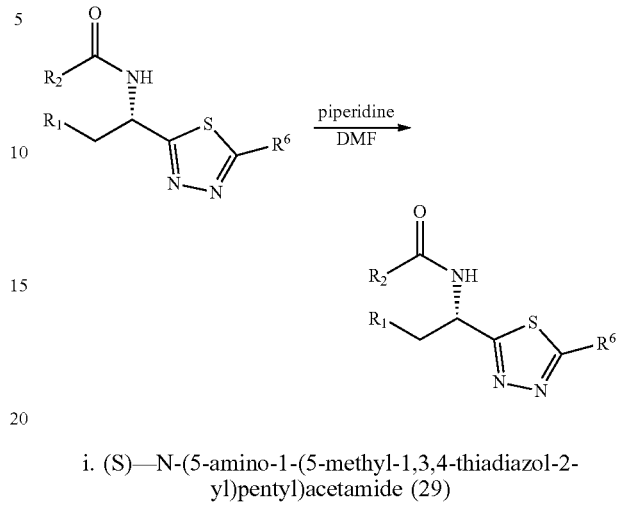

i. (S)—N-(5-amino-1-(5-methyl-1,3,4-thiadiazol-2-yl)pentyl)acetamide (29)

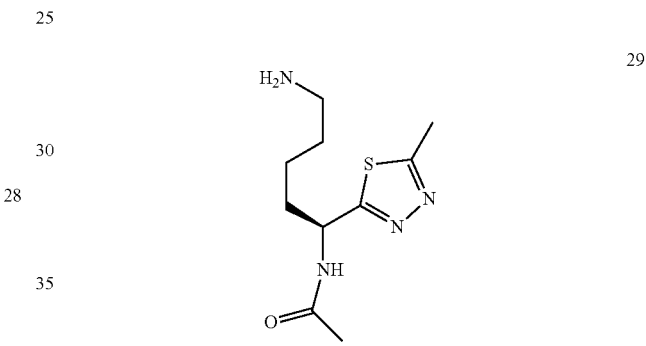

29

To a stirred solution of (S)-(9H-fluoren-9-yl)methyl (5-acetamido-5-(5-methyl-1,3,4-thiadiazol-2-yl)pentyl)carbamate (0.047 g, 0.101 mmol) in DMF (1.775 ml) was added piperidine (0.030 ml, 0.304 mmol) and the reaction mixture was stirred at rt for 2 h. Solvents were removed in vacuo and obtained white solid was washed with diethyl ether to obtain (S)—N-(5-amino-1-(5-methyl-1,3,4-thiadiazol-2-yl)pentyl) acetamide (29) as a white solid. $^1$H NMR (400 MHz, Methanol-d$_4$) δ 5.25 (ddd, J=19.1, 9.0, 5.8 Hz, 1H), 2.73 (s, 3H), 2.70 (d, J=7.1 Hz, 2H), 2.07 (ddt, J=13.7, 9.3, 6.1 Hz, 1H), 1.98 (d, J=7.8 Hz, 3H), 1.96-1.81 (m, 1H), 1.64-1.31 (m, 4H).

ii. (S)—N-(5-amino-1-(5-phenyl-1,3,4-thiadiazol-2-yl)pentyl)acetamide (35)

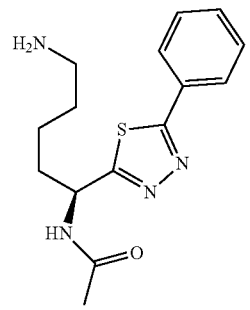 [SMILES: CC(=O)N[C@@H](CCCCN)c1nnc(-c2ccccc2)s1]

To a stirred solution of (S)-(9H-fluoren-9-yl)methyl (5-acetamido-5-(5-phenyl-1,3,4-thiadiazol-2-yl)pentyl)carbamate (26) (0.05 g, 0.095 mmol) in DMF (1.666 ml) was added piperidine (0.028 ml, 0.285 mmol) under inert atmosphere and the reaction mixture was stirred for 2 h. Solvents were removed in vacuo and obtained solid was washed with diethyl ether twice and was purified by prep HPLC using Acetonitrile/water and 0.05% TFA as additive to afford (S)—N-(5-amino-1-(5-phenyl-1,3,4-thiadiazol-2-yl)pentyl) acetamide (35) (0.013 g, 0.043 mmol, 45.0% yield) as a white solid. HRMS: calculated for C15H20N4OS [M+H]$^+$: 304.1358, found 304.1359 1H NMR (400 MHz, DMSO-d6) δ 8.73 (d, J=7.9 Hz, 1H), 7.98-7.88 (m, 2H), 7.61-7.48 (m, 5H), 5.21 (td, J=8.6, 5.8 Hz, 1H), 2.82-2.73 (m, 2H), 2.02 (ddd, J=14.7, 8.8, 4.5 Hz, 1H), 1.89 (s, 4H), 1.56 (p, J=7.5 Hz, 2H), 1.42 (dp, J=15.8, 7.7 Hz, 2H). HPLC: 99.3% ($R_T$)-7.12 min.

5. General Synthesis of Thiadiazoles (Route II)

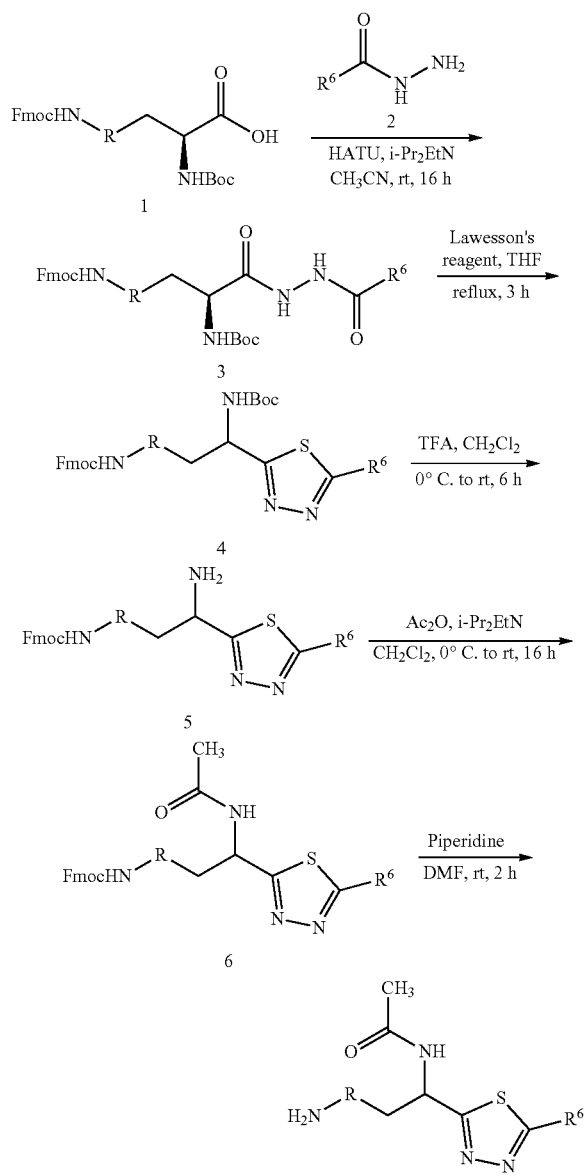

a. Starting Materials

Acid hydrazides were either commercially available or synthesized as shown in Scheme 14A and Scheme 14B below.

SCHEME 14A.

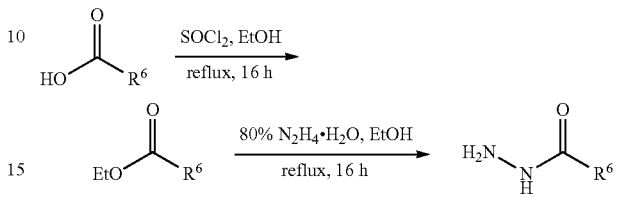

SCHEME 14B.

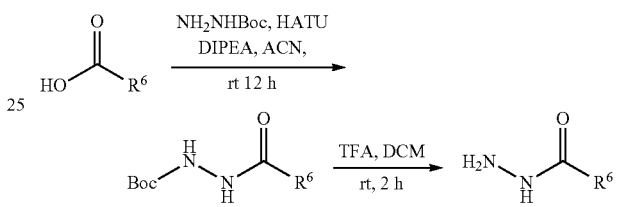

Amino acids were commercially available. If purchased as the Fmoc-protected amine, deprotection was performed after the final step shown above to get the final compounds. In other cases, the final compound was yielded by Step 4. Examples of starting materials include N6-(((9H-fluoren-9-yl)methoxy)carbonyl)-N2-(tert-butoxycarbonyl)-L-lysine, (S)-5-((((9H-fluoren-9-yl)methoxy)carbonyl)amino)-2-((tert-butoxycarbonyl)amino)pentanoic acid, (S)-3-(4-((((9H-fluoren-9-yl)methoxy)carbonyl)amino)phenyl)-2-((tert-butoxycarbonyl)amino)propanoic acid, (S)-3-(4-(((((9H-fluoren-9-yl)methoxy)carbonyl)amino)methyl)phenyl)-2-((tert-butoxycarbonyl)amino)propanoic acid, (S)-2-((tert-butoxycarbonyl)amino)-3-(4-cyanophenyl)propanoic acid, (S)-2-((tert-butoxycarbonyl)amino)-3-(4-fluorophenyl)propanoic acid, and (tert-butoxycarbonyl)-L-phenylalanine.

b. General Procedure for the Preparation of Hydrazines (3)

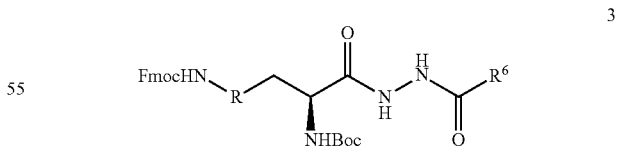

To a mixture of the corresponding amino acid (1) in acetonitrile was added corresponding acid hydrazide (2, 1.1 eq.) followed by DIPEA (3 eq.) and HATU (1.2 eq.) and the reaction mixture was stirred overnight at rt. In some cases, the solid crashed out and was filtered and dried to afford the product. In other cases, the solvent was removed and the obtained residue was purified thorough MPLC to afford the product (3).

c. General Procedure for the Preparation of Thiadiazoles (4)

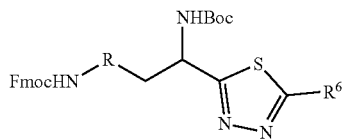

To a stirred mixture of intermediate-3 in either THF or toluene in a sealed tube was added Lawesson's reagent (1.2 eq.) and the reaction mixture was heated for 3-4 h. Solvent was removed and the obtained residue was purified through MPLC to afford the desired compound (4).

d. General Procedure for the Preparation of Amines (5)

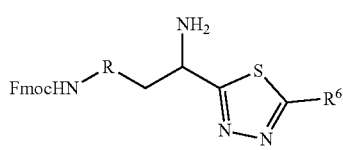

To a stirred solution or mixture of compound (4) in methylene chloride was added trifluoroacetic acid (20 eq.) under inert atmosphere and the reaction mixture was stirred at rt for 2 h. Solvent was removed under vacuum and obtained residue was dissolved in methylene chloride and evaporated again under vacuum and dried at high vacuum. Obtained residue was used in next step without further purification.

e. General Procedure for the Preparation of Amide (6)

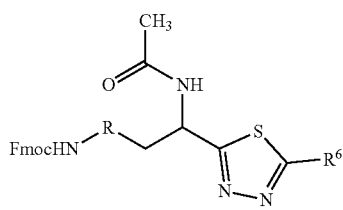

To a stirred solution of compound 5 in methylene chloride was added DIPEA (3 eq.) followed by acetic anhydride (1.2 eq.) and the reaction mixture was stirred at rt overnight. In some cases, the product crashed out and was filtered and dried to afford compound (6). In other cases, the solvent was evaporated and the obtained residue was purified through MPLC to afford compound (6).

f. General Procedure for the Preparation of Deprotected Analogs

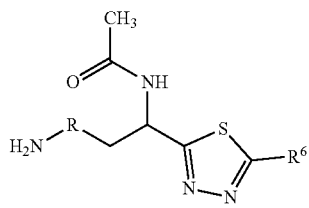

To a solution of compound (6) in DMF was added piperidine (3 eq.) and the reaction mixture was stirred at rt for 2 h under inert atmosphere. Solvent was removed under high vacuum and in some cases, the obtained residue was washed with diethyl ether to afford the compound. In other cases, the residue was subjected to preparatory HPLC using 0.1% TFA in acetonitrile and 0.1% TFA in water as the solvent system.

i. N-(2-(4-Aminophenyl)-1-(5-cyclohexyl-1,3,4-thiadiazol-2-yl)ethyl)acetamide (39137)

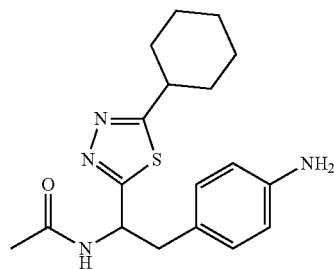 [SMILES: CC(=O)NC(Cc1ccc(N)cc1)c1nnc(C2CCCCC2)s1]

$^1$H NMR (400 MHz, Chloroform-d) δ 6.91-6.84 (m, 2H), 6.60-6.56 (m, 2H), 6.41 (s, 1H), 5.57 (td, J=7.9, 6.3 Hz, 1H), 3.25 (dd, J=13.8, 6.3 Hz, 1H), 3.13-3.05 (m, 2H), 2.09 (d, J=12.2 Hz, 2H), 1.99 (s, 3H), 1.86-1.79 (m, 3H), 1.78-1.69 (m, 1H), 1.53-1.27 (m, 6H). HRMS (ESI): m/z [M+H]+ calcd for $C_{18}H_{25}N_4OS$: 345.17436; found: 345.17383.

ii. N-(4-Amino-1-(5-cyclohexyl-1,3,4-thiadiazol-2-yl)butyl)acetamide (39138)

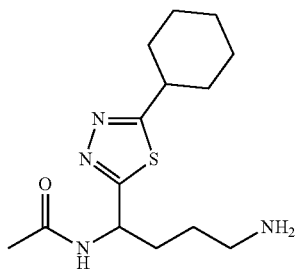 [SMILES: CC(=O)NC(CCCN)c1nnc(C2CCCCC2)s1]

$^1$H NMR (400 MHz, Methanol-d$_4$) δ 5.29 (dd, J=9.1, 5.7 Hz, 1H), 3.13 (tt, J=11.3, 3.6 Hz, 1H), 2.74 (dd, J=7.7, 6.9 Hz, 2H), 2.18-2.03 (m, 3H), 2.00 (s, 3H), 1.98-1.90 (m, 1H), 1.90-1.81 (m, 2H), 1.76 (dtt, J=12.8, 3.3, 1.5 Hz, 1H), 1.71-1.58 (m, 2H), 1.58-1.41 (m, 4H), 1.41-1.26 (m, 1H). HRMS (ESI): m/z [M+H]+ calcd for $C_{14}H_{25}N_4OS$: 297.1749; found: 297.1744.

iii. N-(5-Amino-1-(5-cyclohexyl-1,3,4-thiadiazol-2-yl)pentyl)acetamide (39139)

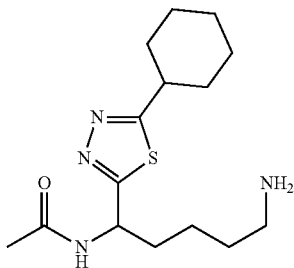 [SMILES: CC(=O)NC(CCCCN)c1nnc(C2CCCCC2)s1]

$^1$H NMR (400 MHz, Methanol-$d_4$) δ 5.28 (dd, J=9.1, 5.7 Hz, 1H), 3.13 (tt, J=11.3, 3.5 Hz, 1H), 2.70 (t, J=7.1 Hz, 2H), 2.15-2.07 (m, 2H), 2.07-2.01 (m, 1H), 1.99 (s, 3H), 1.97-1.90 (m, 1H), 1.90-1.82 (m, 2H), 1.76 (dtt, J=12.7, 3.3, 1.4 Hz, 1H), 1.61-1.56 (m, 2H), 1.56-1.52 (m, 2H), 1.52-1.47 (m, 2H), 1.47-1.41 (m, 2H), 1.40-1.25 (m, 1H). HRMS (ESI): m/z [M+H]+ calcd for $C_{15}H_{27}N_4OS$: 311.1906; found: 311.1900.

iv. N-(5-Amino-1-(5-(2,4-difluorophenyl)-1,3,4-thiadiazol-2-yl)pentyl)acetamide (39425)

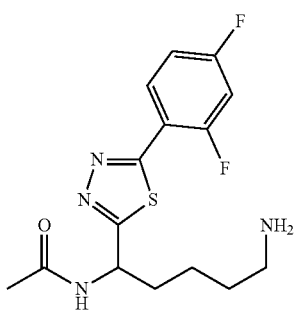 [SMILES: CC(=O)NC(CCCCN)c1nnc(-c2ccc(F)cc2F)s1]

$^1$H NMR (400 MHz, Methanol-$d_4$) δ 8.31 (ddd, J=9.0, 8.2, 6.3 Hz, 1H), 7.30-7.15 (m, 2H), 5.42 (dd, J=8.8, 6.0 Hz, 1H), 2.95 (t, J=7.9 Hz, 2H), 2.22 (ddt, J=13.7, 9.2, 6.4 Hz, 1H), 2.10-2.03 (m, 1H), 2.03 (s, 3H), 1.81-1.68 (m, 2H), 1.67-1.45 (m, 2H). HRMS (ESI): m/z [M+H]+ calcd for $C_{15}H_{19}F_2N_4OS$: 341.1248; found: 341.1243.

v. N-(5-Amino-1-(5-(4-fluorophenyl)-1,3,4-thiadiazol-2-yl)pentyl)acetamide (39261)

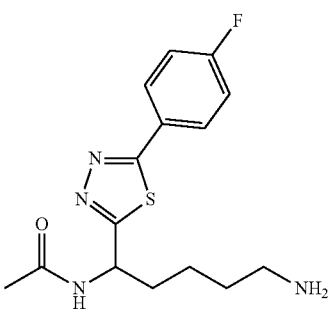 [SMILES: CC(=O)NC(CCCCN)c1nnc(-c2ccc(F)cc2)s1]

$^1$H NMR (400 MHz, Chloroform-d) δ 7.91-7.85 (m, 2H), 7.17-7.11 (m, 2H), 5.42 (td, J=8.1, 5.8 Hz, 1H), 3.25 (s, 5H), 2.84 (t, J=6.6 Hz, 2H), 2.22-2.11 (m, 1H), 2.05 (s, 3H), 1.62 (dtd, J=29.6, 14.8, 8.4 Hz, 4H). HRMS (ESI): m/z [M+H]+ calcd for $C_{15}H_{20}FN_4OS$: 323.13364; found: 323.13413.

vi. N-(2-(4-(aminomethyl)phenyl)-1-(5-cyclohexyl-1,3,4-thiadiazol-2-yl)ethyl)acetamide (39263)

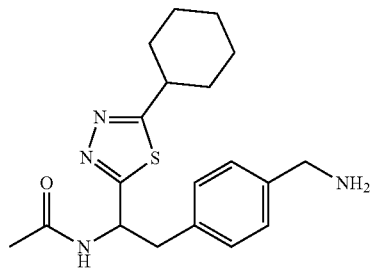 [SMILES: CC(=O)NC(Cc1ccc(CN)cc1)c1nnc(C2CCCCC2)s1]

$^1$H NMR (400 MHz, Chloroform-d) δ 8.30 (d, J=8.2 Hz, 1H), 8.20 (s, 1H), 7.20 (d, J=7.7 Hz, 2H), 7.07 (d, J=7.7 Hz, 2H), 5.54 (q, J=7.8 Hz, 1H), 3.80 (s, 2H), 3.27 (d, J=13.0 Hz, 1H), 3.19-2.98 (m, 2H), 2.06 (d, J=11.4 Hz, 2H), 1.81 (s, 5H), 1.72 (d, J=12.9 Hz, 1H), 1.52-1.30 (m, 4H), 1.24 (q, J=9.7, 7.4 Hz, 1H). HRMS (ESI): m/z [M+H]+ calcd for $C_{19}H_{27}N_4OS$: 359.19001; found: 359.18994.

vii. N,N'-(1-(5-(4-fluorophenyl)-1,3,4-thiadiazol-2-yl)pentane-1,5-diyl)diacetamide (39264)

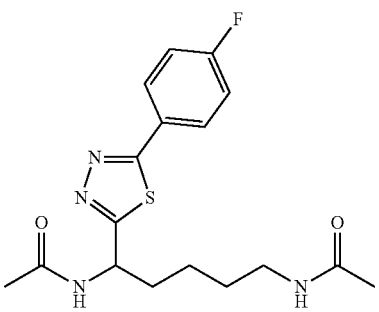 [SMILES: CC(=O)NCCCCC(NC(C)=O)c1nnc(-c2ccc(F)cc2)s1]

Title compound was synthesized from 39261: (S)—N-(5-amino-1-(5-(4-fluorophenyl)-1,3,4-thiadiazol-2-yl)pentyl)acetamide. $^1$H NMR (400 MHz, Chloroform-d) δ 7.97-7.86 (m, 2H), 7.21-7.10 (m, 2H), 6.83 (d, J=7.7 Hz, 1H), 5.75 (s, 1H), 5.39 (td, J=8.2, 5.2 Hz, 1H), 3.38 (dq, J=13.8, 6.8 Hz, 1H), 3.25-3.12 (m, 1H), 2.18 (td, J=14.1, 6.1 Hz, 1H), 2.07 (s, 4H), 1.99 (s, 3H), 1.62-1.52 (m, 2H), 1.52-1.42 (m, 2H). HRMS (ESI): m/z [M+H]+ calcd for $C_{17}H_{22}FN_4O_2S$: 365.1442; found: 365.14511.

viii. N-(2-(4-aminophenyl)-1-(5-(pyridin-2-yl)-1,3,4-thiadiazol-2-yl)ethyl)acetamide (39647)

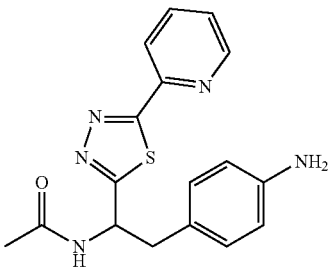 [SMILES: CC(=O)NC(Cc1ccc(N)cc1)c1nnc(-c2ccccn2)s1]

¹H NMR (400 MHz, Methanol-d₄) δ 8.64 (ddd, J=4.9, 1.7, 1.0 Hz, 1H), 8.27 (dt, J=7.9, 1.1 Hz, 1H), 7.98 (td, J=7.8, 1.7 Hz, 1H), 7.52 (ddd, J=7.6, 4.9, 1.2 Hz, 1H), 7.44-7.38 (m, 2H), 7.26-7.20 (m, 2H), 5.66 (dd, J=9.1, 6.4 Hz, 1H), 3.52 (dd, J=13.9, 6.4 Hz, 1H), 3.30-3.26 (m, 1H), 1.93 (s, 3H). HRMS (ESI): m/z [M+H]+ calcd for $C_{17}H_{18}N_5OS$: 340.12266; found: 340.12307.

ix. N-(2-(4-aminophenyl)-1-(5-(thiazol-5-yl)-1,3,4-thiadiazol-2-yl)ethyl)acetamide (39648)

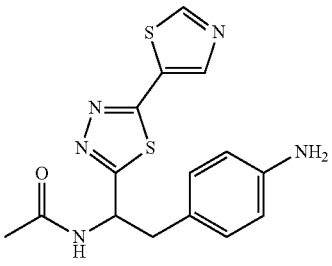 [SMILES: CC(=O)NC(Cc1ccc(N)cc1)c1nnc(-c2cncs2)s1]

¹H NMR (400 MHz, Methanol-d₄) δ 9.17 (d, J=0.7 Hz, 1H), 8.45 (d, J=0.7 Hz, 1H), 7.36 (d, J=8.5 Hz, 2H), 7.15 (d, J=8.4 Hz, 2H), 5.62 (dd, J=9.2, 6.4 Hz, 1H), 3.54-3.47 (m, 1H), 3.29-3.23 (m, 1H), 1.92 (s, 3H). HRMS (ESI): m/z [M+H]+ calcd for $C_{15}H_{16}N_5OS_2$: 346.07908; found: 346.07923.

x. N-(2-(4-aminophenyl)-1-(5-(thiazol-4-yl)-1,3,4-thiadiazol-2-yl)ethyl)acetamide (39577)

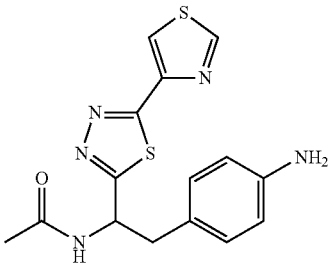 [SMILES: CC(=O)NC(Cc1ccc(N)cc1)c1nnc(-c2cscn2)s1]

¹H NMR (400 MHz, DMSO-d₆) δ 9.28 (d, J=1.9 Hz, 1H), 8.75 (d, J=8.1 Hz, 1H), 8.53 (d, J=1.9 Hz, 1H), 6.90 (d, J=8.4 Hz, 2H), 6.46 (d, J=8.3 Hz, 2H), 5.33 (td, J=8.7, 6.3 Hz, 1H), 4.90 (s, 2H), 3.12 (dd, J=13.9, 6.3 Hz, 1H), 3.00 (dd, J=13.9, 9.0 Hz, 1H), 1.82 (s, 3H). HRMS (ESI): m/z [M+H]+ calcd for $C_{15}H_{16}N_5OS_2$: 346.07908; found: 346.07960.

xi. N-(2-(4-aminophenyl)-1-(5-(1-(4-chlorophenyl)cyclopropyl)-1,3,4-thiadiazol-2-yl)ethyl)acetamide (39649)

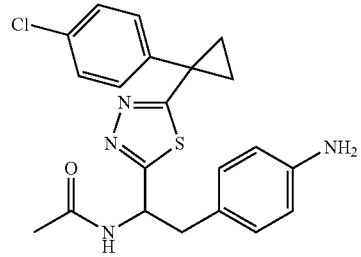 [SMILES: CC(=O)NC(Cc1ccc(N)cc1)c1nnc(C2(c3ccc(Cl)cc3)CC2)s1]

¹H NMR (400 MHz, Methanol-d₄) δ 7.45-7.35 (m, 4H), 6.95-6.89 (m, 2H), 6.65-6.60 (m, 2H), 5.35 (dd, J=9.0, 6.3 Hz, 1H), 3.17 (dd, J=14.0, 6.4 Hz, 1H), 3.01 (dd, J=13.9, 9.1 Hz, 1H), 1.86 (s, 3H), 1.77-1.73 (m, 2H), 1.54-1.50 (m, 2H). HRMS (ESI): m/z [M+H]+ calcd for $C_{21}H_{22}ClN_4OS$: 413.11974; found: 413.12002.

xii. N-(2-(4-(aminomethyl)phenyl)-1-(5-(pyridin-2-yl)-1,3,4-thiadiazol-2-yl)ethyl)acetamide (39650)

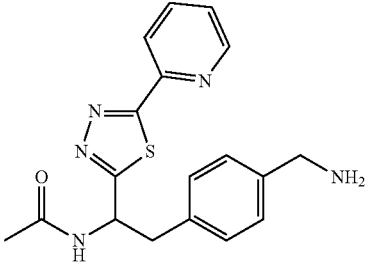 [SMILES: CC(=O)NC(Cc1ccc(CN)cc1)c1nnc(-c2ccccn2)s1]

¹H NMR (400 MHz, Methanol-d₄) δ 8.64 (ddd, J=4.9, 1.7, 1.0 Hz, 1H), 8.26 (dt, J=8.0, 1.1 Hz, 1H), 8.01-7.95 (m, 1H), 7.52 (ddd, J=7.6, 4.9, 1.2 Hz, 1H), 7.39 (s, 4H), 5.70-5.61 (m, 1H), 4.08 (s, 2H), 3.52 (dd, J=13.8, 6.5 Hz, 1H), 3.30-3.26 (m, 1H), 1.93 (s, 3H). HRMS (ESI): m/z [M+H]+ calcd for $C_{18}H_{20}N_5OS$: 354.13831; found: 354.13852.

xiii. N-(2-(4-(aminomethyl)phenyl)-1-(5-(pyridin-3-yl)-1,3,4-thiadiazol-2-yl)ethyl)acetamide (39651)

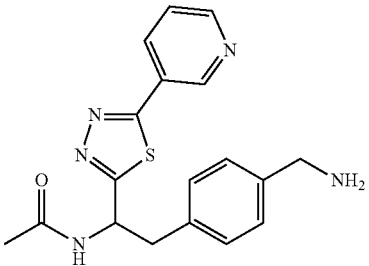 [SMILES: CC(=O)NC(Cc1ccc(CN)cc1)c1nnc(-c2cccnc2)s1]

¹H NMR (400 MHz, Methanol-d₄) δ 9.11 (d, J=2.2 Hz, 1H), 8.71 (dd, J=5.1, 1.6 Hz, 1H), 8.39 (ddd, J=8.0, 2.3, 1.6 Hz, 1H), 7.62 (ddd, J=8.0, 4.9, 0.9 Hz, 1H), 7.40 (s, 4H), 5.67 (dd, J=9.2, 6.3 Hz, 1H), 4.08 (s, 2H), 3.56 (dd, J=13.9, 6.3 Hz, 1H), 3.15-3.11 (m, 1H), 1.91 (s, 3H). HRMS (ESI): m/z [M+H]+ calcd for $C_{18}H_{20}N_5OS$: 354.13831; found: 354.13830.

xiv. N-(4-(2-acetamido-2-(5-(pyridin-4-yl)-1,3,4-thiadiazol-2-yl)ethyl)benzyl)acetamide (39998)

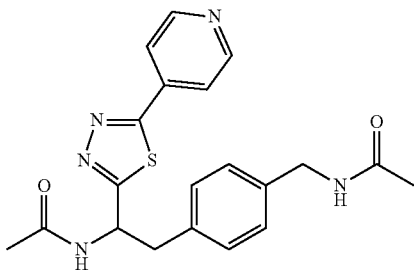 [SMILES: CC(=O)NCc1ccc(CC(NC(C)=O)c2nnc(-c3ccncc3)s2)cc1]

Title compound was synthesized from 39245: (S)—N-(2-(4-(aminomethyl)phenyl)-1-(5-(pyridin-4-yl)-1,3,4-thiadiazol-2-yl)ethyl)acetamide. ¹H NMR (400 MHz, Methanol-d₄) δ 8.73-8.71 (m, 2H), 7.97-7.94 (m, 2H), 7.25 (q, J=8.1 Hz, 4H), 5.64 (dd, J=9.2, 6.2 Hz, 1H), 4.32 (s, 2H), 3.49 (dd, J=13.9, 6.2 Hz, 1H), 3.29-3.21 (m, 1H), 1.97 (s, 3H), 1.92 (s, 3H). HRMS (ESI): m/z [M+H]+ calcd for $C_{20}H_{22}N_5O_2S$: 396.14887; found: 396.14819.

xv. N,N'-(1-(5-cyclohexyl-1,3,4-thiadiazol-2-yl)pentane-1,5-diyl)diacetamide (40004)

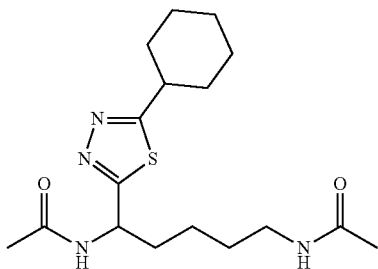 [SMILES: CC(=O)NCCCCC(NC(C)=O)c1nnc(C2CCCCC2)s1]

Title compound was synthesized) from 39263; (S)—N-(2-(4-(aminomethyl)phenyl)-1-(5-(pyridin-4-yl)-1,3,4-thiadiazol-2-yl)ethyl)acetamide. ¹H NMR (400 MHz, Chloroform-d) δ 6.68 (d, J=8.0 Hz, 1H), 5.77 (s, 1H), 5.37 (q, J=7.9 Hz, 1H), 3.34 (dd, J=13.5, 6.8 Hz, 1H), 3.23-3.06 (m, 2H), 2.13 (d, J=12.8 Hz, 3H), 2.05 (d, J=1.4 Hz, 3H), 1.99 (d, J=1.3 Hz, 3H), 1.75 (d, J=13.9 Hz, 2H), 1.54 (dd, J=15.2, 9.3 Hz, 4H), 1.44 (dd, J=16.4, 9.6 Hz, 6H), 1.31 (d, J=13.2 Hz, 1H). HRMS (ESI): m/z [M+H]+ calcd for $C_{17}H_{29}N_4O_2S$: 353.20057; found: 353.19989.

xvi. N-(2-(4-aminophenyl)-1-(5-(3-(trifluoromethoxy)phenyl)-1,3,4-thiadiazol-2-yl)ethyl)acetamide (39999)

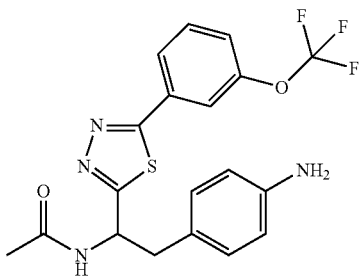 [SMILES: CC(=O)NC(Cc1ccc(N)cc1)c1nnc(-c2cccc(OC(F)(F)F)c2)s1]

¹H NMR (400 MHz, DMSO-d₆) δ 8.78 (d, J=8.0 Hz, 1H), 7.97 (ddd, J=7.7, 1.7, 1.0 Hz, 1H), 7.94 (s, 1H), 7.69 (ddd, J=8.2, 7.7, 0.5 Hz, 1H), 7.59 (ddt, J=8.3, 2.3, 1.1 Hz, 1H), 6.95-6.89 (m, 2H), 6.49-6.43 (m, 2H), 5.33 (ddd, J=9.2, 8.1, 6.1 Hz, 1H), 4.92 (s, 2H), 3.16 (dd, J=13.9, 6.0 Hz, 1H), 3.01 (dd, J=13.9, 9.2 Hz, 1H), 1.82 (s, 3H). HRMS (ESI): m/z [M+H]+ calcd for $C_{19}H_8F_3N_4O_2S$: 423.10971; found: 423.10903.

xvii. N-(2-(4-fluorophenyl)-1-(5-(pyridin-4-yl)-1,3,4-thiadiazol-2-yl)ethyl)acetamide (40050)

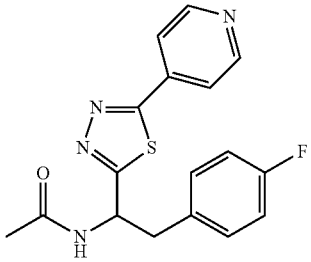 [SMILES: CC(=O)NC(Cc1ccc(F)cc1)c1nnc(-c2ccncc2)s1]

¹H NMR (400 MHz, DMSO-d₆) δ 8.88 (d, J=8.1 Hz, 1H), 8.79-8.72 (m, 2H), 7.96-7.88 (m, 2H), 7.35 (dd, J=8.5, 5.7 Hz, 2H), 7.12 (t, J=8.9 Hz, 2H), 5.49 (ddd, J=9.9, 8.2, 5.6 Hz, 1H), 3.43-3.38 (m, 1H), 3.19 (dd, J=13.9, 9.8 Hz, 1H), 1.81 (s, 3H). HRMS (ESI): m/z [M+H]+ calcd for $C_{17}H_{16}FN_4OS$: 343.10234; found: 343.10210.

xviii. N-(2-(4-(aminomethyl)phenyl)-1-(5-(4-fluorophenyl)-1,3,4-thiadiazol-2-yl)ethyl)acetamide (40051)

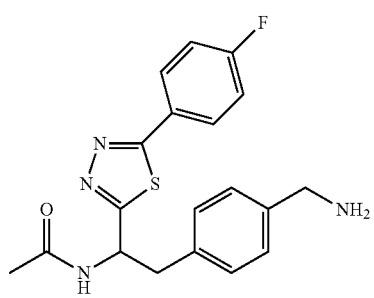 [SMILES: CC(=O)NC(Cc1ccc(CN)cc1)c1nnc(-c2ccc(F)cc2)s1]

¹H NMR (400 MHz, Methanol-d₄) δ 8.03-7.96 (m, 2H), 7.39 (s, 4H), 7.32-7.25 (m, 2H), 5.64 (dd, J=9.2, 6.4 Hz, 1H), 4.07 (s, 2H), 3.53 (dd, J=13.9, 6.4 Hz, 1H), 3.16-3.12 (m, 1H), 1.92 (s, 3H). HRMS (ESI): m/z [M+H]+ calcd for C₁₉H₂₀FN₄OS: 371.13364; found: 371.13347.

xix. N-(2-(4-(aminomethyl)phenyl)-1-(5-(pyridin-4-yl)-1,3,4-thiadiazol-2-yl)ethyl)acetamide (39245)

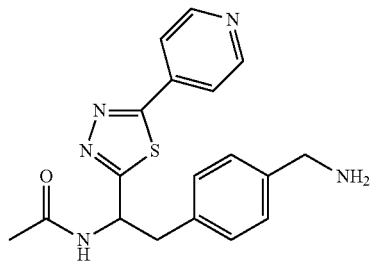 [SMILES: CC(=O)NC(Cc1ccc(CN)cc1)c1nnc(-c2ccncc2)s1]

¹H NMR (400 MHz, Methanol-d₄) δ 8.74-8.71 (m, 2H), 8.54 (s, 1H), 7.99-7.93 (m, 2H), 7.40 (s, 4H), 5.68 (dd, J=9.3, 6.2 Hz, 1H), 4.07 (s, 2H), 3.56 (dd, J=13.9, 6.2 Hz, 1H), 1.92 (s, 3H). HRMS (ESI): m/z [M+H]+ calcd for C₁₈H₂₀N₅OS: 354.13831; found: 354.13747.

xx. N-(2-(3-(aminomethyl)phenyl)-1-(5-phenyl-1,3,4-thiadiazol-2-yl)ethyl)acetamide (40355)

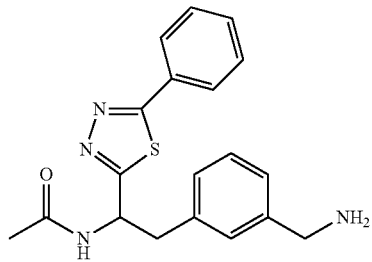 [SMILES: CC(=O)NC(Cc1cccc(CN)c1)c1nnc(-c2ccccc2)s1]

¹H NMR (400 MHz, DMSO-d₆) δ 8.89 (d, J=8.1 Hz, 1H), 8.38 (s, 2H), 7.97-7.92 (m, 2H), 7.58-7.52 (m, 3H), 7.34 (s, 1H), 7.27-7.17 (m, 3H), 5.48 (ddd, J=9.5, 8.4, 5.8 Hz, 1H), 3.79 (s, 2H), 3.39 (d, J=5.6 Hz, 1H), 3.22-3.19 (m, 1H), 1.82 (s, 3H). HRMS (ESI): m/z [M+H]+ calcd for C₁₉H₂₁N₄OS: 353.14306; found: 353.14292.

xxi. N-(2-(3-(aminomethyl)phenyl)-1-(5-(pyridin-4-yl)-1,3,4-thiadiazol-2-yl)ethyl)acetamide (40356)

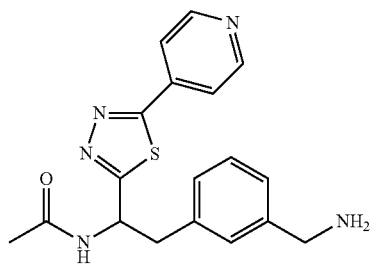 [SMILES: CC(=O)NC(Cc1cccc(CN)c1)c1nnc(-c2ccncc2)s1]

¹H NMR (400 MHz, DMSO-d₆) δ 8.94 (d, J=8.0 Hz, 1H), 8.78-8.71 (m, 2H), 8.33 (s, 1H), 7.93-7.88 (m, 2H), 7.36 (s, 1H), 7.29-7.19 (m, 3H), 5.55-5.45 (m, 1H), 3.83 (s, 2H), 3.36 (d, J=5.7 Hz, 1H), 3.23-3.19 (m, 1H), 1.82 (s, 3H). HRMS (ESI): m/z [M+H]+ calcd for C₁₈H₂₀N₅OS: 354.13831; found: 354.13765.

xxii. N-(2-(3-(aminomethyl)phenyl)-1-(5-(4-(trifluoromethoxy)phenyl)-1,3,4-thiadiazol-2-yl)ethyl)acetamide (SRI-40357)

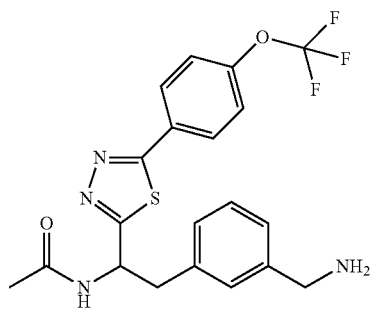 [SMILES: CC(=O)NC(Cc1cccc(CN)c1)c1nnc(-c2ccc(OC(F)(F)F)cc2)s1]

¹H NMR (400 MHz, Methanol-d₄) δ 8.55 (s, 1H), 8.11-8.02 (m, 2H), 7.49-7.40 (m, 3H), 7.40-7.26 (m, 3H), 5.68 (dd, J=9.2, 6.3 Hz, 1H), 4.05 (s, 2H), 3.54 (dd, J=13.9, 6.3 Hz, 1H), 1.93 (s, 3H). HRMS (ESI): m/z [M+H]+ calcd for C₂₀H₂₀F₃N₄O₂S: 437.12536; found: 437.12525.

xxiii. N-(2-(4-(aminomethyl)phenyl)-1-(5-(3-(trifluoromethoxy)phenyl)-1,3,4-thiadiazol-2-yl)ethyl)acetamide (SRI-40000)

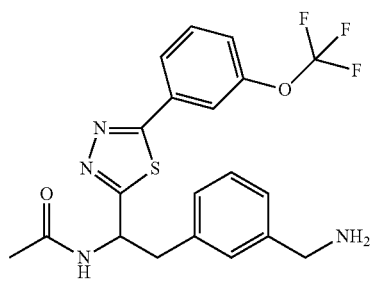 [SMILES: CC(=O)NC(Cc1cccc(CN)c1)c1nnc(-c2cccc(OC(F)(F)F)c2)s1]

¹H NMR (400 MHz, DMSO-d₆) δ 8.89 (d, J=8.1 Hz, 1H), 8.37 (s, 1H), 7.98 (ddd, J=7.7, 1.7, 1.0 Hz, 1H), 7.94 (dd, J=2.4, 1.3 Hz, 1H), 7.70 (ddd, J=8.2, 7.7, 0.5 Hz, 1H), 7.59 (ddt, J=8.2, 2.3, 1.1 Hz, 1H), 7.31 (d, J=1.0 Hz, 4H), 5.48 (ddd, J=9.5, 8.1, 5.6 Hz, 1H), 3.84 (s, 2H), 3.39 (dd, J=13.9, 5.6 Hz, 1H), 3.20 (dd, J=13.9, 9.6 Hz, 1H), 1.81 (s, 3H). HRMS (ESI): m/z [M+H]+ calcd for C₂₀H₂₀F₃N₄O₂S: 437.12536; found: 437.12497.

xxiv. N-(2-(4-(aminomethyl)phenyl)-1-(5-(3,5-difluorophenyl)-1,3,4-thiadiazol-2-yl)ethyl)acetamide (40651)

xxvi. N-(2-(4-(aminomethyl)phenyl)-1-(5-(3,5-bis(trifluoromethyl)phenyl)-1,3,4-thiadiazol-2-yl)ethyl)acetamide (40653)

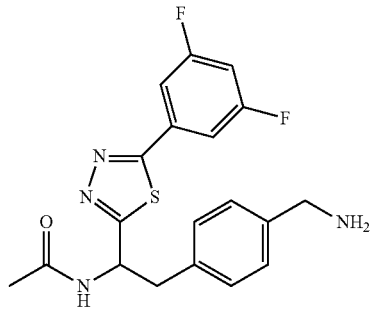 [SMILES: CC(=O)NC(Cc1ccc(CN)cc1)c1nnc(-c2cc(F)cc(F)c2)s1]

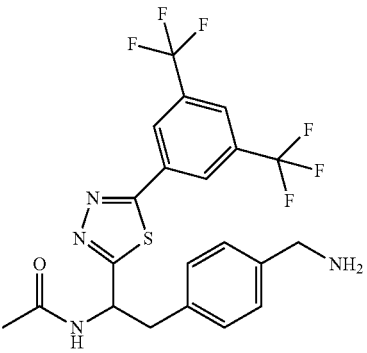

¹H NMR (400 MHz, DMSO-d₆) δ 8.95 (d, J=8.0 Hz, 1H), 8.58 (t, J=1.1 Hz, 2H), 8.35 (s, 1H), 7.34 (s, 4H), 5.51 (ddd, J=9.2, 8.2, 5.4 Hz, 1H), 3.89 (s, 2H), 3.43 (dd, J=13.9, 5.5 Hz, 2H), 3.22 (dd, J=13.9, 9.7 Hz, 2H), 1.82 (s, 3H). HRMS (ESI): m/z [M+H]+ calcd for C₂₁H₁₉F₆N₄OS: 489.11783; found: 489.11754.

¹H NMR (400 MHz, DMSO-d₆) δ 8.90 (d, J=8.1 Hz, 1H), 7.80-7.64 (m, 2H), 7.50 (tt, J=9.2, 2.3 Hz, 1H), 7.28 (d, J=1.9 Hz, 4H), 5.47 (ddd, J=9.6, 8.0, 5.6 Hz, 1H), 3.78 (s, 2H), 3.73 (d, J=4.0 Hz, 1H), 3.38 (dd, J=13.9, 5.6 Hz, 2H), 3.19 (dd, J=13.8, 9.6 Hz, 1H), 1.81 (s, 3H). HRMS (ESI): m/z [M+H]+ calcd for C₁₉H₁₉F₂N₄OS: 389.12421; found: 389.12411.

xxvii. N-(2-(4-cyano-3-fluorophenyl)-1-(5-(3-(trifluoromethoxy)phenyl)-1,3,4-thiadiazol-2-yl)ethyl)acetamide (41176)

xxv. N-(2-(4-(aminomethyl)phenyl)-1-(5-(4-fluoro-3-(trifluoromethoxy)phenyl)-1,3,4-thiadiazol-2-yl)ethyl)acetamide (40652)

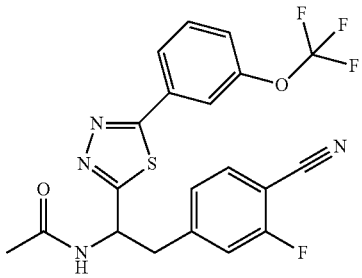

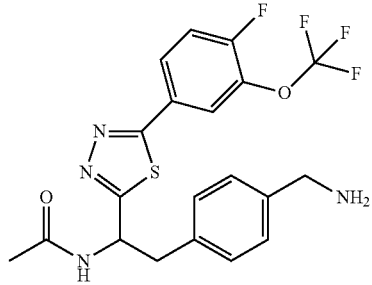 [SMILES: CC(=O)NC(Cc1ccc(CN)cc1)c1nnc(-c2ccc(F)c(OC(F)(F)F)c2)s1]

¹H NMR (400 MHz, Methanol-d₄) δ 7.99-7.84 (m, 2H), 7.75-7.59 (m, 2H), 7.49 (dddd, J=8.3, 3.3, 2.0, 1.0 Hz, 1H), 7.41-7.29 (m, 2H), 5.74 (dd, J=9.7, 5.7 Hz, 1H), 3.66 (dd, J=14.0, 5.7 Hz, 1H), 3.38 (dd, J=14.0, 9.7 Hz, 1H), 1.93 (s, 3H). HRMS (ESI): m/z [M+H]+ calcd for C₂₀H₁₅F₄N₄O₂S: 451.08464; found: 451.08474.

xxviii. N-(2-(4-(aminomethyl)phenyl)-1-(5-(m-tolyl)-1,3,4-thiadiazol-2-yl)ethyl)acetamide (41261)

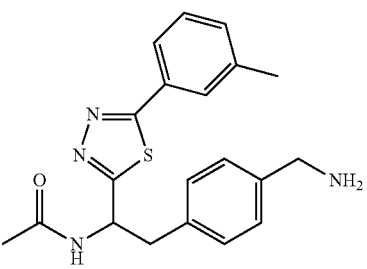 [SMILES: CC(=O)NC(Cc1ccc(CN)cc1)c1nnc(-c2cccc(C)c2)s1]

¹H NMR (400 MHz, DMSO-d₆) δ 8.88 (d, J=8.1 Hz, 1H), 8.16 (d, J=7.3 Hz, 1H), 8.06 (ddd, J=8.7, 4.4, 2.3 Hz, 1H), 7.72 (dd, J=10.1, 8.7 Hz, 1H), 7.28 (d, J=1.5 Hz, 4H), 5.46 (ddd, J=9.3, 8.1, 5.8 Hz, 1H), 3.77 (s, 2H), 3.38 (dd, J=13.9, 5.7 Hz, 2H), 3.19 (dd, J=13.8, 9.6 Hz, 2H), 1.81 (s, 3H). HRMS (ESI): m/z [M+H]+ calcd for C₂₀H₁₉F₄N₄O₂S: 455.11594; found: 455.11580.

¹H NMR (400 MHz, Methanol-d₄) δ 7.76 (tt, J=1.6, 0.8 Hz, 1H), 7.74-7.68 (m, 1H), 7.43-7.35 (m, 6H), 5.64 (dd, J=9.2, 6.3 Hz, 1H), 4.09 (s, 2H), 3.52 (dd, J=13.8, 6.3 Hz, 1H), 3.30-3.25 (m, 1H), 2.42 (s, 3H), 1.92 (s, 3H). HRMS (ESI): m/z [M+H]+ calcd for $C_{20}H_{23}N_4OS$: 367.15871; found: 367.15922.

xxix. N-(2-(4-(aminomethyl)phenyl)-1-(5-(3-chloro-5-(trifluoromethoxy)phenyl)-1,3,4-thiadiazol-2-yl)ethyl)acetamide (42551)

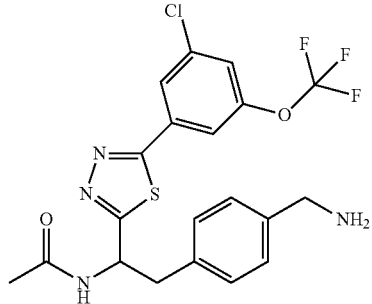 [SMILES: CC(=O)NC(Cc1ccc(CN)cc1)c1nnc(-c2cc(Cl)cc(OC(F)(F)F)c2)s1]

¹H NMR (400 MHz, Methanol-d₄) δ 8.02-7.95 (m, 1H), 7.84 (tt, J=2.3, 1.0 Hz, 1H), 7.58 (tt, J=1.9, 1.0 Hz, 1H), 7.39 (s, 4H), 5.66 (dd, J=9.1, 6.3 Hz, 1H), 4.08 (s, 2H), 3.55 (dd, J=13.9, 6.3 Hz, 1H), 1.91 (s, 3H). HRMS (ESI): m/z [M+H]+ calcd for $C_{20}H_{19}ClF_3N_4O_2S$: 471.0689; found: 471.0689. HPLC: 99.1% (% of AUC).

xxx. N-(2-(4-(aminomethyl)phenyl)-1-(5-(3-chlorophenyl)-1,3,4-thiadiazol-2-yl)ethyl)acetamide (42552)

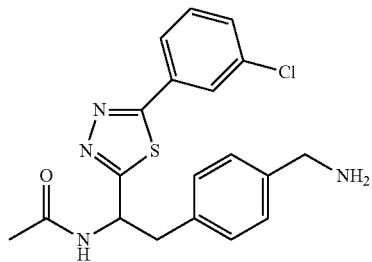

¹H NMR (400 MHz, DMSO-d₆) δ 7.17 (t, J=1.8 Hz, 1H), 7.04 (dt, J=7.5, 1.5 Hz, 1H), 6.79-6.64 (m, 2H), 6.58 (s, 4H), 4.84 (ddd, J=9.0, 6.4, 2.9 Hz, 1H), 3.26 (s, 2H), 2.73 (dd, J=13.9, 6.5 Hz, 1H), 1.10 (s, 3H). HRMS (ESI): m/z [M+H]+ calcd for $C_{19}H_{20}ClN_4OS$: 387.1046; found: 387.1038. HPLC: 99.9% (% of AUC).

xxxi. N-(2-(4-(aminomethyl)phenyl)-1-(5-(4-(trifluoromethoxy)phenyl)-1,3,4-thiadiazol-2-yl)ethyl)acetamide (40348)

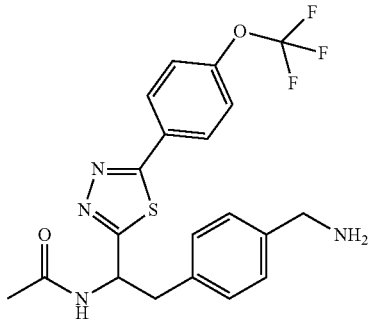 [SMILES: CC(=O)NC(Cc1ccc(CN)cc1)c1nnc(-c2ccc(OC(F)(F)F)cc2)s1]

¹H NMR (400 MHz, Methanol-d₄) δ 8.10-8.01 (m, 2H), 7.50-7.41 (m, 2H), 7.37 (s, 4H), 5.64 (dd, J=9.2, 6.3 Hz, 1H), 4.02 (s, 2H), 3.53 (dd, J=13.9, 6.4 Hz, 1H), 3.27-3.20 (m, 1H), 1.91 (s, 3H). HRMS (ESI): m/z [M+H]+ calcd for $C_{20}H_{20}F_3N_4O_2S$: 437.1259; found: 437.1251. HPLC: 95.7% (% of AUC).

xxxii. N-(2-(4-cyanophenyl)-1-(5-(4-(trifluoromethoxy)phenyl)-1,3,4-thiadiazol-2-yl)ethyl)acetamide (40318)

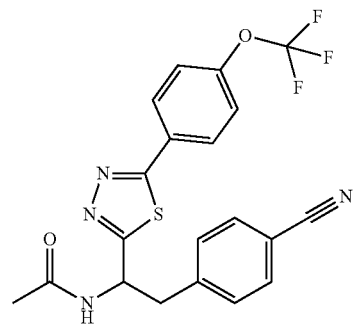 [SMILES: CC(=O)NC(Cc1ccc(C#N)cc1)c1nnc(-c2ccc(OC(F)(F)F)cc2)s1]

¹H NMR (400 MHz, DMSO-d₆) δ 8.86 (d, J=8.3 Hz, 1H), 8.15-8.03 (m, 2H), 7.81-7.73 (m, 2H), 7.58-7.49 (m, 4H), 5.55 (ddd, J=9.9, 8.3, 5.3 Hz, 1H), 3.51 (dd, J=13.8, 5.3 Hz, 2H), 1.78 (s, 3H). HRMS (ESI): m/z [M+H]+ calcd for $C_{20}H_{16}F_3N_4O_2S$: 433.0946; found: 433.0937. HPLC: 97.5% (% of AUC).

xxxiii. N-(2-phenyl-1-(5-phenyl-1,3,4-thiadiazol-2-yl)ethyl)acetamide (41587)

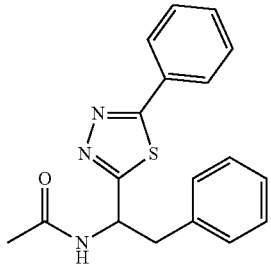 [SMILES: CC(=O)NC(Cc1ccccc1)c1nnc(-c2ccccc2)s1]

¹H NMR (400 MHz, DMSO-d₆) δ 8.82 (d, J=8.1 Hz, 1H), 7.99-7.88 (m, 2H), 7.61-7.45 (m, 3H), 7.36-7.27 (m, 4H), 7.27-7.15 (m, 2H), 5.46 (ddd, J=9.6, 8.2, 5.6 Hz, 1H), 3.38 (dd, J=13.8, 5.6 Hz, 1H), 3.18 (dd, J=13.8, 9.6 Hz, 1H), 1.79 (s, 3H). HRMS (ESI): m/z [M+H]+ calcd for $C_{18}H_{18}N_3OS$: 324.1171; found: 324.1161. HPLC: 98.3% (% of AUC).

xxxiv. N-(2-(4-(aminomethyl)phenyl)-1-(5-(quinolin-4-yl)-1,3,4-thiadiazol-2-yl)ethyl)acetamide (41242)

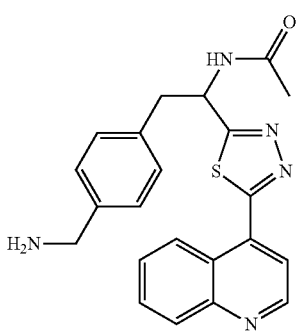 [SMILES: CC(=O)NC(Cc1ccc(CN)cc1)c1nnc(-c2ccnc3ccccc23)s1]

¹H NMR (400 MHz, Methanol-d₄) δ 9.01 (dd, J=4.6, 1.3 Hz, 1H), 8.68 (ddd, J=8.6, 1.4, 0.7 Hz, 1H), 8.18 (ddd, J=8.6, 1.4, 0.7 Hz, 1H), 7.91 (ddd, J=8.4, 6.9, 1.4 Hz, 1H), 7.86 (dd, J=4.6, 1.3 Hz, 1H), 7.76 (ddt, J=8.4, 7.3, 1.4 Hz, 1H), 7.48-7.38 (m, 4H), 5.75 (dd, J=9.3, 6.1 Hz, 1H), 4.09 (s, 2H), 3.62 (dd, J=13.9, 6.1 Hz, 1H), 3.42-3.32 (m, 1H), 1.93 (s, 3H). HRMS (ESI): m/z [M+H]+ calcd for $C_{22}H_{22}N_5OS$: 404.1545; found: 404.1534. HPLC: 99% (% of AUC).

xxxv. N-(2-(4-(aminomethyl)phenyl)-1-(5-(3-methoxy-5-(trifluoromethyl)phenyl)-1,3,4-thiadiazol-2-yl)ethyl)acetamide (42330)

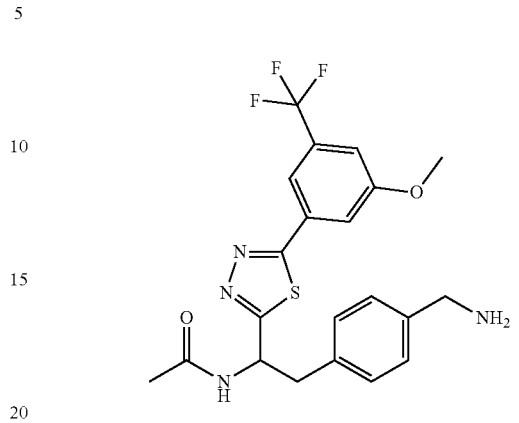

¹H NMR (400 MHz, DMSO-d₆) δ 8.89 (d, J=8.1 Hz, 1H), 8.09 (s, 2H), 7.80 (td, J=1.5, 0.7 Hz, 1H), 7.73 (s, 1H), 7.45 (ddd, J=2.3, 1.6, 0.7 Hz, 1H), 7.36 (d, J=1.1 Hz, 4H), 5.49 (ddd, J=9.7, 8.1, 5.6 Hz, 1H), 3.99 (q, J=5.8 Hz, 3H), 3.92 (s, 4H), 3.42 (dd, J=13.9, 5.6 Hz, 2H), 3.20 (dd, J=13.9, 9.7 Hz, 1H), 1.80 (s, 3H). HRMS (ESI): m/z [M+H]+: 451.14; HPLC: 100% (% of AUC).

xxxvi. N-(2-(3-(aminomethyl)phenyl)-1-(5-(pyridin-3-yl)-1,3,4-thiadiazol-2-yl)ethyl)acetamide (40339)

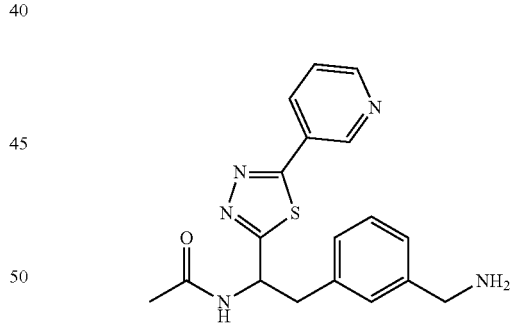

¹H NMR (400 MHz, Methanol-d₄) δ 8.10-8.01 (m, 2H), 7.45 (ddt, J=7.8, 2.0, 1.0 Hz, 2H), 7.37 (s, 4H), 5.64 (dd, J=9.2, 6.3 Hz, 1H), 4.02 (s, 2H), 3.53 (dd, J=13.9, 6.3 Hz, 1H), 3.29-3.18 (m, 1H), 1.91 (s, 3H). HRMS (ESI): m/z [M+H]+ calcd for $C_{18}H_{20}N_5OS$: 353.1310; found: 354.1389. HPLC: 95.3% (% of AUC).

xxxvii. N-(2-(4-aminophenyl)-1-(5-(3-(trifluoromethoxy)phenyl)-1,3,4-thiadiazol-2-yl)ethyl)acetamide (39426)

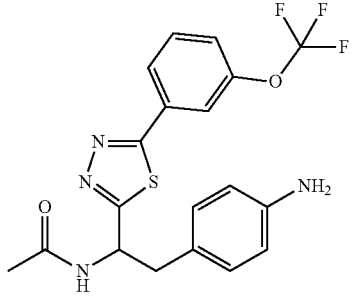 [SMILES: CC(=O)NC(Cc1ccc(N)cc1)c1nnc(-c2cccc(OC(F)(F)F)c2)s1]

$^1$H NMR (400 MHz, DMSO-d$_6$): δ $^1$H NMR (400 MHz, DMSO-d$_6$) δ 8.73 (d, J=8.1 Hz, 1H), 8.25 (ddd, J=7.8, 1.8, 0.5 Hz, 1H), 7.71 (ddd, J=8.4, 7.2, 1.8 Hz, 1H), 7.64-7.47 (m, 2H), 6.96-6.79 (m, 2H), 6.51-6.36 (m, 2H), 5.45-5.25 (m, 1H), 4.87 (s, 2H), 3.14 (dd, J=13.9, 6.1 Hz, 1H), 3.00 (dd, J=13.9, 9.1 Hz, 1H), 1.80 (s, 3H). HRMS (ESI): m/z [M+H]+ calcd for C$_{19}$H$_{18}$F$_3$N$_4$O$_2$S: 423.1103; found: 423.1094. HPLC: 97.2% (% of AUC).

xxxviii. N-(2-(4-cyanophenyl)-1-(5-(2-(trifluoromethoxy)phenyl)-1,3,4-thiadiazol-2-yl)ethyl)acetamide (40311)

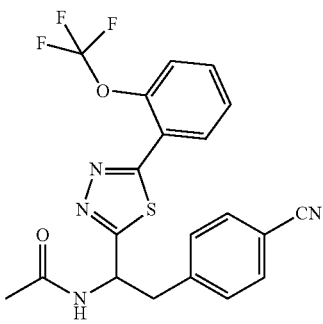 [SMILES: CC(=O)NC(Cc1ccc(C#N)cc1)c1nnc(-c2ccccc2OC(F)(F)F)s1]

$^1$H NMR (400 MHz, DMSO-d$_6$) δ 8.87 (d, J=8.3 Hz, 1H), 8.37-8.19 (m, 1H), 7.79-7.73 (m, 2H), 7.73-7.69 (m, 1H), 7.64-7.57 (m, 2H), 7.54-7.49 (m, 2H), 5.59 (ddd, J=9.9, 8.3, 5.4 Hz, 1H), 3.61-3.38 (m, 2H), 1.77 (s, 3H). HRMS (ESI): m/z [M+H]+ calcd for C$_{20}$H$_{16}$F$_3$N$_4$O$_2$S: 433.0946; found: 433.0935. HPLC: 95.2% (% of AUC).

xxxix. N-(2-(4-(aminomethyl)phenyl)-1-(5-phenyl-1,3,4-thiadiazol-2-yl)ethyl)acetamide (40340)

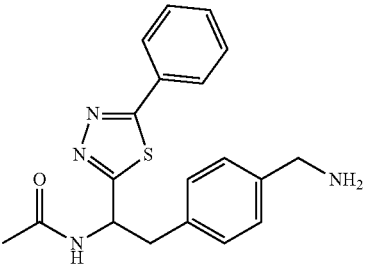 [SMILES: CC(=O)NC(Cc1ccc(CN)cc1)c1nnc(-c2ccccc2)s1]

$^1$H NMR (400 MHz, DMSO-d$_6$) δ $^1$H NMR (400 MHz, DMSO-d$_6$) δ 8.86 (d, J=8.2 Hz, 1H), 8.09 (s, 2H), 7.99-7.85 (m, 2H), 7.60-7.47 (m, 3H), 7.36 (s, 4H), 5.48 (ddd, J=9.5, 8.1, 5.7 Hz, 1H), 3.99 (q, J=5.8 Hz, 2H), 3.21-3.12 (m, 2H), 1.80 (s, 3H). HRMS (ESI): m/z [M+H]+ calcd for C$_{19}$H$_{21}$N$_4$OS: 353.1436; found: 353.1442. HPLC: 98.8% (% of AUC).

xl. N-(1-(5-(3-cyanophenyl)-1,3,4-thiadiazol-2-yl)-2-phenylethyl)acetamide (41670)

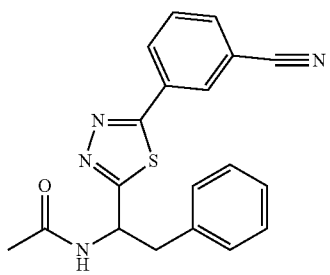 [SMILES: CC(=O)NC(Cc1ccccc1)c1nnc(-c2cccc(C#N)c2)s1]

$^1$H NMR (400 MHz, DMSO-d$_6$) δ $^1$H NMR (400 MHz, DMSO-d$_6$) δ 8.85 (d, J=8.1 Hz, 1H), 8.18-8.10 (m, 2H), 8.04-7.96 (m, 2H), 7.34-7.24 (m, 4H), 7.24-7.16 (m, 1H), 5.48 (ddd, J=9.6, 8.1, 5.5 Hz, 1H), 3.38 (dd, J=13.9, 5.6 Hz, 1H), 3.19 (dd, J=13.9, 9.7 Hz, 1H), 1.79 (s, 3H). HRMS (ESI): m/z [M+H]+ calcd for C$_{19}$H$_{17}$N$_4$OS: 349.1123; found: 349.1117. HPLC: 98.8% (% of AUC).

xli. N-(2-(4-aminophenyl)-1-(5-(pyridin-3-yl)-1,3,4-thiadiazol-2-yl)ethyl)acetamide (39246)

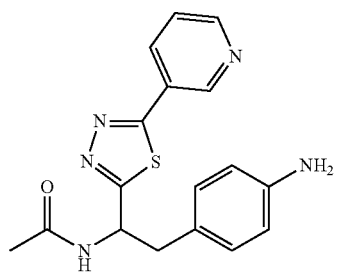 [SMILES: CC(=O)NC(Cc1ccc(N)cc1)c1nnc(-c2cccnc2)s1]

$^1$H NMR (400 MHz, DMSO-d$_6$) δ 9.10 (dd, J=2.3, 0.9 Hz, 1H), 8.79-8.69 (m, 2H), 8.32 (ddd, J=8.0, 2.3, 1.6 Hz, 1H), 7.57 (ddd, J=8.0, 4.8, 0.9 Hz, 1H), 6.94-6.87 (m, 2H), 6.49-6.41 (m, 2H), 5.38-5.21 (m, 1H), 4.88 (s, 2H), 3.17-3.08 (m, 1H), 3.02-2.89 (m, 1H), 1.81 (s, 3H). HRMS (ESI): m/z [M+H]+ calcd for C₁₇H₁₈N₅OS: 340.11232; found: 340.1126. HPLC: 95.1% (% of AUC).

xlii. N-(4-(2-acetamido-2-(5-(3-(trifluoromethoxy)phenyl)-1,3,4-thiadiazol-2-yl)ethyl)benzyl)acetamide (41801)

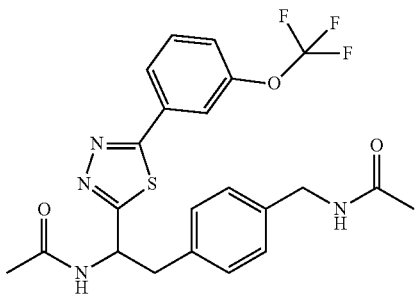 [SMILES: CC(=O)NCc1ccc(CC(NC(C)=O)c2nnc(-c3cccc(OC(F)(F)F)c3)s2)cc1]

Title compound from 40000; (S)—N-(2-(4-(aminomethyl)phenyl)-1-(5-(3-(trifluoromethoxy)phenyl)-1,3,4-thiadiazol-2-yl)ethyl)acetamide. ¹H NMR (400 MHz, DMSO-d₆) δ 8.85 (d, J=8.1 Hz, 1H), 8.18-8.07 (m, 2H), 8.07-7.92 (m, 2H), 7.23 (s, 4H), 5.46 (ddd, J=9.5, 8.0, 5.6 Hz, 1H), 3.68 (s, 2H), 3.16 (dd, J=13.9, 9.6 Hz, 2H), 1.80 (s, 3H). HRMS (ESI): m/z [M+H]+ calcd for C₂₂H₂₂F₃N₄O₃S: 479.1365; found: 479.1363. HPLC: 98.5% (% of AUC).

xliii. N-(2-(4-(aminomethyl)phenyl)-1-(5-(4-cyanophenyl)-1,3,4-thiadiazol-2-yl)ethyl)acetamide (42321)

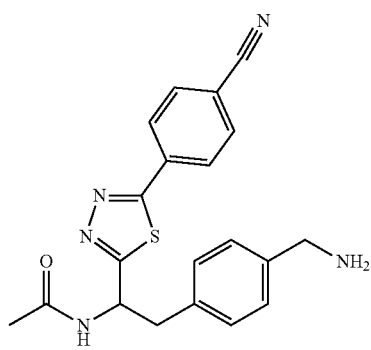 [SMILES: CC(=O)NC(Cc1ccc(CN)cc1)c1nnc(-c2ccc(C#N)cc2)s1]

¹H NMR (400 MHz, DMSO-d₆) δ 8.85 (d, J=8.1 Hz, 1H), 8.18-8.08 (m, 2H), 8.04-7.96 (m, 2H), 7.23 (s, 4H), 5.46 (ddd, J=9.6, 8.0, 5.7 Hz, 1H), 3.68 (s, 2H), 3.16 (dd, J=13.9, 9.6 Hz, 2H), 1.80 (s, 3H). HRMS (ESI): m/z [M+H]+ calcd for C₂₀H₂₀N₅OS: 378.1389; found: 378.1381. HPLC: 90% (% of AUC).

xliv. N-(2-(4-(aminomethyl)phenyl)-1-(5-(4-methyl-3-(trifluoromethyl)phenyl)-1,3,4-thiadiazol-2-yl)ethyl)acetamide (42612)

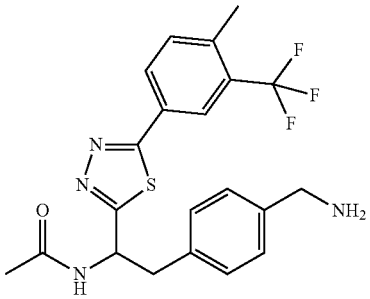 [SMILES: CC(=O)NC(Cc1ccc(CN)cc1)c1nnc(-c2ccc(C)c(C(F)(F)F)c2)s1]

¹H NMR (400 MHz, Methanol-d₄) δ 8.23-8.17 (m, 1H), 8.02 (dd, J=8.1, 2.0 Hz, 1H), 7.55 (ddd, J=8.0, 1.3, 0.6 Hz, 1H), 7.39 (s, 4H), 5.65 (dd, J=9.2, 6.3 Hz, 1H), 4.07 (s, 2H), 3.53 (dd, J=13.9, 6.4 Hz, 1H), 3.27 (d, J=9.2 Hz, 1H), 2.55 (q, J=1.8 Hz, 3H), 1.91 (s, 3H). HRMS (ESI): m/z [M+H]+ calcd for C₂₁H₂₂F₃N₄OS: 435.1466; found: 435.1464. HPLC: 100% (% of AUC).

xlv. N-(2-(4-(aminomethyl)phenyl)-1-(5-(4-fluoro-3-(trifluoromethyl)phenyl)-1,3,4-thiadiazol-2-yl)ethyl)acetamide (42613)

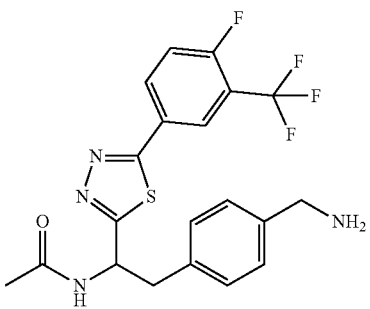 [SMILES: CC(=O)NC(Cc1ccc(CN)cc1)c1nnc(-c2ccc(F)c(C(F)(F)F)c2)s1]

¹H NMR (400 MHz, Methanol-d₄) δ 8.32-8.20 (m, 2H), 7.58-7.49 (m, 1H), 7.39 (s, 4H), 5.65 (dd, J=9.2, 6.3 Hz, 1H), 4.08 (s, 2H), 3.55 (dd, J=13.9, 6.3 Hz, 1H), 3.27 (d, J=9.3 Hz, 1H), 1.91 (s, 3H). HRMS (ESI): m/z [M+H]+ calcd for C₂₀H₁₉F₄N₄OS: 439.1216; found: 439.1219. HPLC: 100% (% of AUC).

6. General Procedure for the Synthesis of Thiadiazoles (Route III)

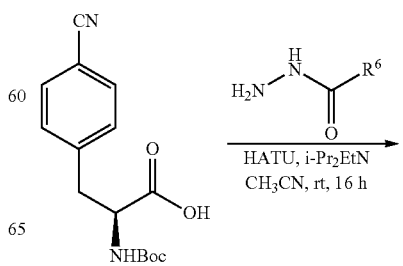

-continued

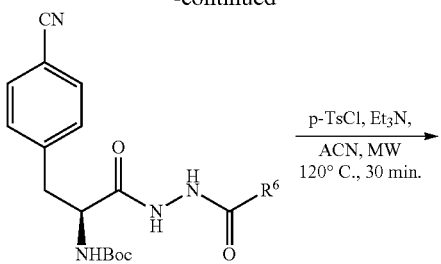

p-TsCl, Et₃N,
ACN, MW
120° C., 30 min.

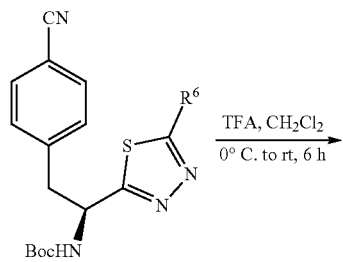

TFA, CH₂Cl₂
0° C. to rt, 6 h

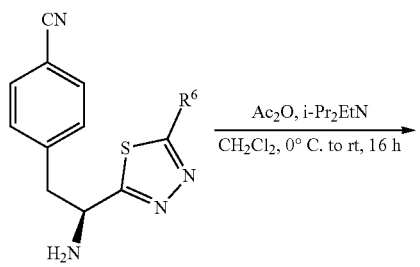

Ac₂O, i-Pr₂EtN
CH₂Cl₂, 0° C. to rt, 16 h

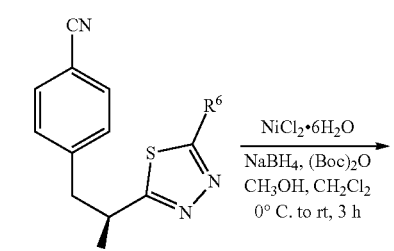

NiCl₂·6H₂O
NaBH₄, (Boc)₂O
CH₃OH, CH₂Cl₂
0° C. to rt, 3 h

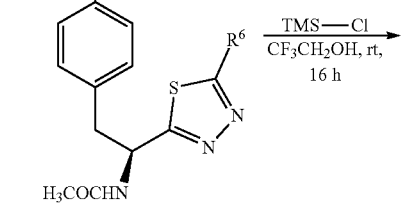

TMS—Cl
CF₃CH₂OH, rt,
16 h

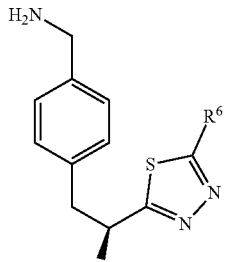

a. N-(5-amino-1-(5-(pyridin-4-yl)-1,3,4-oxadiazol-2-yl)pentyl)acetamide (40074)

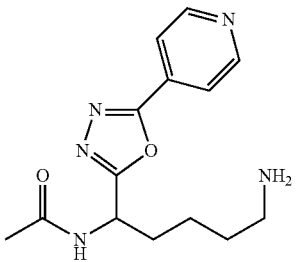 [SMILES: CC(=O)NC(CCCCN)c1nnc(-c2ccncc2)o1]

¹H NMR (400 MHz, Methanol-d₄) δ 8.81 (d, J=5.1 Hz, 2H), 8.07-8.00 (m, 2H), 5.33 (dd, J=8.8, 6.0 Hz, 1H), 2.95 (t, J=7.6 Hz, 2H), 2.15 (ddt, J=13.6, 9.4, 6.2 Hz, 1H), 2.04 (s, 3H), 2.02-1.93 (m, 1H), 1.84-1.64 (m, 2H), 1.64-1.47 (m, 2H). HRMS (ESI): m/z [M+H]+ calcd for C₁₄H₂₀N₅O₂: 290.1617; found: 290.1608.

b. N-(2-(4-cyanophenyl)-1-(5-phenyl-1,3,4-oxadiazol-2-yl)ethyl)acetamide (41139)

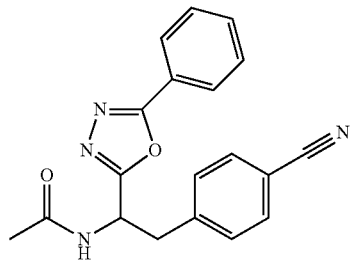 [SMILES: CC(=O)NC(Cc1ccc(C#N)cc1)c1nnc(-c2ccccc2)o1]

¹H NMR (400 MHz, DMSO-d₆) δ ¹H NMR (400 MHz, DMSO-d₆) δ 8.72 (d, J=8.3 Hz, 1H), 7.96 (dd, J=2.0, 1.3 Hz, 1H), 7.94 (d, J=1.8 Hz, 1H), 7.80-7.73 (m, 2H), 7.66-7.57 (m, 3H), 7.53-7.46 (m, 2H), 5.49-5.35 (m, 1H), 3.42 (dd, J=13.7, 6.0 Hz, 1H), 3.28-3.22 (m, 1H), 1.80 (s, 3H). HRMS (ESI): m/z [M+H]+ calcd for C₁₉H₁₇N₄O₂: 333.1352; found: 333.1338. HPLC: 97.7% (% of AUC).

c. N-(2-(4-(aminomethyl)phenyl)-1-(5-phenyl-1,3,4-oxadiazol-2-yl)ethyl)acetamide

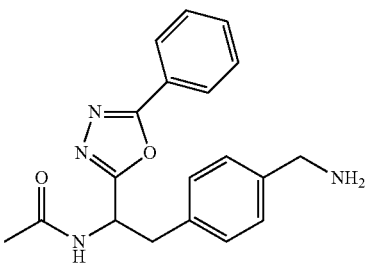 [SMILES: CC(=O)NC(Cc1ccc(CN)cc1)c1nnc(-c2ccccc2)o1]

¹H NMR (400 MHz, Methanol-d₄) δ 8.05-7.95 (m, 2H), 7.65-7.52 (m, 3H), 7.38 (s, 4H), 5.56 (dd, J=8.7, 6.9 Hz, 1H), 4.07 (s, 2H), 3.44 (dd, J=13.8, 6.9 Hz, 1H), 3.29-3.23 (m, d. N-(2-(4-(aminomethyl)phenyl)-1-(5-(3-methoxyphenyl)-1,3,4-oxadiazol-2-yl)ethyl)acetamide Hydrochloride (41234)

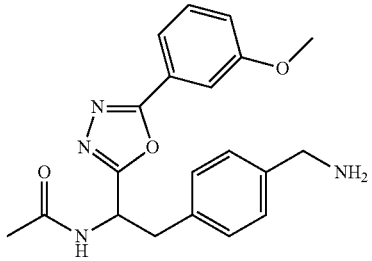 [SMILES: COc1cccc(-c2nnc(C(Cc3ccc(CN)cc3)NC(C)=O)o2)c1]

$^1$H NMR (300 MHz, DMSO-d$_6$): δ 8.85 (d, J=7.6 Hz, 1H), 8.41 (brs, 3H), 7.54 (s, 2H), 7.46 (s, 1H), 7.41-7.40 (m, 2H), 7.34-7.33 (m, 2H), 7.22 (s, 1H), 5.39-5.37 (m, 1H), 3.97 (s, 2H), 3.85 (s, 3H), 3.33-3.30 (m, 1H), 3.21-3.16 (m, 1H), 1.83 (s, 3H); HRMS (ESI): m/z [M+H]+ calcd for C$_{20}$H$_{23}$N$_4$O$_3$: 367.1770; found: 367.1759; MS (MM): m/z 367.0 [M-HCl]+; HPLC: 92.3 (% of AUC).

e. N-(2-(4-(aminomethyl)phenyl)-1-(5-(4-fluoro-3-(trifluoromethoxy)phenyl)-1,3,4-oxadiazol-2-yl)ethyl)acetamide Hydrochloride (41322)

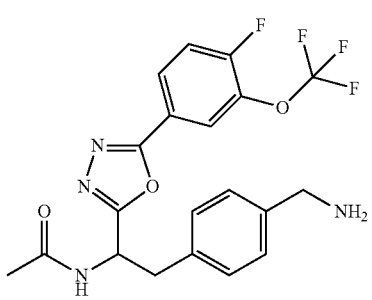 [SMILES: CC(=O)NC(Cc1ccc(CN)cc1)c1nnc(-c2ccc(F)c(OC(F)(F)F)c2)o1]

$^1$H NMR (400 MHz, DMSO-d$_6$): δ 8.78 (d, J=8.0 Hz, 1H), 8.12-8.06 (m, 5H), 7.83-7.78 (m, 1H), 7.36-7.35 (m, 4H), 5.41-5.35 (m, 1H), 3.98 (s, 2H), 3.33-3.30 (m, 1H), 3.19-3.14 (m, 1H), 1.82 (s, 3H); HRMS (ESI): m/z [M+H]+ calcd for C$_{20}$H$_{19}$F$_4$N$_4$O$_3$: 439.1393; found: 439.1384; MS (MM): m/z 439.1 [M-HCl]+; HPLC: 97.4 (% of AUC).

f. N-(2-(4-(aminomethyl)phenyl)-1-(5-(3-(trifluoromethoxy)phenyl)-1,3,4-oxadiazol-2-yl)ethyl)acetamide Hydrochloride (41321)

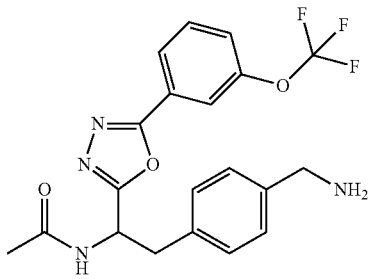 [SMILES: CC(=O)NC(Cc1ccc(CN)cc1)c1nnc(-c2cccc(OC(F)(F)F)c2)o1]

$^1$H NMR (400 MHz, DMSO-d$_6$): δ 8.79 (d, J=8.4 Hz, 1H), 8.17 (brs, 3H), 8.02 (d, J=8.0 Hz, 1H), 7.89 (s, 1H), 7.80-7.76 (m, 1H), 7.70-7.68 (m, 1H), 7.39-7.33 (m, 4H), 5.42-5.36 (m, 1H), 3.98 (s, 2H), 3.33-3.30 (m, 1H), 3.20-3.15 (m, 1H), 1.82 (s, 3H); HRMS (ESI): m/z [M+H]+ calcd for C$_{20}$H$_{20}$F$_3$N$_4$O$_3$: 421.1488; found: 421.1481; MS (MM): m/z 421.1 [M-HCl]+; HPLC: 98.8 (% of AUC).

g. N-(2-(4-(aminomethyl)phenyl)-1-(5-(3-fluorophenyl)-1,3,4-oxadiazol-2-yl)ethyl)acetamide Hydrochloride (41235)

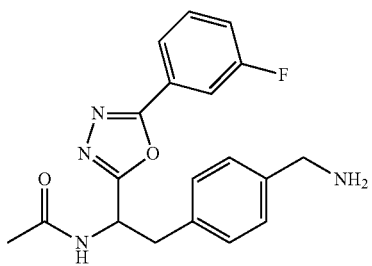

$^1$H NMR (400 MHz, DMSO-d$_6$): δ 8.80 (d, J=8.0 Hz, 1H), 8.23 (brs, 3H), 7.83 (d, J=7.6 Hz, 1H), 7.78-7.76 (m, 1H), 7.70-7.67 (m, 1H), 7.53-7.52 (m, 1H), 7.39-7.33 (m, 4H), 5.39-5.38 (m, 1H), 3.97 (d, J=5.6 Hz, 2H), 3.32-3.30 (m, 1H), 3.20-3.15 (m, 1H), 1.83 (s, 3H); HRMS (ESI): m/z [M+H]+ calcd for C$_{19}$H$_{20}$FN$_4$O$_2$: 355.1570; found: 355.1559; MS (MM): m/z 355.1 [M-HCl]+; HPLC: 96.8 (% of AUC).

h. N-(2-(4-(aminomethyl)phenyl)-1-(5-(3-(trifluoromethyl)phenyl)-1,3,4-oxadiazol-2-yl)ethyl)acetamide Hydrochloride (41236)

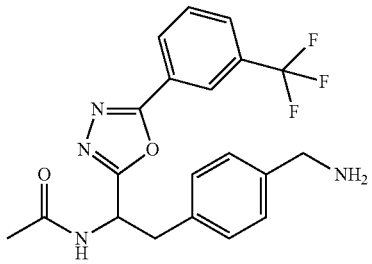 [SMILES: CC(=O)NC(Cc1ccc(CN)cc1)c1nnc(-c2cccc(C(F)(F)F)c2)o1]

$^1$H NMR (300 MHz, DMSO-$d_6$): δ 8.84 (d, J=7.8 Hz, 1H), 8.34-8.28 (m, 4H), 8.22 (s, 1H), 8.05 (d, J=8.1 Hz, 1H), 7.91-7.85 (m, 1H), 7.41-7.33 (m, 4H), 5.44-5.36 (m, 1H), 3.98-3.96 (m, 2H), 3.33-3.30 (m, 1H), 3.22-3.15 (m, 1H), 1.83 (s, 3H); HRMS (ESI): m/z [M+H]+ calcd for $C_{20}H_{20}F_3N_4O_2$: 405.1538; found: 405.1540; MS (MM): m/z 405.1 [M-HCl]$^+$; HPLC: 98.6 (% of AUC).

i. N-(2-(4-(aminomethyl)phenyl)-1-(5-(3,4-difluorophenyl)-1,3,4-oxadiazol-2-yl)ethyl)acetamide Hydrochloride (41237)

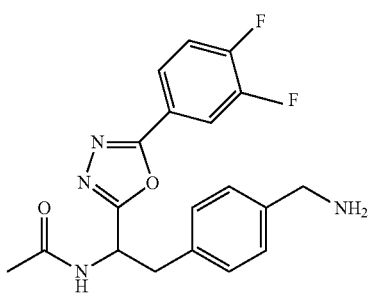

$^1$H NMR (300 MHz, DMSO-$d_6$): δ 8.83 (d, J=8.1 Hz, 1H), 8.38 (brs, 3H), 8.06-8.01 (m, 1H), 7.83 (brs, 1H), 7.76-7.67 (m, 1H), 7.42-7.32 (m, 4H), 5.41-5.33 (m, 1H), 3.97 (s, 2H), 3.31-3.29 (m, 1H), 3.21-3.14 (m, 1H), 1.83 (s, 3H); HRMS (ESI): m/z [M+H]+ calcd for $C_{19}H_{19}F_2N_4O_2$: 373.1476; found: 373.1465; MS (MM) m/z 373.1[M-HCl]$^+$; HPLC: 97.8 (% of AUC).

j. N-(2-(4-cyanophenyl)-1-(5-(4-fluorophenyl)-1,3,4-oxadiazol-2-yl)ethyl)acetamide (41286)

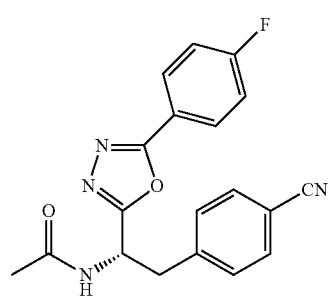 [SMILES: CC(=O)N[C@@H](Cc1ccc(C#N)cc1)c1nnc(-c2ccc(F)cc2)o1]

$^1$H NMR (300 MHz, DMSO-$d_6$): δ 8.73 (d, J=8.1 Hz, 1H), 8.05-8.00 (m, 2H), 7.77 (d, J=7.8 Hz, 2H), 7.52-7.43 (m, 4H), 5.48-5.43 (m, 1H), 3.46-3.39 (m, 1H), 3.29-3.21 (m, 1H), 1.80 (s, 3H); HRMS (ESI): m/z [M+H]+ calcd for $C_{19}H_{16}FN_4O_2$: 351.1257; found: 351.1255; HPLC: 97.1 (% of AUC).

k. N-(2-(4-cyanophenyl)-1-(5-(pyridin-4-yl)-1,3,4-oxadiazol-2-yl)ethyl)acetamide (41287)

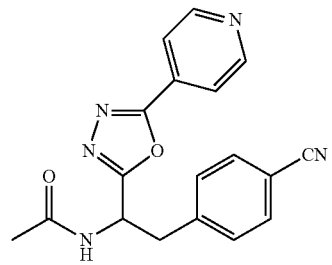 [SMILES: CC(=O)NC(Cc1ccc(C#N)cc1)c1nnc(-c2ccncc2)o1]

$^1$H NMR (300 MHz, DMSO-$d_6$): δ 8.84 (d, J=6.0 Hz, 2H), 8.76 (d, J=8.4 Hz, 1H), 7.90 (d, J=6.0 Hz, 2H), 7.78 (d, J=8.1 Hz, 2H), 7.51 (d, J=7.8 Hz, 2H), 5.47-5.46 (m, 1H), 3.47-3.41 (m, 1H), 3.27-3.23 (m, 1H), 1.81 (s, 3H); HRMS (ESI): m/z [M+H]+ calcd for $C_{18}H_{16}N_5O_2$: 334.1304; found: 334.1294; HPLC: 93.0 (% of AUC).

l. N-(2-(4-(aminomethyl)phenyl)-1-(5-(3,5-bis(trifluoromethyl)phenyl)-1,3,4-oxadiazol-2-yl)ethyl)acetamide (41934)

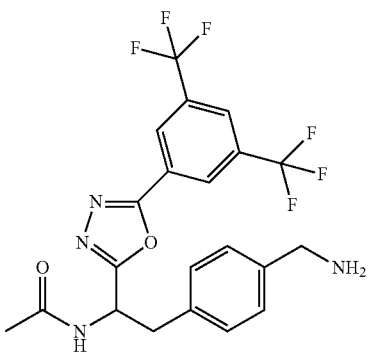 [SMILES: CC(=O)NC(Cc1ccc(CN)cc1)c1nnc(-c2cc(C(F)(F)F)cc(C(F)(F)F)c2)o1]

$^1$H NMR (400 MHz, Methanol-$d_4$) δ 8.58-8.54 (m, 2H), 8.27 (s, 1H), 7.40 (s, 4H), 5.61 (dd, J=9.2, 6.5 Hz, 1H), 4.08 (s, 2H), 3.48 (dd, J=13.8, 6.5 Hz, 1H), 3.29-3.25 (m, 1H), 1.94 (s, 3H). HRMS (ESI): m/z [M+H]+ calcd for $C_{21}H_{19}F_6N_4O_2$: 473.14067; found: 473.14081.

m. N-(2-(3-(aminomethyl)phenyl)-1-(5-(3-(trifluoromethoxy)phenyl)-1,3,4-thiadiazol-2-yl)ethyl)cyclohexanecarboxamide (42461)

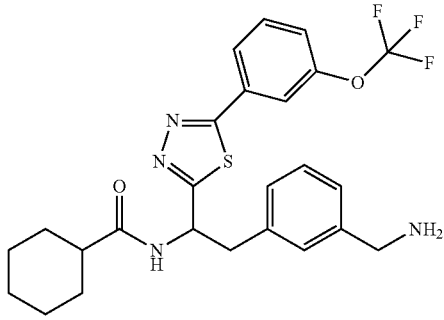 [SMILES: NCc1cccc(CC(NC(=O)C2CCCCC2)c2nnc(-c3cccc(OC(F)(F)F)c3)s2)c1]

$^1$H NMR (400 MHz, DMSO-d$_6$) δ 8.66 (d, J=8.3 Hz, 1H), 8.16-7.86 (m, 2H), 7.68 (t, J=8.0 Hz, 1H), 7.57 (d, J=8.8 Hz, 1H), 7.21 (s, 3H), 5.42 (s, 1H), 3.65 (s, 2H), 3.55-3.37 (m, 2H), 2.07 (s, 1H), 1.93-1.26 (m, 5H), 1.41-0.70 (m, 5H). HRMS (ESI): m/z [M+H]+ calcd for C$_{25}$H$_{28}$F$_3$N$_4$O$_2$S: 505.1807; found: 505.1883. HPLC: 99.69% (% of AUC).

n. N-(2-(3-(aminomethyl)phenyl)-1-(5-(3-(trifluoromethoxy)phenyl)-1,3,4-thiadiazol-2-yl)ethyl)butyramide (42467)

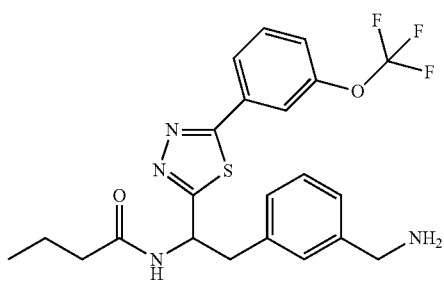 [SMILES: CCCC(=O)NC(Cc1cccc(CN)c1)c1nnc(-c2cccc(OC(F)(F)F)c2)s1]

$^1$H NMR (400 MHz, Chloroform-d) δ 7.87-7.70 (m, 2H), 7.49 (t, J=8.0 Hz, 1H), 7.39-7.28 (m, 1H), 7.26-7.18 (m, 2H), 7.14 (d, J=8.0 Hz, 2H), 6.39 (d, J=7.9 Hz, 1H), 5.73 (q, J=7.2 Hz, 1H), 3.83 (s, 2H), 3.39 (dt, J=14.1, 6.8 Hz, 2H), 2.25-2.12 (m, 2H), 1.63 (q, J=7.4 Hz, 2H), 0.90 (td, J=7.4, 5.2 Hz, 3H). HRMS (ESI): m/z [M+H]+ calcd for C$_{22}$H$_{24}$F$_3$N$_4$O$_2$S: 465.1494; found: 465.1564. HPLC: 94.16% (% of AUC).

o. N-(2-(3-(aminomethyl)phenyl)-1-(5-(3-(trifluoromethoxy)phenyl)-1,3,4-thiadiazol-2-yl)ethyl)cyclopropanecarboxamide (42468)

$^1$H NMR (400 MHz, Chloroform-d) δ 7.82-7.62 (m, 2H), 7.44 (d, J=8.2 Hz, 1H), 7.26 (dd, J=0.8, 0.3 Hz, 2H), 7.14 (d, J=3.9 Hz, 3H), 5.60 (s, 1H), 3.74 (s, 2H), 3.31 (p, J=1.6 Hz, 2H), 1.41 (s, 1H), 0.86 (dd, J=4.5, 2.9 Hz, 2H), 0.70 (dd, J=7.8, 3.1 Hz, 2H). HRMS (ESI): m/z [M+H]+ calcd for C$_{22}$H$_{22}$F$_3$N$_4$O$_2$S: 463.1337; found: 463.1410. HPLC: 100% (% of AUC).

7. General Procedure for the Synthesis of Thiadiazoles (Route IV)

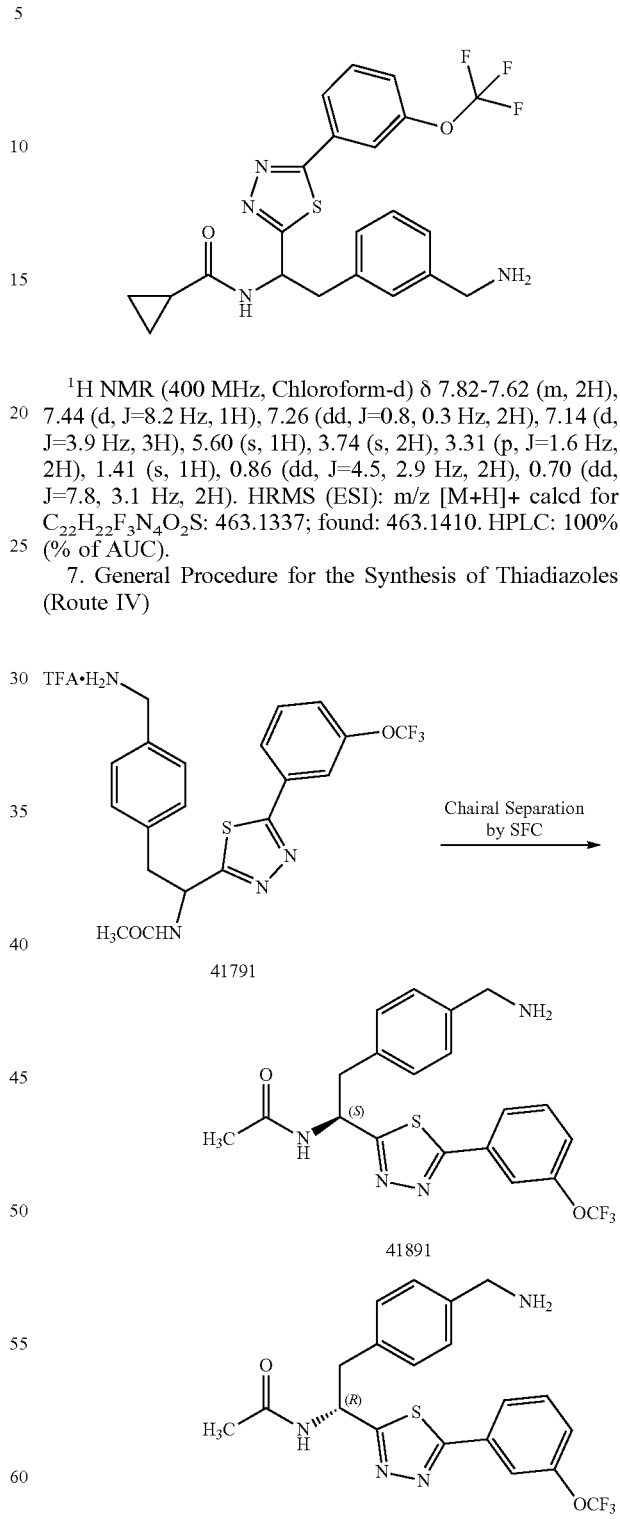

41791 was then subjected to SFC purification as follows: Column: Chiral Pak IA (20×250) mm 5 mm; Co-Solvent (Channel-B)-0.4% DEA in CH$_3$OH; % of Co-Solvent-45%;

Total Flow-70 g/min; Detection UV-265 nm; ABPR-100 Bar; Column Oven Temperature-Ambient; Run Time-5 min; Channel-A-Super Critical Fluid CO₂; Solubility-CH₃OH. Two enantiomers were collected and stereochemistry was assigned arbitrarily.

a. (S)—N-(2-(4-(aminomethyl)phenyl)-1-(5-(3-(trifluoromethoxy)phenyl)-1,3,4-thiadiazol-2-yl)ethyl)acetamide (41891)

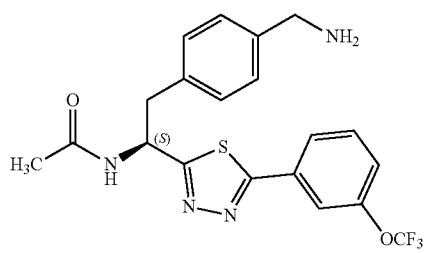

41891

Peak-1: 41891 was isolated as an off-white solid. $^1$H NMR (400 MHz, DMSO-d$_6$): δ 8.86 (d, J=8.0 Hz, 1H), 7.99-7.97 (m, 1H) 7.94 (s, 1H), 7.72-7.68 (m, 1H), 7.61-7.58 (m, 1H), 7.24 (s, 4H), 5.49-5.43 (m, 1H), 3.69 (s, 2H), 3.39-3.35 (m, 1H), 3.20-3.14 (m, 1H), 1.81 (s, 3H); HRMS (ESI): m/z [M+H]+ calcd for C$_{20}$H$_{20}$F$_3$N$_4$O$_2$S: 437.1259; found: 437.1259; MS (MM): m/z 437.1 [M+H]$^+$; HPLC: 97.9 (% of AUC).

b. (R)—N-(2-(4-(aminomethyl)phenyl)-1-(5-(3-(trifluoromethoxy)phenyl)-1,3,4-thiadiazol-2-yl)ethyl)acetamide (41892)

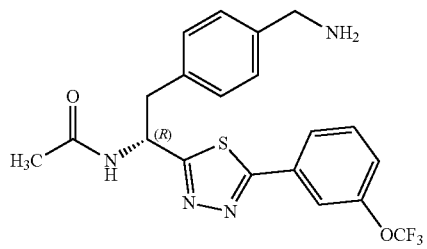

41892

Peak-2: 41892 was isolated as an off-white solid. $^1$H NMR (400 MHz, DMSO-d$_6$): δ 8.86 (d, J=8.0 Hz, 1H), 7.99-7.97 (m, 1H) 7.94 (s, 1H), 7.72-7.68 (m, 1H), 7.60-7.58 (m, 1H), 7.24 (s, 4H), 5.48-5.43 (m, 1H), 3.69 (s, 2H), 3.38-3.37 (m, 1H), 3.20-3.14 (m, 1H), 1.81 (s, 3H); HRMS (ESI): m/z [M+H]+ calcd for C$_{20}$H$_{20}$F$_3$N$_4$O$_2$S: 437.1259; found: 436.1255; MS (MM): m/z 437.1 [M+H]$^+$; HPLC: 96.0 (% of AUC).

8. Synthesis of Compound No. 41792

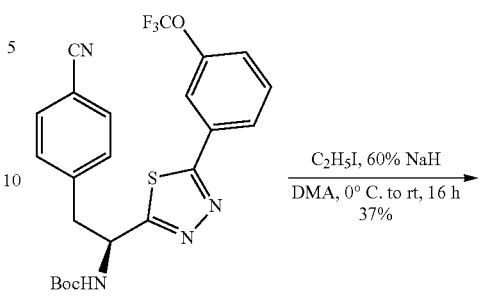

1

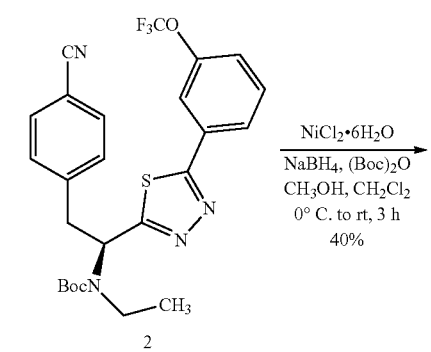

2

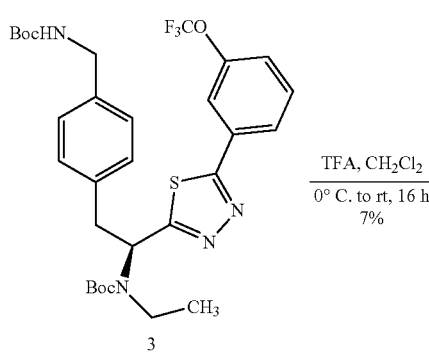

3

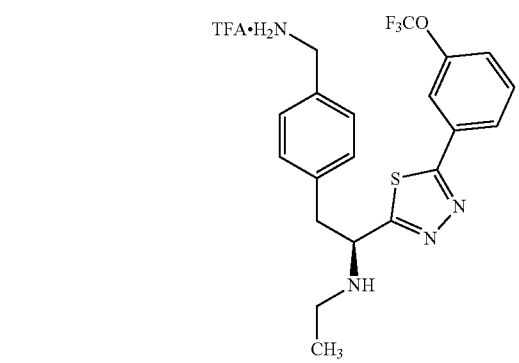

Intermediate 1 was synthesized as detailed above.

a. Preparation of Intermediate 2

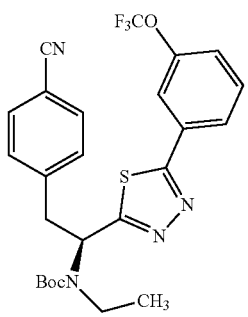

A solution of tert-butyl (S)-(2-(4-cyanophenyl)-1-(5-(3-(trifluoromethoxy)phenyl)-1,3,4-thiadiazol-2-yl)ethyl)carbamate (1, 280 mg, 0.64 mmol) in THF (10 mL) at 0° C. was charged with 60% NaH (77 mg, 1.94 mmol) as portion wise over 2 min and stirred at same temperature for 30 min. To this, EtI (0.12 mL, 1.62 mmol) was added at 0° C. and stirred at room temperature for 16 h. The reaction mixture was quenched with CH$_3$OH (1 mL). Thereafter, the solvents were removed under reduced pressure to get crude, which was purified over silica gel column chromatography (eluting with 15% to 20% EtOAc-hexane) to afford tert-butyl (S)-(2-(4-cyanophenyl)-1-(5-(3-(trifluoromethoxy)phenyl)-1,3,4-thiadiazol-2-yl)ethyl)(ethyl)carbamate in 37% yield as a solid. MS (MM): m/z=461.0 [M-tBu]$^+$.

b. 2-(4-(aminomethyl)phenyl)-N-ethyl-1-(5-(3-(trifluoromethoxy)phenyl)-1,3,4-thiadiazol-2-yl)ethan-1-amine (941792)

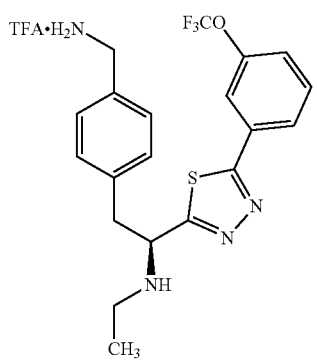

A solution of (tert-butyl (S)-(2-(4-(((tert-butoxycarbonyl)amino)methyl)phenyl)-1-(5-(3-(trifluoromethoxy)phenyl)-1,3,4-thiadiazol-2-yl)ethyl)(ethyl)carbamate (3, 45 mg, 0.07 mmol) in CH$_2$Cl$_2$ (2 mL) at 0° C. was charged with TFA (0.13 mL, 0.18 mmol) as dropwise over 1 min and stirred at room temperature for 16 h. The reaction mixture volatiles were removed under reduced pressure and co-distilled with CH$_2$Cl$_2$ (2×10 mL) to get crude, which was purified by Prep-HPLC to afford trifluoro acetic salt of (S)-2-(4-(aminomethyl)phenyl)-N-ethyl-1-(5-(3-(trifluoromethoxy)phenyl)-1,3,4-thiadiazol-2-yl)ethan-1-amine in 7% yield as a semi solid. $^1$H NMR (400 MHz, CD$_3$OD): δ 7.78-7.76 (m, 2H), 7.54 (t, J=8.0 Hz, 1H), 7.41 (d, J=8.0 Hz, 1H), 7.28 (d, J=8.0 Hz, 2H), 7.19 (d, J=8.0 Hz, 2H), 5.28-5.24 (m, 1H), 3.95 (s, 2H), 3.65-3.61 (m, 1H), 3.33-3.27 (m, 1H), 3.07-3.02 (m, 2H), 1.28 (t, J=7.2 Hz, 3H); MS (MM): m/z 423.1 [M-TFA]$^+$; HPLC: >99 (% of AUC).

9. General Procedure for the Synthesis of Thiadiazoles (Route V)

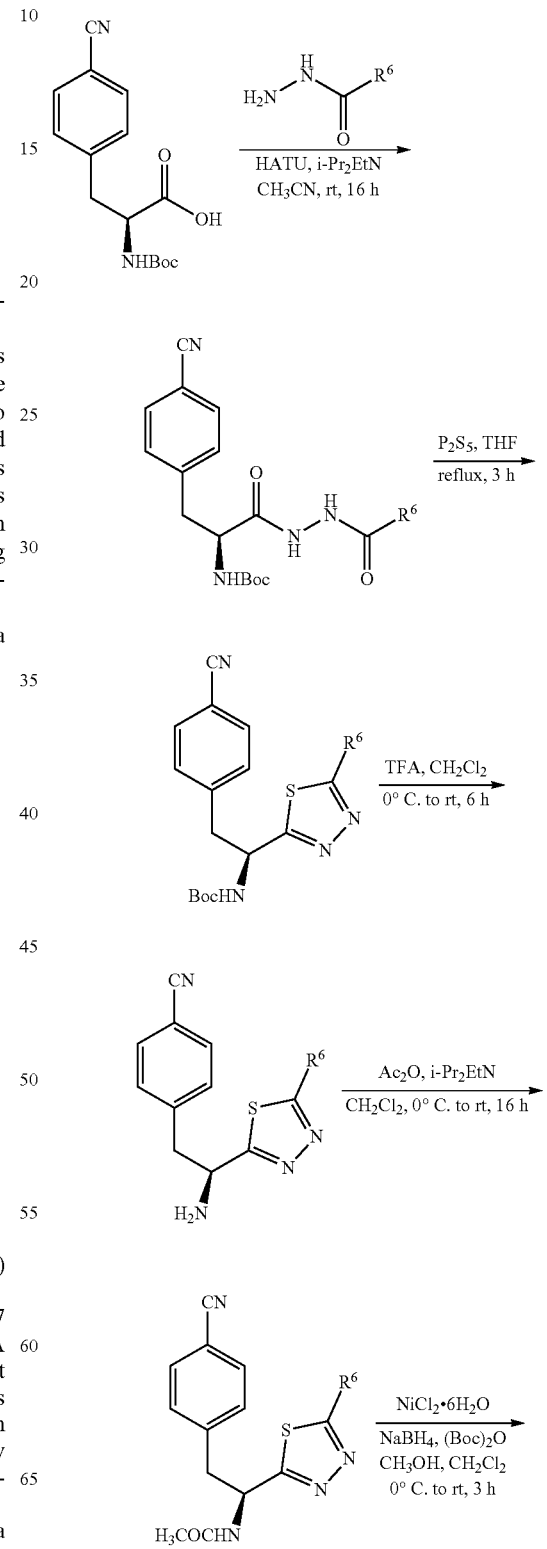

211

-continued

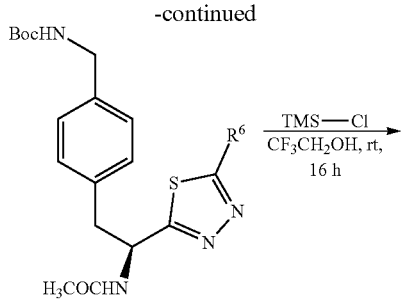

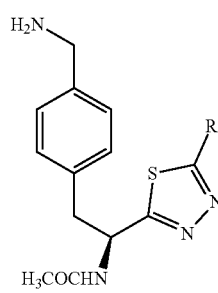

a. N-(2-(4-(aminomethyl)phenyl)-1-(5-(3,4-difluoro-phenyl)-1,3,4-thiadiazol-2-yl)ethyl)acetamide Hydrochloride (41206)

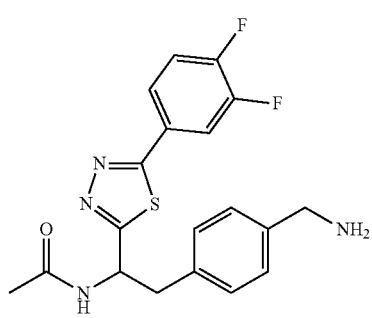 [SMILES: CC(=O)NC(Cc1ccc(CN)cc1)c1nnc(-c2ccc(F)c(F)c2)s1]

¹H NMR (400 MHz, DMSO-d₆): δ 8.94 (d, J=8.4 Hz, 1H), 8.20 (brs, 3H), 8.08-8.05 (m, 1H), 7.85-7.83 (m, 1H), 7.67-7.63 (m, 1H), 7.38 (s, 4H), 5.51-5.45 (m, 1H), 3.99 (d, J=5.6 Hz, 2H), 3.44-3.39 (m, 1H), 3.23-3.17 (m, 1H), 1.80 (s, 3H); HRMS (ESI): m/z [M+H]+ calcd for $C_{19}H_{19}F_2N_4OS$: 389.1248; found: 389.1249; MS (MM): m/z 389.1 [M-HCl]+; HPLC: 94.3 (% of AUC).

212 b. N-(2-(4-(aminomethyl)phenyl)-1-(5-(3-methoxy-phenyl)-1,3,4-thiadiazol-2-yl)ethyl)acetamide Hydrochloride (41149)

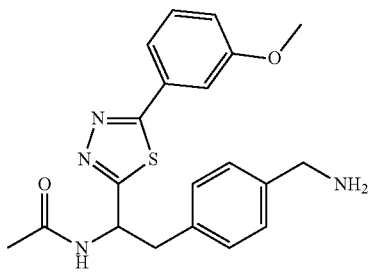 [SMILES: COc1cccc(-c2nnc(C(Cc3ccc(CN)cc3)NC(C)=O)s2)c1]

¹H NMR (300 MHz, DMSO-d₆): δ 8.91 (d, J=8.4 Hz, 1H), 8.21 (brs, 3H), 7.52-7.43 (m, 3H), 7.38 (s, 4H), 7.15 (d, J=7.8 Hz, 1H), 5.49-5.44 (m, 1H), 4.08 (d, J=5.7 Hz, 2H), 3.84 (s, 3H), 3.48-3.33 (m, 1H), 3.24-3.21 (m, 1H), 1.81 (s, 3H); HRMS (ESI): m/z [M+H]+ calcd for $C_{20}H_{23}N_4O_2S$: 383.1542; found: 383.1538; MS (MM): m/z 383.0 [M-HCl]+; HPLC: 91.2 (% of AUC).

c. N-(2-(4-(aminomethyl)phenyl)-1-(5-(3-fluorophe-nyl)-1,3,4-thiadiazol-2-yl)ethyl)acetamide Hydro-chloride (41151)

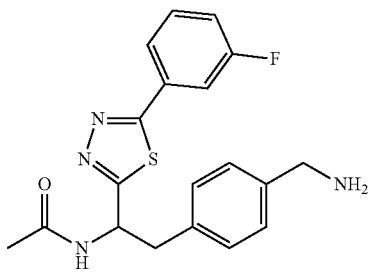 [SMILES: CC(=O)NC(Cc1ccc(CN)cc1)c1nnc(-c2cccc(F)c2)s1]

¹H NMR (400 MHz, DMSO-d₆): δ 8.96 (d, J=8.4 Hz, 1H), 8.20 (brs, 3H), 7.79 (d, J=1.6 Hz, 2H), 7.63-7.58 (m, 1H), 7.46-7.36 (m, 5H), 5.52-5.46 (m, 1H), 3.99 (d, J=5.6 Hz, 2H), 3.44-3.40 (m, 1H), 3.24-3.18 (m, 1H), 1.81 (s, 3H); HRMS (ESI): m/z [M+H]+ calcd for $C_{19}H_{20}FN_4OS$: 371.1342; found: 371.1339; MS (MM): m/z 371.0 [M-HCl]+; HPLC: 91.2 (% of AUC).

d. N-(2-(4-(aminomethyl)phenyl)-1-(5-(3-(trifluo-romethyl)phenyl)-1,3,4-thiadiazol-2-yl)ethyl)acet-amide Hydrochloride (41152)

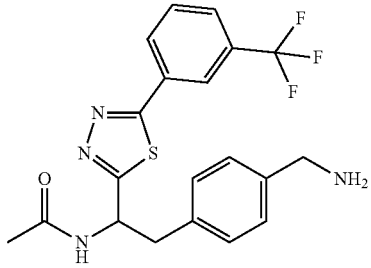 [SMILES: CC(=O)NC(Cc1ccc(CN)cc1)c1nnc(-c2cccc(C(F)(F)F)c2)s1]

¹H NMR (400 MHz, DMSO-d₆): δ 8.95 (d, J=8.0 Hz, 1H), 8.26-8.21 (m, 5H), 7.96 (d, J=4.0 Hz, 1H), 7.83-7.79 (m, 1H), 7.39-7.36 (m, 4H), 5.53-5.47 (m, 1H), 3.99 (d, J=5.6 Hz, 2H), 3.46-3.41 (m, 1H), 3.25-3.19 (m, 1H), 1.81 (s, 3H); HRMS (ESI): m/z [M+H]+ calcd for C₂₀H₁₈F₃N₄OS: 421.1310; found: 421.1307; MS (MM): m/z 421.0 [M-HCl]⁺; HPLC: 91.8 (% of AUC).

e. (N-(2-(4-(aminomethyl)phenyl)-1-(5-(3,5-dimethylphenyl)-1,3,4-thiadiazol-2-yl)ethyl)acetamide Hydrochloride (42182)

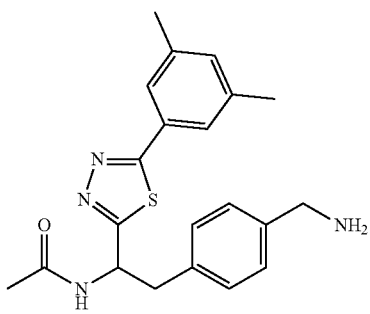 [SMILES: CC(=O)NC(Cc1ccc(CN)cc1)c1nnc(-c2cc(C)cc(C)c2)s1]

¹H NMR (400 MHz, DMSO-d₆) δ: 8.90 (d, J=8.0 Hz, 1H), 8.19 (brs, 3H), 7.56 (s, 2H) 7.38 (s, 4H), 7.21-7.19 (m, 1H), 5.50-5.44 (m, 1H), 4.01-3.97 (m, 2H), 3.44-3.40 (m, 1H), 3.23-3.17 (m, 1H), 2.35 (s, 6H), 1.80 (s, 3H); HRMS (ESI): m/z [M+H]+ calcd for C₂₁H₂₅N₄OS: 381.1749; found: 381.1745; MS (MM): m/z=381 [M-HCl]⁺; HPLC: 95.2% (% of AUC).

f. N-(2-(4-(aminomethyl)phenyl)-1-(5-(3-BROMO-5-(trifluoromethyl)phenyl)-1,3,4-thiadiazol-2-yl)ethyl)acetamide Hydrochloride (42549)

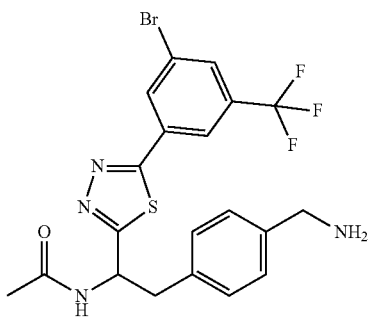

¹H NMR (400 MHz, DMSO-d₆) δ: 9.00 (d, J=8.0 Hz, 1H), 8.45 (s, 1H), 8.32 (brs, 3H), 8.27 (s, 1H), 8.21 (s, 1H), 7.42-7.37 (m, 4H), 5.53-5.47 (m, 1H), 3.98 (s, 2H), 3.46-3.37 (m, 1H), 3.26-3.20 (m, 1H), 1.82 (s, 3H); HRMS (ESI): m/z [M+H]+ calcd for C₂₀H₁₉BrF₃N₄OS: 499.0415; found: 499.0387; MS (MM): m/z=501 [M-HCl]⁺; HPLC: 92.7 (% of AUC).

g. N-(2-(4-(aminomethyl)phenyl)-1-(5-(3-methyl-5-(trifluoromethyl)phenyl)-1,3,4-thiadiazol-2-yl)ethyl)acetamide Hydrochloride (42336)

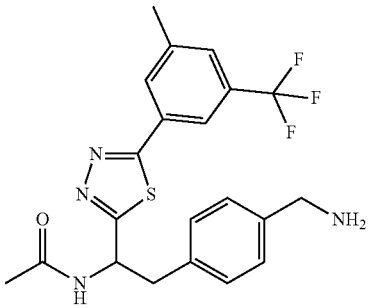 [SMILES: CC(=O)NC(Cc1ccc(CN)cc1)c1nnc(-c2cc(C)cc(C(F)(F)F)c2)s1]

¹H NMR (400 MHz, DMSO-d₆) δ: 8.92 (d, J=8.0 Hz, 1H), 8.15 (brs, 3H), 8.08 (s, 1H), 8.05 (s, 1H), 7.78 (s, 1H), 7.38 (m, 4H), 5.53-5.49 (m, 1H), 4.00-3.99 (m, 2H), 3.46-3.41 (m, 1H), 3.24-3.19 (m, 1H), 2.50 (s, 3H) 1.81 (s, 3H); HRMS (ESI): m/z [M+H]+ calcd for C₂₁H₂₂F₃N₄OS: 435.1466; found: 435.1463; MS (MM): m/z=435 [M-HCl]⁺; HPLC: >99 (% of AUC).

h. N-(2-(4-(aminomethyl)phenyl)-1-(5-(3-chloro-5-(trifluoromethyl)phenyl)-1,3,4-thiadiazol-2-yl)ethyl)acetamide Hydrochloride (42412)

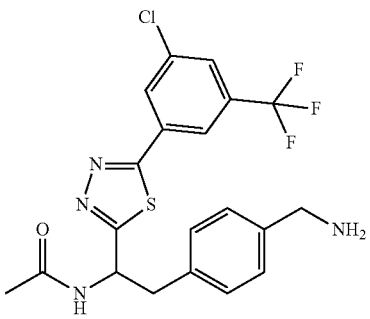 [SMILES: CC(=O)NC(Cc1ccc(CN)cc1)c1nnc(-c2cc(Cl)cc(C(F)(F)F)c2)s1]

¹H NMR (400 MHz, DMSO-d₆) δ: 8.97 (d, J=8.4 Hz, 1H), 8.34 (d, J=1.6 Hz, 1H), 8.24 (brs, 4H) 8.11 (s, 1H), 7.39 (s, 4H), 5.53-5.47 (m, 1H), 3.99 (s, 2H), 3.46-3.41 (m, 1H), 3.26-3.20 (m, 1H), 1.81 (s, 3H); HRMS (ESI): m/z [M+H]+ calcd for C₂₀H₁₉ClF₃N₄OS: 455.0920; found: 455.0915; MS (MM): m/z=455.2 [M-HCl]⁺; HPLC: >99 (% of AUC).

10. Synthesis of Compound No. 42474

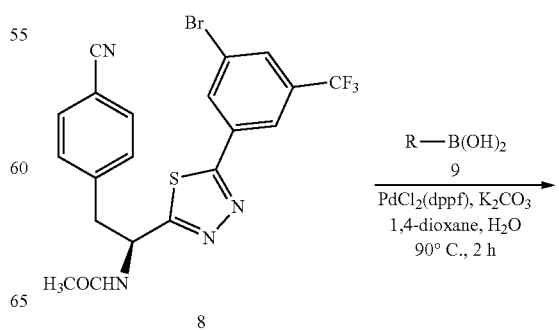

215

-continued

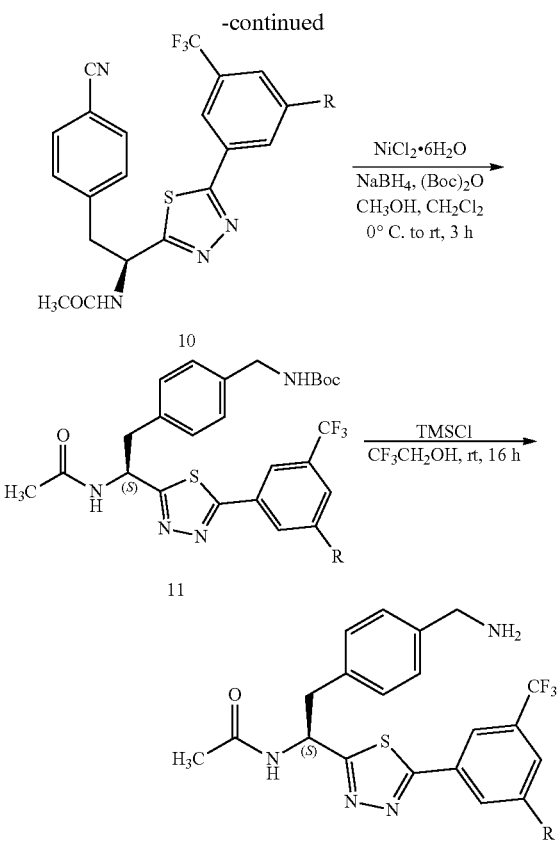

Intermediate 8 was synthesized as detailed above.

a. Preparation of Intermediate 10

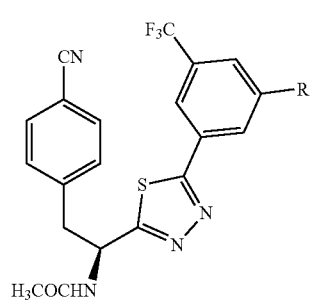

A solution of (S)—N-(1-(5-(3-bromo-5-(trifluoromethyl)phenyl)-1,3,4-thiadiazol-2-yl)-2-(4-cyanophenyl)ethyl)acetamide (8, 0.60 mmol), $K_2CO_3$ (251 mg, 1.81 mmol) and corresponding boronic acid (9, 0.72 mmol) in mixture of 1,4-Dioxane (9 mL) and water (1 mL) was degassed with argon gas for 20 min. To this charged with $PdCl_2$(dppf) (0.06 mmol) and stirred under argon atmosphere at 90° C. for 2 h. Reaction mixture was concentrated under reduced pressure to get crude, this was purified by silica-gel column chromatography eluting with 75% to 80% EtOAC/hexane to afford intermediate 10 as off-white solid. MS (MM): m/z=511.2 [M+H]$^+$. Intermediate 10 and 11 were was used in next step following General procedure for the synthesis of final compound.

216 b. N-(2-(4-(aminomethyl)phenyl)-1-(5-(4'-fluoro-5-(trifluoromethyl)-[1,1'-biphenyl]-3-yl)-1,3,4-thiadiazol-2-yl)ethyl)acetamide Hydrochloride (42474)

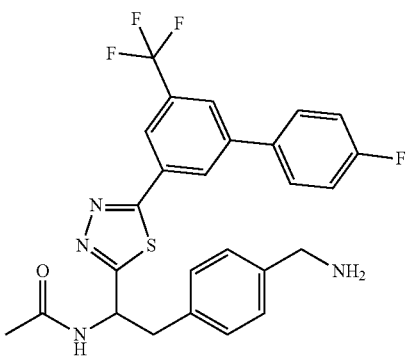 [SMILES: CC(=O)NC(Cc1ccc(CN)cc1)c1nnc(-c2cc(-c3ccc(F)cc3)cc(C(F)(F)F)c2)s1]

$^1$H NMR (400 MHz, DMSO-d$_6$) δ: 8.92 (d, J=8.0 Hz, 1H), 8.42 (s, 1H), 8.25 (s, 1H), 8.18 (s, 4H), 7.96-7.92 (m, 2H), 7.39-7.35 (m, 6H), 5.55-5.49 (m, 1H), 3.99 (s, 2H), 3.48-3.45 (m, 1H), 3.23-3.17 (m, 1H), 1.82 (s, 3H); HRMS (ESI): m/z [M+H]+ calcd for $C_{26}H_{22}F_4N_4OS$: 515.1529; found: 515.1513; MS (MM): m/z=515 [M+H]$^+$; HPLC: 98.9 (% of AUC).

11. Synthesis of Compound No. 42550

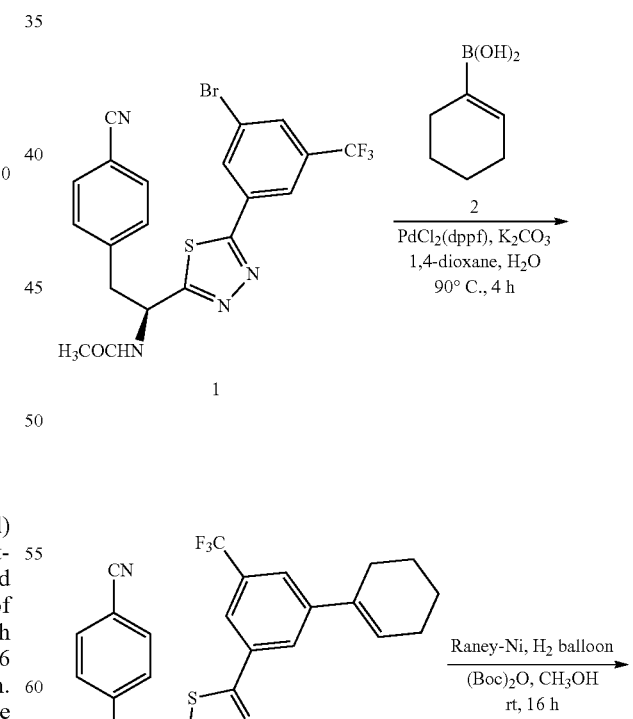

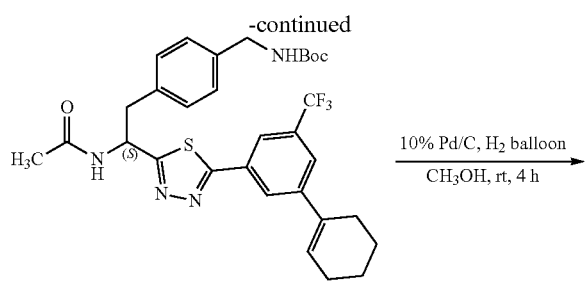

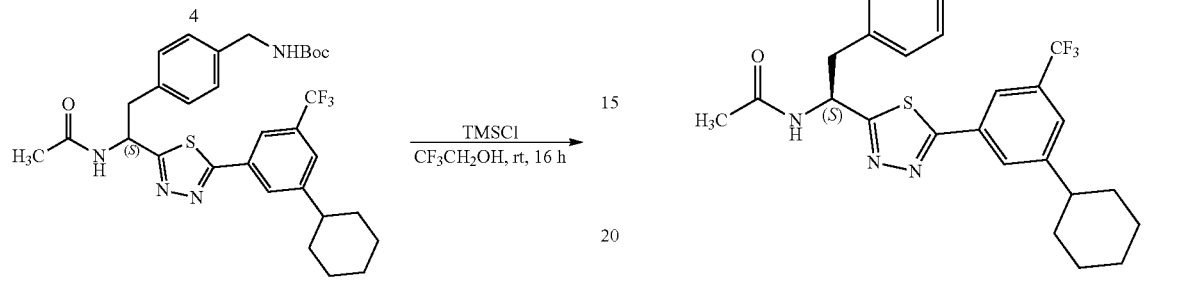

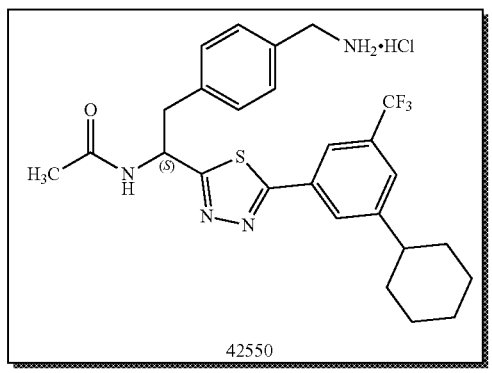

42550 a. Preparation of Intermediate 4

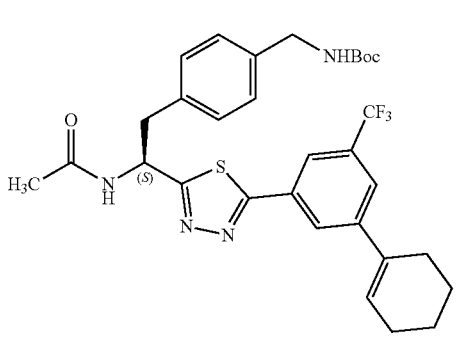

To a solution of (S)—N-(2-(4-cyanophenyl)-1-(5-(5-(trifluoromethyl)-2',3',4',5'-tetrahydro-[1,1'-biphenyl]-3-yl)-1,3,4-thiadiazol-2-yl)ethyl)acetamide (3, 250 mg, 0.50 mmol), Raney-Ni (20 mg) and Boc-anhydride (0.23 mL, 1.00 mmol) in $CH_3OH$ (30 mL) was kept in $H_2$ balloon pressure at room temperature for 16 h. Reaction mixture was filtered through pad of celite bed and washed with $CH_3OH$ (50 mL), concentrated the filtrate under reduced pressure to afford tert-butyl (S)-(4-(2-acetamido-2-(5-(5-(trifluoromethyl)-2', 3',4',5'-tetrahydro-[1,1'-biphenyl]-3-yl)-1,3,4-thiadiazol-2-yl)ethyl)benzyl)carbamate (4, 99% yield) as liquid. MS (MM): m/z=601 $[M+H]^+$.

b. Preparation of Intermediate 5

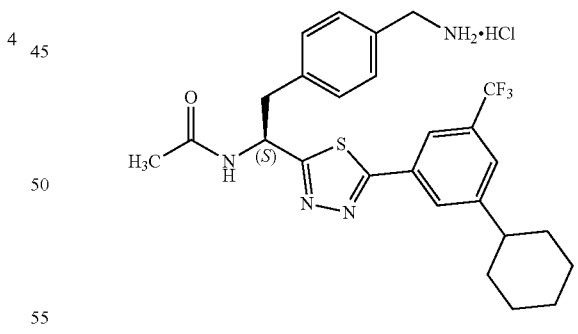

To a solution of tert-butyl (S)-(4-(2-acetamido-2-(5-(5-(trifluoromethyl)-2',3',4',5'-tetrahydro-[1,1'-biphenyl]-3-yl)-1,3,4-thiadiazol-2-yl)ethyl)benzyl)carbamate (4, 250 mg, 0.50 mmol), 10% Pd/C (50% moist) (50 mg) in $CH_3OH$ (30 mL) was kept in $H_2$ balloon pressure at room temperature for 4 h. stirred at for 3 h. Reaction mixture was filtered through pad of celite bed and washed with $CH_3OH$ (50 mL), concentrated the filtrate under reduced pressure to afford tert-butyl (S)-(4-(2-acetamido-2-(5-(3-cyclohexyl-5-(trifluoromethyl)phenyl)-1,3,4-thiadiazol-2-yl)ethyl)benzyl) carbamate (5, 250 mg, 81%) as liquid. MS (MM): m/z=603 $[M+H]^+$.

c. N-(2-(4-(aminomethyl)phenyl)-1-(5-(3-cyclohexyl-5-(trifluoromethyl)phenyl)-1,3,4-thiadiazol-2-yl)ethyl)acetamide Hydrochloride (42550)

$^1H$ NMR (400 MHz, DMSO-$d_6$) δ: 9.02 (d, J=8.0 Hz, 1H), 8.36 (brs, 3H), 8.07 (d, J=4.4 Hz, 2H), 7.78 (s, 1H), 7.45-7.37 (m, 4H), 5.52-5.48 (m, 1H), 3.98 (s, 2H), 3.46-3.42 (m, 1H), 3.26-3.16 (m, 1H), 2.79-2.73 (m, 1H), 1.73-1.70 (m, 7H), 1.56-1.44 (m, 2H), 1.40-1.23 (m, 4H); HRMS (ESI): m/z [M+H]+ calcd for $C_{26}H_{30}F_3N_4OS$: 503.2092; found: 503.2080; MS (MM): m/z=503 $[M-HCl]^+$; HPLC: 91.4 (% of AUC).

12. Synthesis of Compound No. 42320

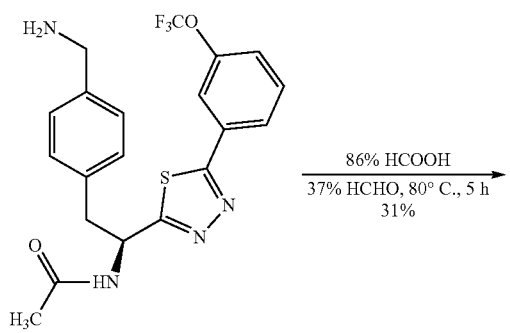

T-18 a. N-(2-(4-((dimethylamino)methyl)phenyl)-1-(5-(3-(trifluoromethoxy)phenyl)-1,3,4-thiadiazol-2-yl)ethyl)acetamide (42320)

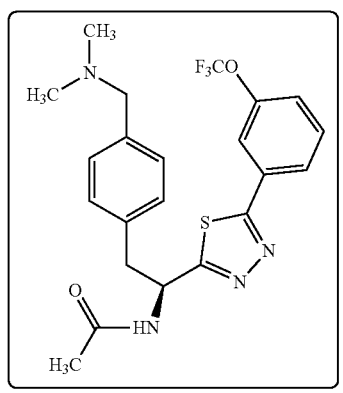

A solution of (S)—N-(2-(4-(aminomethyl)phenyl)-1-(5-(3-(trifluoromethoxy)phenyl)-1,3,4-thiadiazol-2-yl)ethyl)acetamide (SRI-40000, 200 mg, 0.45 mmol) in 86% formic acid (2 mL, 44.8 mmol) was charged with 37% formaldehyde (1 mL, 13.43 mmol) as drop wise over 1 min and stirred at 80° C. for 6 hr. Reaction mixture diluted with ice cold water (20 mL) and basified up to 14 pH with 2N NaOH solution, aqueous layer was extracted with EtOAc (2×30 mL), washed the organic layer with water (30 mL), dried over anhydrous $Na_2SO_4$ and concentrated under reduced pressure to get crude, which was purified by silica-gel column chromatography (eluting with 25% to 30% $CH_3OH$/$CH_2Cl_2$) to afford (S)—N-(2-(4-((dimethylamino)methyl)phenyl)-1-(5-(3-(trifluoromethoxy)phenyl)-1,3,4-thiadiazol-2-yl)ethyl)acetamide in 31% yield as off-white solid.

$^1$H NMR (400 MHz, DMSO-$d_6$): δ 8.88 (d, J=8.0 Hz, 1H), 7.99-7.93 (m, 2H), 7.72-7.68 (m, 1H), 7.60-7.58 (m, 1H), 7.29-7.23 (m, 4H), 5.51-5.46 (m, 1H), 3.52 (s, 2H), 3.41-3.36 (m, 1H), 3.23-3.17 (m, 1H), 2.22 (s, 6H), 1.80 (s, 3H); HRMS (ESI): m/z [M+H]+ calcd for $C_{22}H_{24}F_3N_4O_2S$: 465.1572; found: 465.1565; MS (MM): m/z=465.0 [M+H]$^+$; HPLC: 98.1 (% of AUC).

13. Synthesis of Compound No. 42140

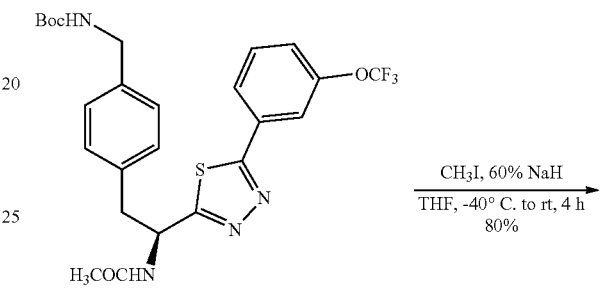

1

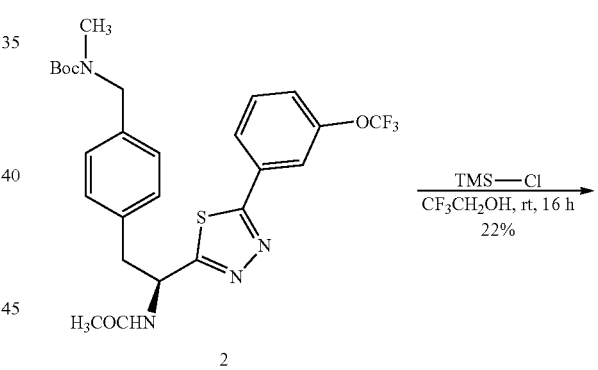

2

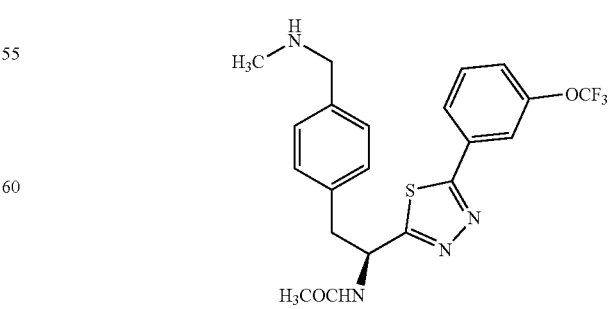

Intermediate 1 was synthesized as detailed above.

221 a. N-(2-(4-((methylamino)methyl)phenyl)-1-(5-(3-(trifluoromethoxy)phenyl)-1,3,4-thiadiazol-2-yl)ethyl)acetamide (42140)

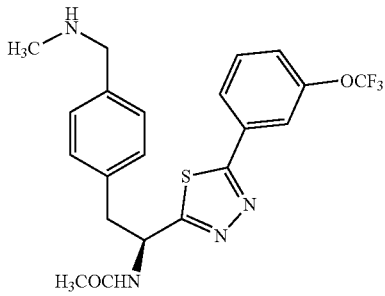

A solution of tert-butyl (S)-(4-(2-acetamido-2-(5-(3-(trifluoromethoxy)phenyl)-1,3,4-thiadiazol-2-yl)ethyl)benzyl)(methyl)carbamate (2, 100 mg, 0.18 mmol) in CF$_3$CH$_2$OH (2 mL) was charged with TMSCl (0.03 mL, 2 vol) as dropwise over 1 min at room temperature and stirred at same temperature for 16 h. Thereafter, the volatiles were removed under reduced pressure to get crude product. The crude product was purified by MS triggered HPLC (HPLC Method: LUNA C18@10 μm (21.2×250 mm, 10 μm); mobile phase, A=0.05% TFA in H$_2$O and B=CH$_3$CN; Flow rate: 20 mL/min, Injection volume: 500 μL, Runtime: 20 min, gradient: 90-15% A, 10-85% B (0.0-15 min); UV detection at 220 nm), obtained pure fractions were concentrated and basified with saturated NaHCO$_3$ solution (3 mL), extracted with CH$_2$Cl$_2$ (2×3 mL), separated organic layer was dried over anhydrous Na$_2$SO$_4$ and concentrated under reduced pressure to afford (S)—N-(2-(4-((methylamino)methyl)phenyl)-1-(5-(3-(trifluoromethoxy)phenyl)-1,3,4-thiadiazol-2-yl)ethyl)acetamide in 22% yield as a liquid. $^1$H NMR (400 MHz, DMSO-d$_6$): δ 7.93 (d, J=8.0 Hz, 1H), 7.88 (s, 1H), 7.67 (t, J=8.0 Hz, 1H), 7.52 (d, J=8.4 Hz, 1H), 7.23 (s, 4H), 6.23-6.12 (m, 1H), 3.70 (s, 2H), 3.57-3.52 (m, 1H), 3.36-3.33 (m, 1H), 2.96 (s, 3H), 1.93 (s, 3H); MS (MM): m/z=451.0 [M+H]$^+$; HPLC: >99 (% of AUC).

14. Synthesis of Compound Nos. 42335 and 42319

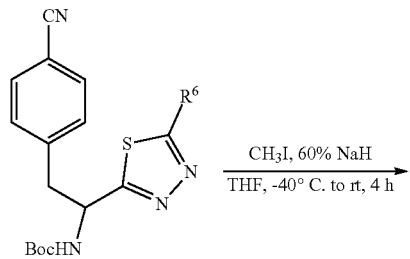

1

222

-continued

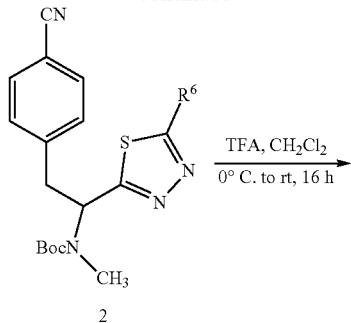

2

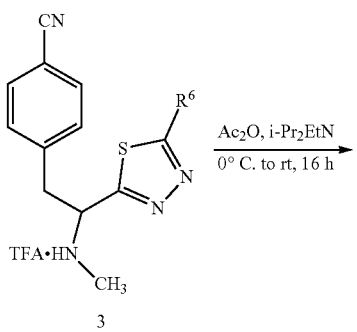

3

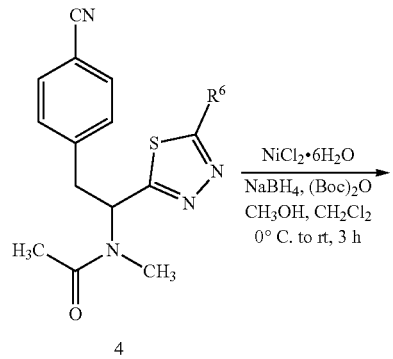

4

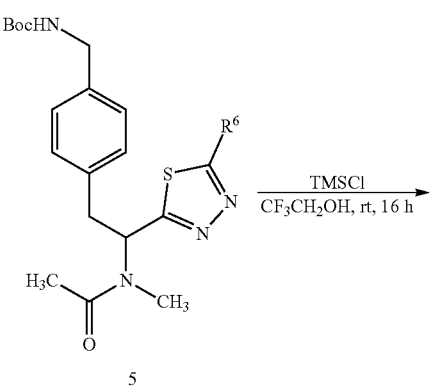

5

-continued

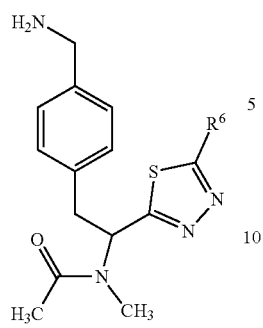

Intermediates 1, 3, 4, and 5 were synthesized as detailed above.

a. Preparation of Intermediate 2

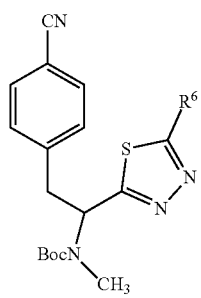

A solution of Intermediate 1 in THF (25 mL) at −40° C. was charged with 60% sodium hydride (6 eq.) as portion wise over 3 min and stirred at same temperature for 30 min. To this, methyl iodide (10 eq.) was added as drop wise at −40° C. and stirred at room temperature for 4 h. Reaction mixture was quenched with CH$_3$OH (5 mL) and concentrated under reduced pressure to get crude, which was purified over silica-gel column chromatography (eluting with 25% to 30% EtOAc/hexane) to afford corresponding intermediate-2.

b. N-(2-(4-(aminomethyl)phenyl)-1-(5-(3-(trifluoromethoxy)phenyl)-1,3,4-thiadiazol-2-yl)ethyl)-N-methylacetamide Hydrochloride (42335)

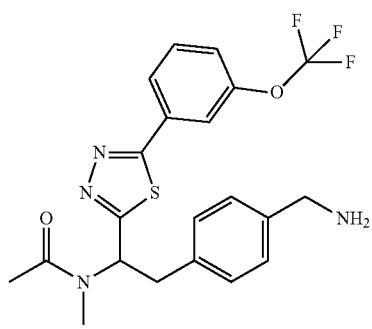 [SMILES: CC(=O)N(C)C(Cc1ccc(CN)cc1)c1nnc(-c2cccc(OC(F)(F)F)c2)s1]

$^1$H NMR (400 MHz, DMSO-d$_6$-VT) δ: 8.18 (brs, 3H), 7.94 (d, J=7.6 Hz, 1H), 7.88 (s, 1H), 7.70-7.66 (m, 1H), 7.53 (d, J=8.0 Hz, 1H), 7.41-7.39 (m, 4H), 6.26-6.24 (m, 1H), 3.98 (s, 2H), 3.63-3.58 (m, 1H), 3.42-3.38 (m, 1H), 2.89 (s, 3H), 1.95 (s, 3H); MS (MM): m/z=451 [M-HCl]; HPLC: 97.3 (% of AUC).

c. N-(2-(4-(aminomethyl)phenyl)-1-(5-(3,5-bis(trifluoromethyl)phenyl)-1,3,4-thiadiazol-2-yl)ethyl)-N-methylacetamide Hydrochloride (42319)

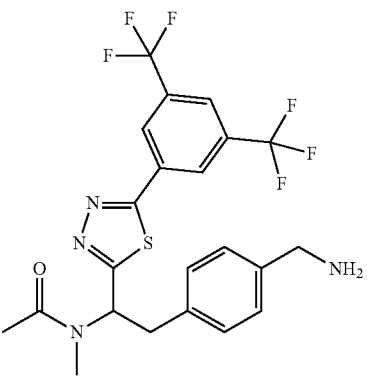 [SMILES: CC(=O)N(C)C(Cc1ccc(CN)cc1)c1nnc(-c2cc(C(F)(F)F)cc(C(F)(F)F)c2)s1]

$^1$H NMR (400 MHz, DMSO-d$_6$-VT) δ: 8.56 (s, 2H), 8.27-8.18 (m, 4H), 7.42 (s, 4H), 6.32 (m, 1H), 4.0.3 (s, 2H), 3.69-3.64 (m, 1H), 3.48-3.42 (m, 1H), 2.97 (s, 3H), 1.99 (s, 3H); HRMS (ESI): m/z [M+H]+ calcd for C$_{22}$H$_{21}$F$_6$N$_4$OS: 503.134; found: 503.1338; MS (MM): m/z=503 [M-HCl]$^+$; HPLC: 98.4% (% of AUC).

15. Evaluation of Inhibitory Activity of Compound 35

Compound 35 was evaluated for its ability to inhibit TGF-β in both ELISA based assays with purified protein components (latent TGFβ and TSP1 or in TSP1-treated cell conditioned media). Briefly, compound 35 demonstrated 15%, 67%, and 67% inhibition at 1 μm, 50 μm, and 100 μm, respectively.

16. Evaluation of Oxadiazole and Thiadiazole Analogs as TGF-Beta Inhibitors

A summary of the inhibitory activity of representative thiadiazole analogs (Tables i and ii) and oxadiazole analogs (Table ii) is shown below.

TABLE I

[Structure: R¹-C(=O)-N(R²)-CH(CH₂-Ar(Rᵃ,Rᵇ))-[1,3,4-thiadiazole]-Rᶜ]

| Compd No. | Rᵃ | Rᵇ | Rᶜ | R² | R¹ | Secondary Assay IC$_{50}$ (nM) |
|---|---|---|---|---|---|---|
| 39245 | —CH$_2$NH$_2$ | H | 4-pyridyl | H | —CH$_3$ | 33 |
| 40051 | —CH$_2$NH$_2$ | H | 4-fluorophenyl | H | —CH$_3$ | 49 |
| 40000 | —CH$_2$NH$_2$ | H | 3-(OCF$_3$)phenyl | H | —CH$_3$ | 28 |
| 40653 | —CH$_2$NH$_2$ | H | 3,5-bis(CF$_3$)phenyl | H | —CH$_3$ | 39 |
| 40652 | —CH$_2$NH$_2$ | H | 3-OCF$_3$-4-F-phenyl | H | —CH$_3$ | NA |
| 41152 | —CH$_2$NH$_2$ | H | 3-(CF$_3$)phenyl | H | —CH$_3$ | 9 |
| 41149 | —CH$_2$NH$_2$ | H | 3-(OCH$_3$)phenyl | H | —CH$_3$ | 183 |
| 42140 | —CH$_2$NHMe | H | 3-(OCF$_3$)phenyl | H | —CH$_3$ | 51 |
| 42320 | —CH$_2$N(CH$_3$)$_2$ | H | 3-(OCF$_3$)phenyl | H | —CH$_3$ | 2 |

TABLE I-continued
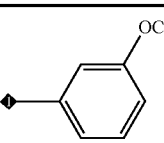
| Compd No. | $R^a$ | $R^b$ | $R^c$ | $R^2$ | $R^1$ | Secondary Assay $IC_{50}$ (nM) |
|---|---|---|---|---|---|---|
| 41791 | —CH$_2$NH$_2$ (racemic) | H | 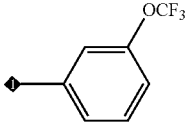 | H | —CH$_3$ | 61 |
| 41891 | —CH$_2$NH$_2$ ((S) randomly assign) | H | 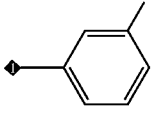 | H | —CH$_3$ | 26 |
| 41892 | —CH$_2$NH$_2$ ((R) randomly assign) | H | 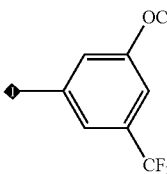 | H | —CH$_3$ | 26.9 |
| 42330 | —CH$_2$NH$_2$ | H | 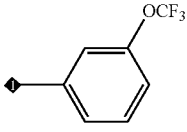 | H | —CH$_3$ | 6 |
| 42335 | —CH$_2$NH$_2$ | H | 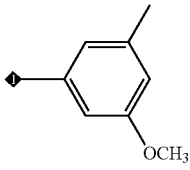 | —CH$_3$ | H | 30 |
| 42473 | —CH$_2$NH$_2$ | H | 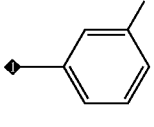 | H | —CH$_3$ | 8 |
| 39999 | —NH$_2$ | H | 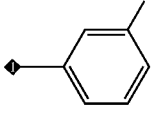 | H | —CH$_3$ | 15 |
| 42461 | —CH$_2$NH$_2$ | H | 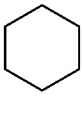 | H |  | 5 |

TABLE I-continued

| Compd No. | $R^a$ | $R^b$ | $R^c$ | $R^2$ | $R^1$ | Secondary Assay $IC_{50}$ (nM) |
|---|---|---|---|---|---|---|
| 42468 | —CH$_2$NH$_2$ | H | 3-OCF$_3$-phenyl | H | cyclopropyl | 8 |
| 42470 | —CH$_2$NH$_2$ | H | 3-OCF$_3$-5-methyl-phenyl | H | —CH$_3$ | 8 |

TABLE II

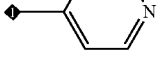

| Cmpd No. | p | $R^3$ | $R^c$ | $R^2$ | $R^1$ | X | Secondary Assay $IC_{50}$ (nM) |
|---|---|---|---|---|---|---|---|
| 40074 | 3 | —NH$_2$ | 4-pyridyl | H | —CH$_3$ | O | >1 µM |
| 38442 | 2 | —NH$_2$ | phenyl | H | —CH$_3$ | S | >1 µM |
| 39139 | 3 | —NH$_2$ | cyclohexyl | H | —CH$_3$ | S | 13 |
| 39261 | 3 | —NH$_2$ | 4-F-phenyl | H | —CH$_3$ | S | 324 |
| 39425 | 3 | —NH$_2$ | 2,4-diF-phenyl | H | —CH$_3$ | S | >1 µM |

17. Screening Assays for Compound Activity

For initial screening, an ELISA-based screening assay was used in which purified human platelet TSP-1 was incubated with compounds and then incubated with recombinant latent TGF-β1 (purchased from R&D Systems). Activity is measured in a commercially available ELISA which detects only active TGF-β (R &D Systems). Activity in the presence of compounds is compared to activity in TSP-1+ latent TGF-β samples without inhibitory compounds (Lu et al. (2016) *Am J Pathol* 186:678-690).

To specifically assess activity of compounds in liver cell specific assays, two different assays were used. In the first, human hepatic stellate cells were incubated overnight in low serum media to condition the media with secreted latent TGF-β. Purified TSP1 either pre-incubated with compounds or not will be added to cultures and then conditioned media harvested to assess TGF-β biological activity using the R&D Systems ELISA as above. Hepatic stellate cells will be purchased from commercial sources. Although hepatic stellate cells are the primary drivers of liver fibrosis, conditions which drive liver fibrosis can induce hepatocyte TSP-1 expression which can then have paracrine effects on controlling TGF-β activation in hepatic stellate cells. Furthermore, TGF-β can negatively impact hepatocyte regeneration following injury. Therefore, the ability of compounds to blockTSP-1 activation of latent TGF-β will also be assessed in cultured primary human hepatocytes following the protocol described for the hepatic stellate cells. Similar approaches have successfully been used to screen compounds which inhibit human myeloma cell derived latent TGF-β activation by TSP-1 (Lu et al. (2016) *Am J Pathol* 186:678-690).

18. TSP1 and TGF-b Decrease Osteoblast Differentiation and TSP1 Inhibitory Peptide LSKL Increases Osteoblast Differentiation by MSCs Under Osteogenic Conditions Referring to FIG. 1A, MSCs were grown to confluence in basal (control) media. Cells were treated with control growth media, osteogenic media, or osteogenic media with TGF-β (5 ng/mL) or stripped TSP1 (10 nM), TSP1+LSKL (25 μM), TSP1+SLLK (25 μM control peptide), or TSP1+anti-TGF-β (5 μg/mL). Cultures were fed daily for 20 days. Alkaline phosphatase staining is representative of triplicate wells.

Figure 1B:
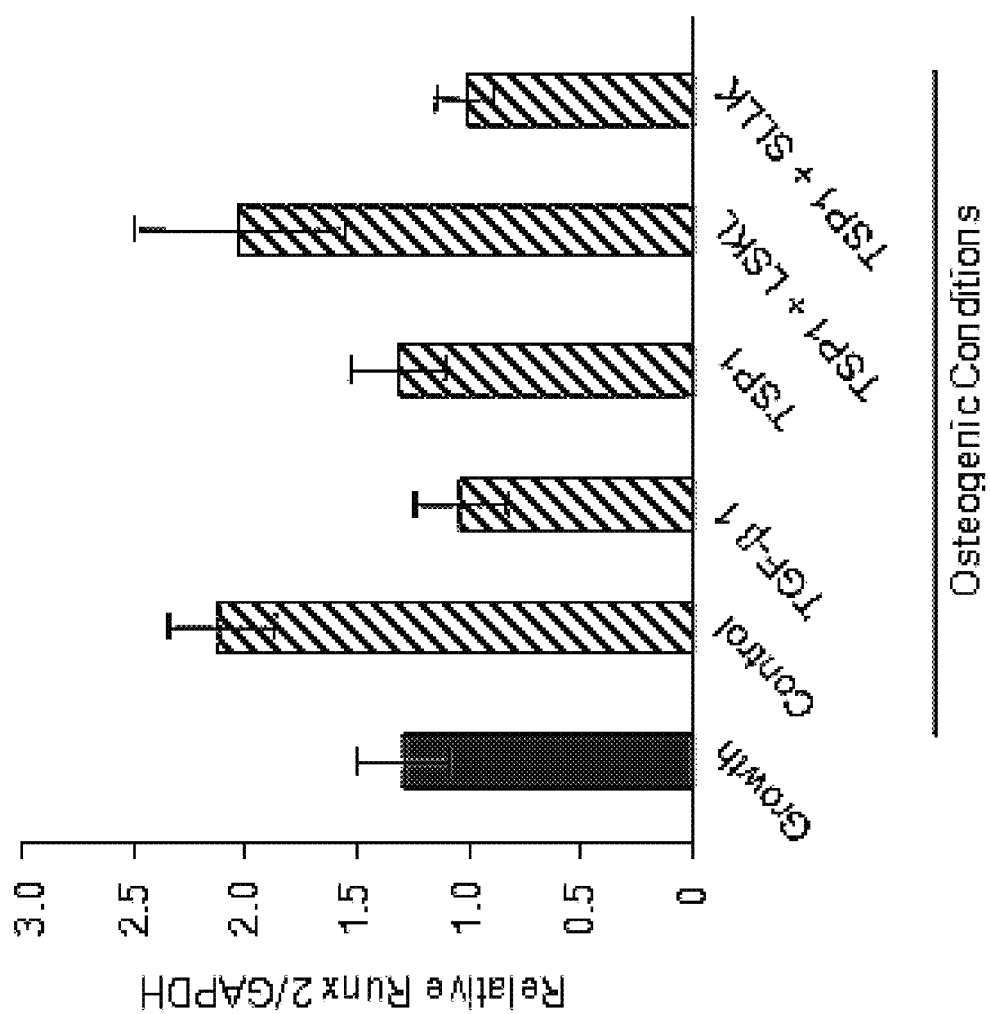

Referring to FIG. 1B, cells were treated every 2 days for 20 days with MSC growth media (control) or osteogenic media with TGF-β (5 ng/mL) or TSP1 (10 nM)±daily treatment with 25 μM LSKL or SLLK peptides. RNA isolated from cells was used for RT-PCR analysis of Runx2 expression. Samples were run in duplicate and each experimental treatment in triplicate.

19. LSKL Peptide Treatment Reduces MM Tumor Burden in the SCID-Tibia MM Model

Figures 2A, 2B:
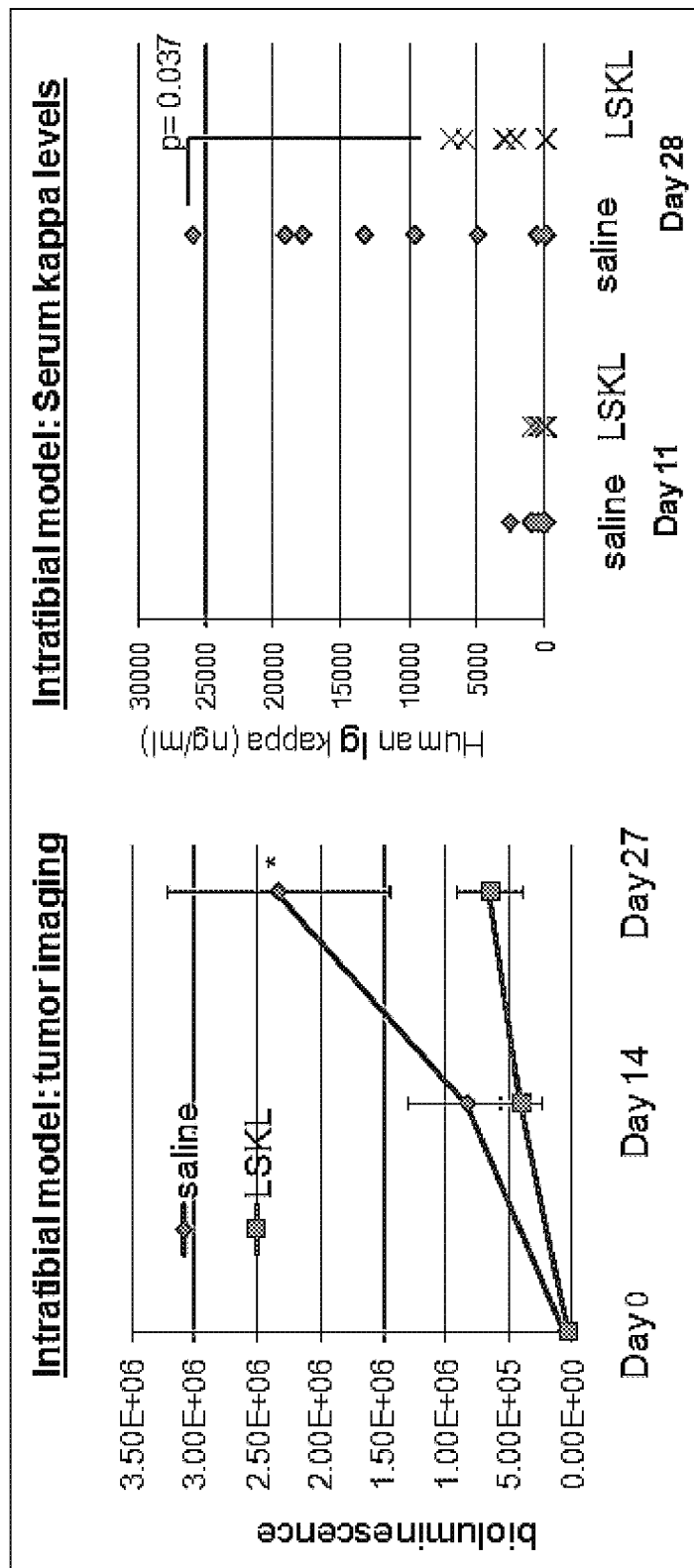
FIG. 2A and FIG. 2B show representative data illustrating the impact of LSKL treatment on tumor burden in the SCID-tibia MM model.

Referring to FIG. 2A and FIG. 2B, CAG human myeloma cells were injected into the intratibial marrow space of SCID mice. After 2 weeks, tumors were imaged by bioluminescence and serum lg kappa levels measured. Mice were randomized to equalize lg kappa levels. Osmotic pumps were implanted subcutaneously to deliver saline or LSKL peptide (30 mg/kg/day) (n=10/group). Tumors were imaged and serum lg kappa levels measured at 2 and 4 weeks of treatment. Data are means±SEM. Bioluminescence; *p=0.019 ANOVA, serum kappa; p=0.037, t-test.

20. LSKL Reduces Phospho-Smad 2 in the Bone Marrow

Figure 3A:
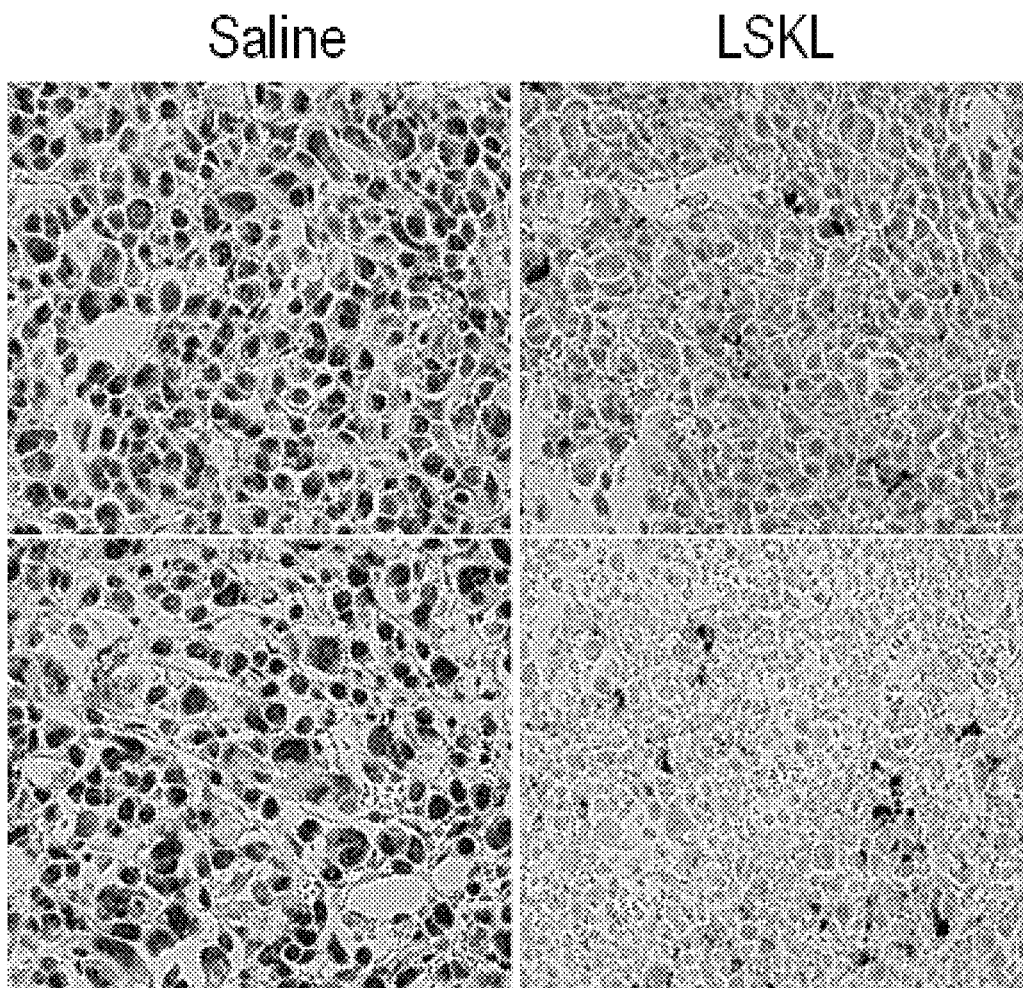
FIG. 3A-C show representative data illustrating the impact of LSKL treatment on Smad 2 phosphorylation in bone marrow myeloma cells.
Figures 3B, 3C:
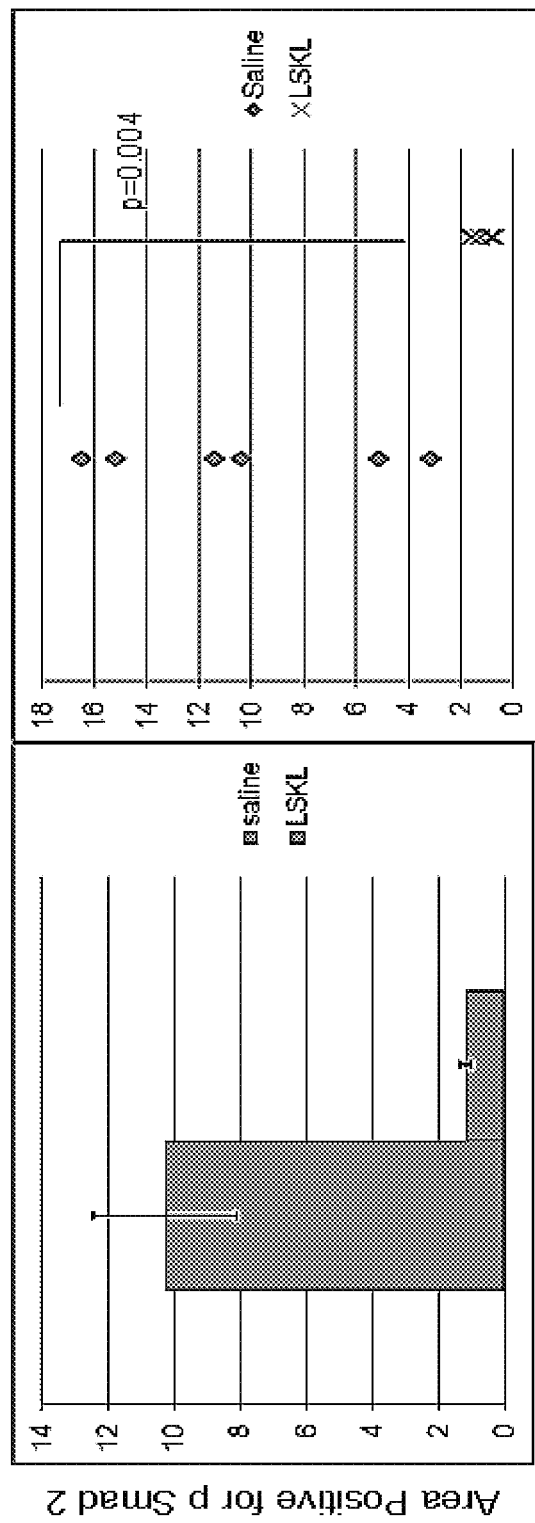

Referring to FIG. 3A-C, at 4 weeks of treatment, tibiae from mice injected with CAG MM cells were fixed and stained with antibody to phosphor-Smad 2. Left panels are from 2 different saline treated mice and the right panels are from LSKL-treated mice. Pixels of brown staining were quantified in 4 fields per animal. 5-6 animals per group were analyzed. Data are the percent area exceeding the threshold for positive staining (FIG. 3A). FIG. 3B represents the mean±SEM and FIG. 3C shows the data for individuals. P=0.004.

21. TSP1 Induces TGF-b Activity in CAG MM Cells and LSKL Reduces TGF-b Activity

Figures 4A, 4B:
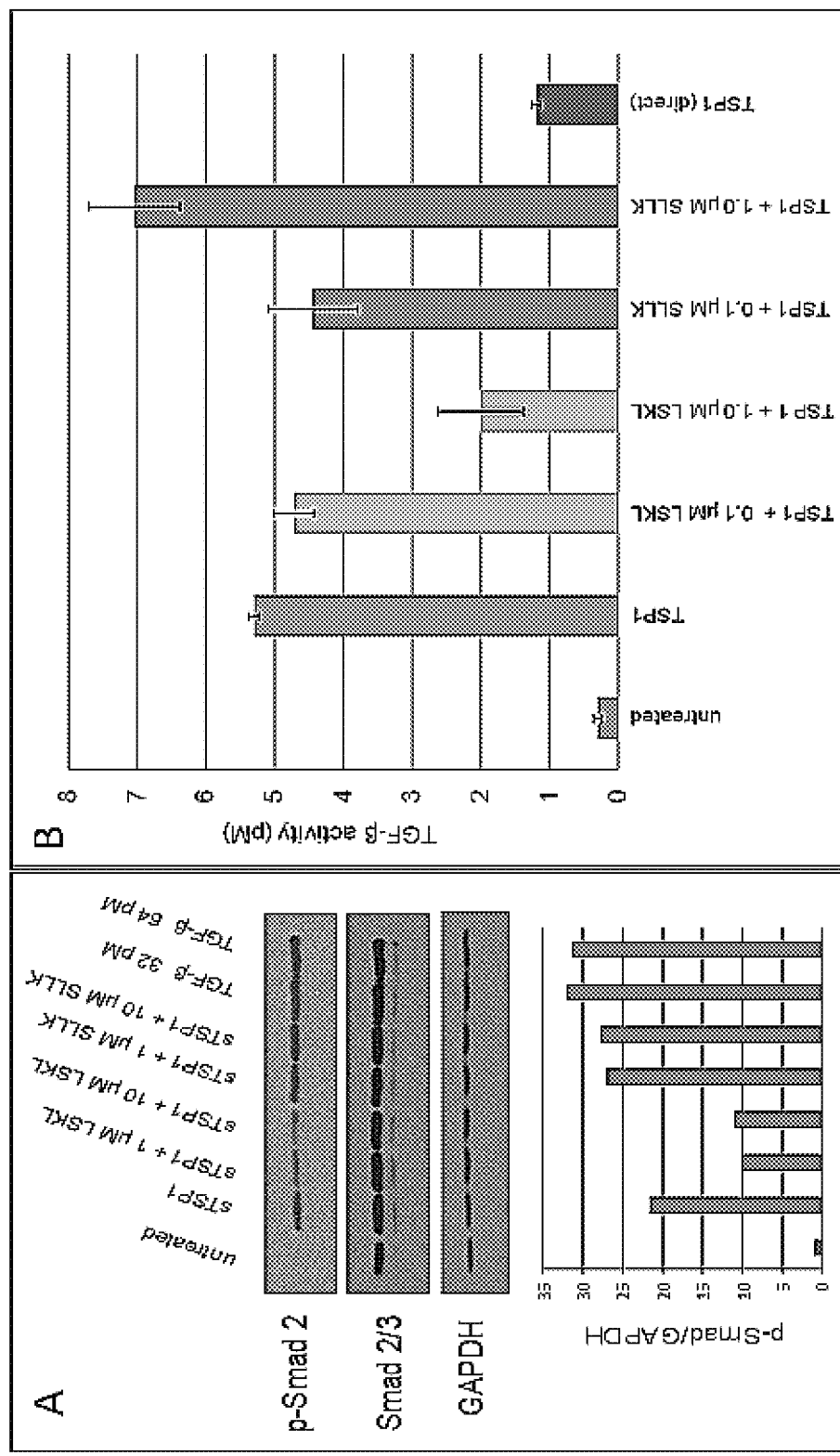
FIG. 4A and FIG. 4B show representative data illustrating the impact of TSP1 and LSKL on TGF-β activity in CAG MM cells.
Figure 5:
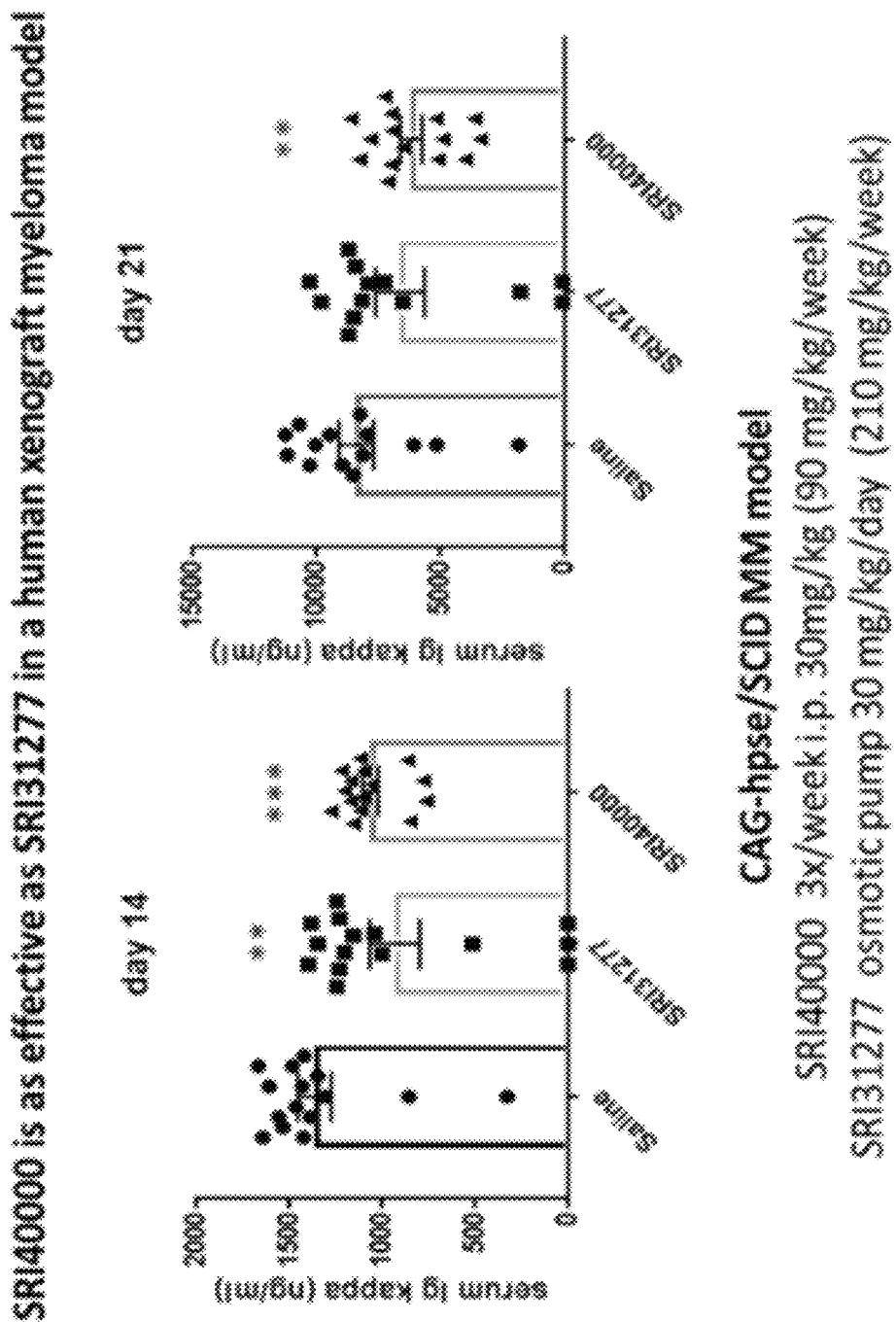
FIG. 5 shows representative data illustrating that SRI-40000 reduces myeloma tumor burden as measured by serum human Ig kappa in a systemic xenograft model of myeloma.

Referring to FIG. 4A, CAG MM cells were incubated with 30 nM TSP1 for 6 hrs±LSKL or SLLK. Cell lysates were immunoblotted for phosphor-Smad 2. Blots were stripped and reprobed for total Smad 2/3 and GAPDH. Results are normalized to GAPDH (untreated controls=1). LSKL reduces TSP1 induced treatment or luciferase activity in cells treated with active TGF-β (not shown).

Referring to FIG. 4B, CAG-heparanase MM cells were treated with 67 nM TSP1 and conditioned media were assessed for TGF-β activity using PAI-1 promoter luciferase reporter assay. There is ~1.19 pM TGF-β in the added TSP1 and LSKL blocks 80% of the CAG-heparanase MM cell generated TGF-β activity.

22. Pharmacokinetic Evaluation of Compound No. 42140 Following a Single Oral and Intravenous Administration to CD1 Mouse a. Formulation Preparation A NMP stock solution was prepared by adding 1.136 mL of NMP to 5.68 mg of compound no. 42140 with vortexing and sonification, to obtain a solution with a concentration at 5 mg/mL of 42140:01. Next, to prepare an intravenous formulation, 0.100 mL of the 5 mg/mL stock solution was placed in a new vial. 0.100 mL of NMP and 0.400 mL of PEG400 were added with vortexing and sonification, followed by addition of 0.400 mL of saline with vortexing and sonification. This resulted in a final solution with a concentration of 0.5 mg/mL of compound no. 42140:01. Alternatively, to prepare an oral formulation, 0.200 mL of the 5 mg/mL stock solution was placed in a new vial. 0.400 mL of PEG400 was added with vortexing and sonification, followed by addition of 0.400 mL of saline with vortexing and sonification. This resulted in a final solution with a concentration of 1.0 mg/mL of compound no. 42140:01.

TABLE 1

| Route | Sample Name | Dilution Factor | Nominal (mg/mL) | Measured (mg/mL) | Mean (mg/mL) |
|---|---|---|---|---|---|
| IV | Dose_IV_1 | 10000 | 0.5 | 0.583 | 0.577 |
|  | Dose_IV_2 | 10000 |  | 0.579 |  |
|  | Dose_IV_3 | 10000 |  | 0.569 |  |
| PO | Dose_PO_1 | 10000 | 1 | 1.16 | 1.12 |
|  | Dose_PO_2 | 10000 |  | 1.08 |  |
|  | Dose_PO_3 | 10000 |  | 1.11 |  |

| Route | Sample Name | Accuracy (%) | SD (mg/mL) | CV (%) |
|---|---|---|---|---|
| IV | Dose_IV_1 | 115 | 0.007 | 1.25 |
|  | Dose_IV_2 |  |  |  |
|  | Dose_IV_3 |  |  |  |
| PO | Dose_PO_1 | 112 | 0.04 | 3.62 |
|  | Dose_PO_2 |  |  |  |
|  | Dose_PO_3 |  |  |  | b. Analytical Method

Briefly, the desired serial concentrations of working solutions were achieved by diluting a stock solution of the compound with 100% acetonitrile. 3 μL of working solutions (5, 10, 20, 50, 100, 500, 1000, 5000, 10000 ng/mL) were added to 30 μL of the blank CD1 mouse plasma to achieve calibration standards of 0.5-1000 ng/mL (0.5, 1, 2, 5, 10, 50, 100, 500, 1000 ng/mL) in a total volume of 33 μL. Five quality control samples at 1 ng/mL, 2 ng/mL, 5 ng/mL, 50 ng/mL and 800 ng/mL for plasma were prepared independently of those used for the calibration curves. These QC samples were prepared on the day of analysis in the same way as calibration standards.

Next, 33 μL standards, 33 μL QC samples, and 33 μL unknown samples (30 μL plasma with 3 μL blank solution) were added to 200 μL of acetonitrile containing IS mixture for precipitating protein, respectively. Then the samples were vortexed for 30 s. After centrifugation at 4 degree Celsius, 4000 rpm for 15 min, 3 μL of supernatant was injected into the LC/MS/MS system for quantitative analysis.

HPLC analysis was performed using 100% water with 0.1% formic acid (Solution A) and 100% acetonitrile with 0.1% formic acid (Solution B) with a flow rate of 0.6 mL/min. The gradient is shown in Table 2 below.

TABLE 2

| Time (min) | A (%) | B (%) |
|---|---|---|
| 0.01 | 90.0 | 10.0 |
| 0.30 | 90.0 | 10.0 |
| 1.80 | 35.0 | 65.0 |
| 2.10 | 35.0 | 65.0 |
| 2.11 | 90.0 | 10.0 |
| 2.50 | 90.0 | 10.0 | c. Results

Figure 6A:
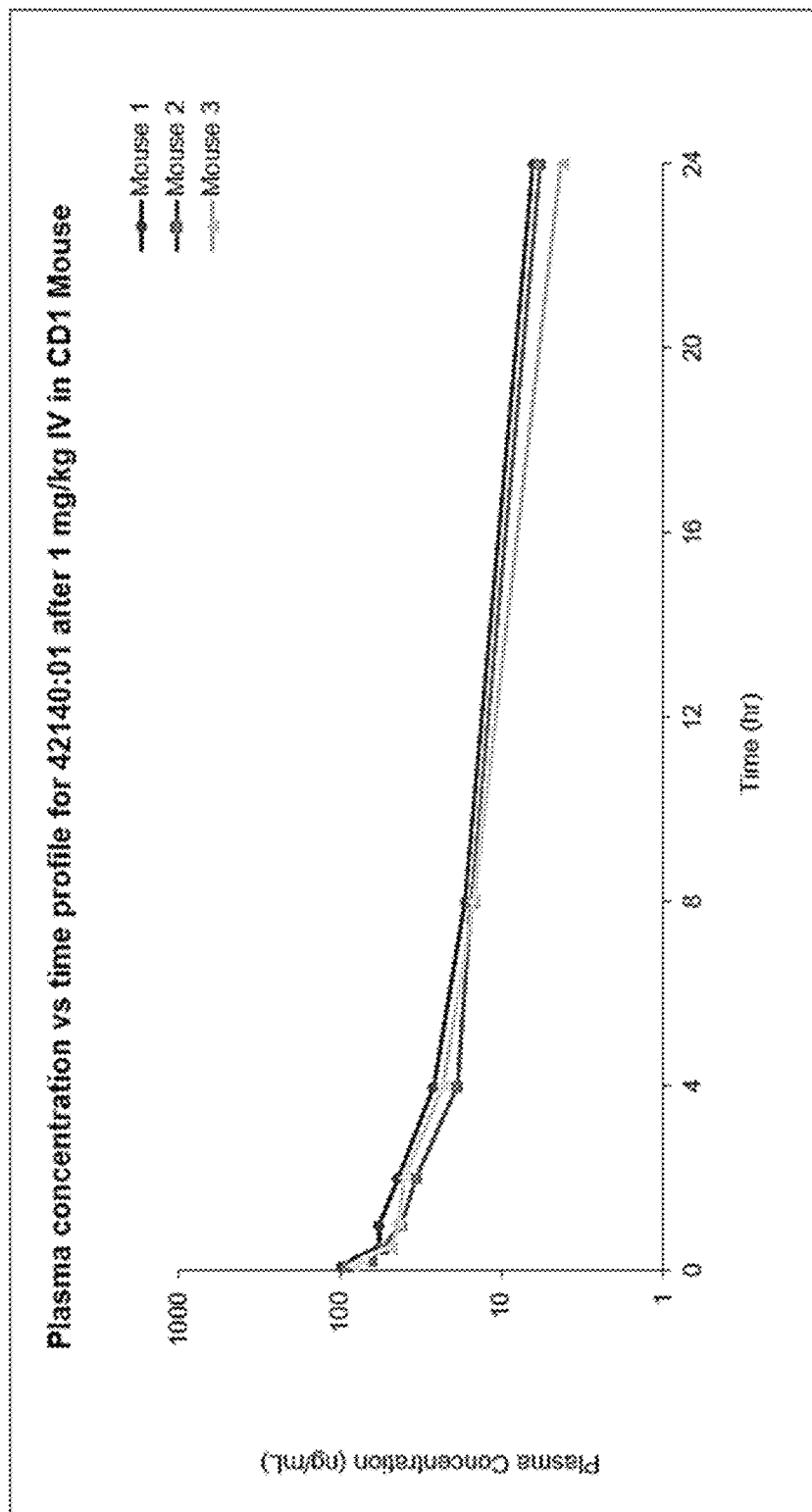
FIG. 6A-C show representative pharmacokinetic data for compound no. 42140 after IV (FIG. 6A), p.o.
Figure 6B:
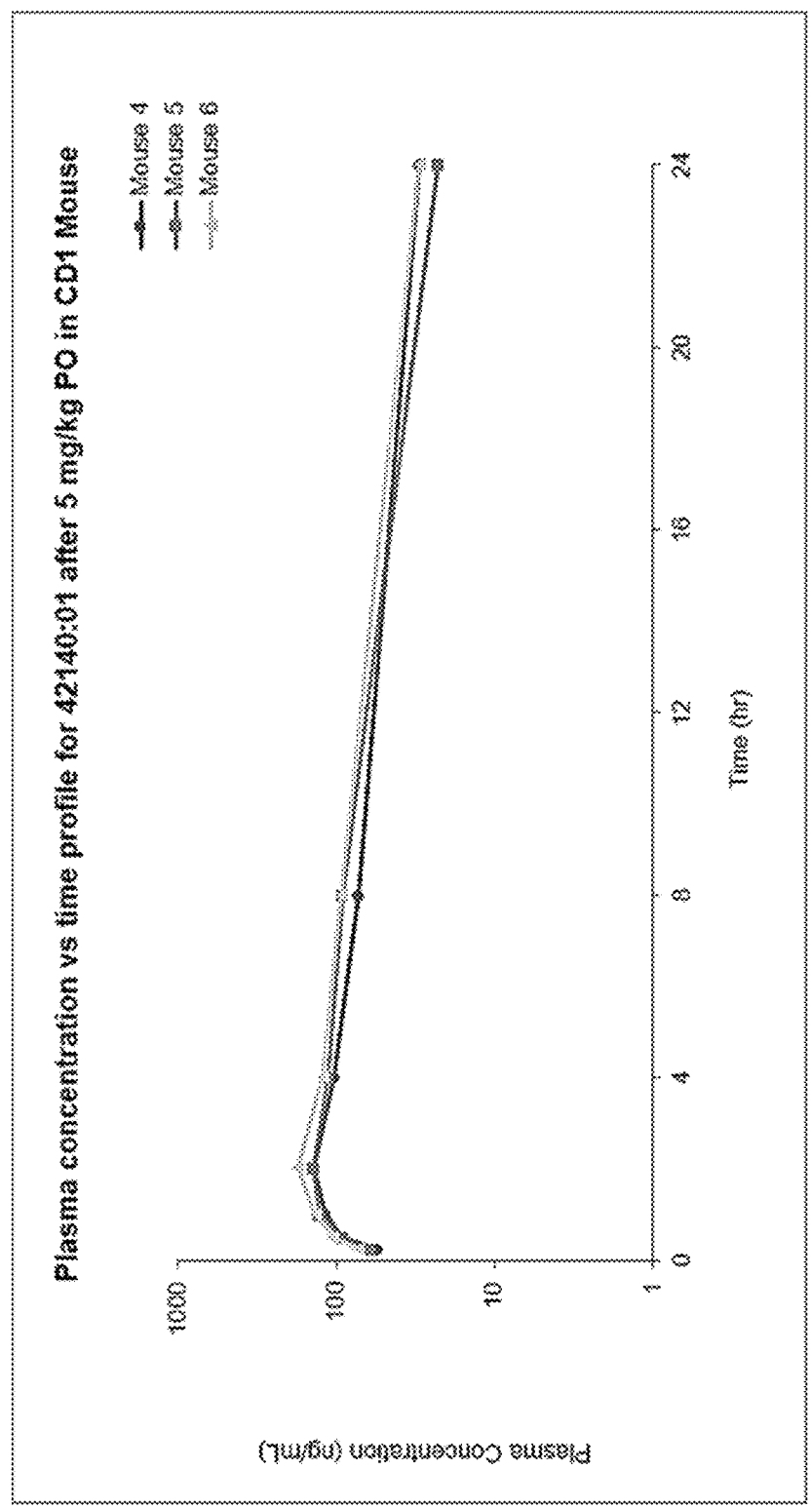
Figure 6C:
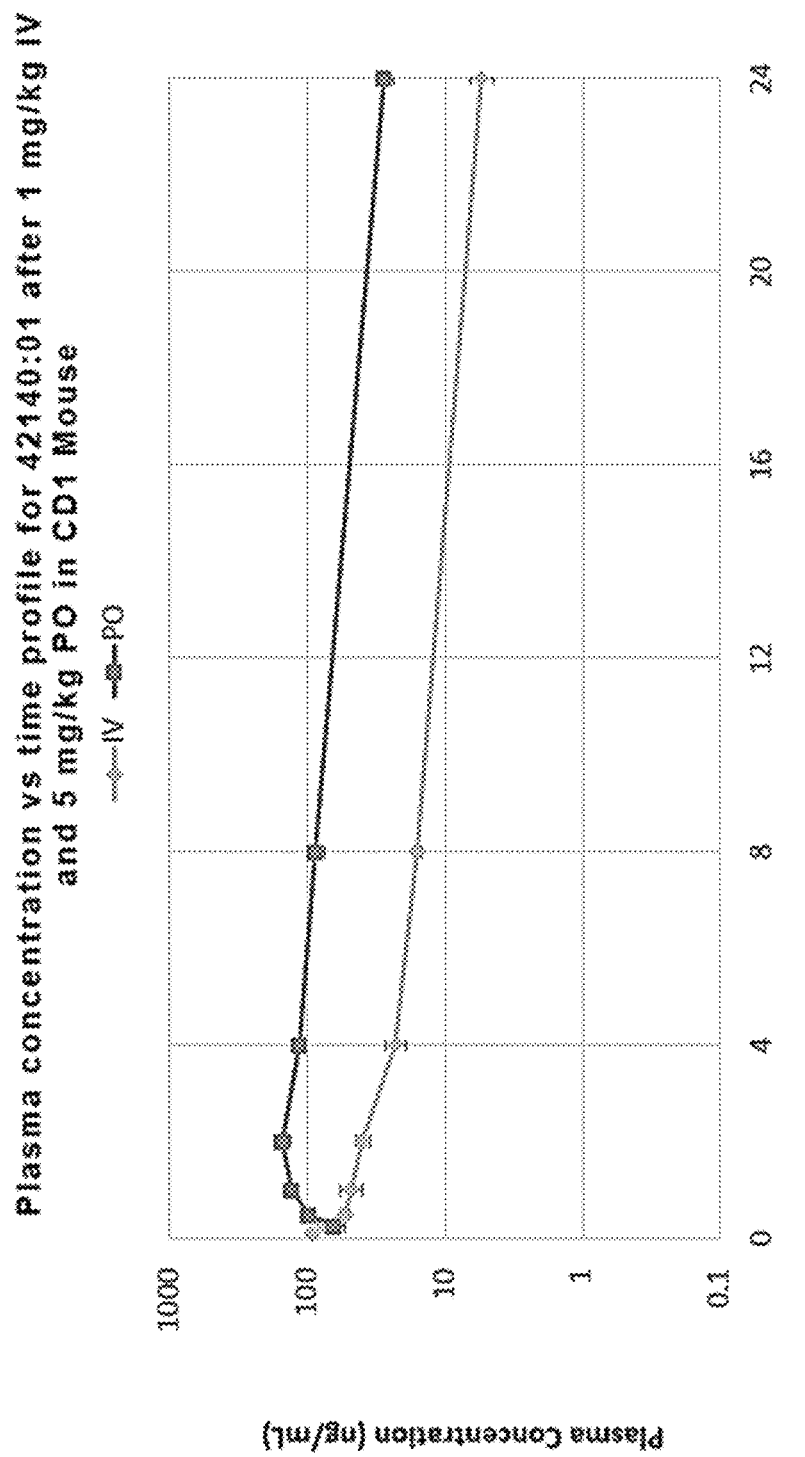

The IV plasma concentration profile of compound no. 42140 is shown in Table 3, FIG. 6A, and FIG. 6C. A summary of the IV pharmacokinetic parameters is shown in Table 4.

TABLE 3

| | IV Dose: 1 mg/kg | | | | | |
|---|---|---|---|---|---|---|
| Time | Concentration (ng/mL) | | | Mean | SD | CV |
| (h) | Mouse 1 | Mouse 2 | Mouse 3 | (ng/mL) | (ng/mL) | (%) |
| 0.0833 | 96.6 | 89.5 | 86.3 | 90.8 | 5.3 | 5.81 |
| 0.25 | 81.5 | 65.0 | 74.2 | 73.6 | 8.3 | 11.2 |
| 0.5 | 57.2 | 53.8 | 48.1 | 53.0 | 4.6 | 8.67 |
| 1 | 57.8 | 42.1 | 43.7 | 47.9 | 8.6 | 18.0 |
| 2 | 43.7 | 34.1 | 39.9 | 39.2 | 4.8 | 12.3 |
| 4 | 26.1 | 18.8 | 23.3 | 22.7 | 3.7 | 16.2 |
| 8 | 16.9 | 15.5 | 14.9 | 15.8 | 1.0 | 6.51 |
| 24 | 6.40 | 5.76 | 4.27 | 5.48 | 1.09 | 20.0 |

TABLE 4

| | IV Dose: 1 mg/kg | | | | | |
|---|---|---|---|---|---|---|
| PK parameters | Unit | Mouse 1 | Mouse 2 | Mouse 3 | Mean | SD | CV(%) |
| $Cl\_obs$ | mL/min/kg | 29.9 | 34.3 | 37.4 | 33.9 | 3.8 | 11.1 |
| $T_{1/2}$ | h | 10.3 | 11.6 | 8.36 | 10.1 | 1.6 | 16.0 |
| $C_0$ | ng/mL | 105 | 105 | 93 | 101 | 7 | 6.87 |
| $AUC_{last}$ | h*ng/mL | 462 | 389 | 394 | 415 | 41 | 9.83 |
| $AUC_{Inf}$ | h*ng/mL | 557 | 486 | 445 | 496 | 57 | 11.4 |
| $AUC\_\%_{Extrap}\_obs$ | % | 17.0 | 19.8 | 11.6 | 16.1 | 4.2 | 26.0 |
| $MRT_{Inf}\_obs$ | h | 12.1 | 13.7 | 9.69 | 11.8 | 2.0 | 16.9 |
| $AUC_{last}/D$ | h*mg/mL | 462 | 389 | 394 | 415 | 41 | 9.83 |
| $V_{ss}\_obs$ | L/kg | 21.8 | 28.1 | 21.8 | 23.9 | 3.7 | 15.3 |

The p.o. plasma concentration profile of compound no. 42140 is shown in Table 5, FIG. 6B, and FIG. 6C. A summary of the p.o. pharmacokinetic parameters is shown in Table 6.

TABLE 5

| | PO Dose: 5 mg/kg | | | | | |
|---|---|---|---|---|---|---|
| Time | Concentration (ng/mL) | | | Mean | SD | CV |
| (h) | Mouse 4 | Mouse 5 | Mouse 6 | (ng/mL) | (ng/mL) | (%) |
| 0.25 | 54.5 | 60.6 | 73.1 | 62.7 | 9.5 | 15.1 |
| 0.5 | 92.2 | 91.9 | 106 | 97 | 8 | 8.33 |
| 1 | 117 | 129 | 136 | 127 | 10 | 7.55 |
| 2 | 139 | 140 | 175 | 151 | 21 | 13.5 |
| 4 | 103 | 112 | 123 | 113 | 10 | 8.89 |
| 8 | 72.7 | 91.4 | 93.5 | 85.9 | 11.5 | 13.3 |
| 24 | 29.8 | 22.7 | 29.6 | 27.4 | 4.0 | 14.8 |

TABLE 6

| | PO Dose: 5 mg/kg | | | | | |
|---|---|---|---|---|---|---|
| PK parameters | Unit | Mouse 4 | Mouse 5 | Mouse 6 | Mean | SD | CV(%) |
| $T_{1/2}$ | h | 11.5 | 8.47 | 9.71 | 9.9 | 1.5 | 15.5 |
| $T_{max}$ | h | 2.00 | 2.00 | 2.00 | 2.00 | 0.00 | 0.000 |
| $C_{max}$ | ng/mL | 139 | 140 | 175 | 151 | 21 | 13.5 |
| $AUC_{last}$ | h*ng/mL | 1619 | 1788 | 1963 | 1790 | 172 | 9.62 |
| $AUC_{Inf}$ | h*ng/mL | 2114 | 2065 | 2378 | 2186 | 168 | 7.70 |
| $AUC\_\%_{Extrap}\_obs$ | % | 23.4 | 13.4 | 17.4 | 18.1 | 5.0 | 27.8 |
| $MRT_{Inf}\_obs$ | h | 15.8 | 11.4 | 13.1 | 13.4 | 2.21 | 16.5 |
| $AUC_{last}/D$ | h*mg/mL | 324 | 358 | 393 | 358 | 34 | 9.62 |
| F | % | 78.0 | 83.3 | 95.9 | 85.7 | 9.2 | 10.7 |

23. Pharmacokinetic Evaluation of Compound No. 42320 Following a Single Oral and Intravenous Administration to CD1 Mouse a. Formulation Preparation A NMP stock solution was prepared by adding 2.092 mL of NMP to 10.46 mg of compound no. 42320 with vortexing and sonification, to obtain a solution with a concentration at 5 mg/mL of 42140:01. Next, to prepare an intravenous formulation, 0.100 mL of the 5 mg/mL stock solution was placed in a new vial. 0.100 mL of NMP and 0.400 mL of PEG400 were added with vortexing and sonification, followed by addition of 0.400 mL of saline with vortexing and sonification. This resulted in a final solution with a concentration of 0.5 mg/mL of compound no. 42320:01. Alternatively, to prepare an oral formulation, 0.200 mL of the 5 mg/mL stock solution was placed in a new vial. 0.400 mL of PEG400 was added with vortexing and sonification, followed by addition of 0.400 mL of saline with vortexing and sonification. This resulted in a final solution with a concentration of 1.0 mg/mL of compound no. 42320:01.

TABLE 7

| Route | Sample Name | Dilution Factor | Nominal (mg/mL) | Measured (mg/mL) | Mean (mg/mL) |
|---|---|---|---|---|---|
| IV | Dose_IV_1 | 10000 | 0.5 | 0.513 | 0.493 |
|  | Dose_IV_2 | 10000 |  | 0.477 |  |
|  | Dose_IV_3 | 10000 |  | 0.490 |  |
| PO | Dose_PO_1 | 10000 | 1 | 0.960 | 0.962 |
|  | Dose_PO_2 | 10000 |  | 0.963 |  |
|  | Dose_PO_3 | 10000 |  | 0.962 |  |

| Route | Sample Name | Accuracy (%) | SD (mg/mL) | CV (%) |
|---|---|---|---|---|
| IV | Dose_IV_1 | 98.7 | 0.018 | 3.70 |
|  | Dose_IV_2 |  |  |  |
|  | Dose_IV_3 |  |  |  |
| PO | Dose_PO_1 | 96.2 | 0.002 | 0.159 |
|  | Dose_PO_2 |  |  |  |
|  | Dose_PO_3 |  |  |  | b. Analytical Method

Briefly, the desired serial concentrations of working solutions were achieved by diluting a stock solution of the compound with 100% acetonitrile. 3 µL of working solutions (5, 10, 20, 50, 100, 500, 1000, 5000, 10000 ng/mL) were added to 30 µL of the blank CD1 mouse plasma to achieve calibration standards of 0.5-1000 ng/mL (0.5, 1, 2, 5, 10, 50, 100, 500, 1000 ng/mL) in a total volume of 33 µL. Five quality control samples at 1 ng/mL, 2 ng/mL, 5 ng/mL, 50 ng/mL, and 800 ng/mL for plasma were prepared independently of those used for the calibration curves. These QC samples were prepared on the day of analysis in the same way as calibration standards.

Next, 33 µL standards, 33 µL QC samples, and 33 µL unknown samples (30 µL plasma with 3 µL blank solution) were added to 200 µL of acetonitrile containing IS mixture for precipitating protein, respectively. Then the samples were vortexed for 30 s. After centrifugation at 4 degree Celsius, 4000 rpm for 15 min, 3 µL of supernatant was injected into the LC/MS/MS system for quantitative analysis.

HPLC analysis was performed using 100% water with 0.1% formic acid (Solution A) and 100% acetonitrile with 0.1% formic acid (Solution B) with a flow rate of 0.6 mL/min. The gradient is shown in Table 8 below.

TABLE 8

| Time (min) | A (%) | B (%) |
|---|---|---|
| 0.01 | 90.0 | 10.0 |
| 0.30 | 90.0 | 10.0 |
| 1.80 | 40.0 | 60.0 |
| 2.10 | 40.0 | 60.0 |
| 2.11 | 90.0 | 10.0 |
| 2.50 | 90.0 | 10.0 | c. Results

Figure 7A:
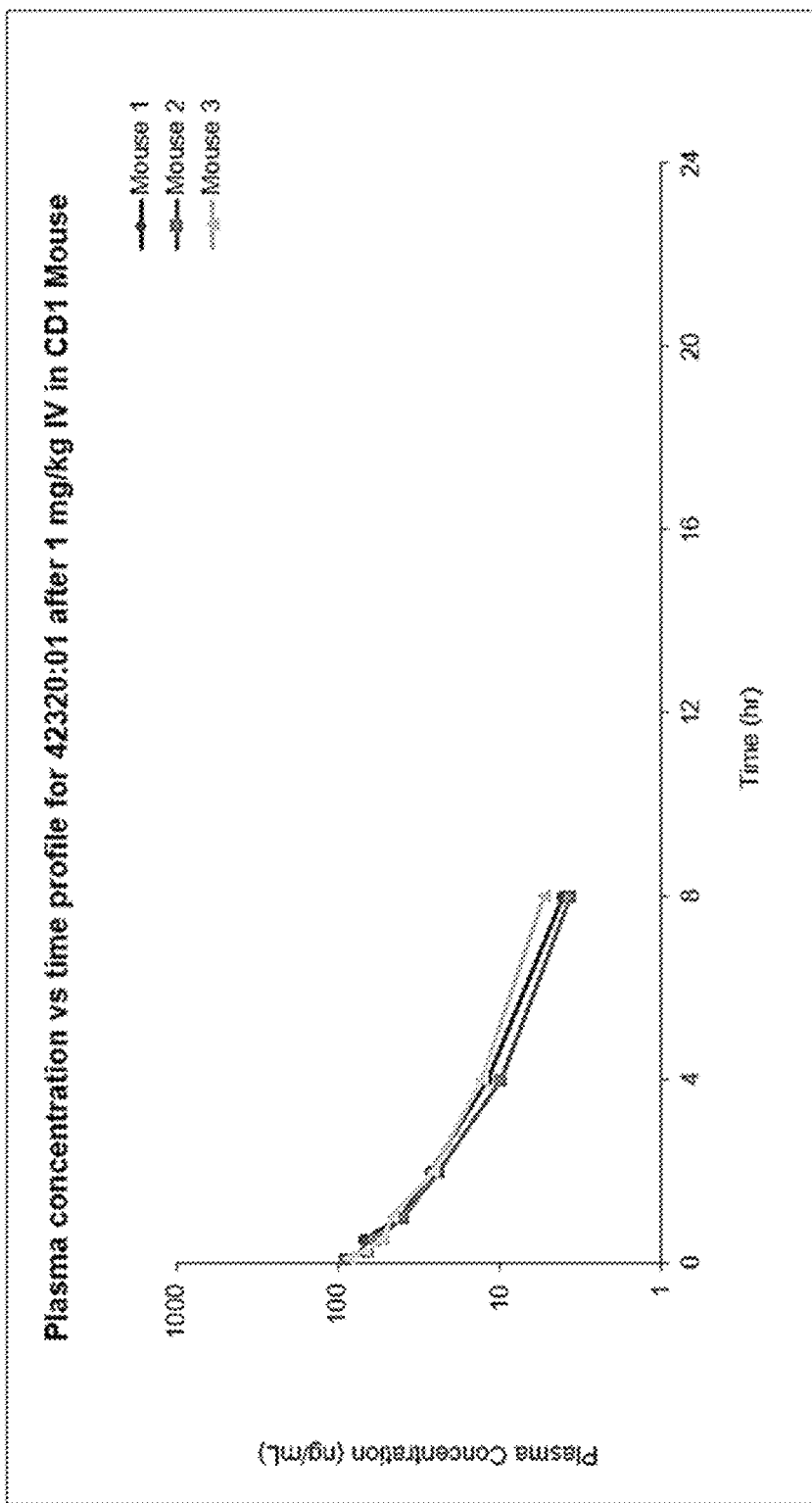
FIG. 7A-C show representative pharmacokinetic data for compound no. 42320 after IV (FIG. 7A), p.o.
Figure 7B:
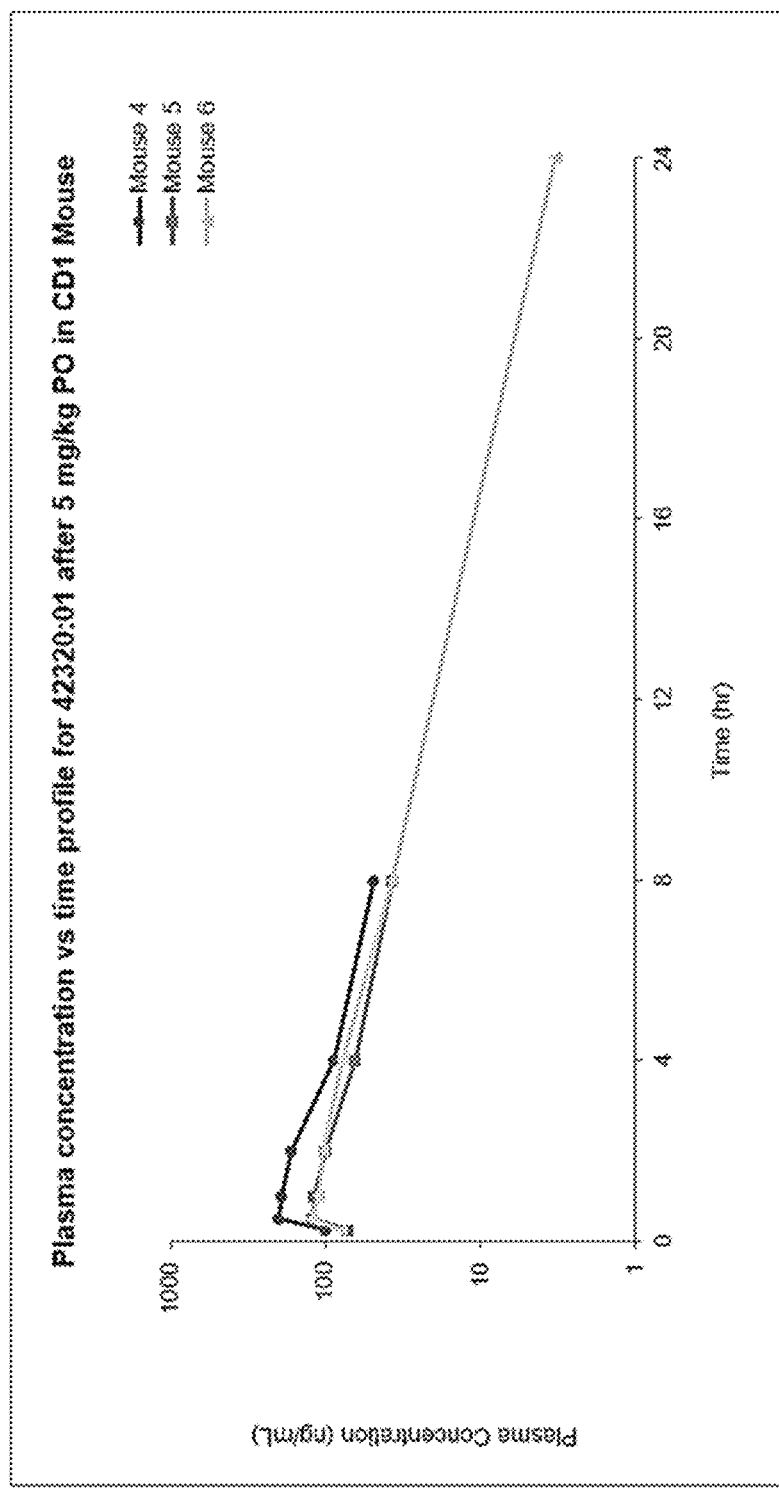
Figure 7C:
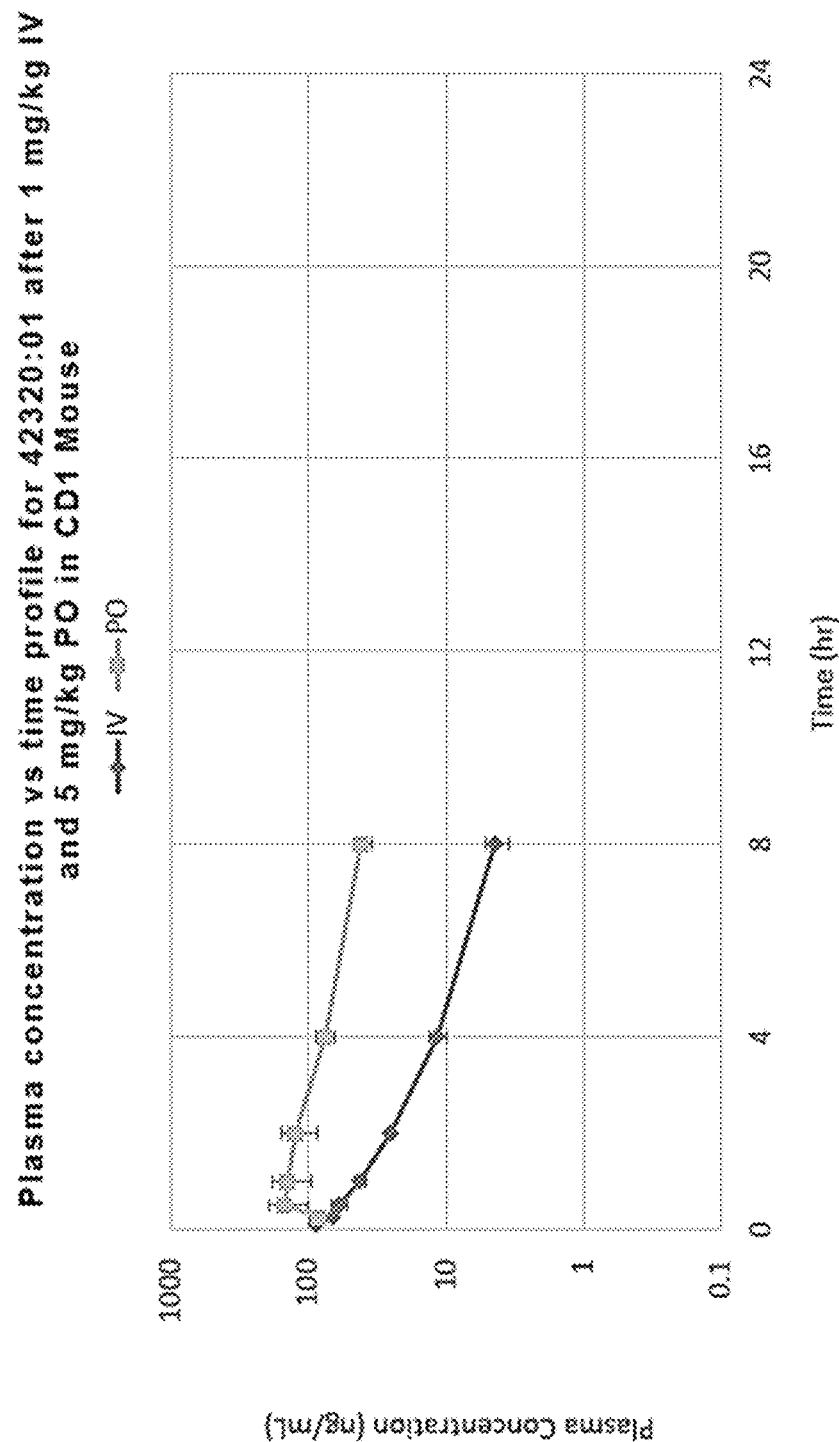

The IV plasma concentration profile of compound no. 42320 is shown in Table 9, FIG. 7A, and FIG. 7C. A summary of the IV pharmacokinetic parameters is shown in Table 10.

TABLE 9

| | IV Dose: 1 mg/kg | | | | | |
|---|---|---|---|---|---|---|
| Time | Concentration (ng/mL) | | | Mean | SD | CV |
| (h) | Mouse 1 | Mouse 2 | Mouse 3 | (ng/mL) | (ng/mL) | (%) |
| 0.0833 | 86.9 | 90.3 | 85.7 | 87.6 | 2.4 | 2.72 |
| 0.25 | 68.4 | 65.0 | 68.3 | 67.2 | 1.9 | 2.88 |
| 0.5 | 68.0 | 59.2 | 52.7 | 60.0 | 7.7 | 12.8 |
| 1 | 41.2 | 39.4 | 47.1 | 42.6 | 4.0 | 9.46 |
| 2 | 26.5 | 23.9 | 25.9 | 25.4 | 1.4 | 5.35 |
| 4 | 11.9 | 9.71 | 13.0 | 11.5 | 1.7 | 14.5 |
| 8 | 4.08 | 3.66 | 5.31 | 4.35 | 0.86 | 19.7 |
| 24 | BLOQ | BLOQ | BLOQ | NA | NA | NA |

TABLE 10

| | IV Dose: 1 mg/kg | | | | | |
|---|---|---|---|---|---|---|
| PK parameters | Unit | Mouse 1 | Mouse 2 | Mouse 3 | Mean | SD | CV(%) |
| Cl_obs | mL/min/kg | 91.3 | 101 | 86.3 | 93 | 7 | 7.90 |
| $T_{1/2}$ | h | 2.27 | 2.29 | 2.68 | 2.41 | 0.23 | 9.68 |
| $C_0$ | ng/mL | 97.9 | 106 | 96.0 | 100 | 6 | 5.54 |
| $AUC_{last}$ | h*ng/mL | 169 | 153 | 172 | 165 | 10 | 6.22 |
| $AUC_{Inf}$ | h*ng/mL | 183 | 165 | 193 | 180 | 14 | 7.74 |
| $AUC_{\_\%\ Extrap}\_obs$ | % | 7.32 | 7.31 | 10.6 | 8.4 | 1.9 | 22.9 |
| $MRT_{Inf}\_obs$ | h | 2.66 | 2.59 | 3.17 | 2.81 | 0.32 | 11.3 |
| $AUC_{last}/D$ | h*mg/mL | 169 | 153 | 172 | 165 | 10 | 6.22 |
| $V_{ss}\_obs$ | L/kg | 14.6 | 15.7 | 16.4 | 15.6 | 0.9 | 5.94 |

The p.o. plasma concentration profile of compound no. 42140 is shown in Table 11, FIG. 7B, and FIG. 7C. A summary of the p.o. pharmacokinetic parameters is shown in Table 12.

TABLE 11

PO Dose: 5 mg/kg

| Time (h) | Concentration (ng/mL) | | | Mean (ng/mL) | SD (ng/mL) | CV (%) |
|---|---|---|---|---|---|---|
| | Mouse 4 | Mouse 5 | Mouse 6 | | | |
| 0.25 | 100 | 71.4 | 78.6 | 83 | 15 | 17.9 |
| 0.5 | 201 | 121 | 122 | 148 | 46 | 31.0 |
| 1 | 193 | 119 | 112 | 141 | 45 | 31.8 |
| 2 | 165 | 100 | 105 | 123 | 36 | 29.4 |
| 4 | 88.4 | 64.2 | 77.7 | 76.8 | 12.1 | 15.8 |
| 8 | 49.0 | 37.2 | 37.4 | 41.2 | 6.8 | 16.4 |
| 24 | BLOQ | BLOQ | 3.26 | NA | NA | NA |

TABLE 12

PO Dose: 5 mg/kg

| PK parameters | Unit | Mouse 4 | Mouse 5 | Mouse 6 | Mean | SD | CV(%) |
|---|---|---|---|---|---|---|---|
| $T_{1/2}$ | h | 3.56 | 4.31 | 4.42 | 4.10 | 0.47 | 11.4 |
| $T_{max}$ | h | 0.500 | 0.500 | 0.500 | 0.500 | 0.000 | 0.000 |
| $C_{max}$ | ng/mL | 201 | 121 | 122 | 148 | 46 | 31.0 |
| $AUC_{last}$ | h*ng/mL | 856 | 569 | 940 | 788 | 194 | 24.6 |
| $AUC_{Inf}$ | h*ng/mL | 1108 | 801 | 961 | 956 | 153 | 16.0 |
| $AUC\_\%_{Extrap}\_obs$ | % | 22.7 | 28.9 | 2.16 | 17.9 | 14.0 | 78.1 |
| $MRT_{Inf}\_obs$ | h | 5.27 | 6.33 | 5.84 | 5.81 | 0.53 | 9.15 |
| $AUC_{last}/D$ | h*mg/mL | 171 | 114 | 188 | 158 | 39 | 24.6 |
| F | % | 104 | 69.0 | 107 | 93 | 21 | 22.5 |

24. Activity of SRI-40000 in a Rat Model of Lung Fibrosis a. Experimental Methods Animal:

Species and quality level: SD rats, SPF grade; Gender and number: male, 12; Purchasing body weight range: 260-280 g; Company Certificate No.: SCXX (zhe) 2018-0001, Zhejiang Vital River Laboratory Animal Technology Co., Ltd.

Animal Housing:

Rats were housed in the Animal House Facility of the KCI Biotech Inc. under international standards for temperature, humidity and light control system. The animal use protocol has been reviewed and approved by the Institutional Animal Care and Use Committee (IACUC) of KCI Biotech Inc. All experimental procedures were conducted in conformity with institutional guidelines of KCI Biotech Inc.

Model Establishment:

This study was carried out in strict accordance with the SOP institutional guidelines for the care and use of laboratory animals. Rats were anesthetized by intraperitoneal injection of pentobarbital sodium at dose of 50 mg/kg. Then rat neck skin was disinfected and opened in layers. The trachea was exposed carefully. Bleomycin (BLM) was directly injected into left main bronchus at a dose of 3 mg/kg body weight in volume of 1.0 ml/kg via a cannula. After closing the trachea and skin in layers the animal was moved on an electric heat pad at 37° C. to wait waking up from anesthesia before returning to holding cages with free access to water and diet.

Experiment Grouping:

Rats were assigned into two groups: Model (Group-1, n=6), CPD-X (Group-2, 10 mg/kg/d, n=6) (Table 13).

TABLE 13

| Group | N | BLM (3.0 mg/kg) | CPD dosing | CPD | Route | Dosage mg/kg | Dosing rate |
|---|---|---|---|---|---|---|---|
| G1 | 6 | Yes | No | Saline | ip | | QD |
| G2 | 6 | Yes | Yes | CPD-X | ip | 10 | QD |

Drug Administration:

A Test article, CPD-X was designed as an intraperitoneal injection once a day starting from day-8 of modeling for 14 days (Table 13). The saline as a vehicle for model group via a ip injection once a day for 14 days.

Left Lung Collection for Pathology Analysis:

One day after the last dosing all animals were euthanized according to the standard SOP at KCI. After confirming the animal death the left lung BALF was collected according the standard SOP at KCI. The BALF was frozen in liquid nitrogen and stored at −80° C. The left lungs then were perfused with equal volume of 10% formaldehyde solution (3 mL for each lung).

Lung pathology was processed after lung fixation. All animal hearts were collected at same time, weighted, and fixed in 10% formaldehyde solution for histology examination.

Figure 8:
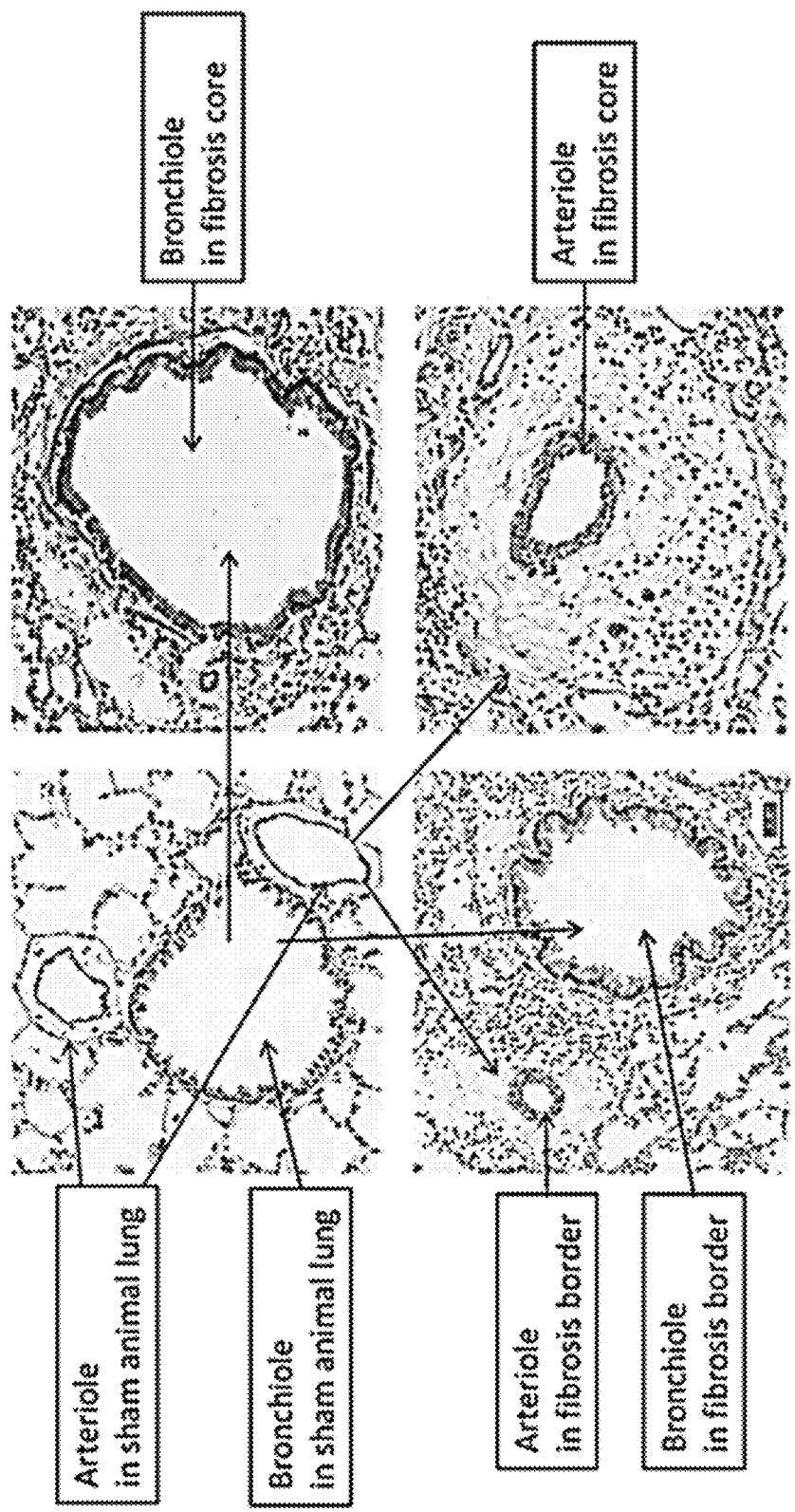
FIG. 8 shows representative images illustrating the criteria of histological features for the bronchiole and pulmonary arteriole damage and inflammation.
Figure 9:
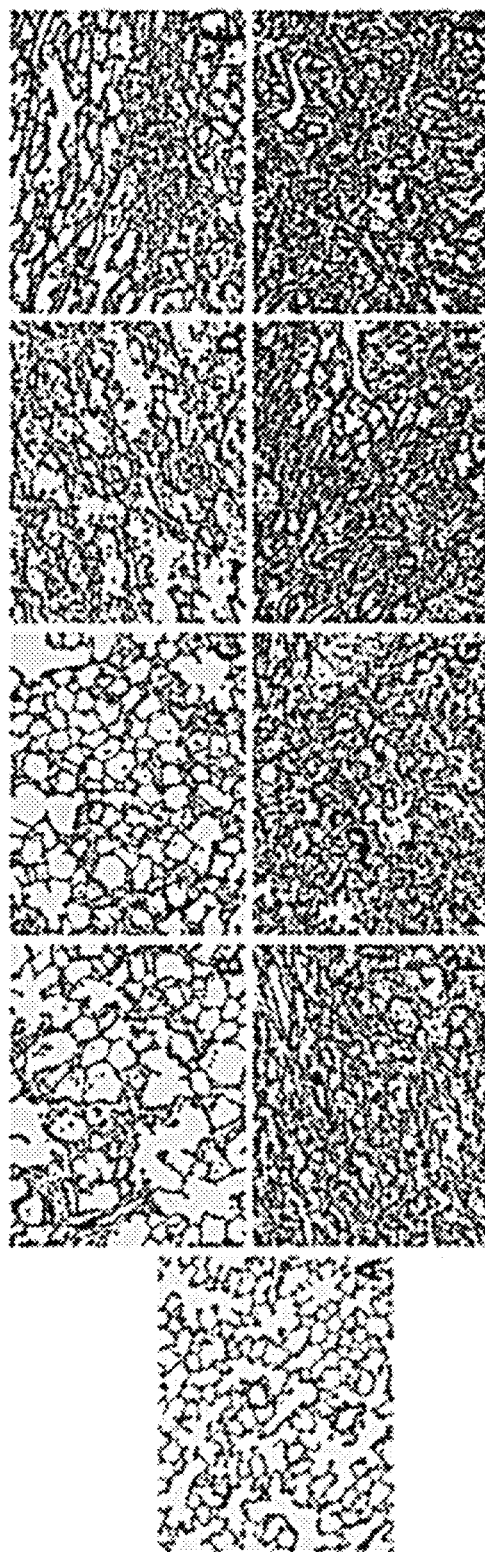
FIG. 9 shows representative images illustrating the criteria of histological features for lung fibrosis screening (A: Normal; B: score 1; C: score 2; D: score 3; E: score 4; F: score 5; G: score 6; H: score 7; I: score 8).

Left Lung Pathology Assay:

The whole left lung was dehydrated and wax embedded following KCI pathology SOP, then sectioned at 3 m in thickness. HE and Masson Trichrome staining were processed following KCI pathology standard staining SOPs, whole slides were then scanned by Hamamatsu NanoZoomer Digital Pathology S210 slide scanner after staining. Bronchiole and pulmonary arteriole damage and inflammatory cell infiltration in fibrosis core and fibrotic board area were scored with H&E stained slides (Table 14 and Table 15, FIG. 8), for which 5 different areas were selected in each lung slide. BLM induced left lung injury area and Ashcraft scoring for fibrosis were evaluated with Masson Trichrome stained slides (Table 16 and FIG. 9), for which 10 different areas were selected in each lung slide.

TABLE 14

| Score | |
|---|---|
| | The damage of terminal bronchiole wall |
| 0 | Normal structure |
| 1 | Normal structure with less than ½ of the terminal bronchiole wall area injury and characterized by bronchial epithelial cells damage and epithelium regeneration, wall edema, medium layer of the mucosal muscle degeneration or regeneration. |

TABLE 14-continued

| Score | |
|---|---|
| 2 | Normal structure with more than ½ of the terminal bronchiole wall area injury and characterized by bronchial epithelial cells damage and epithelium regeneration, wall edema, medium layer of the mucosal muscle degeneration or regeneration. |
| 3 | Normal structure with more than ½ area of the terminal bronchiole wall area injury and characterized by bronchial epithelial cells damage and epithelium regeneration, wall edema, medium layer of the mucosal muscle degeneration or regeneration, granulomas formation or fibrosis. |
| | The terminal bronchiole wall inflammatory cells infiltration |
| 0 | Normal structure with no inflammatory cells infiltration |
| 1 | The terminal bronchiole outside wall with a few scattered inflammatory cell infiltration (less than 10) but no focal. |
| 2 | The terminal bronchiole outside wall with a lot scattered inflammatory cell infiltration which is focal or diffuse and totaled less than ½ area of the terminal bronchiole wall. |
| 3 | The terminal bronchiole outside wall with diffuse infiltration of inflammatory cells and totaled more than ½ area of the terminal bronchiole wall, inflammatory cells infiltration in the inner and medium layer of the membrane. |

TABLE 15

| Score | |
|---|---|
| | Pulmonary small arteries wall damage |
| 0 | The structure of pulmonary small arteries is clear and complete |
| 1 | The parts endothelial cells exfoliate |
| 2 | The endothelial cells exfoliate, medium layer of the smooth muscle degeneration, regeneration or small focal necrosis. |
| 3 | The endothelial cells exfoliate, medium layer of the smooth muscle degeneration, regeneration or small focal necrosis, medium layer of the smooth muscle degeneration, regeneration or small focal necrosis, medium layer granulomas formation or fibrosis. |
| | Pulmonary arteriole inflammatory infiltration |
| 0 | Normal structure of pulmonary small arteries |
| 1 | The pulmonary small arteries outside wall with a few scattered inflammatory cell infiltration (less than 10) but no focal. |
| 2 | The pulmonary small arteries outside wall with a lot scattered inflammatory cell infiltration which is focal or diffuse and totaled less than ½ area of the artery wall. |
| 3 | The pulmonary small arteries outside wall with diffuse infiltration of inflammatory cells and totaled more than ½ area of the pulmonary small artery wall, inflammatory cells infiltration in the medium layer of the membrane. |

TABLE 16

| Grade of fibrosis | Ashcroft scoring criteria |
|---|---|
| 0 | Alveolar septum: no fibrosis lesion<br>Structure: normal |
| 1 | Alveolar septum: Isolated and Simple Pulmonary fibrosis ( alveolar walls thicken but less than of triple times normal lung)<br>Structure: Large alveolar areas, little exudate, no fibrosis material. |
| 2 | Alveolar septum: Clear fibrosis change (alveolar walls thicken and lager than of triple times normal lung), small nodule formation but no connection.<br>Structure: Large alveolar areas, little exudate, no fibrosis material. |
| 3 | Alveolar septum: Early stage fibrosis forms in all alveolar (alveolar walls thicken and lager than of triple times normal lung)<br>Structure: Large alveolar areas, little exudate, no fibrosis material. |
| 4 | Alveolar septum: Alveolar septum is still visible.<br>Structure: Isolated fibrosis nodule formation in alveolar (≤10% at high magnification) |
| 5 | Alveolar septum: Alveolar septum is still visible.<br>Structure: Integrate fibrosis nodule formation in alveolar (>10% and ≤50% at high magnification). Lung structure is substantially impaired but exists. |
| 6 | Alveolar septum: seen but barely existed.<br>Structure: Integrate fibrosis nodule formation in alveolar (>50% at high magnification). Lung structure is barely exists. |
| 7 | Alveolar septum: Not exist.<br>Structure: Pulmonary alveoli and interstitial fibrosis proliferation were seen but there are still 5 vacuole structure. |
| 8 | Alveolar septum: Not exist.<br>Structure: Pulmonary alveoli and interstitial fibrosis proliferation were seen at high magnification. |

The animal hearts were dehydrated and wax embedded following KCI pathology SOP, then sectioned at 3 m in thickness. HE staining was processed following KCI pathology standard staining SOPs, whole slides were then scanned by Hamamatsu NanoZoomer Digital Pathology S210 slide scanner after staining. The thickness of left ventricle wall (LV), septum and right ventricle wall (RV) were measured at five different points and calculated the average thickness of LV, septum and RV.

Statistical Analysis:

A Statistical analysis was performed using Graphpad prism 6.0 software. Descriptive results were expressed as mean±sem or mean±sd. Statistical comparisons were performed using t-test, two-way ANOVA analysis. The p value <0.05 was considered as statistically significant.

b. Results

Animal Clinical Observation During Experiment:

There was no obviously physical and behavior abnormality change in all experiment rats during experiment.

Figure 10:
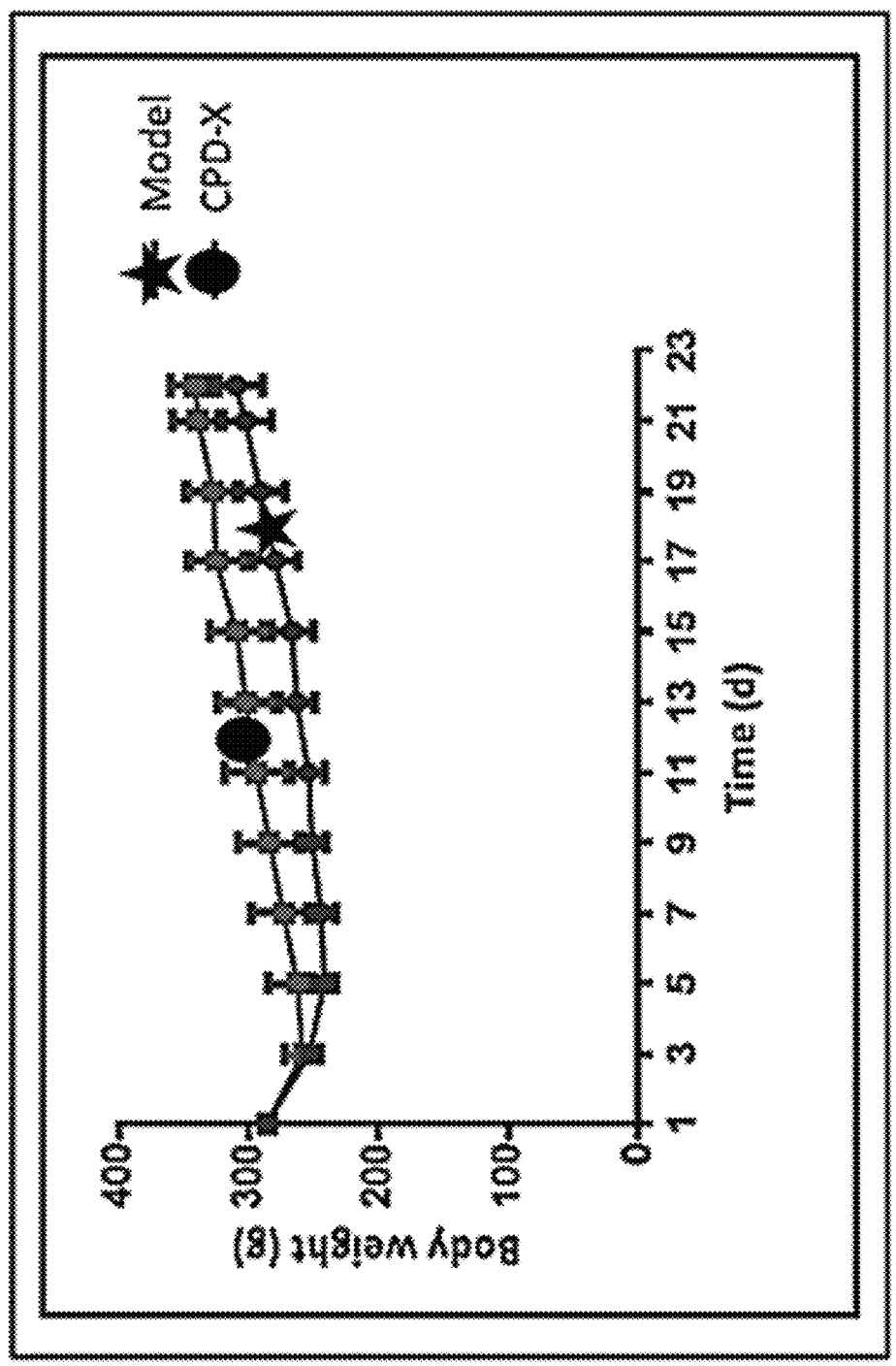
FIG. 10 shows representative data illustrating the changes in animal body weight during the experiment.
Figure 11:
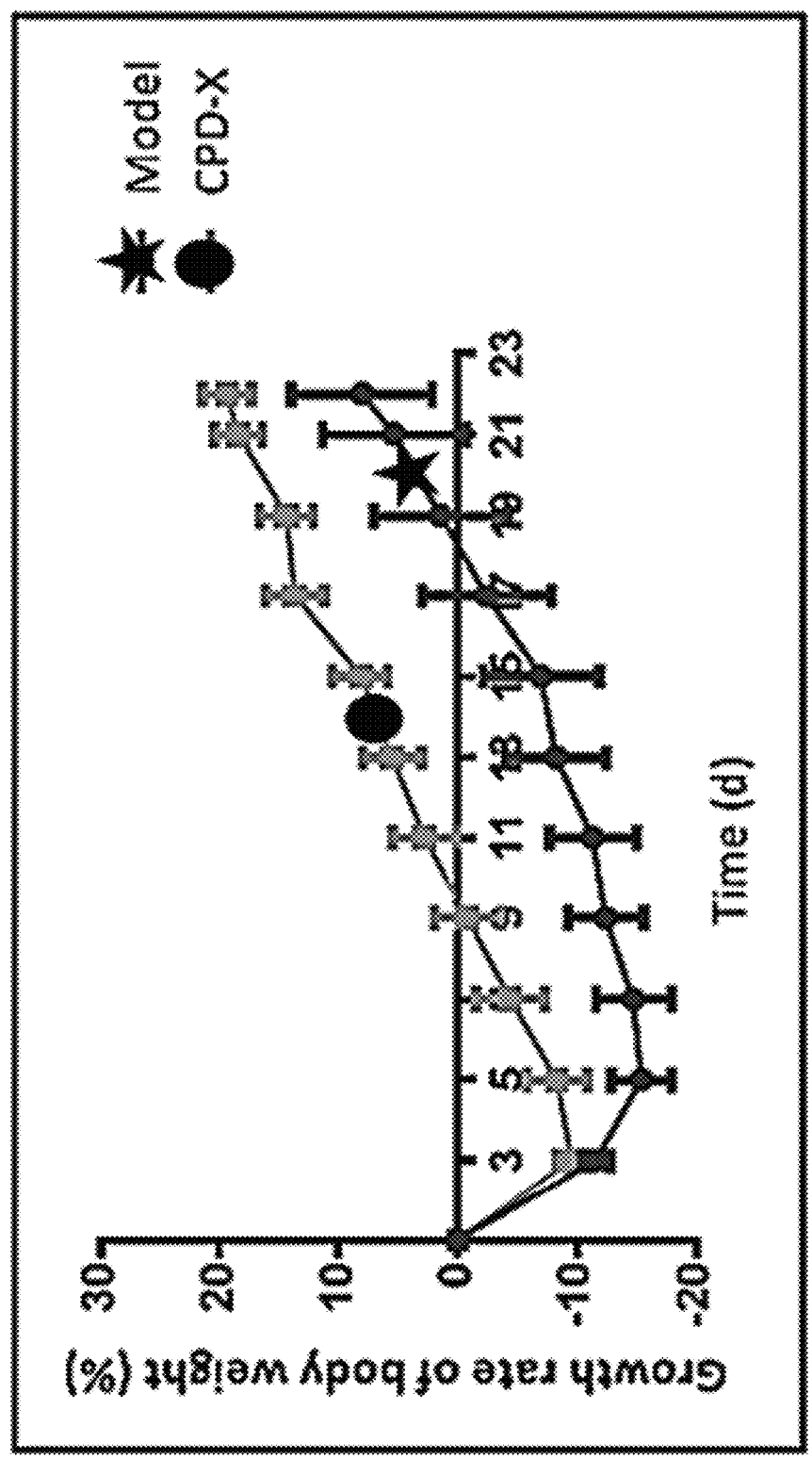
FIG. 11 shows representative data illustrating the growth rate of animal body weight during the experiment.
Figures 12A, 12B:
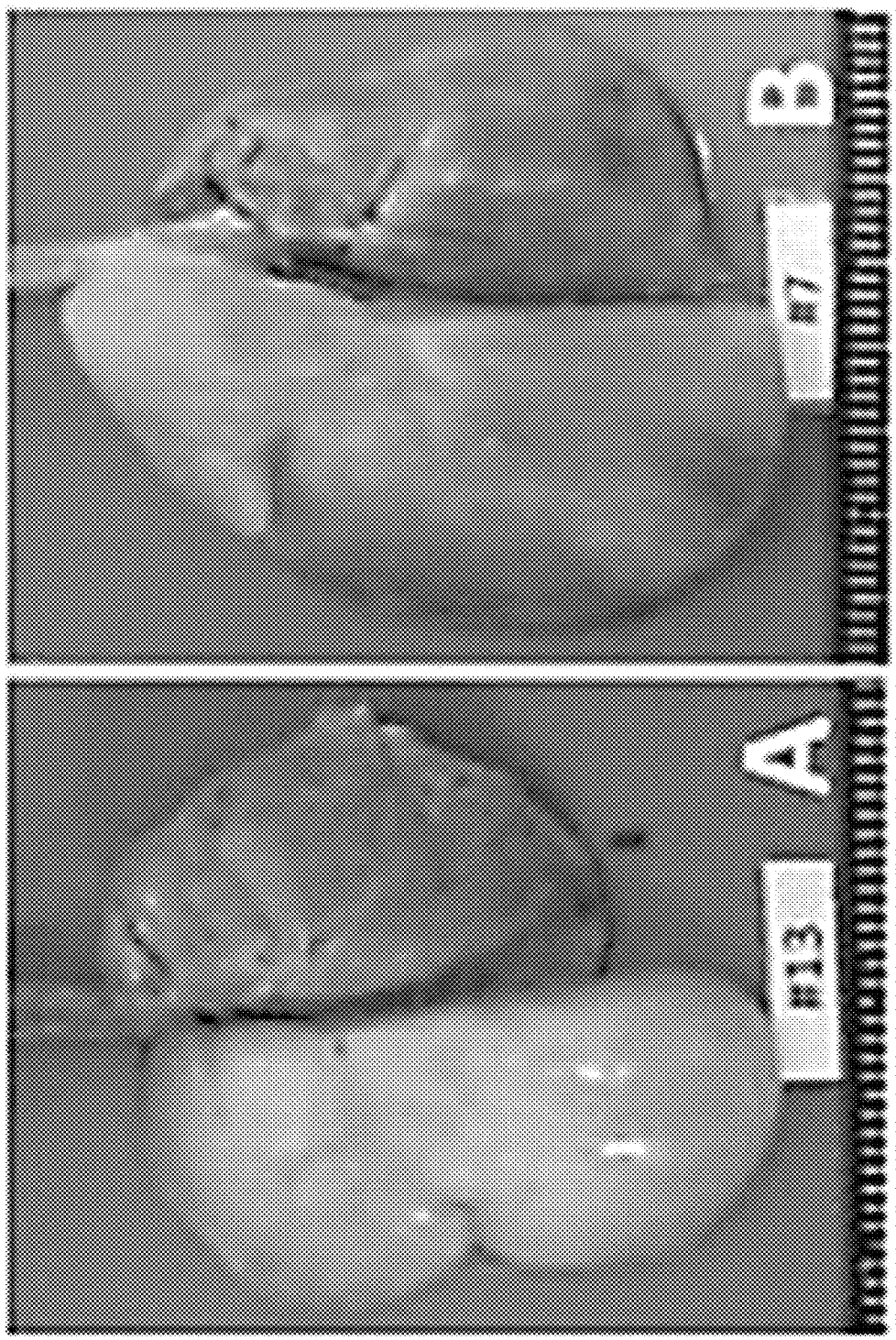
FIG. 12A-D show representative images illustrating BLM-induced left lung damage in a model group (FIG. 12A and FIG. 12C) and a CPD-X group (FIG. 12B and FIG. 12D).
Figures 12C, 12D:
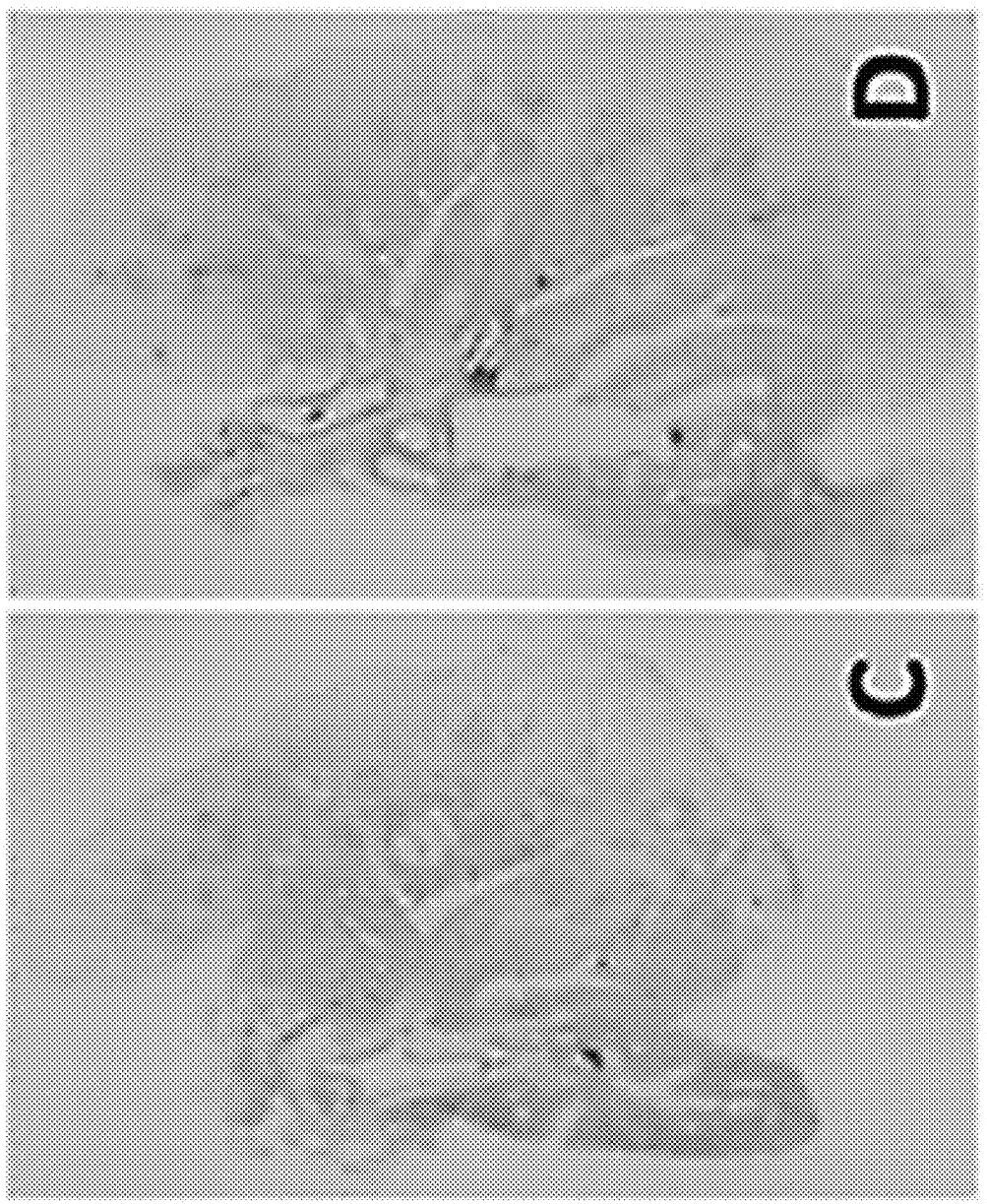
Figures 13A, 13B:
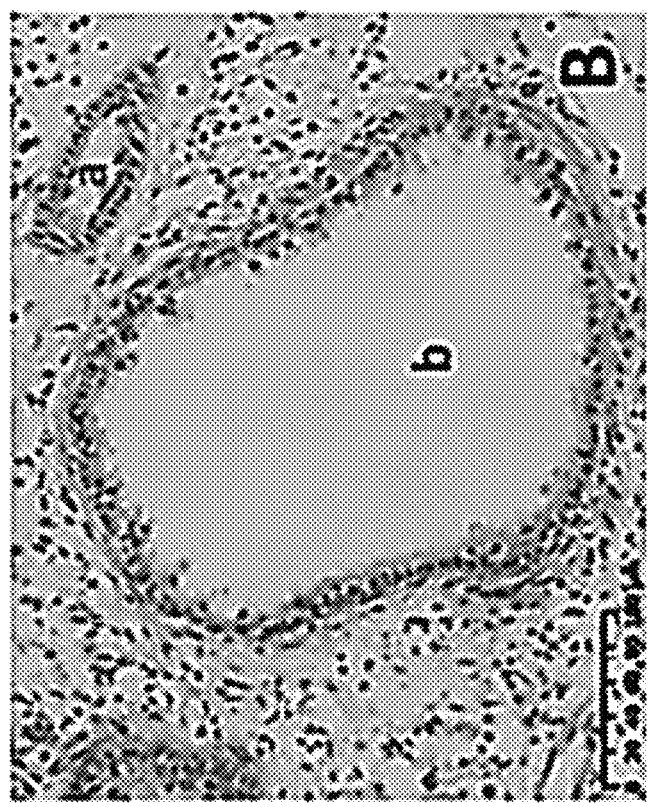

Changes in Body Weight in all Experiment Rats:

All rat body weights were reduced slightly over first six to seven days after surgery during experiment period. Then all rat body weight began to recover gradually with the experiment process. There was a significant difference in body recovery between the CPD-X treatment group and model group (Table 17, FIG. 10, and FIG. 11).

TABLE 17

| | Group | | | |
|---|---|---|---|---|
| | Model | | CPD-X 10 mg/kg/d | |
| day | (n = 6) | Changes in the ratio (%) | (n = 6) | Changes in the ratio (%) |
| 0 | 281.3 ± 7.8 | 0 | 286.0 ± 6.1 | 0 |
| 2 | 253.2 ± 12.7 | −11.6 ± 2.7 | 258.7 ± 13.4 | −9.6 ± 3.6 |
| 5 | 242.3 ± 21.1 | −15.4 ± 6.1 | 262.4 ± 22.6 | −8.3 ± 6.7 |
| 7 | 244.3 ± 25.3 | −14.7 ± 7.7 | 273.6 ± 24.9 | −4.4 ± 7.6 |
| 9 | 251.0 ± 26.5 | −12.4 ± 7.9 | 283.9 ± 24.5 | −0.8 ± 7.5 |
| 11 | 254.2 ± 29.3 | −11.3 ± 9.0 | 294.1 ± 23.5 | 2.8 ± 7.0 |
| 13 | 263.0 ± 33.7 | −8.3 ± 10.4 | 302.0 ± 22.0 | 5.5 ± 6.4 |
| 15 | 266.8 ± 39.5 | −7.0 ± 12.1 | 309.0 ± 20.4 | 8.2 ± 6.1 |
| 17 | 279.8 ± 43.2 | −2.5 ± 13.3 | 325.3 ± 21.2 | 13.7 ± 6.4 |
| 19 | 291.0 ± 45.2 | 1.4 ± 13.8 | 327.3 ± 20.7 | 14.4 ± 5.9 |
| 21 | 302.3 ± 48.3 | 5.4 ± 14.7 | 338.9 ± 19.4 | 18.4 ± 5.3 |
| 22 | 310.0 ± 48.2 | 8.0 ± 14.6 | 341.6 ± 18.8 | 19.4 ± 5.4 |

Figure 14:
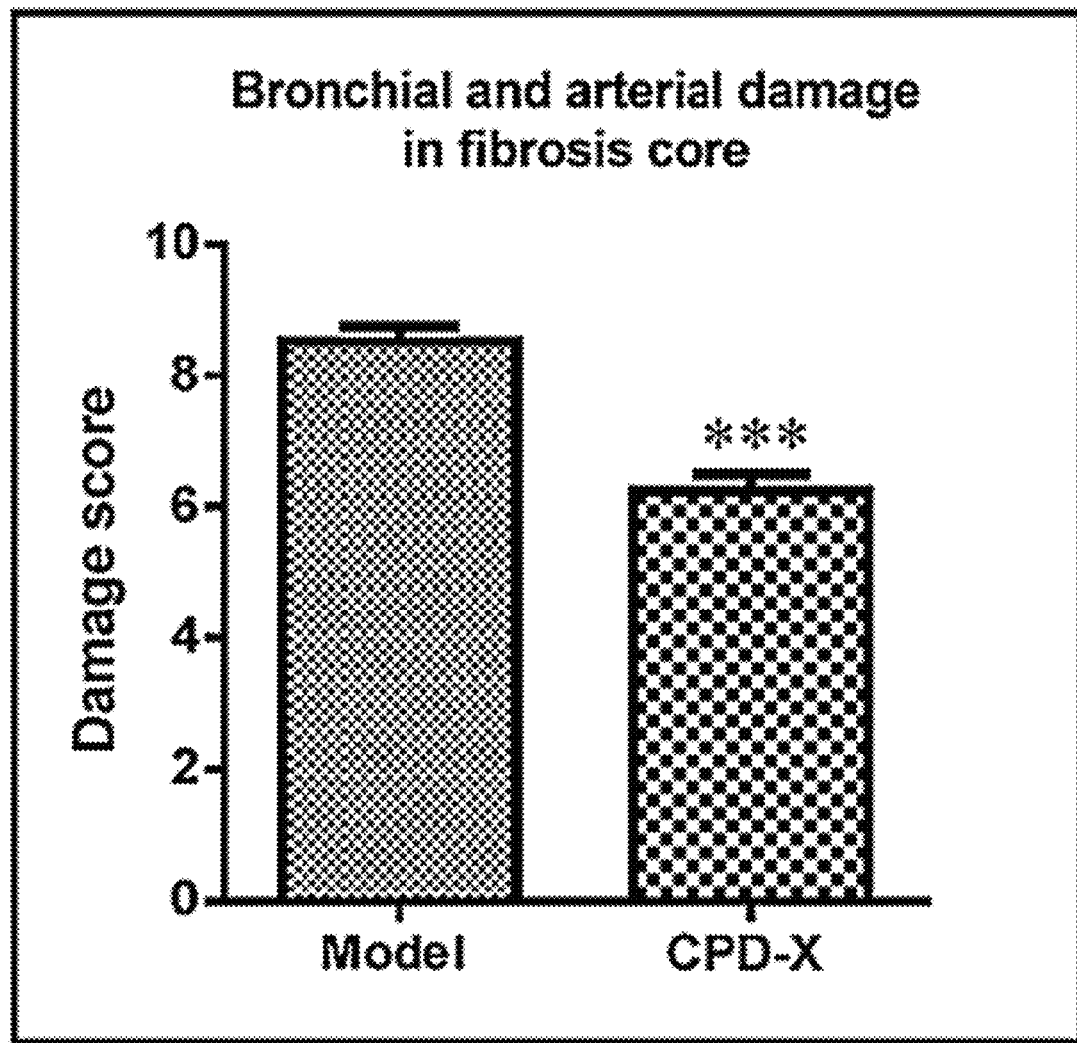
FIG. 14 shows representative data illustrating the change of left lung bronchial and arteriole damages in the fibrotic core. T-test: ***$p<0.001$ vs. model group.
Figure 15:
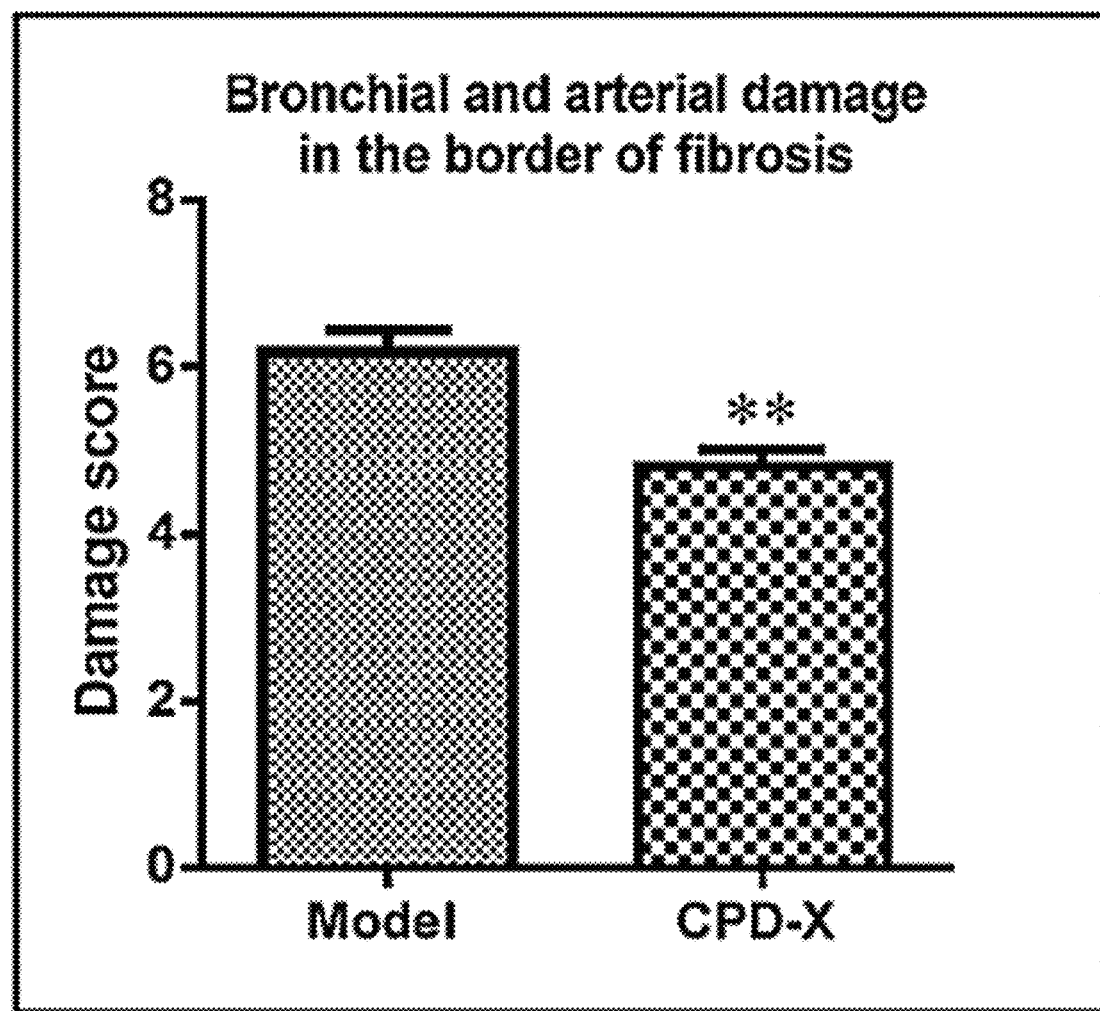
FIG. 15 shows representative data illustrating the change of left lung bronchial and arteriole damages in the border of the fibrosis core. T-test: **$p<0.01$ vs. model group.
Figure 16D:
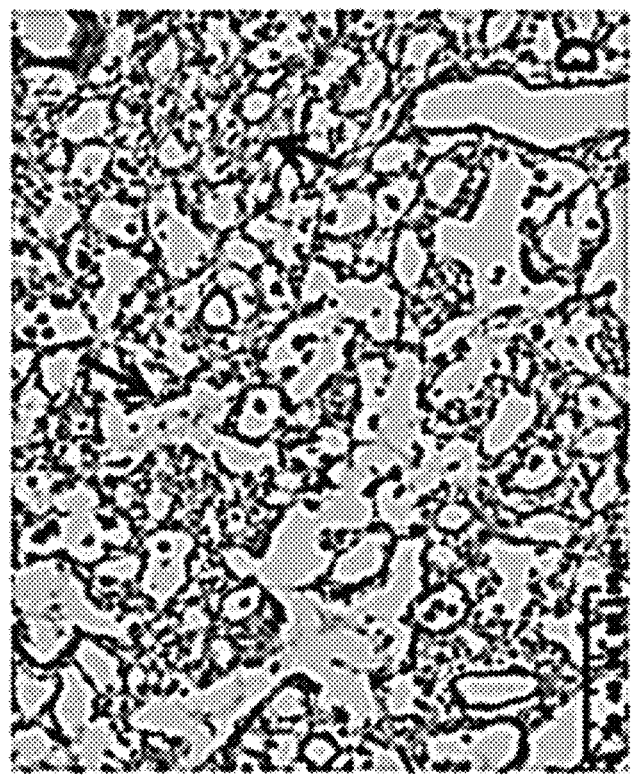
Figure 16C:
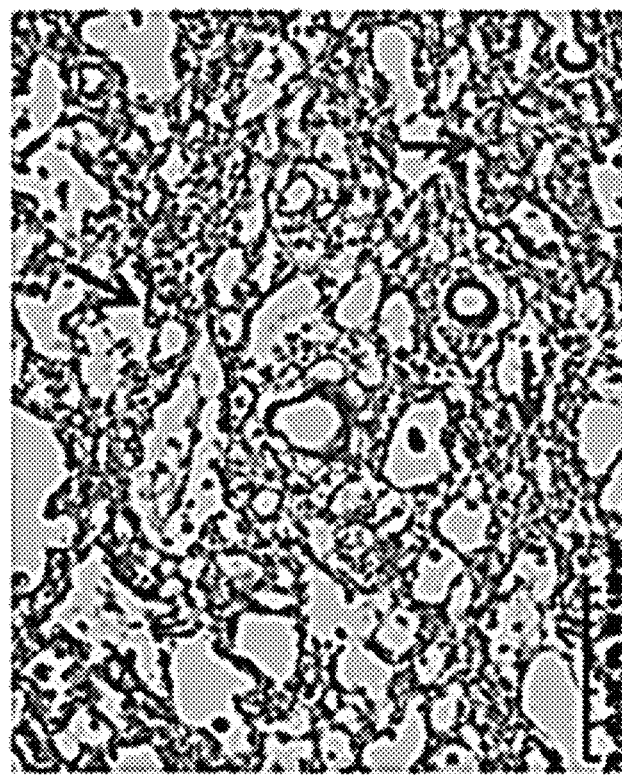
Figure 17:
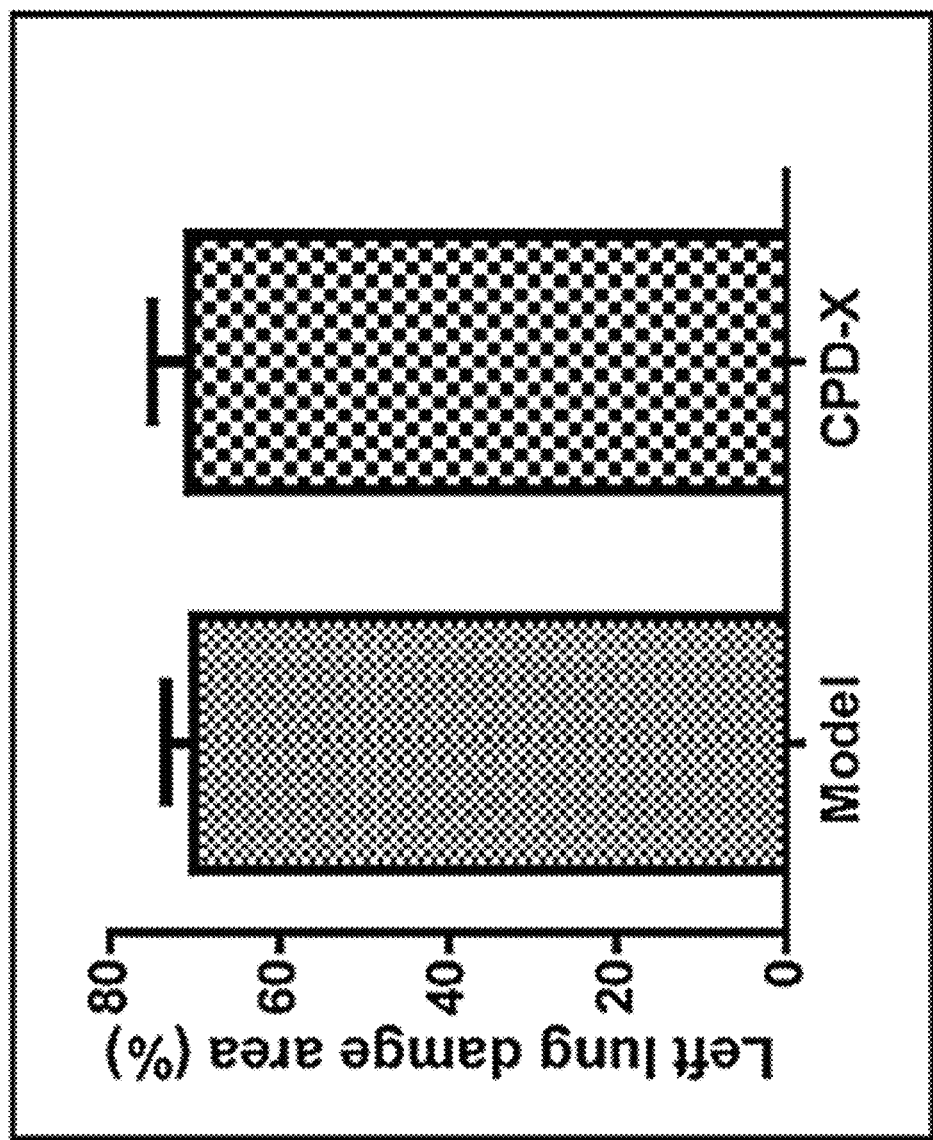
FIG. 17 shows representative data illustrating the BLM-induced left lung damage area (%).

Pathological Analysis of Bronchi and Arterioles in Left Lung:

A Left lung histology represented a significant lung injury with a clear damage board (FIG. 12A-D) which showed as a different degree of bronchial hyperplasia, terminal fine bronchus and alveolar duct epithelial cell hyperplasia, different quantity of mucus in bronchial lumen. Different degree of inflammatory cell infiltration on bronchial walls, especially in the adventitia area; partial bronchial wall thickness with granulation tissue were observed. Alveolar damages in fibrosis core were represented as alveolar epithelial denudation, regeneration, alveolar wall inflammatory cell infiltration and fibrosis. Inflammatory exudation in the alveolar cavities with fibrotic mass was also recognized widely. A different degree of arteriole endothelial cell denudation and proliferation were seen both in fibrosis core and fibrosis board with a different degree of inflammatory cell infiltration, mostly located in the adventitia area (FIG. 13A-D). CPD-X treatment had a significant therapeutic effect on reduction of bronchial and arteriole damages both in fibrotic core and in the border of fibrosis (p<0.001) (Table 18, FIG. 14, and FIG. 15).

TABLE 18

|  | In the fibrosis core (n = 6) | In the border of fibrosis (n = 6) |
| --- | --- | --- |
| Model | 8.53 ± 0.53 | 6.17 ± 0.66 |
| CPD-X | 6.23 ± 0.67*** | 4.8 ± 0.54** |

T-test: p < 0.01 vs. model, *p < 0.001 vs. model

Figure 18:
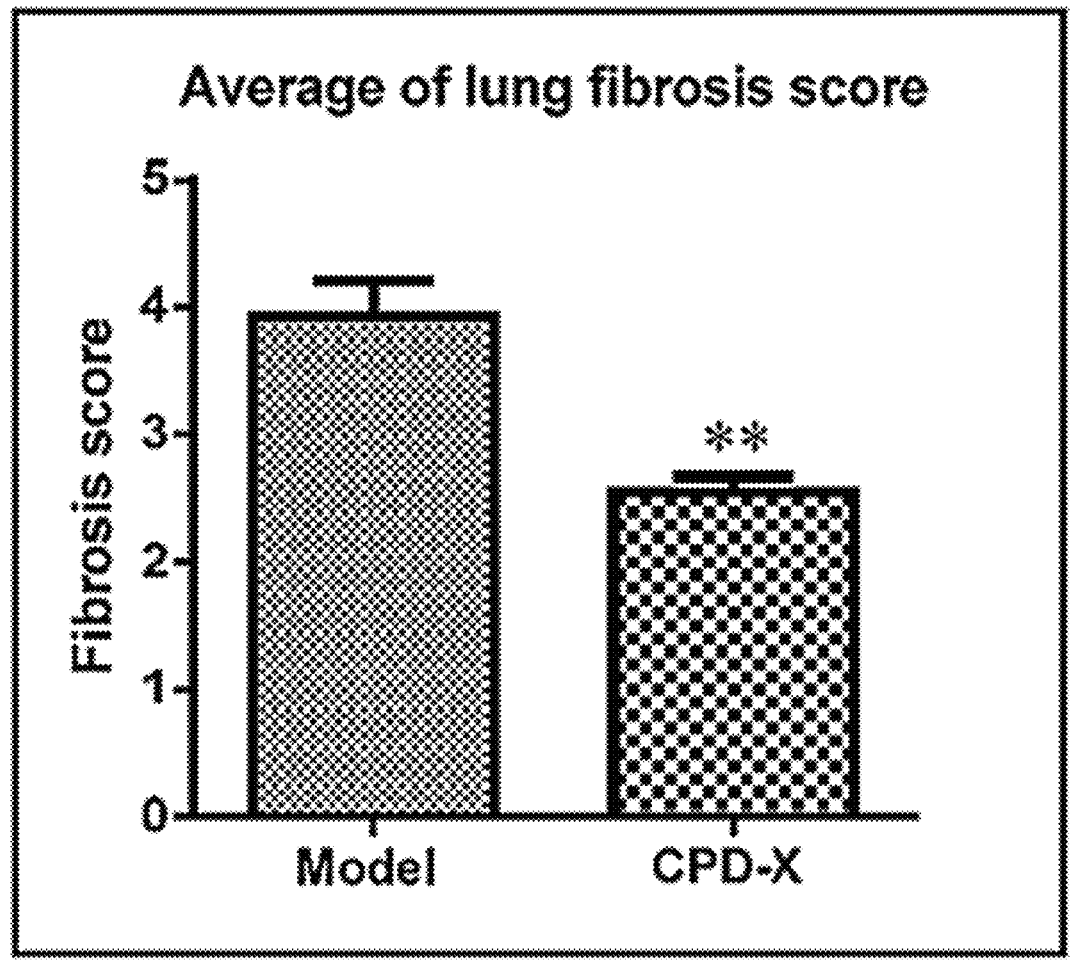
FIG. 18 shows representative data illustrating the change in left lung Ashcroft fibrosis core. T-test: **$p<0.01$ vs. model.
Figure 19:
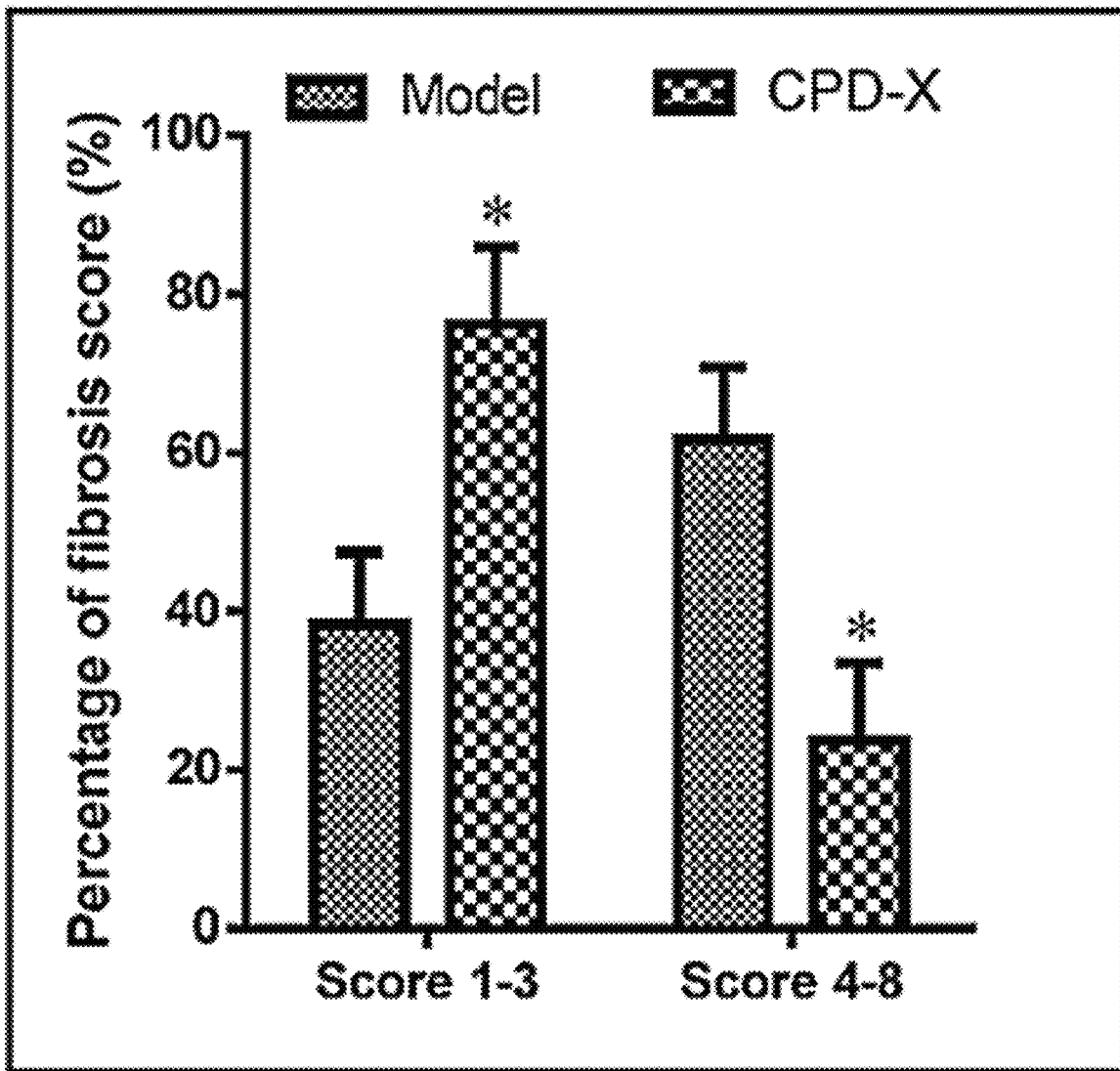
FIG. 19 shows representative data illustrating the ratio of left lung fibrosis score. Two-way ANOVA: *$p<0.05$ vs. model.

Pathological Analysis of Left Lung Fibrosis Core:

With Masson Trichrome staining the left lung fibrosis was scored according to Ashcraft scoring methods. A significant alveolar damage with fibrosis was recognized (FIGS. 16A-D and FIG. 17). Ashcraft scoring data indicated a significant reduction in fibrosis after CPD-X treatment (Table 19, FIG. 18). Based on the Ashcraft scoring criteria the fibrosis scores were divided two sections such as in section-I the score was ≤3, meaning the original alveolar structure was preserved with a different damage and fibrosis, and in section-II the score was ≥4, meaning the alveolar structure was damaged partially or totally with a different damage and fibrosis. The data showed over sixty percent of Ashcraft score was ≥4 in model group. The CPD-X treatment group's fibrosis score was about 80%≤3. The statistical analysis showed that there was a significantly difference between CPD-X treated group and model group (FIG. 19).

TABLE 19

|  | Lung damage area (%) | Ashcroft fibrosis score | % of fibrosis score (≤3) | % of fibrosis score (≥4) |
| --- | --- | --- | --- | --- |
| Model | 70.12 ± 8.33 | 3.92 ± 0.72 | 38.3 ± 22.29 | 61.67 ± 22.29 |
| CPD-X | 70.69 ± 10.66 | 2.55 ± 0.29** | 90 ± 10.95* | 10 ± 10.95* |

T-test: *p < 0.05 vs. model; **p < 0.01 vs. model

Figures 20A, 20B:
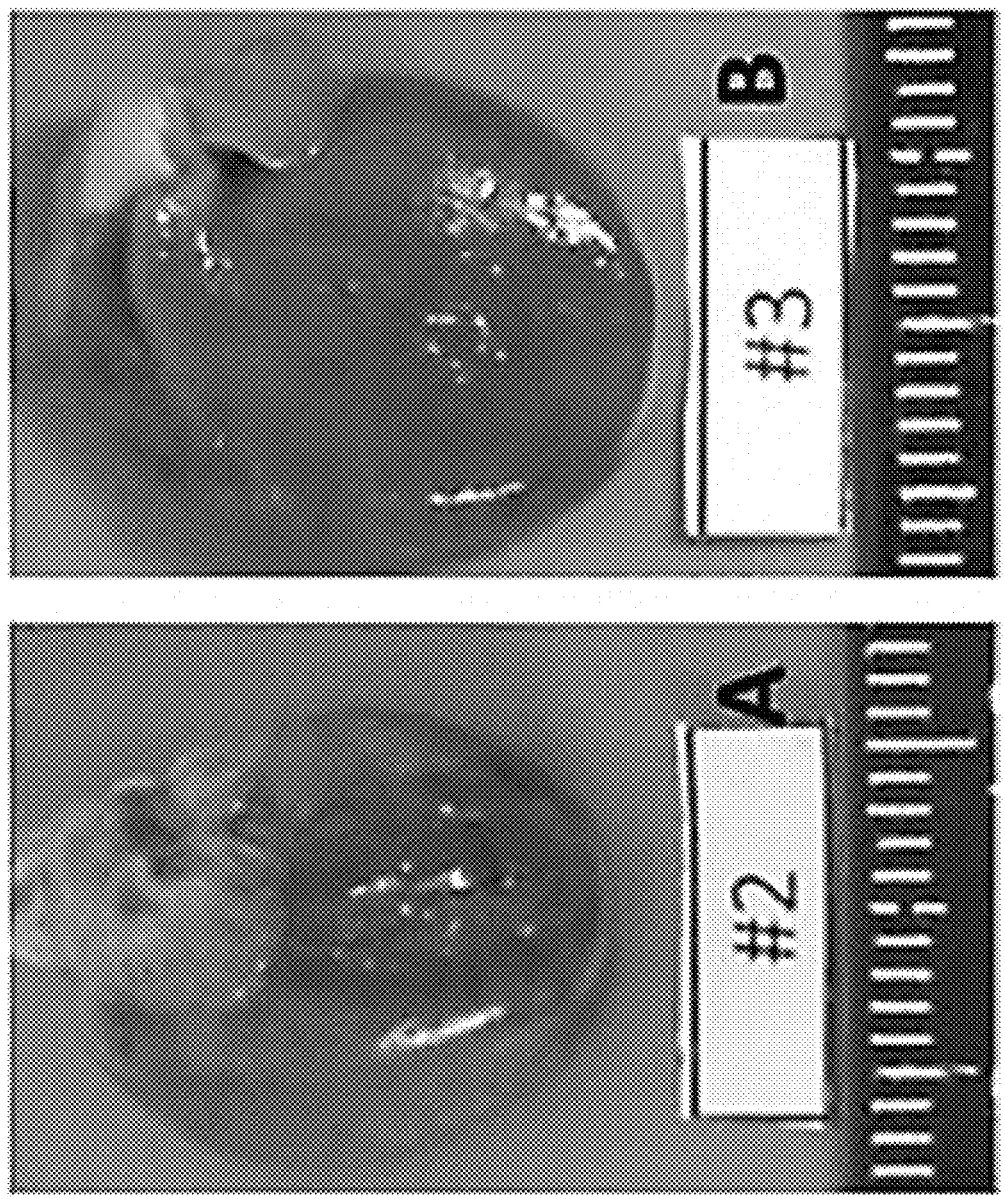
FIG. 20A and FIG. 20B show representative images illustrating the gross images of hearts in a model group (FIG. 20A) and a CPD-X group (FIG. 20B).
Figure 21:
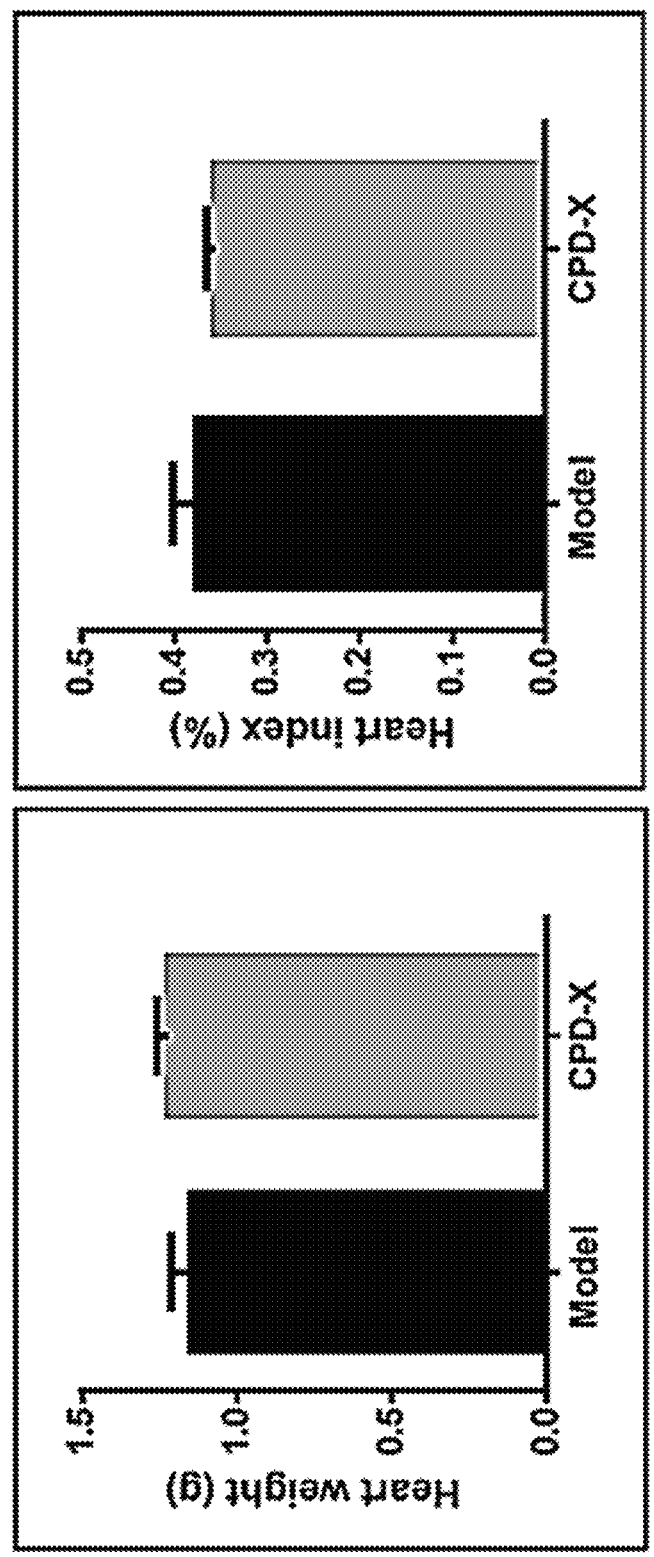
FIG. 21 shows representative data illustrating the changes in the heart weight and heart index (%).

Pathological Analysis of Hearts:

Heart gross pathologic examination did not show a significant difference between two groups (FIG. 20A, FIG. 20B, and FIG. 21).

Thus, without wishing to be bound by theory, successful BLM induced unilateral lung fibrosis model was achieved. CPD-X was administrated via intraperitoneal injection starting on the day-8 of modeling for 14 days indicated a significant therapeutic effect, showing a significant improvement in bronchial and arteriole damage and alveolar fibrosis. CPD-X treatment slightly limited the right ventricle wall thickness due to lung fibrosis. However, there was no statistic difference as compared to model group animals.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula selected from:

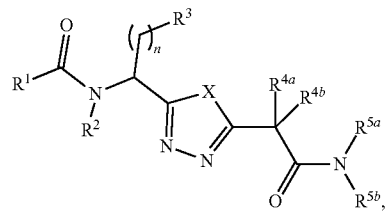

wherein n is selected from 1, 2, 3, and 4;
wherein X is selected from O and S;
wherein $R^1$ is selected from C1-C8 alkyl and $Cy^1$;
   wherein $Cy^1$, when present, is selected from C3-C8 cycloalkyl and aryl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
wherein $R^2$ is selected from hydrogen, C1-C4 alkyl, and amine protecting group;
wherein $R^3$ is selected from $NR^{20a}R^{20b}$, $NHCOR^{21}$, $NHPG^1$, and $Ar^1$;
   wherein $PG^1$ is an amine protecting group;
   wherein each of $R^{20a}$ and $R^{20b}$, when present, is independently selected from hydrogen, C1-C4 alkyl, $Cy^2$, and amine protecting group;
     wherein $Cy^2$, when present, is selected from C3-C8 cycloalkyl and aryl and is substituted with 0-4 non-hydrogen groups independently selected from halogen, $NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
   wherein $R^{21}$, when present, is selected from C1-C4 alkyl, cycloalkyl, and heterocycloalkyl and is substituted with 0-4 non-hydrogen groups independently selected from halogen, —$NH_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
   wherein $Ar^1$, when present, is selected from aryl and heteroaryl and is substituted with 0-4 non-hydrogen groups independently selected from halogen, —CN, C1-C4 alkyl, C, 1-C4 haloalkyl, C1-C4 hydroxyalkyl, C1-C4 alkoxy, —$(CH_2)_mNH_2$, —$(CH_2)_m$(C1-C4 alkylamino), —$(CH_2)_m[(C1-C4)(C1-C4)$ dialkylamino], —$(CH_2)_mNH(C=O)(C1-C4$ alkyl), —$(CH_2)_mN(C1-C4$ alkyl)(C=O)(C1-C4 alkyl), and $Cy^5$;

wherein m is selected from 0 and 1;
wherein Cy⁵, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
wherein each of $R^{4a}$ and $R^{4b}$ is independently selected from hydrogen and C1-C4 alkyl;
or wherein each of $R^{4a}$ and $R^{4b}$ are optionally covalently bonded together and, together with the intermediate atoms, comprise a 3- to 7-membered cycloalkyl substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
wherein each of $R^{5a}$ and $R^{5b}$ is independently selected from hydrogen, C1-C4 alkyl, and Cy³; and
wherein Cy³, when present, is selected from C3-C8 cycloalkyl and aryl and is substituted with 0-4 non-hydrogen groups independently selected from halogen, —NH$_2$, C1-C4 alkyl, C1-C4 haloalkyl, C1-C4 hydroxyalkyl, C1-C4 alkoxy, C1-C4 alkylamino, and (C1-C4)(C1-C4) dialkylamino;
or a pharmaceutically acceptable salt thereof.

2. The compound of claim 1, wherein R³ is selected from $NR^{20a}R^{20b}$, $NHCOR^{21}$, and Ar¹;
wherein Ar¹, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), and —(CH$_2$)$_m$[(C1-C4)(C1-C4) dialkylamino].

3. The compound of claim 1, wherein R¹ is methyl.

4. The compound of claim 1, wherein R³ is selected from $NR^{20a}R^{20b}$ and Ar¹.

5. The compound of claim 1, wherein Ar¹, when present, is selected from aryl and heteroaryl and is substituted with 1-4 non-hydrogen groups independently selected from halogen, —CN, C1-C4 alkyl, C1-C4 haloalkyl, C1-C4 hydroxyalkyl, C1-C4 alkoxy, —(CH$_2$)$_m$NH$_2$, —(CH$_2$)$_m$(C1-C4 alkylamino), —(CH$_2$)$_m$[(C1-C4)(C1-C4) dialkyl amino], —(CH$_2$)$_m$NH(C=O)(C1-C4 alkyl), —(CH$_2$)$_m$N(C1-C4 alkyl)(C=O)(C1-C4 alkyl), and Cy⁵.

6. The compound of claim 1, having a structure represented by a formula selected from:

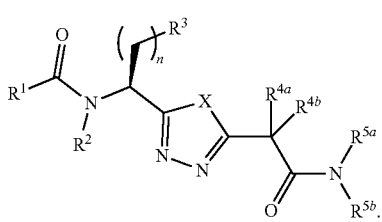

7. The compound of claim 1, having a structure represented by a formula:

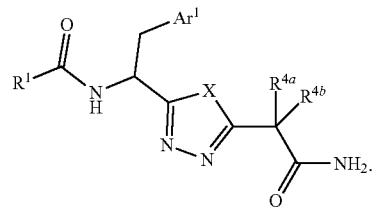

8. The compound of claim 1, having a structure represented by a formula:

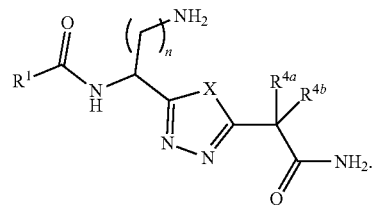

9. The compound of claim 1, wherein the compound is selected from:

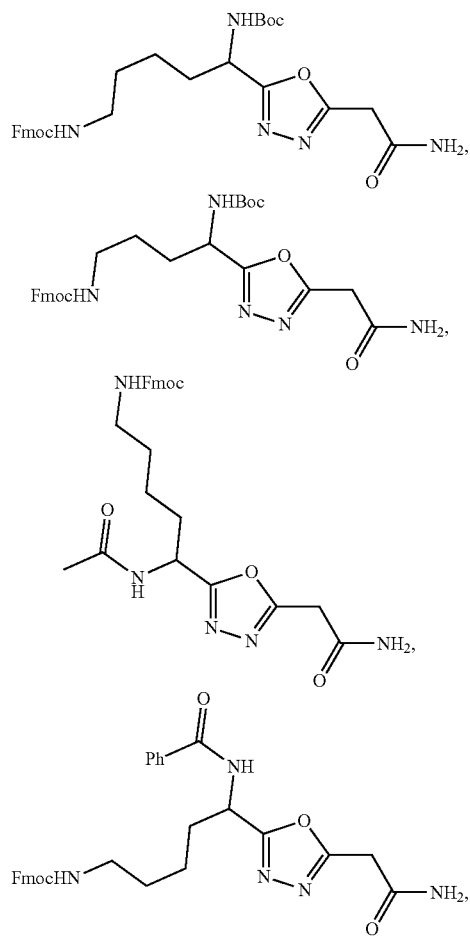

245
-continued
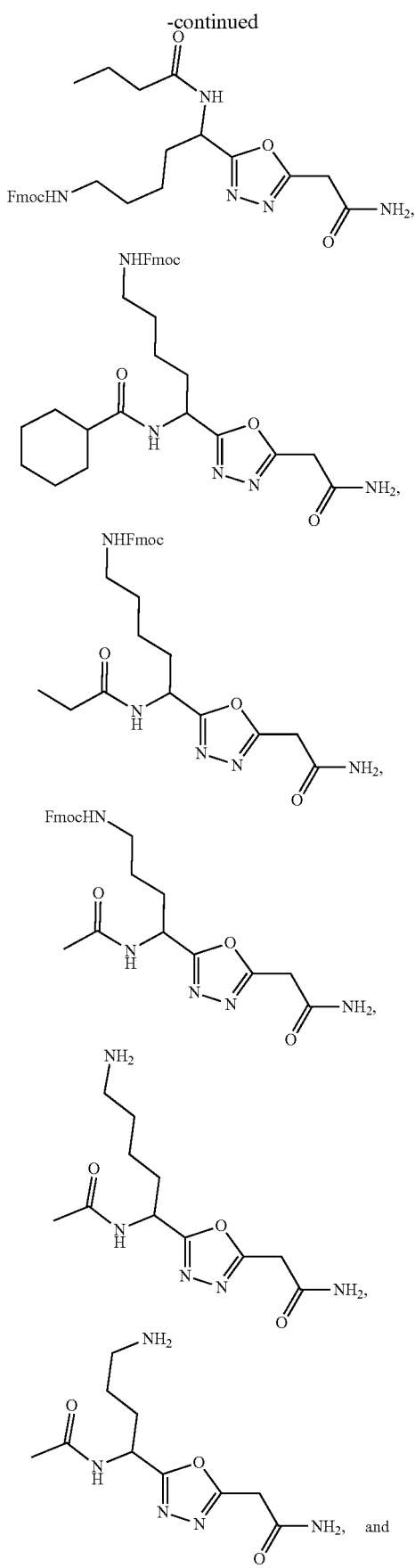
246
-continued
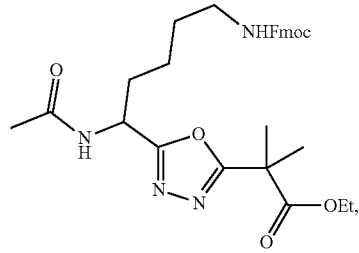
or a pharmaceutically acceptable salt thereof.
10. A compound selected from:
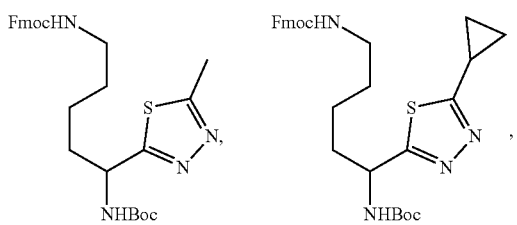
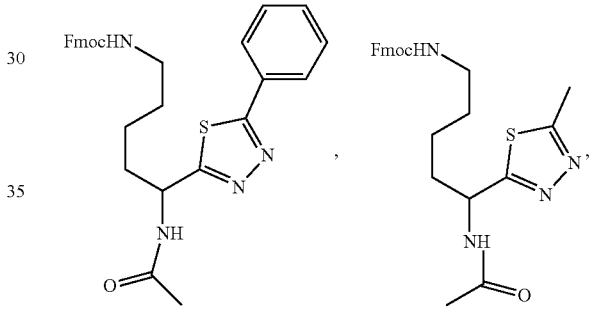
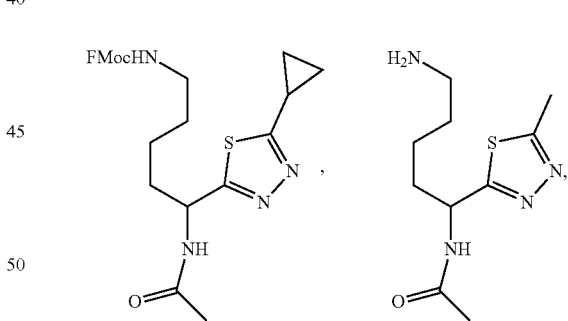
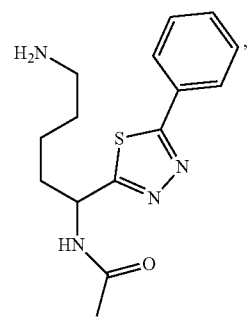

247
-continued
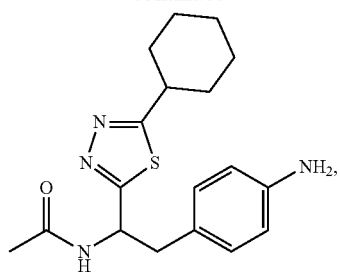
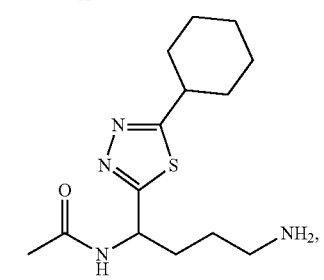
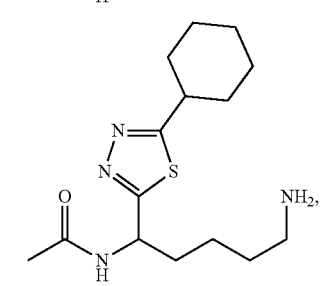
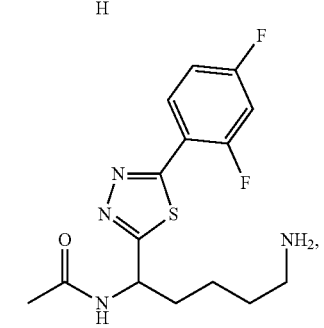
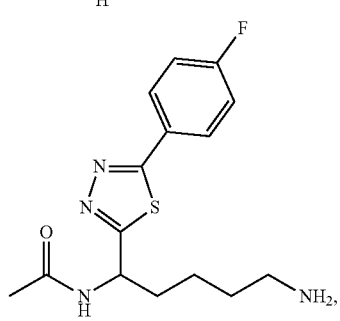
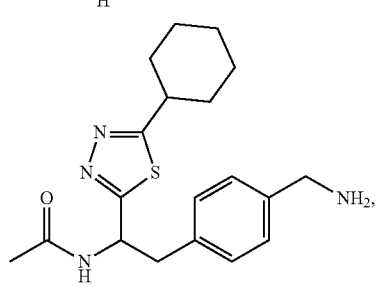
248
-continued
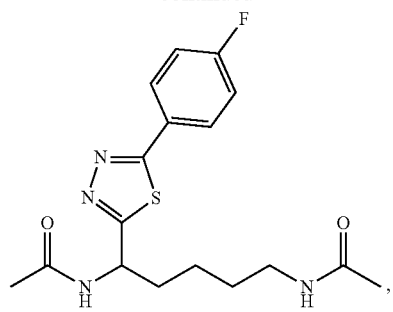
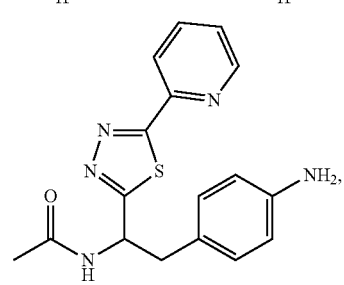
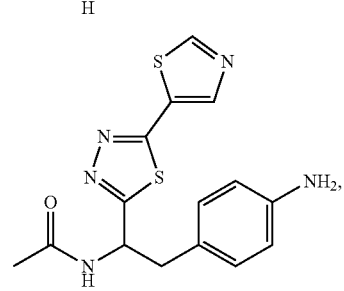
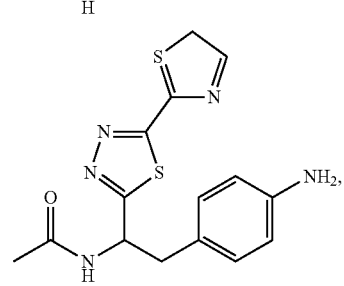
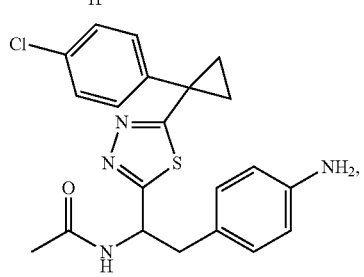
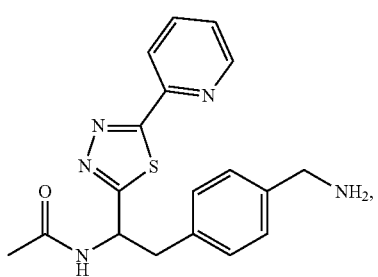

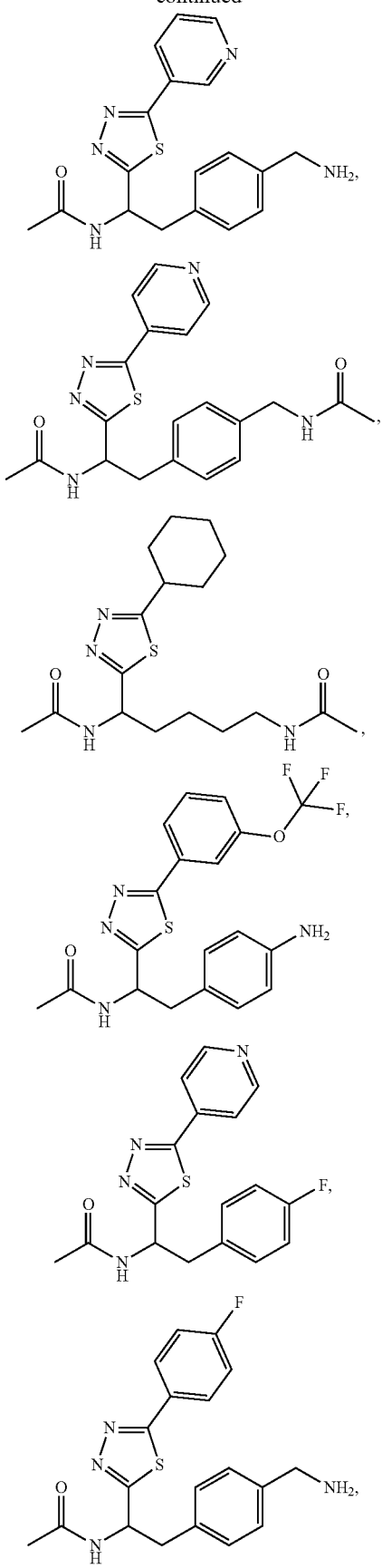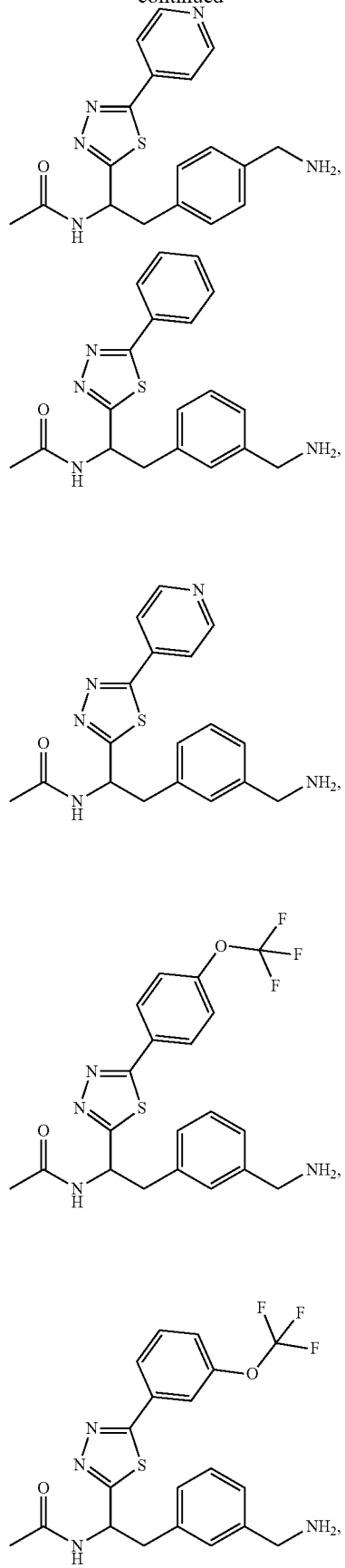

251
-continued
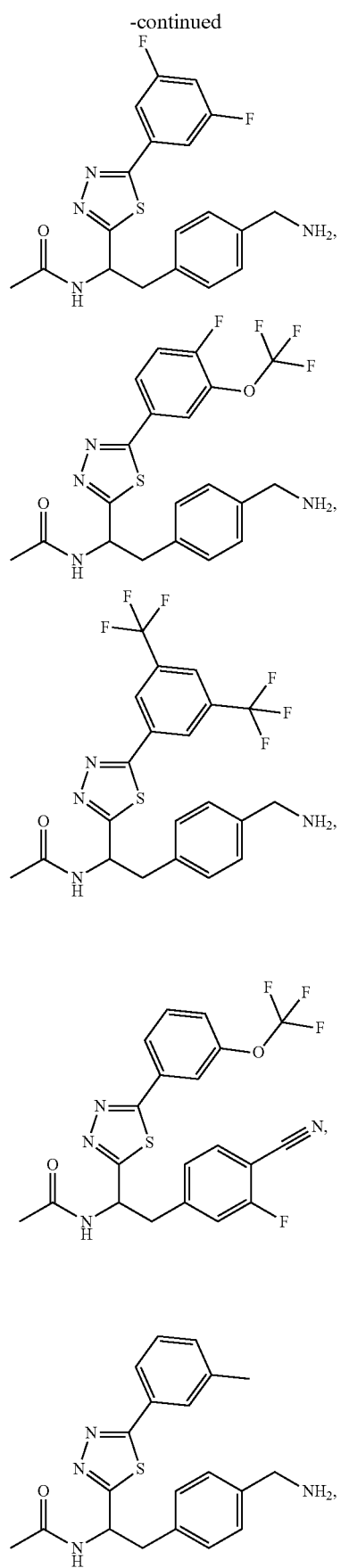
252
-continued
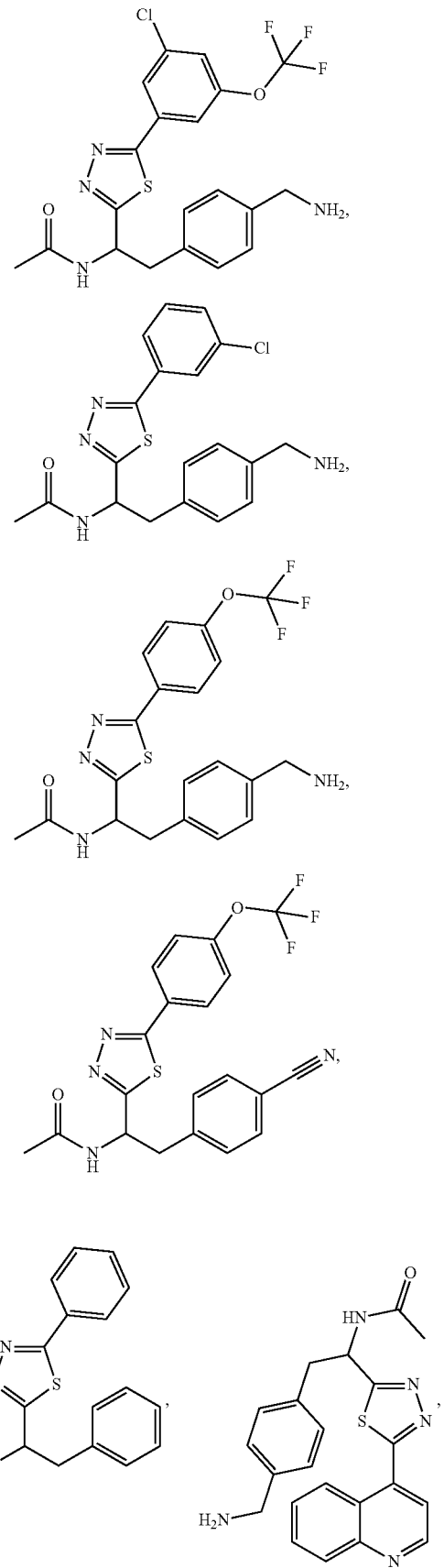

253
-continued
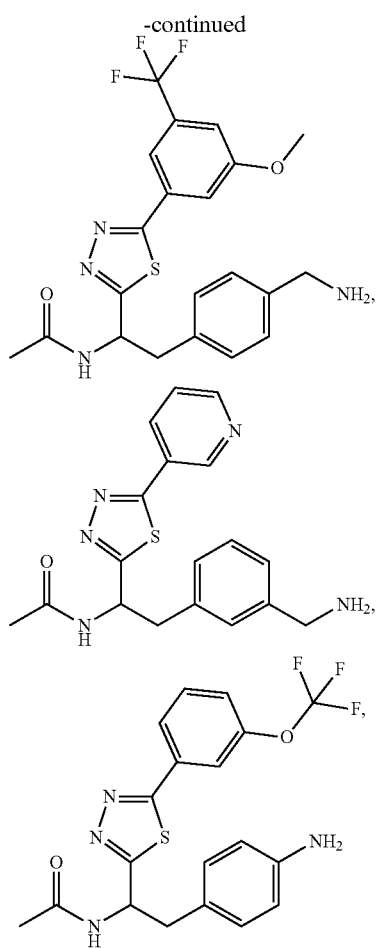
254
-continued
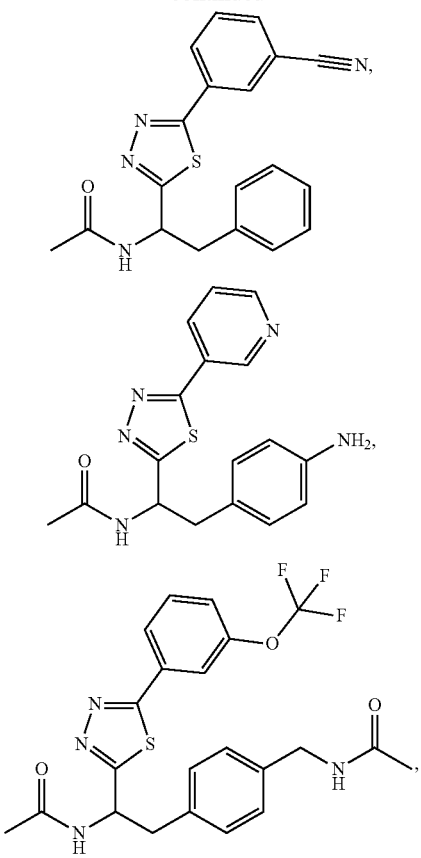
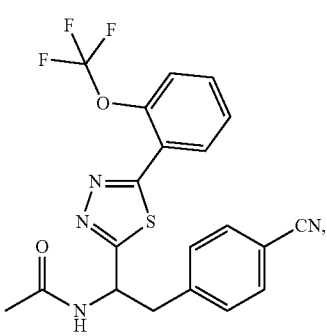
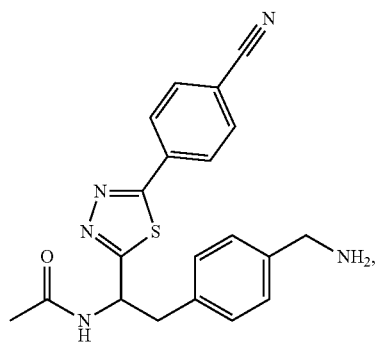
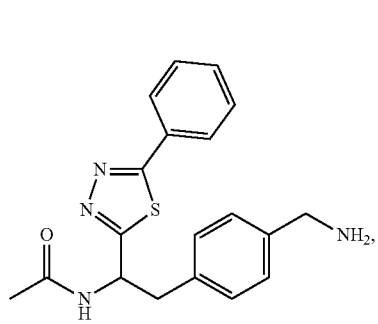
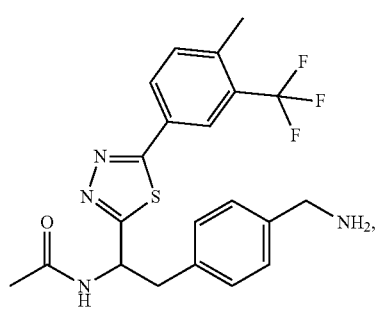

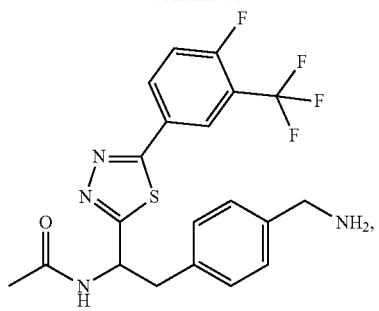
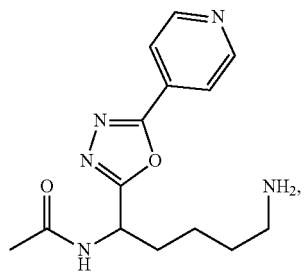
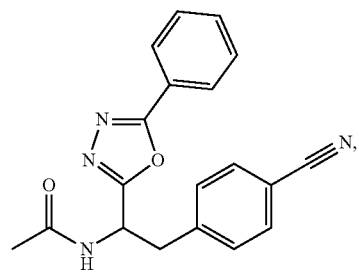
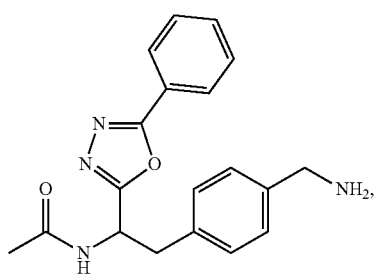
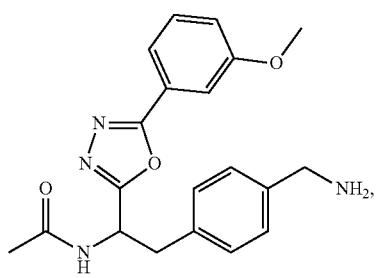
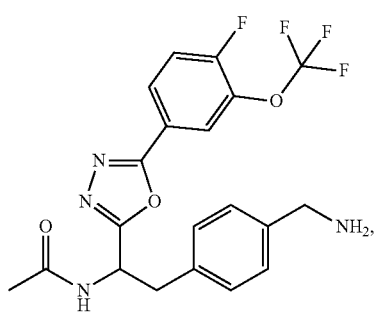
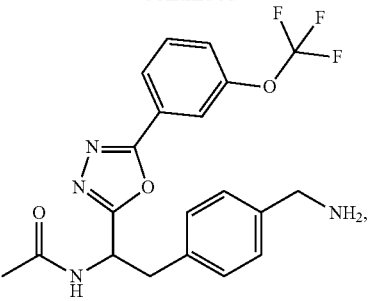
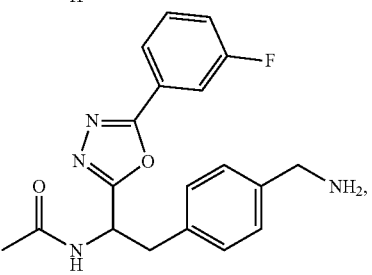
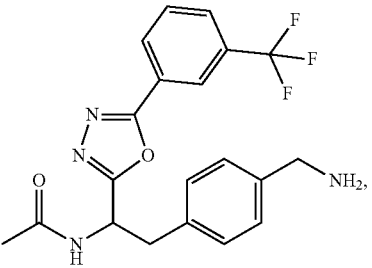
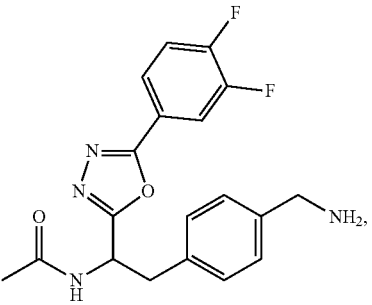
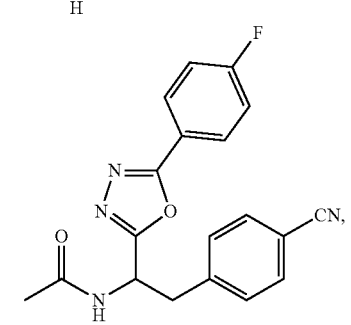

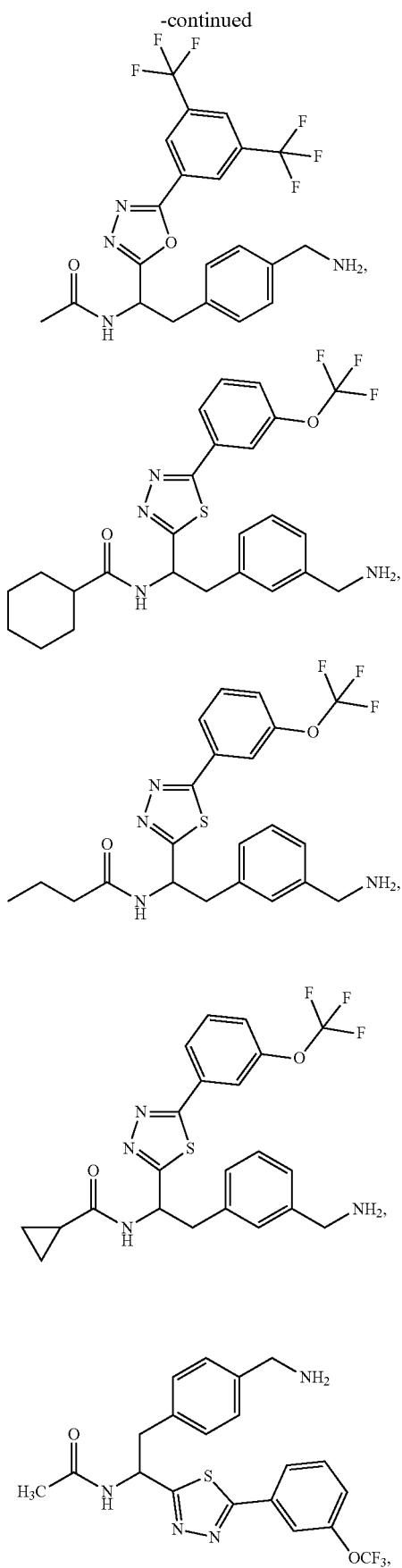
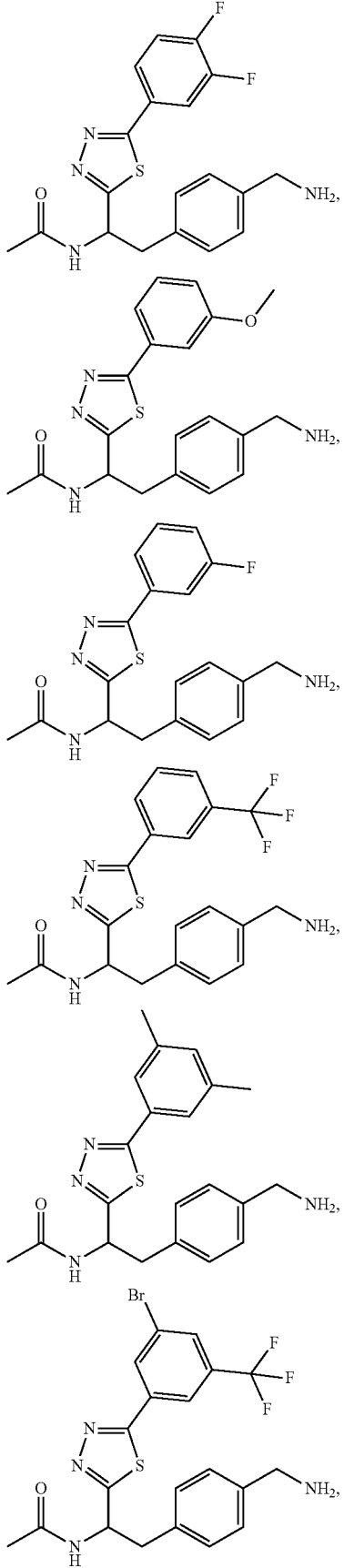

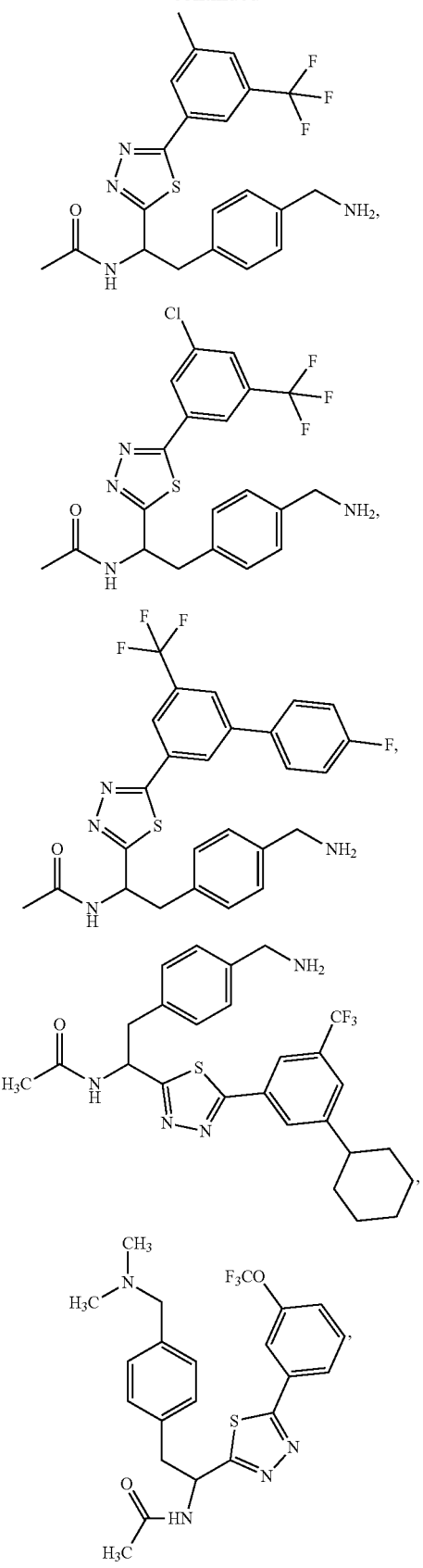
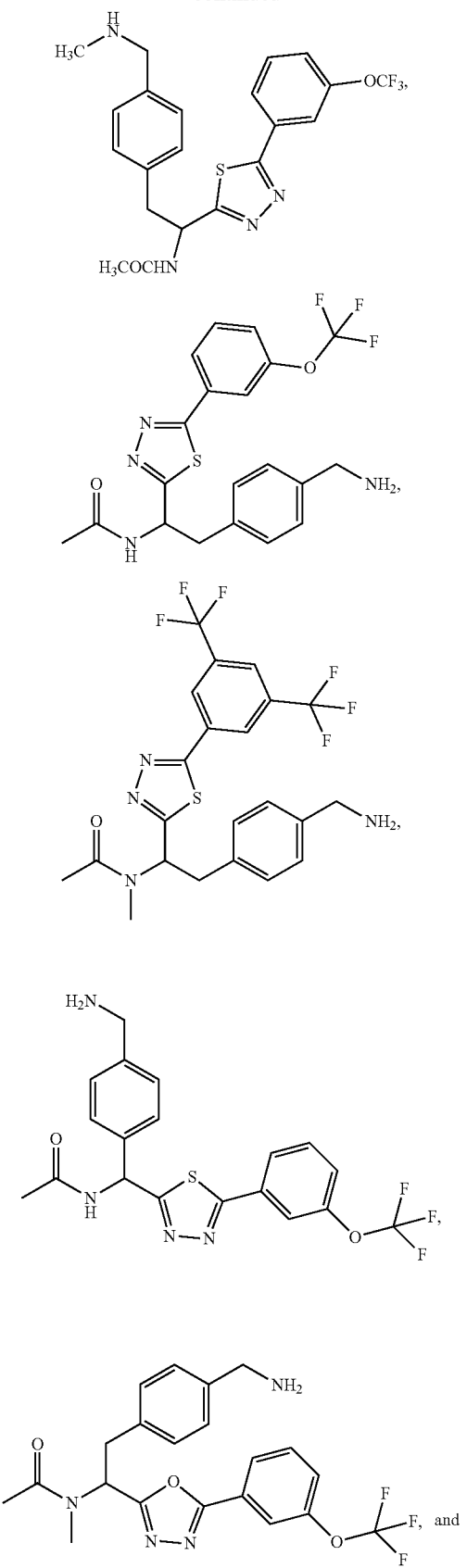

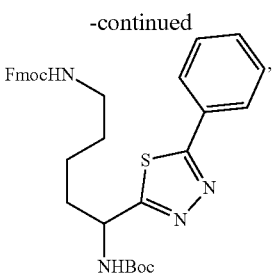

or a pharmaceutically acceptable salt thereof.

11. A pharmaceutical composition comprising a therapeutically effective amount of at least one compound of claim 1 and a pharmaceutically acceptable carrier.

12. A method for treating a disorder associated with TGF-β activity in a subject, the method comprising the step of administering to the subject an effective amount of at least one compound of claim 1.

13. The method of claim 12, wherein $R^3$ is selected from $NR^{20a}R^{20b}$, $NHCOR^{21}$, and $Ar^1$;
wherein $Ar^1$, when present, is selected from aryl and heteroaryl and is substituted with 1-4 non-hydrogen groups independently selected from halogen, C1-C4 alkyl, C1-C4 haloalkyl, C1-C4 hydroxyalkyl, C1-C4 alkoxy, $-(CH_2)_mNH_2$, $-(CH_2)_m(C1-C4$ alkylamino), and $-(CH_2)_m[(C1-C4)(C1-C4)$ dialkylamino].

14. The method of claim 12, wherein the disorder is a cancer, a fibrotic disorder, or an immune dysfunction.

15. The method of claim 12, wherein the subject has been diagnosed with a need for treatment of the disorder prior to the administering step.

16. The method of claim 12, further comprising the step of identifying a subject in need of treatment of the disorder.

17. A method for inhibiting TGF-β activity in a subject, the method comprising the step of administering to the subject an effective amount of at least one compound of claim 1, thereby inhibiting TGF-β activity in the subject.

18. The method of claim 17, wherein the subject has been diagnosed with a need for treatment of a disorder selected from a cancer, a fibrotic disorder, and an immune dysfunction prior to the administering step.

19. A pharmaceutical composition comprising a therapeutically effective amount of at least one compound of claim 10 and a pharmaceutically acceptable carrier.

20. A method for treating a disorder associated with TGF-β activity in a subject, the method comprising the step of administering to the subject an effective amount of at least one compound of claim 10.

21. The method of claim 20, wherein the disorder is a cancer, a fibrotic disorder, or an immune dysfunction.

22. The method of claim 20, wherein the subject has been diagnosed with a need for treatment of the disorder prior to the administering step.

23. The method of claim 20, further comprising the step of identifying a subject in need of treatment of the disorder.

* * * * *